United States Patent
Chen et al.

(10) Patent No.: US 10,730,832 B2
(45) Date of Patent: Aug. 4, 2020

(54) ALIPHATIC PROLINAMIDE DERIVATIVES

(71) Applicant: ORION OPHTHALMOLOGY LLC, New York, NY (US)

(72) Inventors: Austin Chih-Yu Chen, San Marcos, CA (US); Robert Gomez, North Vancouver (CA); Renata Marcella Oballa, Coquitlam (CA); David Andrew Powell, Vancouver (CA); Jeffrey Roger Roppe, Temecula (CA); Thomas Jon Seiders, San Diego, CA (US); Tao Sheng, Coquitlam (CA)

(73) Assignee: ORION OPHTHALMOLOGY LLC, New York, NY (US)

( * ) Notice: Subject to any disclaimer, the term of this patent is extended or adjusted under 35 U.S.C. 154(b) by 0 days.

(21) Appl. No.: 16/312,259

(22) PCT Filed: Jun. 15, 2017

(86) PCT No.: PCT/US2017/037773
§ 371 (c)(1),
(2) Date: Dec. 20, 2018

(87) PCT Pub. No.: WO2017/222917
PCT Pub. Date: Dec. 28, 2017

(65) Prior Publication Data
US 2019/0330146 A1    Oct. 31, 2019

Related U.S. Application Data

(60) Provisional application No. 62/352,965, filed on Jun. 21, 2016.

(51) Int. Cl.
*C07D 207/16* (2006.01)
*C07D 401/04* (2006.01)
(Continued)

(52) U.S. Cl.
CPC ......... *C07D 207/16* (2013.01); *C07D 401/04* (2013.01); *C07D 401/14* (2013.01);
(Continued)

(58) Field of Classification Search
CPC ............................. C07D 207/16; C07D 401/04
See application file for complete search history.

(56) References Cited

U.S. PATENT DOCUMENTS

| 5,948,886 A | 9/1999 | Peet et al. |
| 7,012,066 B2 * | 3/2006 | Saksena ............... C07K 5/0812 514/1.3 |

(Continued)

FOREIGN PATENT DOCUMENTS

| EP | 1 881 002 A1 | 1/2008 |
| WO | WO 98/17679 | 4/1998 |

(Continued)

OTHER PUBLICATIONS

Search Report dated Nov. 12, 2019 in corresponding European Application No. 17815963.8.
(Continued)

*Primary Examiner* — Golam M Shameem
(74) *Attorney, Agent, or Firm* — Haug Partners LLP

(57) ABSTRACT

This invention is directed to novel aliphatic prolinamide derivatives of Formula I, and pharmaceutically acceptable salts, solvates, solvates of the salt and prodrugs thereof, useful in the prevention (e.g., delaying the onset of or reducing the risk of developing) and treatment (e.g., controlling, alleviating, or slowing the progression of) of age-related macular degeneration (AMD) and related diseases of the eye. These diseases include dry-AMD, wet-AMD, geographic atrophy, diabetic retinopathy, retinopathy of prematurity, polypoidal choroidal vasculopathy, and degeneration of retinal or photoreceptor cells. The invention disclosed herein is further directed to methods of prevention, slowing the progress of, and treatment of dry-AMD, wet-AMD, and geographic atrophy, diabetic retinopathy, retinopathy of prematurity, polypoidal choroidal vasculopathy, and degeneration of retinal or photoreceptor cells, comprising: administration of a therapeutically effective amount of compound of the invention. The compounds of the invention are inhibitors of HTRA1. Thus, the compounds of the invention are useful in the prevention and treatment of a wide range of diseases mediated (in whole or in part) by HTRA1. The compounds of the invention are also useful for inhibiting HTRA1 protease activity in an eye or locus of an arthritis or related condition.

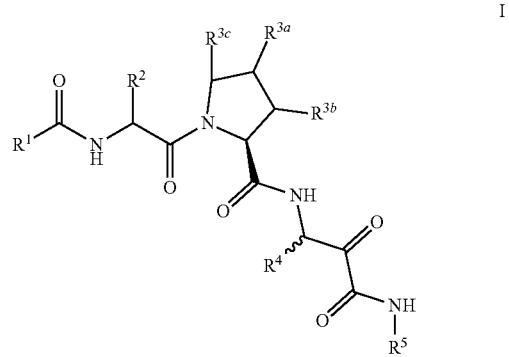

16 Claims, No Drawings

(51) Int. Cl.
    *C07D 401/14*     (2006.01)
    *C07D 403/04*     (2006.01)
    *C07D 403/14*     (2006.01)
    *C07D 405/14*     (2006.01)
    *C07D 409/14*     (2006.01)
    *C07D 413/14*     (2006.01)
    *C07D 471/04*     (2006.01)

(52) U.S. Cl.
    CPC ......... *C07D 403/04* (2013.01); *C07D 403/14* (2013.01); *C07D 405/14* (2013.01); *C07D 409/14* (2013.01); *C07D 413/14* (2013.01); *C07D 471/04* (2013.01)

(56) References Cited

U.S. PATENT DOCUMENTS

| | | | |
|---|---|---|---|
| 7,964,624 B1 | 6/2011 | Cottrell et al. | |
| 10,526,315 B2 * | 1/2020 | Gomez | C07D 471/04 |
| 2007/0032433 A1 | 2/2007 | Saksena et al. | |
| 2014/0294763 A1 | 10/2014 | Babine et al. | |

FOREIGN PATENT DOCUMENTS

| | | |
|---|---|---|
| WO | WO 2004/062601 A2 | 7/2004 |
| WO | WO 2005/087731 A1 | 9/2005 |
| WO | WO 2007/089618 A2 | 8/2007 |
| WO | WO 2007/139585 A1 | 12/2007 |
| WO | WO 2008/106130 A2 | 9/2008 |
| WO | WO 2009/064414 A1 | 5/2009 |
| WO | WO 2012/040242 A1 | 3/2012 |
| WO | WO 2013/053372 A1 | 4/2013 |
| WO | WO 2016/100555 A1 | 6/2016 |

OTHER PUBLICATIONS

Official Action dated Nov. 26, 2019 in corresponding Eurasian Application No. 201990070.

Sellanes, D. et al., "Preparation and Biological Evaluation of Key Fragments and Open Analogs of Scleritodermin A", Tetrahedron, 2010, vol. 66, No. 29, pp. 5384-5395.

International Search Report and Written Opinion dated Sep. 25, 2017 in corresponding International Application No. PCT/US2017/037773.

\* cited by examiner

ALIPHATIC PROLINAMIDE DERIVATIVES

CROSS-REFERENCE TO RELATED APPLICATIONS

This application is the National Stage entry under 35 U.S.C. § 371 of International Application No. PCT/US2017/037773 filed on Jun. 15, 2017, published on Dec. 28, 2017 under Publication Number WO 2017/222917, which claims the benefit of U.S. Provisional Application No. 62/352,965 filed Jun. 21, 2016, the entireties of which are herein incorporated by reference.

BACKGROUND OF THE INVENTION

Field of the Invention

The present disclosure is directed to novel aliphatic prolinamide derivatives, pharmaceutical compositions containing such novel compounds, as well as methods for preventing and treating age-related macular degeneration (AMD) and related diseases of the eye.

Description of the Related Art

Age-related macular degeneration (AMD) is the leading cause of severe loss of vision in people over the age of 60. Age is the major risk factor for the onset of AMD: the likelihood of developing AMD triples after age 55. Many factors, however, contribute to the likelihood that an individual will develop AMD.

As summarized in WO2001/006262, "environmental" conditions may modulate the rate at which an individual develops AMD or the severity of the disease. Light exposure has been proposed as a possible risk factor, since AMD most severely affects the macula, where light exposure is high. (See Young, R. W. (1988), Surv. Ophthalmol. 32(4), 252-69; Taylor, H. R. et al., (1990), Trans. Amer. Ophthalmol. Soc. 88, 163-73; Schalch W. (1992), Exs, 62, 280-98). The amount of time spent outdoors is associated with increased risk of choroidal neovascularization in men, and wearing hats and/or sunglasses is associated with a decreased incidence of soft drusen (Cruickshanks, K. et al., (1993), Arch. Ophthalmol., 111, 514-518). Accidental exposure to microwave irradiation has also been shown to be associated with the development of numerous drusen (Lim, J. et al., (1993), Retina. 13, 230-3). Cataract removal and light iris pigmentation has also been reported as a risk factor in some studies (Sandberg, M. et al., (1994), Invest. Ophthalmol. Vis. Sci. 35(6), 2734-40). This suggests that: 1) eyes prone to cataracts may be more likely to develop AMD; 2) the surgical stress of cataract removal may result in increased risk of AMD, due to inflammation or other surgically-induced factors; or 3) cataracts prevent excessive light exposure from falling on the macula, and are in some way prophylactic for AMD. While it is possible that dark iris pigmentation may protect the macula from light damage, it is difficult to distinguish between iris pigmentation alone and other, co-segregating genetic factors which may be actual risk factors.

Smoking, gender (women are at greater risk), obesity, and repeated exposure to UV radiation also increase the risk of AMD.

More recently, a number of HTRA1 single nucleotide polymorphs (SNP) have been found to be associated with an increased risk of AMD. See, for example, WO2008/013893A2, WO2008/067040A2 and WO2008/094370A2. These SNP's include rs11200638, rs10490924, rs3750848, rs3793917 and rs932275. In particular, the risk allele rs11200638, was found to be associated with increased HTRA1 mRNA and protein expression, and HTRA1 is present in drusen in patients with AMD. (See Dewan et al., (2006), Science 314:989-992; Yang et al., (2006), Science 314:992-993). These disclosures provide evidence that HTRA1 is an important factor in AMD and the progression thereof.

In broad terms, there are two forms of AMD: dry AMD and wet AMD. The dry form is the more common, and accounts for 85-90% of the patients with AMD, and does not typically result in blindness. In dry AMD, (also called non-neovascular AMD or non-exudative AMD) drusen appear in the macula of the eye, the cells in the macula die, and vision becomes blurry. Dry AMD can progress in three stages: 1) early, 2) intermediate, and 3) advanced dry AMD. Dry AMD can also progress into wet AMD during any of these stages.

Wet AMD (also called neovascular or exudative AMD), is associated with pathologic posterior segment neovascularization. The posterior segment neovascularization (PSNV) found in exudative AMD is characterized as pathologic choroidal neovascularization. Leakage from abnormal blood vessels forming in this process damages the macula and impairs vision, eventually leading to blindness.

The end stage of AMD is characterized by a complete degeneration of the neurosensory retina and of the underlying retinal pigment epithelium in the macular area. Advanced stages of AMD can be subdivided into geographic atrophy (GA) and exudative AMD. Geographic atrophy is characterized by progressive atrophy of the retinal pigment epithelium (RPE). While GA is typically considered less severe than the exudative AMD because its onset is less sudden, to date no treatment has been effective at halting or slowing its progression.

Currently, treatment of dry AMD includes the administration of antioxidant vitamins and/or zinc. For example, one study at the National Eye Institute assessed a composition comprising vitamin C, β-carotene, zinc oxide and cupric oxide.

Treatment of wet AMD is also wanting. Available drug therapies include: bevacizumab (Avastin®, Genentech, CA), ranibizumab (Lucentis®, Genentech, CA), pegaptanib (Macugen® Bausch & Lomb, NJ), and aflibercept (Eylea®, Regeneron, NY). In each instance, the medication is injected into the eye. Injections may be repeated every four to eight weeks to maintain the beneficial effect of the medication. Those with a positive result may partially recover vision as the blood vessels shrink and the fluid under the retina is absorbed, allowing retinal cells to regain some function.

Pharmacologic therapy for the treatment of macular edema associated with AMD is lacking. The current standard of care is laser photocoagulation, which is used to stabilize or resolve macular edema and retard the progression to later stage disease. Laser photocoagulation may reduce retinal ischemia by destroying healthy tissue and thereby decreasing metabolic demand; it also may modulate the expression and production of various cytokine and trophic factors. There are no current treatments for preventing loss of vision after dry AMD enters an advanced stage. There are also no definitive methods for preventing progression of dry AMD to an advanced stage, other than by avoiding and/or reducing risk factors and using dietary supplements, which cannot guarantee or be relied on to stop AMD progression. Thus, there is a need for therapeutics that can treat dry AMD and prevent progression of dry to wet AMD.

The compound (1-{3-cyclohexyl-2-[naphthalene-2-carbonyl)-amino]-propionyl}-pyrrolidine-2-carboxylic acid [5-(3-cyclohexyl-ureido)-1-dihydroxyboranyl-pentyl]-amide is disclosed in Grau, S. et. al., (2006), J. Biol. Chem., 281(10): 6124-6129 and in WO2012/078540 (identified therein as NVP-LB976) as an inhibitor of HTRA1.

In addition to AMD, a number of publications have described a potential role of HTRA1 and disease, including retinal angiomatous proliferation (Ohkuma, Y., et al., (2014) Clin. Ophthalmol., 8:143-8), foveomacular proliferation (Chowers, I., et al., (2015) Progress in Retinal and Eye Research, 47:64-85), musculoskeletal diseases, including osteoarthritis, spinal disk degeneration rheumatoid arthritis, muscular dystrophy and osteoporosis (Taiden, A. N. and Richards, P. J. (2013) Am. J. Pathology, 182(5):1482-8), and treatment of autologous chondrocytes prior to intraarticular implantation (Ollitrault, D. et al., (2015) Tissue Engineering, Part C Methods, 21(2):133-47). An HTRA1 inhibitor thus may demonstrate a therapeutic benefit in these additional indications.

SUMMARY OF THE INVENTION

The present disclosure is directed to novel aliphatic prolinamide derivatives of Formula I, and pharmaceutically acceptable salts, solvates, solvates of the salts and prodrugs thereof, pharmaceutical compositions comprising a compound of Formula I, as well as methods for preventing and treating age-related macular degeneration (AMD) and related diseases of the eye comprising administering to a patient in need thereof a therapeutically effective amount of a compound of Formula I. These diseases include, but are not limited to, dry-AMD, wet-AMD, geographic atrophy, diabetic retinopathy, retinopathy of prematurity, polypoidal choroidal vasculopathy, and degeneration of retinal or photoreceptor cells. The compounds of the present disclosure are inhibitors of HTRA1, and are useful in the prevention and treatment of diseases mediated (in whole or in part) by HTRA1. The compounds of the present disclosure are also useful for inhibiting HTRA1 protease activity in an eye or locus of an arthritis or related condition.

DETAILED DESCRIPTION OF THE PREFERRED EMBODIMENT

In a first embodiment the present disclosure provides compounds of Formula

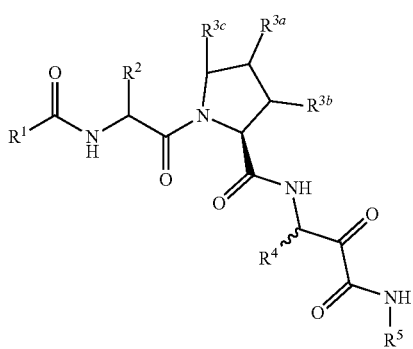

(I)

or a pharmaceutically acceptable salt, solvate, solvate of the salt or prodrug thereof wherein:

$R^1$ is selected from the group consisting of:
(a) -aryl and
(b) -heteroaryl;
wherein the aryl and heteroaryl of choices (a) and (b) are each optionally substituted with 1 to 3 substituents independently selected from the group consisting of:
(i) -halogen,
(ii) —CN,
(iii) —$C_{1-6}$alkyl,
(iv) —$C_{2-6}$alkenyl,
(v) —$C_{2-6}$alkynyl,
(vi) —C(O)$R^8$,
(vii) —CO$_2R^8$,
(viii) —CONR$^5R^6$,
(ix) —OH,
(x) —O—$C_{1-6}$alkyl,
(xi) —SH,
(xii) —S(O)$_p$—$C_{1-6}$alkyl,
(xiii) —S(O)$_2$NR$^5R^6$,
(xiv) —NO$_2$,
(xv) —NR$^5R^6$,
(xvi) —NHC(O)$R^8$,
(xvii) —NHC(O)O$R^8$,
(xviii) —NHC(O)NR$^5R^6$, and
(xix) —NHSO$_2C_{1-6}$alkyl,
wherein each of the alkyl group of choices (iii), (x), (xii) and (xix) is optionally substituted with 1 to 5 substituents independently selected from -halogen, -halo$C_{1-4}$alkyl, —COR$^8$, —CO$_2R^8$, —CONR$^5R^6$, —NR$^5R^6$, —OH, —O—$C_{1-4}$alkyl, —SH and —S—$C_{1-4}$alkyl;

$R^2$ is selected from the group consisting of:
(a) —$C_{3-8}$alkyl,
(b) —$C_{0-6}$alkyl-$R^7$, and
(c) —(CH$_2$)$_{1-6}$—N($R^{13}$)($R^{13}$),
wherein each of the alkyl group of choices (a) and (b) is optionally substituted with 1 to 5 substituents independently selected from:
(i) -halogen,
(ii) —$C_{1-4}$alkyl,
(iii) -halo$C_{1-4}$alkyl,
(iv) —OH,
(v) —O—$C_{1-4}$alkyl,
(vi) —SH, and
(vii) —S—$C_{1-4}$alkyl;

$R^{3b}$ and $R^{3c}$ together represent —(CH$_2$)$_{2-3}$—, and $R^{3a}$ is H; or
$R^{3b}$ and $R^{3c}$ are each H, and $R^{3a}$ is selected from the group consisting of:

(a) —H, (b) -aryl, (c) 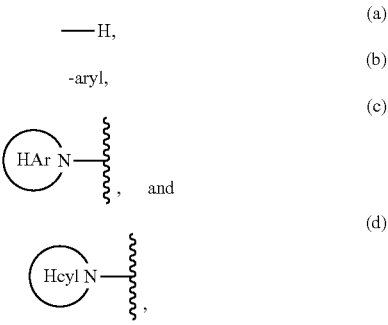 and (d)

wherein HAr is heteroaryl and Hcyl is heterocycle, wherein each of the aryl of choice (b), HAr and Hcyl is optionally substituted with 1 to 3 groups independently selected from the group consisting of:

(i) -halogen,
(ii) —OH,
(iii) —CR$^{10}$R$^{11}$R$^{12}$,
(iv) —(CH$_2$)$_{0-3}$—NHSO$_2$—C$_{1-4}$alkyl, and
(v) —(CH$_2$)$_{0-3}$—SO$_2$—C$_{1-4}$alkyl;

R$^4$ is selected from the group consisting of:
(a) —C$_{1-6}$alkyl,
(b) -haloC$_{1-6}$alkyl,
(c) —C$_{2-6}$alkenyl,
(d) —C$_{2-6}$alkynyl,
(e) —C$_{1-6}$alkyl-C$_{3-6}$cycloalkyl,
(f) —C$_{1-6}$alkyl-aryl, wherein aryl is optionally substituted with nitro or —N(R$^{13}$)(R$^{13}$)
(g) —C$_{1-6}$alkyl-R$^9$, and
(h) -haloC$_{1-6}$alkyl-R$^9$;

each R$^5$ and each R$^6$ are independently selected from the group consisting of:
(a) —H,
(b) —C$_{1-6}$alkyl,
(c) —C$_{0-6}$alkyl-C$_{3-12}$cycloalkyl,
(d) —C$_{0-6}$alkyl-heterocyclyl,
(e) —C$_{0-6}$alkyl-heteroaryl, and
(f) —C$_{0-6}$alkyl-aryl,
wherein the alkyl group of choices (b)-(f) is optionally substituted with 1 to 3 groups independently selected from:
(i) -halogen,
(ii) —C(O)C$_{1-4}$alkyl,
(iii) —C(O)OC$_{1-4}$alkyl,
(iv) —OH,
(v) —OC$_{1-4}$alkyl,
(vi) —SH,
(vii) —SC$_{1-4}$alkyl,
(viii) —NH$_2$,
(ix) —NH(C$_{1-4}$alkyl), and
(x) —N(C$_{1-4}$alkyl)(C$_{1-4}$alkyl); or R$^5$, R$^6$ and the nitrogen atom to which they are attached together form a 3- to 7-membered monocyclic or 6- to 11-membered bicyclic heterocycle optionally having an additional heteroatomic moiety selected from —O—, —S(O)$_p$—, and —NR$^{13}$—, and wherein said heterocycle is optionally substituted with 1 to 2 groups independently selected from halogen, -haloC$_{1-4}$alkyl, —OH, —O—C$_{1-4}$alkyl, —SH and —S—C$_{1-4}$alkyl;

R$^7$ is selected from the group consisting of:
(a) —C$_{3-10}$cycloalkyl, and
(b) -heterocyclyl,
wherein each of choices (a) and (b) is optionally substituted with 1 to 3 substituents independently selected from the group consisting of:
(i) —C$_{1-4}$alkyl,
(ii) -halogen,
(iii) —OH,
(iv) —O—C$_{1-4}$alkyl,
(v) —SH, and
(vi) —S—C$_{1-4}$alkyl;

R$^8$ is selected from the group consisting of:
(a) —C$_{1-6}$alkyl,
(b) —C$_{0-6}$alkyl-C$_{3-12}$cycloalkyl,
(c) —C$_{0-6}$alkyl-heterocyclyl,
(d) —C$_{0-6}$alkyl-heteroaryl, and
(e) —C$_{0-6}$alkyl-aryl,
wherein each of the alkyl group of choices (a)-(e) is optionally substituted with 1 to 3 groups independently selected from:
(i) -halogen,
(ii) —OH,
(iii) —OC$_{1-4}$alkyl,
(iv) —SH, and
(v) —SC$_{1-4}$alkyl;

R$^9$ is selected from the group consisting of:
(a) —NH$_2$,
(b) —NH—C$_{1-4}$alkyl,
(c) —N(C$_{1-4}$alkyl)$_2$,
(d) —NH—C(=O)—NH$_2$,
(e) —NH—C(=O)—NH—C$_{1-4}$alkyl,
(f) —NH—C(=O)—N(C$_{1-4}$alkyl)$_2$,
(g) —NH—C(=O)—NH—C$_{3-5}$alkenyl,
(h) —NH—C(=O)—NH—C$_{3-5}$alkynyl,
(i) —NH—C(=O)—NH—C$_{3-6}$cycloalkyl,
(j) —NH—C(=O)—NH-aryl,
(k) —NH—C(=O)—NH-heterocycle,
(l) —NH—C(=O)—NH-heteroaryl,
(m) —NH—C(=O)—NH—SO$_2$—C$_{1-4}$alkyl,
(n) —NH—C(=O)—NH—SO$_2$—C$_{3-6}$cycloalkyl,
(o) —NH—C(=O)—O—C$_{1-4}$alkyl,
(p) —NH—C(=O)—O—C$_{1-4}$alkylaryl,
(q) —NH—C(=O)—C$_{1-4}$alkyl,
(r) —NH—C(=O)—C$_{3-6}$cycloalkyl,
(s) —NH—C(=O)-aryl,
(t) —NH—C(=O)-heterocycle,
(u) —NH—C(=O)-heteroaryl, and
(v) —NH—SO$_2$—C$_{1-4}$alkyl,
wherein each of choices (b) to (v) is optionally substituted with 1 to 3 substituents independently selected from the group consisting of:
(i) —C$_{1-4}$alkyl,
(ii) -halogen,
(iii) —OH,
(iv) —O—C$_{1-4}$alkyl,
(v) —SH,
(vi) —S—C$_{1-4}$alkyl;
(vii) —NO$_2$, and
(viii) —CN;
(ix)

R$^{10}$, R$^{11}$, and R$^{12}$ are independently selected from the group consisting of: H, halogen, —OH and —C$_{1-6}$ alkyl; or R$^{10}$, R$^{11}$ and the carbon atom to which they are attached together form a C$_{3-12}$cycloalkyl or a heterocyclyl group;

R$^{13}$ is selected from the group consisting of:
(a) —H,
(b) —C$_{1-4}$alkyl,
(c) —C(O)—C$_{1-4}$alkyl,
(d) —C(O)NH$_2$,
(e) —C(O)—NH(C$_{1-4}$alkyl),
(f) —C(O)—NH(C$_{3-6}$cycloalkyl),
(g) —C(O)—N(C$_{1-4}$alkyl)$_2$,
(h) —C(O)O—C$_{1-4}$alkyl, and
(i) —C(O)O—C$_{1-4}$alkylaryl;

p is 0, 1 or 2.

In a second embodiment, for a compound of the first embodiment, R$^1$ is selected from the group consisting of:
(a) -aryl and
(b) -heteroaryl;
Wherein the aryl and heteroaryl of choices (a) and (b) are each optionally substituted with 1 to 3 substituents independently selected from the group consisting of:
(i) -halogen,
(ii) —CN,
(iii) —C(O)R$^8$,
(iv) —CONR$^5$R$^6$,
(v) —OH,
(vi) —O—C$_{1-6}$alkyl,
(vii) —S(O)$_p$—C$_{1-6}$alkyl,
(viii) —S(O)$_2$NR$^5$R$^6$, (ix) —NHC(O)R$^8$,
(x) —NHC(O)OR$^8$,
(xi) —NHSO$_2$C$_{1-6}$alkyl, wherein each of the alkyl group of choices (iii), (x), (xii) and (xix) is optionally substituted with 1 to 5 substituents independently selected from -halogen, -haloC$_{1-4}$alkyl, —COR$^8$, —CO$_2$R$^8$, —CONR$^5$R$^6$, —NR$^5$R$^6$, —OH, —O—C$_{1-4}$alkyl, —SH and —S—C$_{1-4}$alkyl.

In a third embodiment, for a compound of any of the preceding embodiments, R$^2$ is selected from the group consisting of:
(a) —C$_{1-6}$alkyl-R$^7$, and
(b) —(CH$_2$)$_{1-6}$—N(R$^{13}$)(R$^{13}$), wherein the alkyl group of choice (a) is optionally substituted with 1 to 5 substituents independently selected from:
(i) -halogen,
(ii) —C$_{1-4}$alkyl,
(iii) -haloC$_{1-4}$alkyl,
(iv) —OH,
(v) —O—C$_{1-4}$alkyl,
(vi) —SH, and
(vii) —S—C$_{1-4}$alkyl.

In a fourth embodiment, for a compound of any of the preceding embodiments, R$^2$ is selected from the group consisting of:
(a) —(CH$_2$)$_{1-6}$—R$^7$, and
(b) —(CH$_2$)$_{1-6}$—N(R$^{13}$)(R$^{13}$).

In a fifth embodiment, for a compound of any of the preceding embodiments, R$^{3b}$ and R$^{3c}$ are each H, and R$^{3a}$ is selected from the group consisting of:

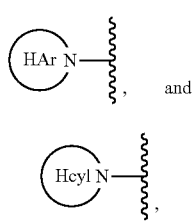

wherein HAr is heteroaryl and Hcyl is heterocycle, wherein each of HAr and Hcyl is optionally substituted with 1 to 3 groups independently selected from the group consisting of:
(i) -halogen,
(ii) —OH,
(iii) —CR$^{10}$R$^{11}$R$^{12}$,
(iv) —(CH$_2$)$_{0-3}$—NHSO$_2$—C$_{1-4}$alkyl, and
(v) —(CH$_2$)$_{0-3}$—SO$_2$—C$_{1-4}$alkyl.

In a sixth embodiment, for a compound of any of the preceding embodiments, R$^4$ is selected from the group consisting of:
(a) —C$_{1-6}$alkyl,
(b) —C$_{2-6}$alkenyl,
(c) —C$_{1-6}$alkyl-C$_{3-6}$cycloalkyl,
(d) —C$_{1-6}$alkyl-aryl, wherein aryl is optionally substituted with nitro or —N(R$^{13}$)(R$^{13}$) and
(e) —C$_{1-6}$alkyl-R$^9$.

In a seventh embodiment, for a compound of any of the preceding embodiments, R$^4$ is —C$_{1-6}$alkyl-R$^9$.

In an eighth embodiment, for a compound of the first embodiment is a compound having the Formula (Ia):

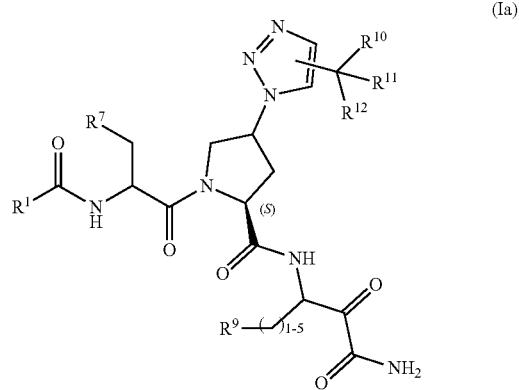

or a pharmaceutically acceptable salt, solvate, solvate of the salt or prodrug thereof; wherein
R$^1$ is selected from the group consisting of:
(a) -aryl and
(b) -heteroaryl;

wherein the aryl and heteroaryl of choices (a) and (b) are each optionally substituted with 1 to 3 substituents independently selected from the group consisting of:
(i) -halogen,
(ii) —CN,
(iii) —C$_{1-6}$alkyl,
(iv) —C$_{2-6}$alkenyl,
(v) —C$_{2-6}$alkynyl,
(vi) —C(O)R$^8$,
(vii) —CO$_2$R$^8$,
(viii) —CONR$^5$R$^6$,
(ix) —OH,
(x) —O—C$_{1-6}$alkyl,
(xi) —SH,
(xii) —S(O)$_p$—C$_{1-6}$alkyl,
(xiii) —S(O)$_2$NR$^5$R$^6$,
(xiv) —NO$_2$,
(xv) —NR$^5$R$^6$,
(xvi) —NHC(O)R$^8$,
(xvii) —NHC(O)OR$^8$,
(xviii) —NHC(O)NR$^5$R$^6$, and
(xix) —NHSO$_2$C$_{1-6}$alkyl, wherein each of the alkyl group of choices (iii), (x), (xii) and (xix) is optionally substituted with 1 to 5 substituents independently selected from -halogen, -haloC$_{1-4}$alkyl, —COR$^5$, —CO$_2$R$^8$, —CONR$^5$R$^6$, —NR$^5$R$^6$, —OH, —O—C$_{1-4}$alkyl, —SH and —S—C$_{1-4}$alkyl;

each R$^5$ and each R$^6$ are independently selected from the group consisting of:
(a) —H,
(b) —C$_{1-6}$alkyl,
(c) —C$_{0-6}$alkyl-C$_{3-12}$cycloalkyl,
(d) —C$_{0-6}$alkyl-heterocyclyl,
(e) —C$_{0-6}$alkyl-heteroaryl, and
(f) —C$_{0-6}$alkyl-aryl, wherein each of the alkyl groups of choices (b)-(f) is optionally substituted with 1 to 3 groups independently selected from:
(i) -halogen,
(ii) —C(O)C$_{1-4}$alkyl,
(iii) —C(O)OC$_{1-4}$alkyl,
(iv) —OH,
(v) —OC$_{1-4}$alkyl,
(vi) —SH, (vii) —S$C_{1-4}$alkyl,
(viii) —N$H_2$,
(ix) —NH($C_{1-4}$alkyl), and
(x) —N($C_{1-4}$alkyl)($C_{1-4}$alkyl); or $R^5$, $R^6$ and the nitrogen atom to which they are attached together form a 3- to 7-membered monocyclic or 6- to 11-membered bicyclic heterocycle optionally having an additional heteroatomic moiety selected from —O—, —S(O)$_p$—, and N$R^{13}$—, and wherein said heterocycle is optionally substituted with 1 to 2 groups independently selected from halogen, -halo$C_{1-4}$alkyl, —OH, —O—$C_{1-4}$alkyl, —SH and —S—$C_{1-4}$alkyl;

$R^7$ is selected from the group consisting of:
(a) —$C_{3-10}$ cycloalkyl, and
(b) —$C_{4-10}$ heterocyclyl,
wherein each of choices (a) and (b) is optionally substituted with 1 to 3 substituents independently selected from the group consisting of:
(i) —$C_{1-4}$alkyl,
(ii) -halogen,
(iii) —OH,
(iv) —O—$C_{1-4}$alkyl,
(v) —SH, and
(vi) —S—$C_{1-4}$alkyl;

$R^8$ is selected from the group consisting of:
(a) —$C_{1-6}$alkyl,
(b) —$C_{0-6}$alkyl-$C_{3-12}$cycloalkyl,
(c) —$C_{0-6}$alkyl-heterocyclyl,
(d) —$C_{0-6}$alkyl-heteroaryl, and
(e) —$C_{0-6}$alkyl-aryl,
wherein the alkyl group of choices (a)-(e) is optionally substituted with 1 to 3 groups independently selected from:
(i) -halogen,
(ii) —OH,
(iii) —O$C_{1-4}$alkyl,
(iv) —SH, and
(v) —S$C_{1-4}$alkyl;

$R^9$ is selected from the group consisting of:
(a) —N$H_2$,
(b) —NH—$C_{1-4}$alkyl,
(c) —N($C_{1-4}$alkyl)$_2$,
(d) —NH—C(=O)—N$H_2$,
(e) —NH—C(=O)—NH—$C_{1-4}$alkyl,
(f) —NH—C(=O)—N($C_{1-4}$alkyl)$_2$,
(g) —NH—C(=O)—NH—$C_{3-5}$alkenyl,
(h) —NH—C(=O)—NH—$C_{3-5}$alkynyl,
(i) —NH—C(=O)—NH—$C_{3-6}$cycloalkyl,
(j) —NH—C(=O)—NH-aryl,
(k) —NH—C(=O)—NH-heterocycle,
(l) —NH—C(=O)—NH-heteroaryl,
(m) —NH—C(=O)—NH—S$O_2$—$C_{1-4}$alkyl,
(n) —NH—C(=O)—NH—S$O_2$—$C_{3-6}$cycloalkyl,
(o) —NH—C(=O)—O—$C_{1-4}$alkyl,
(p) —NH—C(=O)—O—$C_{1-4}$alkylaryl,
(q) —NH—C(=O)—$C_{1-4}$alkyl,
(r) —NH—C(=O)—$C_{3-6}$cycloalkyl,
(s) —NH—C(=O)-aryl,
(t) —NH—C(=O)-heterocycle,
(u) —NH—C(=O)-heteroaryl, and
(v) —NH—S$O_2$—$C_{1-4}$alkyl,
wherein each of choices (b) to (v) is optionally substituted with 1 to 3 substituents independently selected from the group consisting of:
(i) —$C_{1-4}$alkyl,
(ii) -halogen,
(iii) —OH,
(iv) —O—$C_{1-4}$alkyl,
(v) —SH,
(vi) —S—$C_{1-4}$alkyl;
(vii) —N$O_2$, and
(viii) —CN;

$R^{10}$, $R^{11}$, and $R^{12}$ are independently selected from the group consisting of: H, halogen, —OH and —$C_{1-6}$ alkyl; or $R^{10}$, $R^{11}$ and the carbon atom to which they are attached together form a $C_{3-12}$cycloalkyl or a heterocyclyl group;

$R^{13}$ is selected from the group consisting of:
(a) —H,
(b) —$C_{1-4}$alkyl,
(c) —C(O)—$C_{1-4}$alkyl,
(d) —C(O)N$H_2$,
(e) —C(O)—NH($C_{1-4}$alkyl),
(f) —C(O)—NH($C_{3-6}$cycloalkyl),
(g) —C(O)—N($C_{1-4}$alkyl)$_2$,
(h) —C(O)O—$C_{1-4}$alkyl, and
(i) —C(O)O—$C_{1-4}$alkylaryl; and
p is 0, 1 or 2.

In a ninth embodiment, for a compound of any of the preceding embodiments having the formula (Ia), $R^1$ is selected from the group consisting of:
(a) -aryl, and
(b) -heteroaryl;
wherein the aryl and heteroaryl of choices (a) and (b) are each optionally substituted with 1 to 3 substituents independently selected from the group consisting of:
(i) -halogen,
(ii) —CN,
(iii) —C(O)$R^8$,
(iv) —CON$R^5R^6$,
(v) —OH,
(vi) —O—$C_{1-6}$alkyl,
(vii) —S(O)$_p$—$C_{1-6}$alkyl,
(viii) —S(O)$_2$N$R^5R^6$,
(ix) —NHC(O)$R^8$,
(x) —NHC(O)O$R^8$, and
(xi) —NHS$O_2C_{1-6}$alkyl,
wherein each of the alkyl group of choices (vi), (vii), and (xi) is optionally substituted with 1 to 5 substituents independently selected from -halogen, -halo$C_{1-4}$alkyl, —CO$R^8$, —C$O_2R^8$, —CON$R^5R^6$, —N$R^5R^6$, —OH, —O—$C_{1-4}$alkyl, —SH and —S—$C_{1-4}$alkyl;

$R^7$ is —$C_{3-10}$cycloalkyl;

$R^9$ is selected from the group consisting of:
(a) —NH—C(=O)—NH—$C_{1-4}$alkyl,
(b) —NH—C(=O)—N($C_{1-4}$alkyl)$_2$,
(c) —NH—C(=O)—NH—$C_{3-8}$alkenyl,
(d) —NH—C(=O)—NH—$C_{3-8}$alkynyl,
(e) —NH—C(=O)—NH—$C_{3-6}$cycloalkyl,
(f) —NH—C(=O)—NH-aryl,
(g) —NH—C(=O)—NH-heterocycle,
(h) —NH—C(=O)—NH-heteroaryl,
(i) —NH—C(=O)—NH—S$O_2$—$C_{1-4}$alkyl,
(j) —NH—C(=O)—NH—S$O_2$—$C_{3-6}$cycloalkyl,
(k) —NH—C(=O)—O—$C_{1-4}$alkyl, and
(l) —NH—C(=O)—O—$C_{1-4}$alkylaryl,
wherein each of choices (a) to (l) is optionally substituted with 1 to 3 substituents independently selected from the group consisting of:
(i) —$C_{1-4}$alkyl,
(ii) -halogen,
(iii) —OH,
(iv) —O—$C_{1-4}$alkyl, (v) —SH, and
(vi) —S—$C_{1-4}$alkyl;
$R^{10}$ and $R^{11}$ are each —$C_{1-4}$alkyl, or
$R^{10}$, $R^{11}$ and the carbon atom to which they are attached together form a $C_{3-6}$cycloalkyl or a 4- to 6-membered heterocycle, and
$R^{12}$ is —OH.

In a tenth embodiment, the compound of the first embodiment is a compound having the formula (Ib):

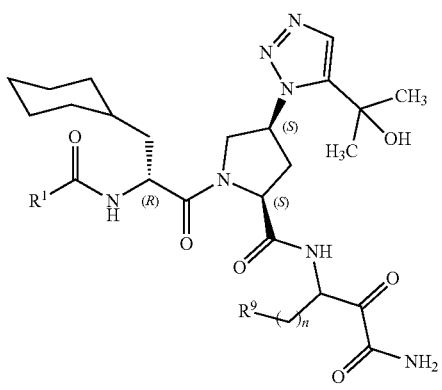

(Ib)

or a pharmaceutically acceptable salt, solvate, solvate of the salt or prodrug thereof, wherein $R^1$ is selected from the group consisting of:
(a) -aryl, and
(b) -heteroaryl;
wherein the aryl and heteroaryl of choices (a) and (b) are each optionally substituted with 1 to 3 substituents independently selected from the group consisting of:
(i) -halogen,
(ii) —CN,
(iii) —C(O)$R^8$,
(iv) —CONR$^5$R$^6$,
(v) —OH,
(vi) —O—$C_{1-6}$alkyl,
(vii) —S(O)$_p$—$C_{1-6}$alkyl,
(viii) —S(O)$_2$NR$^5$R$^6$,
(ix) —NHC(O)$R^8$,
(x) —NHC(O)O$R^8$,
(xi) —NHSO$_2$$C_{1-6}$alkyl, and
(xii) $C_{1-4}$alkyl;
wherein each of the alkyl group of choices (vi), (vii), and (xi) is optionally substituted with 1 to 5 substituents independently selected from -halogen, -halo$C_{1-4}$alkyl, —COR$^8$, —CO$_2$R$^8$, —CONR$^5$R$^6$, —NR$^5$R$^6$, —OH, —O—$C_{1-4}$alkyl, —SH and —S—$C_{1-4}$alkyl;
$R^9$ is selected from the group consisting of:
(a) —NH—C(═O)—NH—$C_{1-4}$alkyl,
(b) —NH—C(═O)—N($C_{1-4}$alkyl)$_2$,
(c) —NH—C(═O)—NH—$C_{3-8}$alkenyl,
(d) —NH—C(═O)—NH—$C_{3-5}$alkynyl,
(e) —NH—C(═O)—NH—$C_{3-6}$cycloalkyl,
(f) —NH—C(═O)—NH-aryl,
(g) —NH—C(═O)—NH-heterocycle,
(h) —NH—C(═O)—NH-heteroaryl,
(i) —NH—C(═O)—NH—SO$_2$—$C_{1-4}$alkyl,
(j) —NH—C(═O)—NH—SO$_2$—$C_{3-6}$cycloalkyl,
(k) —NH—C(═O)—O—$C_{1-4}$alkyl, and
(l) —NH—C(═O)—O—$C_{1-4}$alkylaryl,
wherein each of choices (a) to (l) is optionally substituted with 1 to 3 substituents independently selected from the group consisting of:

(i) —$C_{1-4}$alkyl,
(ii) -halogen,
(iii) —OH,
(iv) —O—$C_{1-4}$alkyl,
(v) —SH, and
(vi) —S—$C_{1-4}$alkyl; and
n is 1 to 5.

In an eleventh embodiment, for a compound of the tenth embodiment n is 4.

In a twelfth embodiment, for a compound of the tenth or eleventh embodiment, $R^1$ is phenyl optionally substituted with 1 to 3 substituents independently selected from the group consisting of:
(i) -halogen,
(ii) —CN,
(iii) —C(O)$R^8$,
(iv) —CONR$^5$R$^6$,
(v) —OH,
(vi) —O—$C_{1-6}$alkyl,
(vii) —S(O)$_p$—$C_{1-6}$alkyl, and
(viii) —S(O)$_2$NR$^5$R$^6$;
wherein each of the alkyl group of choices (vi) and (vii) is optionally substituted with 1 to 5 substituents independently selected from -halogen, -halo$C_{1-4}$alkyl, —COR$^5$, —CO$_2$R, —CONH$_2$, —OH, and —O—$C_{1-4}$alkyl.

In a thirteenth embodiment, for a compound of the tenth or eleventh embodiment $R^1$ is naphthyl.

In a fourteenth embodiment, for a compound of the tenth or eleventh embodiment $R^1$ is selected from the group consisting of:
(a) 5- or 6-membered monocyclic heteroaryl ring having a heteroatom selected from N, O and S, and optionally 1, 2 or 3 additional N atoms; and
(b) 8-, 9-, or 10-membered fused bicyclic heteroaryl ring having a heteroatom selected from N, O and S, and optionally 1, 2 or 3 additional N atoms;
wherein each of choices (a) and (b) is optionally substituted with a group selected from: OH and $C_{1-4}$alkyl.

In a fifteenth embodiment, the compound of the first embodiment is a compound selected from:
(2S)-1-((R)-2-(2-naphthamido)-3-cyclohexylpropanoyl)-N-(1-amino-4-methyl-1,2-dioxopentan-3-yl)pyrrolidine-2-carboxamide;
methyl (3-((S)-1-((R)-2-(2-naphthamido)-3-cyclohexylpropanoyl)pyrrolidine-2-carboxamido)-4-methyl-2-oxopentanoyl)glycinate;
(2S)-1-((R)-2-(2-naphthamido)-3-cyclohexylpropanoyl)-N-(1-((2-methoxyethyl)amino)-4-methyl-1,2-dioxopentan-3-yl)pyrrolidine-2-carboxamide;
(2S,4R)-1-((R)-2-(2-naphthamido)-3-cyclohexylpropanoyl)-N-(1-amino-4-methyl-1,2-dioxopentan-3-yl)-4-phenylpyrrolidine-2-carboxamide;
(2S,4R)-1-((R)-2-(2-naphthamido)-3-cyclohexylpropanoyl)-N-(1-amino-4-methyl-1,2-dioxopentan-3-yl)-4-(piperidin-1-yl)pyrrolidine-2-carboxamide;
(2S,4R)-1-((R)-2-(2-naphthamido)-3-cyclohexylpropanoyl)-N-(1-amino-7-(3-cyclohexylureido)-2-hydroxy-1-oxoheptan-3-yl)-4-(piperidin-1-yl)pyrrolidine-2-carboxamide;
(2S,4R)-1-((R)-2-(2-naphthamido)-3-cyclohexylpropanoyl)-N-(4-amino-1-cyclobutyl-3,4-dioxobutan-2-yl)-4-(piperidin-1-yl)pyrrolidine-2-carboxamide;
(2S,4R)-1-((R)-2-(2-naphthamido)-3-cyclohexylpropanoyl)-N-(1-amino-4-methyl-1,2-dioxohexan-3-yl)-4-(piperidin-1-yl)pyrrolidine-2-carboxamide;

(2S,4R)-1-((R)-2-(2-naphthamido)-3-cyclohexylpropanoyl)-N-(4-amino-3,4-dioxo-1-phenylbutan-2-yl)-4-(piperidin-1-yl)pyrrolidine-2-carboxamide;

(2S,4S)-1-((R)-2-(2-naphthamido)-3-cyclohexylpropanoyl)-N-(4-amino-1-cyclobutyl-3,4-dioxobutan-2-yl)-4-(piperidin-1-yl)pyrrolidine-2-carboxamide;

(2S,4S)-1-((R)-2-(2-naphthamido)-3-cyclohexylpropanoyl)-N-(1-amino-7-(3-cyclopropylureido)-1,2-dioxoheptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-7-(3-isobutylureido)-1,2-dioxoheptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-7-(3-cyclohexylureido)-1,2-dioxoheptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-1,2-dioxo-7-(3-(pyridin-4-yl)ureido)heptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-7-(3-ethylureido)-1,2-dioxoheptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-7-(3-(1-methyl-1H-pyrazol-3-yl)ureido)-1,2-dioxoheptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-7-(3-(isoxazol-3-yl)ureido)-1,2-dioxoheptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-1,2-dioxo-7-(3-(tetrahydro-2H-pyran-4-yl)ureido)heptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-1,2-dioxo-7-(3-(pyrimidin-5-yl)ureido)heptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-7-(3-(1-oxidotetrahydro-2H-thiopyran-4-yl)ureido)-1,2-dioxoheptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-1,2-dioxo-7-(3-(tetrahydro-2H-thiopyran-4-yl)ureido)heptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-1,2-dioxo-7-(3-(pyridin-3-yl)ureido)heptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-1,2-dioxo-7-(3-(pyridin-2-yl)ureido)heptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-1,2-dioxo-7-(3-(prop-2-yn-1-yl)ureido)heptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-7-(3-(5-(tert-butyl)isoxazol-3-yl)ureido)-1,2-dioxoheptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(7-(3-allylureido)-1-amino-1,2-dioxoheptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-7-(3-(cyanomethyl)ureido)-1,2-dioxoheptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-7-(3-cyclobutylureido)-1,2-dioxoheptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-1,2-dioxo-7-((trifluoromethyl)sulfonamido)heptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-7-(3-(cyclopropylsulfonyl)ureido)-1,2-dioxoheptan-3-yl)-4-(5-(2-hydroxypropan-2-yl)-1H-1,2,3-triazol-1-yl)pyrrolidine-2-carboxamide;

benzyl (5-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (5-((2S,4S)-1-((R)-2-(2-naphthamido)-3-cyclohexylpropanoyl)-4-(4-(2-hydroxypropan-2-yl)-1H-1,2,3-triazol-1-yl)pyrrolidine-2-carboxamido)-7-amino-6,7-dioxoheptyl)carbamate;

benzyl (5-((2S,4R)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (5-((2S,4R)-1-((R)-2-(2-naphthamido)-3-cyclohexylpropanoyl)-4-(4-(2-hydroxypropan-2-yl)-1H-1,2,3-triazol-1-yl)pyrrolidine-2-carboxamido)-7-amino-6,7-dioxoheptyl)carbamate;

(2S,4S)-1-((R)-2-(2-naphthamido)-3-cyclohexylpropanoyl)-N-(1-amino-1,2-dioxohex-5-en-3-yl)-4-(5-(2-hydroxypropan-2-yl)-1H-1,2,3-triazol-1-yl)pyrrolidine-2-carboxamide;

N-((2R)-1-((2S,4S)-2-((7-(3-propargylureido)-1-amino-1,2-dioxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)isonicotinamide;

(2S,4S)—N-(7-(3-propargylureido)-1-amino-1,2-dioxoheptan-3-yl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide;

(2S,4S)—N-(1-amino-1,2-dioxo-7-(3-(prop-2-yn-1-yl)ureido)heptan-3-yl)-1-((R)-3-cyclohexyl-2-(4-(2,2,2-trifluoro-1,1-dihydroxyethyl)benzamido)propanoyl)-4-(5-(2-hydroxypropan-2-yl)-1H-1,2,3-triazol-1-yl)pyrrolidine-2-carboxamide;

benzyl (5-((2S,4S)-1-((R)-2-(1H-benzo[d]imidazole-2-carboxamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (7-amino-5-((2S,4S)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (5-((2S,4S)-1-((R)-2-(1H-benzo[d]imidazole-4-carboxamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (5-((2S,4S)-1-((R)-2-(1H-benzo[d]imidazole-6-carboxamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (7-amino-5-((2S,4S)-1-((R)-3-cyclohexyl-2-(1,6-naphthyridine-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1,6-naphthyridine-8-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1,8-naphthyridine-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoxaline-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinazoline-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoxaline-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1,5-naphthyridine-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1,6-naphthyridine-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1,8-naphthyridine-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1,7-naphthyridine-3-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1,5-naphthyridine-3-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoxaline-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(4-oxo-3,4-dihydroquinazoline-7-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1,5-naphthyridine-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1-methyl-1H-imidazole-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1-methyl-1H-imidazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1-methyl-1H-imidazole-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-pyrrolo[3,2-c]pyridine-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-indole-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-indole-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-indole-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-indazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-indazole-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-indazole-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-indazole-7-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (5-((2S,4S)-1-((R)-2-(1-naphthamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (7-amino-5-((2S,4S)-1-((R)-3-cyclohexyl-2-(isoxazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(oxazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(oxazole-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-2-(3-carbamoylbenzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-2-(4-carbamoylbenzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-2-(2-cyanobenzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-2-(3-cyanobenzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-2-(4-cyanobenzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(2-fluorobenzamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(4-fluorobenzamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(2-methoxybenzamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(3-methoxybenzamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(4-methoxybenzamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(2-((methylperoxy)thio)benzamido)-propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(3-((methylperoxy)thio)benzamido)-propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(4-((difluoromethyl)sulfonyl)benzamido)-propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(4-((2-methoxyethyl)sulfonyl)benzamido)-propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-2-(4-((2-amino-2-oxoethyl)sulfonyl)benzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(4-(isopropylsulfonyl)benzamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(nicotinamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(picolinamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(isonicotinamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(pyrimidine-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(isoquinoline-1-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoline-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoline-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(isoquinoline-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(isoquinoline-8-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoline-8-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoline-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1-oxo-1,2-dihydroisoquinoline-3-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(isoquinoline-3-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoline-3-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(2-oxo-1,2-dihydroquinoline-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(isoquinoline-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(isoquinoline-7-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(imidazo[1,2-a]pyridine-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoline-7-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(pyrido[2,3-b]pyrazine-8-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(pyrido[2,3-b]pyrazine-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(pyrido[2,3-b]pyrazine-7-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-1,2,3-triazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1-methyl-1H-1,2,3-triazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

(2S,4S)—N-(1-amino-7-(3-cyclopropylureido)-1,2-dioxoheptan-3-yl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide;

(2S,4S)—N-(1-amino-7-(3-cyclopropylureido)-1,2-dioxoheptan-3-yl)-1-((R)-2-(4-cyanobenzamido)-3-cyclohexylpropanoyl)-4-(5-(2-hydroxypropan-2-yl)-1H-1,2,3-triazol-1-yl)pyrrolidine-2-carboxamide;

N-((2R)-1-((2S,4S)-2-((1-amino-7-(3-cyclopropylureido)-1,2-dioxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)imidazo[1,2-a]pyridine-6-carboxamide;

N-((2R)-1-((2S,4S)-2-((1-amino-7-(3-cyclopropylureido)-1,2-dioxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)quinoline-3-carboxamide;

(2S,4S)-1-((R)-2-(4-((2-amino-2-oxoethyl)sulfonyl)benzamido)-3-cyclohexylpropanoyl)-N-(1-amino-7-(3-cyclopropylureido)-1,2-dioxoheptan-3-yl)-4-(5-(2-hydroxypropan-2-yl)-1H-1,2,3-triazol-1-yl)pyrrolidine-2-carboxamide;

(2S,4S)—N-(1-amino-7-(3-cyclopropylureido)-1,2-dioxoheptan-3-yl)-1-((R)-3-cyclohexyl-2-(4-((difluoromethyl)sulfonyl)benzamido)propanoyl)-4-(5-(2-hydroxypropan-2-yl)-1H-1,2,3-triazol-1-yl)pyrrolidine-2-carboxamide;

N-((2R)-1-((2S,4S)-2-((1-amino-7-(3-cyclopropylureido)-1,2-dioxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)-1H-indazole-7-carboxamide;

(2S,4S)—N-(1-amino-7-(3-cyclopropylureido)-1,2-dioxoheptan-3-yl)-1-((R)-3-cyclohexyl-2-(4-((2-methoxyethyl)sulfonyl)benzamido)propanoyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(4-amino-1-(4-nitrophenyl)-3,4-dioxobutan-2-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(4-acetamidophenyl)-4-amino-3,4-dioxobutan-2-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(4-amino-1-(4-(3-cyclohexylureido)phenyl)-3,4-dioxobutan-2-yl)-4-(5-(2-hydroxypropan-2-yl)-1H-1,2,3-triazol-1-yl)pyrrolidine-2-carboxamide;

benzyl (2-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-4-amino-3,4-dioxobutyl)carbamate;

benzyl (7-amino-5-((3S)-2-((R)-3-cyclohexyl-2-(4-(methylsulfonyl)benzamido)propanoyl)-2-azabicyclo[2.2.1]heptane-3-carboxamido)-6,7-dioxoheptyl)carbamate;

benzyl (5-((2S,4S)-1-(2-(2-naphthamido)-4-((1S,4R)-bicyclo[2.2.1]heptan-2-yl)butanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (5-((2S,4S)-1-((R)-2-(2-naphthamido)-3-(((benzyloxy)carbonyl)amino)propanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (5-((2S,4S)-1-(2-(2-naphthamido)-3-(tetrahydro-2H-pyran-4-yl)propanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (5-((2S,4S)-1-(2-(2-naphthamido)-3-((3S,5S,7S)-adamantan-1-yl)propanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (5-((2S,4S)-1-(2-(2-naphthamido)-3-((1S,2R,5S)-6,6-dimethylbicyclo[3.1.1]heptan-2-yl)propanoyl)-4-(5-(2-hydroxypropan-2-yl)-1H-1,2,3-triazol-1-yl)pyrrolidine-2-carboxamido)-7-amino-6,7-dioxoheptyl)carbamate; and benzyl (5-((2S,4S)-1-(2-(2-naphthamido)-3-(3-methyloxetan-3-yl)propanoyl)-4-(5-(2-hydroxypropan-2-yl)-1H-1,2,3-triazol-1-yl)pyrrolidine-2-carboxamido)-7-amino-6,7-dioxoheptyl)carbamate;

or a pharmaceutically acceptable salt, solvate, salt of the solvate or prodrug thereof.

In a sixteenth embodiment, the present disclosure provides a pharmaceutical composition comprising a compound of any of the first through the fifteenth embodiments, and a pharmaceutically acceptable carrier.

In a seventeenth embodiment, the present disclosure provides a method of preventing, or treating a disease of the eye selected from dry-AMD, wet-AMD, geographic atrophy, diabetic retinopathy, retinopathy of prematurity, polypoidal choroidal vasculopathy, and degeneration of retinal or photoreceptor cells, comprising: administering to a subject in need thereof a therapeutically effective amount of a compound according to any of the first through the fifteenth embodiments, or a pharmaceutically acceptable salt, solvate, solvate of the salt or prodrug thereof, or the pharmaceutical composition of the sixteenth embodiment.

In a eighteenth embodiment, for the method of the seventeenth embodiment, the method of prevention is selected from delaying the onset of disease and reducing the risk of developing a disease of the eye, wherein the disease of the eye is selected from dry-AMD, wet-AMD, geographic atrophy, diabetic retinopathy, retinopathy of prematurity, polypoidal choroidal vasculopathy, and degeneration of retinal or photoreceptor cells.

In a nineteenth embodiment, for the method of the seventeenth embodiment the method of treating a disease of the eye is selected from controlling, alleviating, and slowing the progression of, wherein the disease is selected from dry-AMD, wet-AMD, geographic atrophy, diabetic retinopathy, retinopathy of prematurity, polypoidal choroidal vasculopathy, and degeneration of retinal or photoreceptor cells.

In a twentieth embodiment, for the method of any one of the seventeenth through the nineteenth embodiments, the disease is geographic atrophy.

In a twenty-first embodiment, the present disclosure provides a method of inhibiting HtrAl protease activity in an eye, comprising administering to a subject in need thereof a therapeutically effective amount of any one of the compounds of the first through the fifteenth embodiments or a pharmaceutically acceptable salt, solvate, solvate of the salt or prodrug thereof, or the pharmaceutical composition of the sixteenth embodiment.

Any of the features of an embodiment is applicable to all embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other embodiments. Any embodiment of a method can comprise another embodiment of a compound, and any embodiment of a compound can be configured to perform a method of another embodiment.

DEFINITIONS

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

The term "patient" includes mammals such as mice, rats, cows, sheep, pigs, rabbits, goats, horses, monkeys, dogs, cats, and humans.

The term "halo" or "halogen" refers to any radical of fluorine, chlorine, bromine or iodine.

The term "alkyl" refers to a saturated hydrocarbon chain that may be a straight chain or branched chain, containing the indicated number of carbon atoms. For example, $C_{1-6}$alkyl indicates that the group may have from 1 to 6 (inclusive) carbon atoms in it. In some embodiments, an alkyl is a $C_{1-6}$alkyl which represents a straight-chain or branched saturated hydrocarbon radical having 1 to 6 carbon atoms. Examples of alkyl include without limitation methyl, ethyl, n-propyl, isopropyl, n-butyl, isobutyl, sec-butyl, and tert-butyl. The notation "$C_{0-n}$alkyl" indicates the absence of an alkyl moiety, or the presence of an alkyl moiety having 1 to n carbon atoms. Thus, for example, the term "$C_{0-6}$alkyl-$R^5$" indicates that the $R^5$ group is attached directly to the parent moiety, or that there is an intervening alkyl group of 1 to 6 carbon atoms between $R^5$ and the parent moiety; such an intervening group may be, for example, —CH$_2$—, —CH$_2$CH$_2$—, —CH(CH$_3$)— and —C(CH$_3$)$_2$—.

The term "haloalkyl" refers to an alkyl group in which at least one hydrogen atom is replaced by halo. In some embodiments, more than one hydrogen atom (e.g., 2, 3, 4, 5, 6, 7, 8, 9, 10, 11, 12, 13, or 14) are replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl).

As referred to herein, the term "alkoxy" refers to a group of formula —O-(alkyl). Alkoxy can be, for example, methoxy, ethoxy, propoxy, isopropoxy, butoxy, iso-butoxy, sec-butoxy, pentoxy, 2-pentoxy, 3-pentoxy, or hexyloxy.

Likewise, the term "thioalkoxy" refers to a group of formula —S-(alkyl). The terms "haloalkoxy" and "thiohaloalkoxy" refer to —O-(haloalkyl) and —S-(haloalkyl), respectively. The term "sulfhydryl" refers to —SH.

The term "aralkyl" refers to an alkyl moiety in which an alkyl hydrogen atom is replaced by an aryl group. One of the carbons of the alkyl moiety serves as the point of attachment of the aralkyl group to another moiety. Non-limiting examples of "aralkyl" include benzyl, 2-phenylethyl, and 3-phenylpropyl groups.

The term "alkenyl" refers to a straight or branched hydrocarbon chain containing the indicated number of carbon atoms and having one or more carbon-carbon double bonds. Alkenyl groups can include, e.g., vinyl, allyl, 1-butenyl, and 2-hexenyl. In some embodiments, an alkenyl is a C2-6alkenyl.

The term "alkynyl" refers to a straight or branched hydrocarbon chain containing the indicated number of carbon atoms and having one or more carbon-carbon triple bonds. Alkynyl groups can include, e.g., ethynyl, propargyl, 1-butynyl, and 2-hexynyl. In some embodiments, an alkynyl is a C2-6alkynyl.

The term "heterocycle", "heterocyclyl" or "heterocyclic" as used herein except where noted, represents a stable 4-, 5-, 6- or 7-membered monocyclic- or a stable 6-, 7-, 8-, 9-, 10-, 11-, or 12-membered bicyclic heterocyclic ring system which comprises at least one non-aromatic (i.e. saturated or partially unsaturated) ring which consists of carbon atoms and from one to four, preferably up to three, heteroatoms selected from the group consisting of N, O and S, wherein the nitrogen and sulfur atoms may optionally be oxidized as N-oxide, sulfoxide or sulfone, and wherein the nitrogen atom may optionally be quaternized. A heterocycle can be bonded via a ring carbon atom or, if available, via a ring nitrogen atom. Bicyclic heterocyclic ring systems may be fused, bridged, or spiro bicyclic heterocyclic ring system(s). In some embodiments, heterocyclyl is monocyclic having 4 to 7, preferably 4 to 6, ring atoms, of which 1 or 2 are heteroatoms independently selected from the group consisting of N, O and S. In some embodiments, a heterocyclyl group is bicyclic, and in which case, the second ring may be an aromatic or a non-aromatic ring which consists of carbon atoms and from one to four, preferably up to three, heteroatoms independently selected from the group consisting of N, O and S, or the second ring may be a benzene ring, or a "cycloalkyl", or a "cycloalkenyl", as defined herein. Examples of such heterocyclic groups include, but are not limited to azetidine, chroman, dihydrofuran, dihydropyran, dioxane, dioxolane, hexahydroazepine, imidazolidine, imidazoline, indoline, isochroman, isoindoline, isothiazoline, isothiazolidine, isoxazoline, isoxazolidine, morpholine, oxazoline, oxazolidine, oxetane, piperazine, piperidine, dihydropyridine, tetrahydropyridine, dihydropyridazine, pyran, pyrazolidine, pyrazoline, pyrrolidine, pyrroline, tetrahydrofuran, tetrahydropyran, thiamorpholine, tetrahydrothiophene, thiazoline, thiazolidine, thiomorpholine, thietane, thiolane, sulfolane, 1,3-dioxolane, 1,3-oxazolidine, 1,3-thiazolidine, tetrahydrothiopyran, tetrahydrotriazine, 1,3-dioxane, 1,4-dioxane, hexahydrotriazine, tetrahydro-oxazine, tetrahydropyrimidine, perhydroazepine, perhydro-1,4-diazepine, perhydro-1,4-oxazepine, 7-azabicyclo[2.2.1]heptane, 3-azabicyclo[3.2.0]heptane, 7-azabicyclo[4.1.0]heptane, 2,5-diazabicyclo[2.2.1]heptane, 2-oxa-5-azabicyclo[2.2.1]heptane, tropane, 2-oxa-6-azaspiro[3.3]heptane, dihydrobenzofuran, diydrobenzimidazolyl, dihydrobenzoxazole, and dihydrobenzothiazolyl, and N-oxides or sulfones or sulfoxides thereof.

The term "cycloalkyl" refers to a fully saturated monocyclic, bicyclic, tricyclic or other polycyclic hydrocarbon group having the indicated number of ring carbon atoms. Multicyclic cycloalkyl may be fused, bridged or spiro ring systems. Cycloalkyl groups include, but are not limited to, cyclopropyl, cyclobutyl, cyclopentyl, cyclohexyl, cycloheptyl, cyclooctyl, norbornyl (bicyclo[2.2.1]heptyl), decalinyl, adamantyl, spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, bicyclo[4.2.0]octyl, bicyclo[2.2.2]octyl, and spiro[3.5]nonyl. In some embodiments, cycloalkyl is a monocyclic C3-8cycloalkyl. In other embodiments, cycloalkyl is a bi- or tricyclic C5-12cycloalkyl. In other embodiments, cycloalkyl is a spirocyclic C5-12cycloalkyl.

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Cycloalkenyl moieties can include, e.g., cyclopentenyl, cyclohexenyl, cyclohexadienyl, or norbornenyl. In some embodiments, a cycloalkenyl is a C4-10cycloalkenyl. In other embodiments, a cycloalkenyl is a C4-6cycloalkenyl. In some embodiments, a cycloalkenyl is monocyclic. In some embodiments, a cycloalkenyl is bicyclic.

The term "aryl" as used herein, is intended to mean any stable monocyclic or bicyclic carbon ring of up to 6 members in each ring, wherein at least one ring is aromatic. Examples of aryl include phenyl, naphthyl, tetrahydronaphthyl, indanyl, or biphenyl.

The term "heteroaryl", as used herein except where noted, represents a stable 5-, 6- or 7-membered monocyclic- or stable 9 or 10-membered fused bicyclic ring system which comprises at least one aromatic ring, which consists of carbon atoms and from one to four, preferably up to three, heteroatoms selected from the group consisting of N, O and S wherein the nitrogen and sulfur heteroatoms may optionally be oxidized, and the nitrogen heteroatom may optionally be quaternized. In the case of a "heteroaryl" which is a bicyclic group, the second ring need not be aromatic and need not comprise a heteroatom. Accordingly, bicyclic "heteroaryl" includes, for example, a stable 5- or 6-membered monocyclic aromatic ring consisting of carbon atoms and from one to four, preferably up to three, heteroatoms, as defined immediately above, fused to a benzene ring, or a second monocyclic "heteroaryl", or a "heterocyclyl", a "cycloalkyl", or a "cycloalkenyl", as defined above. Examples of heteroaryl groups include, but are not limited to, benzimidazole, benzopyrazole, benzisothiazole, benzisoxazole, benzofuran, isobenzofuran, benzothiazole, benzothiophene, benzotriazole, benzoxazole, cinnoline, furan, furazan, imidazole, indazole, indole, indolizine, isoquinoline, isothiazole, isoxazole, naphthyridine, oxadiazole, oxazole, phthalazine, pteridine, purine, pyrazine, pyrazole, pyridazine, pyridine, pyrimidine, pyrrole, quinazoline, quinoline, quinoxaline, tetrazole, thiadiazole, thiazole, thiophene, triazine, triazole, benzimidazole, benzothiadiazole, isoindole, pyrrolopyridines, imidazopyridines such as imidazo[1,2-a]pyridine, pyrazolopyridine, pyrrolopyrimidine and N-oxides thereof.

The term "acyl", as used herein, refers to those groups derived from an organic acid by removal of the hydroxy portion of the acid. Accordingly, acyl is meant to include, for example, acetyl, propionyl, butyryl, decanoyl, pivaloyl, benzoyl and the like.

As used herein, the term "fused" refers to a connectivity between two rings in which two adjacent atoms sharing at least one bond (saturated or unsaturated) are common to the rings. For example, in the following structure, rings A and B are fused

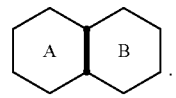

Examples of fused ring structures include, but are not limited to, decahydronaphthalene, 1H-indole, quinolone, chromane, bicyclo[2.1.0]pentane and 6,7,8,9-tetrahydro-5H-benzo[7]annulene.

As used herein, the term "bridged" refers to a connectivity wherein three or more atoms are shared between two rings. The following structures

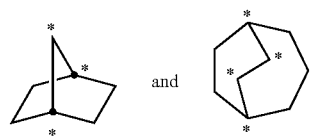 [SMILES: C1C[C@H]2CC[C@H]1C2 ; C1CC2CCC(C1)CC2]

are examples of "bridged" rings because the indicated atoms are shared between at least two rings. Examples of bridged ring structures include, but are not limited to, bicyclo[1.1.1]pentane, 2-oxabicyclo[1.1.1]pentane, 5-azabicyclo[2.1.1]hexane, 6-azabicyclo[3.1.1]heptane, adamantane and norbornane.

As used herein, the term "spiro" refers to a connectivity between two rings wherein the rings have only one atom in common. For example, in the structure

rings C and D are joined by a spiro connection. Examples of spiro connected ring structures include, but are not limited to, spiro[3.3]heptane, 2,6-diazaspiro[3.3]heptane, 2-oxa-6-azaspiro[3.3]heptane, spiro[4.5]decane and 2,6-dioxaspiro[3.3]heptane.

For each of the organic radicals defined above, any atom can be optionally substituted, e.g., by one or more substituents.

Unless otherwise specified, when a bond is depicted in a chemical structure with ∿∿, it is meant that the bond is located at a stereocenter in which the structure may have either the S or R configuration as understood under the Cahn-Ingold System for naming enantiomers. For example, the ∿∿ notation can indicate that the bond at the given position can be either a ⫶⫶⫶ or a ◢. The presence of the ∿∿ does not limit the exemplified compound to only a racemate, but can include all possible stereoconfigurations.

The term "treating", "treat", or "treatment" refers generally to controlling, alleviating, ameliorating, slowing the progress of or eliminating a named condition once the condition has been established. In addition to its customary meaning, the term "preventing", "prevent", or "prevention" also refers to delaying the onset of, or reducing the risk of developing a named condition or of a process that can lead to the condition, or the recurrence of symptoms of a condition.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

Compound Forms and Salts

The compounds of this disclosure may contain one or more asymmetric centers and thus occur as racemates and racemic mixtures, enantiomerically enriched mixtures, single enantiomers, individual diastereomers and diastereomeric mixtures. The compounds of the present disclosure may, either by nature of asymmetric centers or by restricted rotation, be present in the form of isomers (e.g., enantiomers, diastereomers).

It will also be appreciated that when two or more asymmetric centers are present in the compounds of the disclosure, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the disclosure.

All isomers, whether separated, pure, partially pure, or in racemic mixture, of the compounds of this disclosure are encompassed within the scope of this disclosure. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

The compounds of the present disclosure include all cis, trans, syn, anti, entgegen (E), and zusammen (Z) isomers as well as mixtures thereof. The compounds of the present disclosure may also be represented in multiple tautomeric forms, in such instances, the present disclosure expressly includes all tautomeric forms of the compounds described herein, even though only a single tautomeric form may be represented. In addition, where a term used in the present disclosure encompasses a group that may tautomerize, all tautomeric forms are expressly included thereunder. For example, hydroxy substituted heteroaryl includes 2-hydroxypyridine as well as 2-pyridone, 1-hydroxyisoquinoline as well as 1-oxo-1,2-dihyroisoquinoline, 4-hydroxyquinazoline as well as 4-oxo-3,4-dihydroquinazoline, and the like. All such isomeric forms of such compounds are expressly included in the present disclosure.

The compounds of the present disclosure include the compounds themselves, as well as their salts, solvate, solvate of the salt and their prodrugs, if applicable. Salts for the purposes of the present disclosure are preferably pharmaceutically acceptable salts of the compounds according to the present disclosure. Salts which are not themselves suitable for pharmaceutical uses but can be used, for example, for isolation or purification of the compounds according to the disclosure are also included. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. When the compound of the present disclosure is basic, pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfonic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, benzenesulfonic, toluenesulfonic, naphthalenedisulfonic, methanesulfonic, ethanesulfonic, ethanedisulfonic, camphorsulfonic, gluconic, mandelic, mucic, pantothenic, oxalic, isethionic, and the like.

When the compound of the present disclosure is acidic, salts may be prepared from pharmaceutically acceptable non-toxic bases, including inorganic and organic bases. Such salts that may be prepared include lithium salt, sodium salt, potassium salt, magnesium salt, calcium salt, dicyclohexylamine salt, N-methyl-D-glucamine salt, tris(hydroxymethyl)methylamine salt, arginine salt, lysine salt, and the like.

Lists of suitable salts may be found in Remington's Pharmaceutical Sciences, 17th ed., Mack Publishing Company, Easton, Pa., 1985, p. 1418; S. M. Berge et al., "Pharmaceutical Salts", J. Pharm. Sci. 1977, 66, 1-19; and "Pharmaceutical Salts: Properties, Selection, and Use. A Handbook"; Wermuth, C. G. and Stahl, P. H. (eds.) Verlag Helvetica Chimica Acta, Zurich, 2002 [ISBN 3-906390-26-8]; each of which is incorporated herein by reference in its entirety.

Solvates in the context of the present disclosure are designated as those forms of the compounds according to the present disclosure which form a complex in the solid or liquid state by stoichiometric coordination with solvent molecules. Hydrates are a specific form of solvates, in which the coordination takes place with water. Hydrates are preferred solvates in the context of the present disclosure. The formation of solvates is described in greater detail in "Solvents and Solvent Effects in Organic Chemistry"; Reichardt, C. and Welton T.; John Wiley & Sons, 2011 [ISBN: 978-3-527-32473-6], the contents of which is incorporated herein by reference in its entirety. A person of ordinary skill in the art would recognize the solvates of the present disclosure.

The present disclosure also encompasses all suitable isotopic variants of the compounds according to the present disclosure, whether radioactive or not. An isotopic variant of a compound according to the present disclosure is understood to mean a compound in which at least one atom within the compound according to the present disclosure has been exchanged for another atom of the same atomic number, but with a different atomic mass than the atomic mass which usually or predominantly occurs in nature. Examples of isotopes which can be incorporated into a compound according to the present disclosure are those of hydrogen, carbon, nitrogen, oxygen, fluorine, chlorine, bromine and iodine, such as $^2$H (deuterium), $^3$H (tritium), $^{13}$C, $^{14}$C, $^{15}$N, $^{17}$O, $^{18}$O, $^{18}$F, $^{36}$Cl, $^{82}$Br, $^{123}$I, $^{124}$I, $^{125}$I, $^{129}$I and $^{131}$I. Particular isotopic variants of a compound according to the present disclosure, especially those in which one or more radioactive isotopes have been incorporated, may be beneficial, for example, for the examination of the mechanism of action or of the active compound distribution in the body. Due to comparatively easy preparability and detectability, especially compounds labelled with $^3$H, $^{14}$C and/or $^{18}$F isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required. Such modifications of the compounds according to the present disclosure may therefore in some cases also constitute a preferred embodiment of the present disclosure. In some embodiments, hydrogen atoms of the compounds described herein may be replaced with deuterium atoms. Isotopic variants of the compounds according to the present disclosure can be prepared by processes known to those skilled in the art, for example by the methods described below and the methods described in the working examples, by using corresponding isotopic modifications of the particular reagents and/or starting compounds therein.

The present disclosure includes within its scope prodrugs of the compounds of Formula I. Prodrugs are generally drug precursors that, following administration to a subject are converted to an active, or a more active species via some process, such as conversion by chemical hydrolysis or a metabolic pathway. Thus, in the methods of treatment of the present disclosure, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985 (Amsterdam, NL). Examples of prodrugs include $C_{1-6}$ alkyl esters of carboxylic acid groups and esters of boronic acids, which, upon administration to a subject, are capable of providing active compounds.

Compounds of Formula I may be prepared as prodrugs of the ketoamide moiety. Examples of ketone prodrugs include but are not limited to ketimine, oxime, aminal, ketal, hemiaminal, hemiketal, thioketal, hydrated ketone which, upon administration to a subject, are capable of providing active compounds. Carbonyl derivatives of ketoamides are illustrated by Formula IIa and IIb:

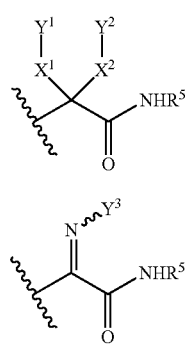

wherein:

$X_1$ and $X_2$ are each independently selected from O, N and S;

$Y_1$ and $Y_2$ are each independently selected from hydrogen, optionally substituted $C_{1-6}$alkyl, $C_{3-10}$cycloalkyl, $C_{1-6}$heterocycle, or $Y_1$ and $Y_2$ are joined together to form the group:

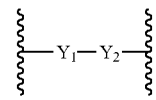

wherein $Y_1$ and $Y_2$ forms an optionally substituted $C_{2-6}$alkyl, or an optionally substituted heterocycle. The optional substituents include, for example, hydroxyl, halogen and $C_{1-3}$alkoxy;

$Y_3$ is H, $C_{1-4}$alkyl, —OH or O—$C_{1-4}$alkyl.

Illustrating the ketone prodrugs are:

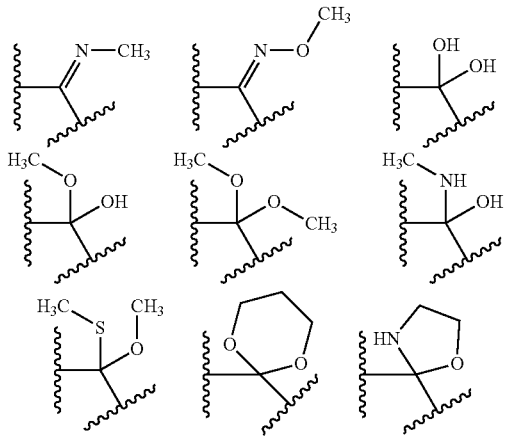

Pharmaceutical Compositions

The term "pharmaceutical composition" as used herein is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure, or a pharmaceutically acceptable salt, or solvate or solvate of the salt thereof, and a pharmaceutically acceptable carrier.

The term "pharmaceutically acceptable carrier" refers to a carrier or an adjuvant that may be administered to a patient, together with a compound of the present disclosure, or a pharmaceutically acceptable salt, solvate, salt of the solvate or prodrug thereof, and which does not destroy the pharmacological activity thereof and is nontoxic when administered in doses sufficient to deliver a therapeutic amount of the compound.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. For convenience, the total daily dosage may be divided and administered in portions during the day if desired.

Pharmaceutical compositions of the present disclosure for injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These pharmaceutical compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin. If desired, and for more effective distribution, the compounds can be incorporated into slow release or targeted delivery systems such as polymer matrices, liposomes, and microspheres.

The pharmaceutical compositions that are injectable formulations can be sterilised, for example, by filtration through a bacterial-retaining filter, or by incorporating sterilising agents in the form of sterile solid pharmaceutical compositions that can be dissolved or dispersed in sterile water or other sterile injectable medium just prior to use.

Solid dosage forms of the instant pharmaceutical compositions for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid pharmaceutical compositions of a similar type may also be employed as fillers in soft and hard-filled gelatin capsules using such excipients as lactose or milk sugar as well as high molecular weight polyethylene glycols and the like.

The solid dosage forms of the instant pharmaceutical compositions of tablets, dragees, capsules, pills, and granules can be prepared with coatings and shells such as enteric coatings and other coatings well known in the pharmaceutical formulating art. They may optionally contain opacifying agents and can also be of a formulation that they release the active ingredient(s) only, or preferentially, in a certain part of the intestinal tract, optionally, in a delayed manner. Examples of embedding pharmaceutical compositions which can be used include polymeric substances and waxes.

The active compounds can also be in microencapsulated form, if appropriate, with one or more of the above-mentioned excipients.

Liquid dosage forms of the instant pharmaceutical compositions for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral pharmaceutical compositions can also include adjuvants such as wetting agents, emulsifying and suspending agents, sweetening, flavouring, and perfuming agents.

Suspensions of the instant compounds, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Pharmaceutical compositions for rectal or vaginal administration are preferably suppositories which can be prepared by mixing the compounds with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound or pharmaceutical composition of the present disclosure include powders, patches, sprays, ointments and inhalants. The active compound is mixed under sterile conditions with a pharmaceutically acceptable carrier and any needed preservatives, buffers, or propellants which may be required.

Dosage forms for application to the eye include solutions, suspensions, ointments, gels, emulsions, strips, inserts such as contact lenses, and implants, which may be administered topically, intravitreally, perioccularly, and the like.

Uses

The present disclosure is directed to novel aliphatic prolinamide derivatives of Formula I, and pharmaceutically acceptable salts, solvates, salts of solvates and prodrugs thereof, useful in the prevention (e.g., delaying the onset of or reducing the risk of developing) and treatment (e.g., controlling, alleviating, or slowing the progression of) of age-related macular degeneration (AMD) and related diseases of the eye. These diseases include dry-AMD, wet-AMD, geographic atrophy, diabetic retinopathy, retinopathy of prematurity, polypoidal choroidal vasculopathy, diabetic macula edema (DME), other retinopathies such as choroidal neovascularisation (CNV), choroidal neovascular membrane (CNVM), cystoid macular edema (CME), epi-retinal membrane (ERM) and macular hole, hypertrophic changes of the retinal pigment epithelium (RPE), atrophic changes of the retinal pigment epithelium, retinal detachment, choroidal vein occlusion, retinal vein occlusion, corneal angiogenesis following, for example, keratitis, cornea transplantation or keratoplasty, corneal angiogenesis due to hypoxia (e.g., induced by extensive contact lens wearing), pterygium conjunctivae, subretinal edema, intraretinal edema, Stargardt disease and degeneration of retinal or photoreceptor cells. The present disclosure disclosed herein is further directed to methods of prevention, slowing the progress of, and treatment of dry-AMD, wet-AMD, and geographic atrophy, diabetic retinopathy, retinopathy of prematurity, polypoidal choroidal vasculopathy, diabetic macula edema (DME), other retinopathies such as choroidal neovascularisation (CNV), choroidal neovascular membrane (CNVM), cystoid macular edema (CME), epi-retinal membrane (ERM) and macular hole, hypertrophic changes of the retinal pigment epithelium (RPE), atrophic changes of the retinal pigment epithelium, retinal detachment, choroidal vein occlusion, retinal vein occlusion, corneal angiogenesis following, for example, keratitis, cornea transplantation or keratoplasty, corneal angiogenesis due to hypoxia (e.g., induced by extensive contact lens wearing), pterygium conjunctivae, subretinal edema, intraretinal edema, Stargardt disease and degeneration of retinal or photoreceptor cells, comprising: administration of a therapeutically effective amount of compound of the present disclosure. The compounds of the present disclosure are inhibitors of HTRA1. Thus, the compounds of the present disclosure are useful in the prevention and treatment of a wide range diseases mediated (in whole or in part) by HTRA1. The compounds of the present disclosure are also useful for inhibiting HTRA1 protease activity in an eye and elsewhere. By virtue of their activity profile, the compounds of the present disclosure are particularly suitable for the treatment and/or prevention of ocular disorders, such as age-related macular degeneration (AMD) like wet-AMD or dry-AMD, geographic atrophy, diabetic retinopathy, Stargardt disease, choroidal neovascularisation (CNV), and diabetic macula edema (DME).

Additionally, compounds of the present disclosure may be useful in the treatment of other diseases in which HTRA1 may be involved, including retinal angiomatous proliferation, foveomacular proliferation, musculoskeletal diseases, including osteoarthritis, spinal disk degeneration rheumatoid arthritis, muscular dystrophy and osteoporosis, and treatment of autologous chondrocytes prior to intraarticular implantation.

Administration

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg) every 4 to 120 hours, or according to the requirements of the particular drug, dosage form, and/or route of administration. The interrelationship of dosages for animals and humans (based on milligrams per meter squared of body surface) is described by Freireich et al., Cancer Chemother. Rep. 50, 219-244 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or by injection. The methods herein contemplate administration of an effective amount of compound or compound composition to achieve the desired or stated effect. Typically, the pharmaceutical compositions of the present disclosure will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, and the judgment of the treating physician.

Dosage forms include from about 0.001 milligrams to about 2,000 milligrams (including, from about 0.001 milligrams to about 1,000 milligrams, from about 0.001 milligrams to about 500 milligrams, from about 0.01 milligrams to about 250 milligrams, from about 0.01 milligrams to about 100 milligrams, from about 0.05-milligrams to about 50 milligrams, and from about 0.1 milligrams to about 25 milligrams) of a compound of Formula I (and/or a compound of any of the other formulae described herein) or a salt (e.g., a pharmaceutically acceptable salt) thereof as defined anywhere herein. The dosage forms can further include a pharmaceutically acceptable carrier and/or an additional therapeutic agent.

With regard to ophthalmic preparation, because AMD and related diseases (including dry-AMD, wet-AMD, geographic atrophy, diabetic retinopathy, retinopathy of prematurity, polypoidal choroidal vasculopathy, and degeneration of retinal or photoreceptor cells) primarily afflict the back of the eye, local administration such as topical administration, trans-scleral drug delivery and intravitreal administration may be preferable over systemic administration. Intravitreal administration can be further divided into intravitreal injection and intravitreal implants. Of these, intravitreal injection appears to be the most widely used. Products utilizing intravitreal injection include Trivaris® (triamcinolone acetonide), Triescence® (triamcinolone acetonide, Alcon Fort Worth, Tex.), Macugen® (pegaptanib sodium, Bausch and Lomb, Rochester, N.Y.), Lucentis® (ranibizumab injection, Genentech, South San Francisco, Calif.), Ozurdex® (dexamethasone, Allergan, Inc., Irvine, Calif.) and Iluvien® (flucinolone acetonide, Alimera Sciences, Alpharetta, Ga.). The preferred dosage range for local administration to the back of the eye ranges from 0.001 mg to 100 mg (including from about 0.01 milligrams to about 500 milligrams, from about 0.05 milligrams to about 250 milligrams, from about 0.05 milligrams to about 100 milligrams, from about 0.1 milligrams to about 50 milligrams, from about 0.1 milligrams to about 25 milligrams, and from about 0.1 milligrams to about 10 milligrams). References on the subject of ophthalmic drug delivery include: Kompella U. B. et al., Recent Advances in Ophthalmic Drug Delivery, Ther. Deliv. 2010 1(3): 435-456; Gaudana R. et al., Ocular Drug Delivery, AAPS Journal, Vol. 12, No. 3: 348-360 (2010); Haghjou N. et al., Sustained Release Intraocular Drug Delivery Devices for Treatment of Uveitis, J. Ophthalmic Vis. Res. 2011; 6 (4): 317-329; Kuno N. and Fujii S. Recent Advances in Ocular Drug Delivery Systems, Polymers (2011), 3:193-

221; Patel A. et al., Ocular Drug Delivery Systems: An Overview, World J. Pharmacol. (2013) 2:47-64; Morrison P. W. J. and Khutoryanskiy V. V. Advances in Ophthalmic Drug Delivery, Ther. Deliv. (2014) 5:1297-1315; Chen H. Recent Developments in Ocular Drug Delivery, J. Drug Target (2015), 23:597-604; all of which are incorporated by reference.

For the treatment and/or prevention of ocular disorders, as described above, the preferred route for administering the compounds of the present disclosure is topically at the eye or by an ocular drug delivery system. Intraocular injections are another way to administer the compounds of the present disclosure that is suitable for such purposes.

Delivery to areas within the eye can be accomplished by injection, employing a cannula or another invasive device designed to introduce precisely metered amounts of a desired formulation to a particular compartment or tissue within the eye (e.g., posterior chamber or retina). An intraocular injection may be into the vitreous (intravitreal), under the conjunctiva (subconjunctival), behind the eye (retrobulbar), into the sclera, or under the Capsule of Tenon (sub-Tenon), and may be in a depot form. Other intraocular routes of administration and injection sites and forms are also contemplated and are within the scope of the present disclosure.

The compounds according to the present disclosure may be formulated in a manner known to those skilled in the art so as to give adequate delivery to the back of the eye, which may be by regular dosing, such as with eye drops, or by using a delivery system to give a controlled release, such as slow release, of the compounds according to the present disclosure.

Preferred ocular formulations for the compounds of the present disclosure include aqueous solutions, suspensions or gels of these compounds in the form of drops of liquid, liquid washes, sprays, ointments or gels, in a mixture with excipients suitable for the manufacture and use of such application forms. Alternatively, the compounds of the present disclosure may be applied to the eye via liposomes or other ocular delivery systems that are known in the art.

Appropriate dosage levels may be determined by any suitable method known to one skilled in the art of treating eye diseases. Preferably, the active substance is administered at a frequency of 1 to 4 times per day for topical administration, or less often if a drug delivery system is used. Typically, an ocular formulation intended for topical application contains the active ingredient in a concentration range of about 0.001% to 10%.

Nevertheless, actual dosage levels and time course of administration of the active ingredients in the pharmaceutical compositions of the present disclosure may be varied so as to obtain an amount of the active ingredient which is effective to achieve the desired therapeutic response for a particular patient, composition and mode of administration, without being toxic to the patient. It may therefore be necessary where appropriate to deviate from the stated amounts, in particular as a function of age, gender, body weight, diet and general health status of the patient, route of administration, individual response to the active ingredient, nature of the preparation, and time or interval over which administration takes place. Thus, it may be satisfactory in some cases to manage with less than the aforementioned minimum amount, whereas in other cases the stated upper limit must be exceeded. It may in the event of administration of larger amounts be advisable to divide these into multiple individual doses spread over the day.

In one aspect the compounds of the present disclosure may be co-administered with one or more additional agents. The additional agents include, but are not limited to Acuvail® (ketorolac tromethamine ophthalmic solution), AK-Con-A®/OcuHist® (pheniramine maleate-naphazoline HCl, ophthalmic solution), Akten® (lidocaine HCl ophthalmic gel), Alamast® (pemirolast potassium ophthalmic solution), Alphagan® (brimonidine tartrate ophthalmic solution), Bepreve® (bepotastine besilate ophthalmic solution), Besivance® (besifloxacin ophthalmic suspension), Betaxon® (levobetaxolol HCl ophthalmic suspension), Cosopt® (dorzolamide HCl-timolol maleate, ophthalmic solution), Cystaran® (cysteamine HCl ophthalmic solution), Durezol® (difluprednate ophthalmic emulsion), Eylea® (aflibercept intravitreal injection), Jetrea® (ocriplasmin intravitreal injection), Lotemax® (loteprednol etabonate ophthalmic suspension), Lucentis® (ranibizumab injection), Lumigan® (bimatoprost ophthalmic solution), Macugen® (pegaptanib intravitreal injection), Ocuflox® (ofloxacin ophthalmic solution), Omidria® (phenylephrine and ketorolac injection), Ozurdex® (dexamethasone intravitreal implant), Quixin® (levofloxacin ophthalmic solution), Rescula® (unoprostone isopropyl ophthalmic solution 0.15%), Restasis® (cyclosporine ophthalmic emulsion), Salagen® (pilocarpine HCl tablets), Travatan® (travoprost ophthalmic solution), Valcyte® (valganciclovir HCl tablets and oral solution), Vistide® (cidofovir tablets), Visudyne® (verteporfin injection), Vitrasert® (ganciclovir implant), Vitravene® (fomivirsen injection), Zioptan® (tafluprost ophthalmic solution), Zirgan® (ganciclovir ophthalmic gel), and Zymaxid® (gatifloxacin ophthalmic solution). Furthermore the compounds of the disclosure may be co-administered with one or more inhibitors of VEGF-mediated angiogenesis, such as, for example, ACTB-1003 (Edding Pharm, CN), apatinib, axitinib, bevacizumab, bevasiranib, BMS-690514 (Bristol-Myers Squibb (BMS), NY), brivanib, cediranib, CT-322 (Adnexus/BMS, MA), dovitinib, lenvatinib, foretinib, KH-902/conbercept (approved in CN for exudative macular degeneration), linifanib, MGCD-265 (Mirati Therapeutics, CA), motesanib, elpamotide, pazopanib, pegaptanib, ranibizumab, regorafenib, ruboxystaurin, sorafenib, SU-14813 (Pfizer, Conn.), sunitinib, telatinib, TG-100801, tivozanib, TSU-68 (Taiho Pharmaceuticals, JP), vandetanib, vargatef, vatalanib and Carbometyx® (cabozantinib tablets, Exelixis, CA), or with inhibitors of other signaling pathways, such as disulfiram, fenretinide, mecamylamine, PF-04523655 (Pfizer, Conn.), sonepcizumab, tandospirone and volociximab.

Additional agents which may be utilized for co-administration include: known vitamins and antioxidants such as AREDS/AREDS2 (supplements used in Age-Related Eye Disease Study/Study 2, National Eye Institute, US), omega-3 fatty acids, lutein, zeaxanthin, vitamin A; visual-cycle modulators such as emixustat (ACU-4429, Acucela, WA); anti-inflammatory agents such as Illuvien® (fluocinolone acetonide), sirolimus, Triesence®/Trivaris® (triamcinolone acetonide); complement modulators such as lampalizumab, Soliris® (eculizumab, Alexion, CT); amyloid-modulators such as GSK933776 (GlaxosmithKline, PA), RN6G (PF-04382923, Pfizer, CT) and platelet-derived growth factor modulators such as, for example, Fovista® (pegpleranib, Ophthotech, NY).

In certain embodiments, the additional agents may be administered separately (e.g., sequentially; on different overlapping schedules), as part of a multiple dose regimen, from the compounds of the present disclosure (e.g., one or more compounds of Formula (I) and/or a compound of any of the other formulae, including any subgenera or specific compounds thereof). In other embodiments, these agents may be part of a single dosage form, mixed together with the compounds of the present disclosure in a single composition. In still another embodiment, these agents can be given as a separate dose that is administered at about the same time as that of one or more compounds of Formula (I) (and/or a compound of any of the other formulae, including any subgenera or specific compounds thereof) are administered (e.g., simultaneously with the administration of one or more compounds of Formula (I) (and/or a compound of any of the other formulae, including any subgenera or specific compounds thereof)). When the compositions of the present disclosure include a combination of a compound of the formulae described herein and one or more additional therapeutic or prophylactic agents, both the compound and the additional agent can be present at dosage levels of between about 1 to 100%, and more preferably between about 5 to 95% of the dosage normally administered in a monotherapy regimen.

The compositions of the present disclosure may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions of the present disclosure may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase and then combined with emulsifying and/or suspending agents. If desired, certain sweetening and/or flavoring and/or coloring agents may be added.

Biological Function

The utility of the present disclosure can be demonstrated by one or more of the following methods or other methods known in the art:

Full Length HTRA1 Assay

Serial dilutions (1/3) from 1000 μM down to 0.051 μM of test compounds were prepared in dimethyl sulfoxide (DMSO). Then 2 μL of solution from each dilution were added to 100 μL of 4 nM full-length human His-HTRA1 in assay buffer (50 mM Tris, pH 7.5, 200 mM NaCl and 0.25% 3-[(3-cholamidopropyl)dimethylammonio]-1-propanesulfonate or CHAPS) in white non-binding 96-well plates. The assay solutions were mixed for 5 seconds on a shaker plate and incubated for 10 minutes at room temperature. Mca-H2OPT (Mca-Ile-Arg-Arg-Val-Ser-Tyr-Ser-Phe-Lys(Dnp)-Lys-OH trifluoroacetate salt) (Mca=7-methoxycoumarin-4-acetic acid; Dnp=dinitrophenyl) (5 μM) in 100 μL of assay buffer was added to the assay solutions. The reaction mixture was shaken for 5 seconds on a shaker plate and cleavage of Mca-H2OPT was monitored by spectrofluorometry (SpectraMax M3 by Molecular Devices, CA) for 10 minutes (Exλ=330 nm; Emλ=420 nm). Percent inhibition was calculated by fitting values to a standard mathematical model for determining the dose response curve.

| Example | HtrA1 IC$_{50}$ (μM) |
|---|---|
| 1 | 0.013 |
| 2 | 0.14 |
| 3 | 0.057 |
| 4 | 0.11 |
| 5 | 0.013 |
| 6 | 0.051 |
| 7 | 0.017 |
| 8 | 0.028 |
| 9 | 0.058 |
| 10 | 0.15 |
| 11 | 0.050 |
| 12 | 0.029 |
| 13 | 0.044 |
| 14 | 0.05 |
| 15 | 0.057 |
| 16 | 0.055 |
| 17 | 0.034 |
| 18 | 0.062 |
| 19 | 0.076 |
| 20 | 0.10 |
| 21 | 0.043 |
| 22 | 0.022 |
| 23 | 0.021 |
| 24 | 0.023 |
| 25 | 0.020 |
| 26 | 0.025 |
| 27 | 0.069 |
| 28 | 0.013 |
| 29 | 0.035 |
| 30 | 0.083 |
| 31 | 0.017 |
| 32 | 0.018 |
| 33 | 0.021 |
| 34 | 0.015 |
| 35 | 0.071 |
| 36 | 0.076 |
| 37 | 0.33 |
| 38 | 0.051 |
| 39 | 0.07 |
| 40 | 0.02 |
| 41 | 0.097 |
| 42 | 0.053 |
| 43 | 0.091 |
| 44 | 0.21 |
| 45 | 0.17 |
| 46 | 0.12 |
| 47 | 0.072 |
| 48 | 0.067 |
| 49 | 0.11 |
| 50 | 0.095 |
| 51 | 0.42 |
| 52 | 0.15 |
| 53 | 0.13 |
| 54 | 0.059 |
| 55 | 0.12 |
| 56 | 0.18 |
| 57 | 0.13 |
| 58 | 0.38 |
| 59 | 0.41 |
| 60 | 0.14 |
| 61 | 0.02 |
| 62 | 0.023 |
| 63 | 0.014 |
| 64 | 0.043 |
| 65 | 0.034 |
| 66 | 0.024 |
| 67 | 0.030 |
| 68 | 0.040 |
| 69 | 0.073 |
| 70 | 0.11 |
| 71 | 0.19 |
| 72 | 0.077 |
| 73 | 0.054 |
| 74 | 0.13 |
| 75 | 0.028 |
| 76 | 0.024 |
| 77 | 0.037 |
| 78 | 0.024 |

-continued

| Example | HtrA1 IC$_{50}$ (μM) |
|---|---|
| 79 | 0.050 |
| 80 | 0.029 |
| 81 | 0.029 |
| 82 | 0.15 |
| 83 | 0.041 |
| 84 | 0.015 |
| 85 | 0.020 |
| 86 | 0.027 |
| 87 | 0.019 |
| 88 | 0.053 |
| 89 | 0.079 |
| 90 | 0.040 |
| 91 | 0.15 |
| 92 | 0.060 |
| 93 | 0.061 |
| 94 | 0.062 |
| 95 | 0.060 |
| 96 | 0.063 |
| 97 | 0.075 |
| 98 | 0.040 |
| 99 | 0.038 |
| 100 | 0.045 |
| 101 | 0.037 |
| 102 | 0.064 |
| 103 | 0.027 |
| 104 | 0.023 |
| 105 | 0.043 |
| 106 | 0.044 |
| 107 | 0.23 |
| 108 | 0.22 |
| 109 | 0.081 |
| 110 | 0.13 |
| 111 | 0.14 |
| 112 | 0.060 |
| 113 | 0.047 |
| 114 | 0.20 |
| 115 | 0.078 |
| 116 | 0.072 |
| 117 | 0.063 |
| 118 | 0.064 |
| 119 | 0.052 |
| 120 | 0.13 |
| 121 | 1.1 |
| 122 | 0.063 |
| 123 | 0.13 |
| 124 | 0.089 |
| 125 | 0.014 |
| 126 | 0.092 |
| 127 | 0.91 |
| 128 | 0.011 |
| 129 | 0.017 |
| 130 | 1.4 |

Synthesis

The starting materials used for the synthesis were either prepared or obtained from commercial sources, such as, but not limited to, Sigma-Aldrich, Fluka, Acros Organics, Alfa Aesar, VWR Scientific, and the like. Nuclear Magnetic Resonance (NMR) analysis was conducted using a Varian Mercury 300 MHz spectrometer with an appropriate deuterated solvent. LCMS analysis was conducted using a Waters Acquity UPLC with a QDA MS detector using a Waters C18 BEH 1.7 M, 2.1×50 mm column, eluting with 95:5 to 0:100 H$_2$O:MeCN+0.1% formic acid at a flow rate of 0.6 mL/min over 3.5 minutes. The QDA MS detector was set up to scan under both positive and negative mode ions ranging from 100-1200 Daltons. General methods for the preparation of compounds can be modified by the use of appropriate reagents and conditions for the introduction of the various moieties found in the structures as provided herein.

Abbreviations

Approx. approximately
Boc tert-butyl carbonate
C celcius
Cbz carboxybenzyl
Cp* pentamethylcyclopentadiene
DBU 1,8-diazabicyclo[5.4.0]undec-7-ene
DME dimethoxyethane
DMF dimethylformamide
DMP Dess-Martin Periodinane
DMSO dimethylsulfoxide
EDC 1-ethyl-3-(3-dimethylaminopropyl)carbodiimide
EtOAc ethyl acetate
Et ethyl
equiv equivalents
h hours
HATU 1-[bis(dimethylamino)methylene]-1H-1,2,3-triazolo[4,5-b]pyridinium 3-oxid hexafluorophosphate
HOBt hydroxybenzotriazole
IBX 2-iodoxybenzoic acid
g grams
L liter
LCMS liquid chromatography-mass spectrometry
LiHMDS lithium bis(trimethylsilyl)amide
liq. liquid
M molar
Me methyl
MeCN acetonitrile
mg milligrams
mL milliliter
mmol millimoles
mol moles
Ms, Mes or Mesyl methanesulfonyl
MS mass spectrometry
MTBE methyl tert-butyl ether
NHS N-hydroxysuccinimide
NMM N-methyl morpholine
Pr or iPr propyl or isopropyl
Ph phenyl
Room temperature ambient temperature, approximately 21-25° C.
sat. saturated
THF tetrahydrofuran
TLC thin layer chromatography (normally silica gel based)
TFA trifluoroacetic acid
Tf$_2$O trifluoromethanesulfonic anhydride
μL microliter
wt % weight percentage General Synthetic Scheme In some embodiments, compounds described herein can be prepared as outlined in the following general synthetic schemes. These compounds may be viewed as consisting of four units as shown in the general structure: A—the R$^1$—C(O) group, B—an α-amino acyl group, C—the prolyl group, and D—an α-aminoketoamide group. All the variables in the general structure and in the synthetic schemes are, unless otherwise specified, as defined in the claims.

General Structure

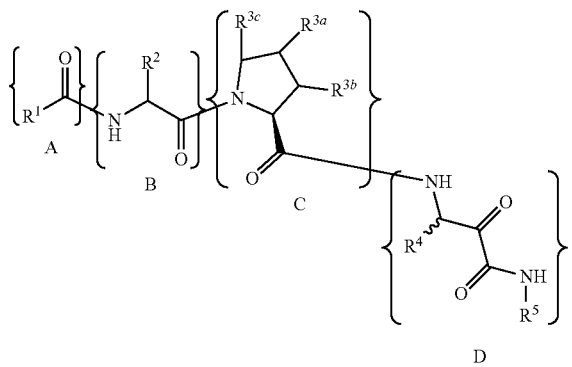

In the schemes, unless otherwise specified, PG is a conventional protecting group (e.g., BOC or CBz for amino group, alkyl ester for carboxylic or boronic acid group); LG is a leaving group (e.g., methanesulfonyloxy); Nuc is a nucleophile (e.g., $N_3$ or piperidine); and R is a protecting group or one or more of optionally protected A, B, C, D units.

Method A: Synthesis of amino-2-hydroxy-amides

A suitably protected α-amino acid (commercially available, or otherwise prepared from the corresponding ketone using a known procedures such as Naydenova, E. D., et al. Eur. J. Med. Chem. 2008, 43, 1199-1205) can be reduced to the primary alcohol (e.g. via $LiAH_4$) and then oxidized to the aldehyde via an appropriate oxidation reagent (e.g. Dess Martin Periodinane). Alternatively, the α-amino acid can be converted to the aldehyde via reduction. For example, the acid can be coupled with N,O-dimethylhydroxylamine via amide coupling conditions described in the literature (e.g. Valeur, E., et al. Chem. Soc. Rev. 2009, 38, 606-631), yielding a Weinreb amide, which is reduced (e.g. via $LiAH_4$) to afford the α-amino aldehyde. The resulting α-amino aldehyde is reacted with a cyanide salt (e.g. KCN) under aqueous acidic condition (such as aqueous $NaHSO_3$) to give a 1-amino 2-hydroxycyanide. The cyanide is hydrolyzed to the hydroxyacetamide (e.g. via an oxidative condition such as hydrogen peroxide). The subsequent N-protected 1-amino 2-hydroxyacetamide is converted to 1-amino 2-hydroxyacetamide or a salt thereof by removal of the nitrogen protecting group (e.g. with a strong acid such as HCl for a Boc group).

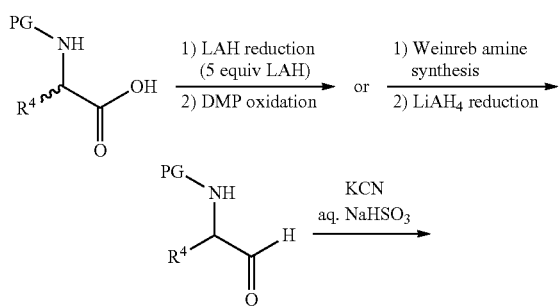

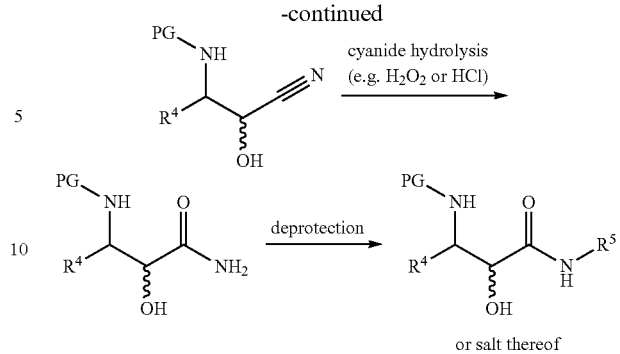

Method B: Amide Coupling

In multiple instances, key bonds within the compounds of the present invention can be assembled via standard amide coupling chemistry. For example a substituted proline analog (or salt thereof) can be joined together with an appropriate carboxylic acid to afford the coupled product under standard amide coupling conditions (e.g. HATU, $EtN(iPr)_2$, $CH_2Cl_2$). Typical amide coupling conditions have been described in the literature, including the review article by Eric Valeur and Mark Bradley in Chemical Society Reviews, 2009, 38, 606-631.

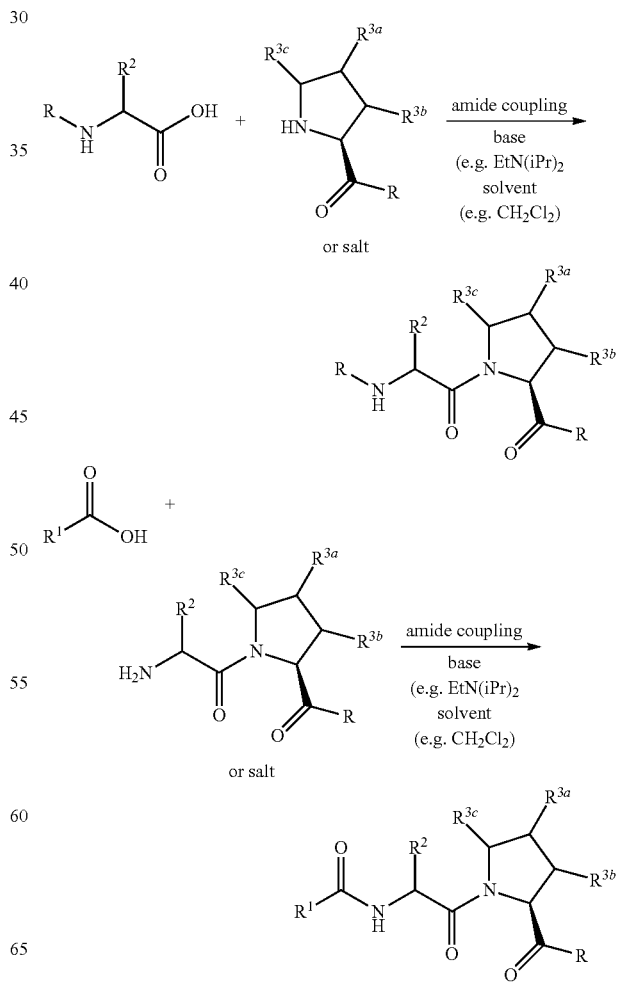

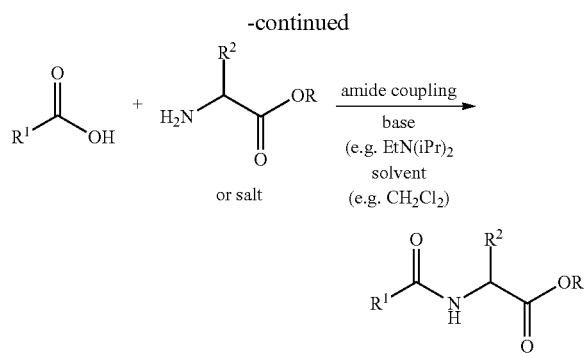

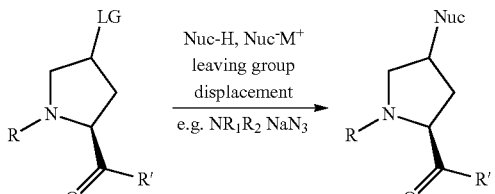

R' is either OR or NHR

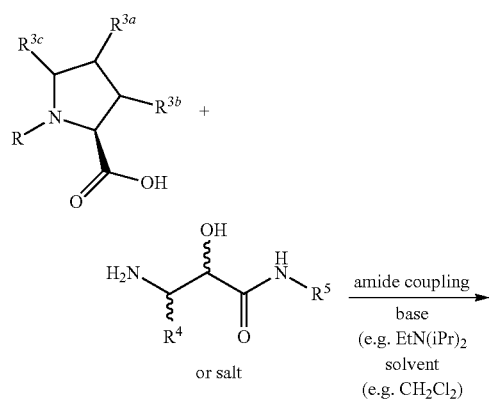

Method D: Synthesis of 4-Triazole Substituted Proline Analogs

An appropriate 4-azido proline analog, prepared as in Method C, is reacted with a terminal alkyne (such as 2-methyl-3-butyn-2-ol) under transition metal catalyzed cycloaddition conditions (such as Cp*RuCl(PPh$_3$)$_2$, as described in the literature: Boren, B. C., et al. *J. Am. Chem. Soc.* 2008, 130, 8923-8930), resulting in the 1,5-isomer of the 4-triazole substituted proline analogs. Alternatively, by applying another transition metal catalytic system (such as CuSO$_4$/L-ascorbic acid, as described in the literature: Rostovtsev, V. V., et al. *Angew. Chem. Int. Ed.* 2002, 41, 2596-2599) the 1,4-cycloaddition product can be facilitated.

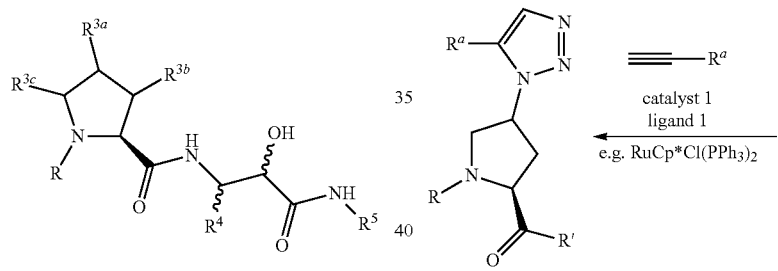

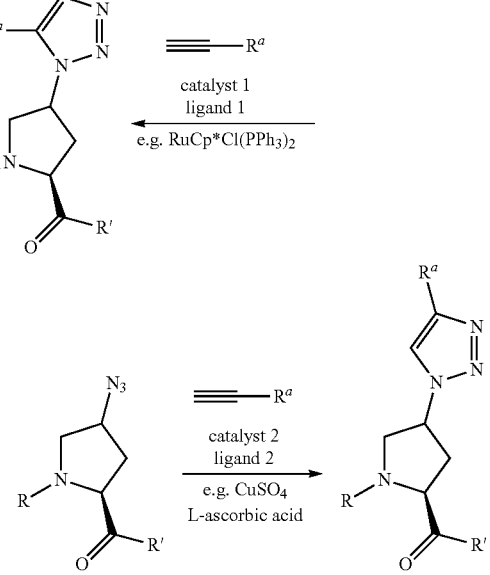

R is a substituent for heteroaryl group, as defind under formula (I) R' is either OR or NHR

Method C: Synthesis of 4-Substituted Proline Analogs Via Nucleophilic Displacement The alcohol moiety from a 4-hydroxyproline analog is converted into a suitable leaving group (e.g. mesylate) under standard conditions and then reacted in the presence of a suitable nucleophile (e.g. an amine, azide) in the presence of a base (e.g. Et$_3$N or NaH) to afford a 4-substituted proline derivative. The proline may be protected at the proline nitrogen (e.g. Boc, Cbz) or may be further functionalized with an α-amino acid or derivative. The proline may contain a 2-amide or 2-ester moiety.

Method E: Modification of Amines at R$^4$

In certain examples, the substituent close to the ketoamide or amino 2-hydroxy amide can be further functionalized. For example, an amine can then be reacted with a range of acylating reagents, including isocyanates, acyl chlorides and sulfonyl chlorides to generate further functionalized analogs.

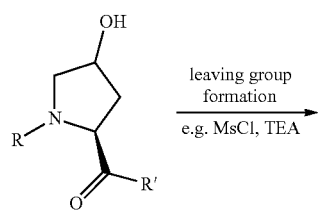

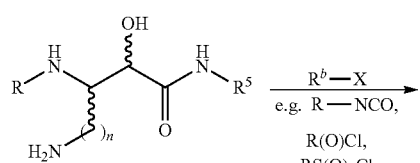
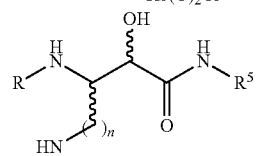
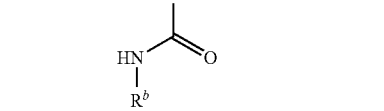
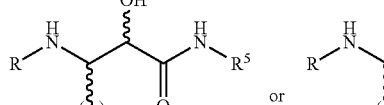

$R^b$ is a group for ureas, amides and sulfonamides as provided in the definition of $R^9$ for formula (I).

Method F: Synthesis of α-Monosubstituted α-Amino Acid Derivatives

A series of α-monosubstituted α-amino acid derivatives can be obtained via a three-step synthesis from a primary alcohol. The alcohol is firstly oxidized to an aldehyde under standard alcohol oxidation conditions (e.g. DMP oxidation). The resulting aldehyde can react with an α-phosphoryl-α-amino acid derivatives via a Horner-Wadsworth-Emmons reaction following standard literature procedures (e.g. St. Jean Jr. D. J., et al. *J. Med. Chem.*, 2014, 57, 309-324). A subsequent olefin hydrogenation of the α,β-unsaturated β-amino ester can be facilitated under conventional heterogeneous catalytic hydrogenation condition (e.g. Pd/C, $H_2$ balloon), affording the α-monosubstituted α-amino acid derivative.

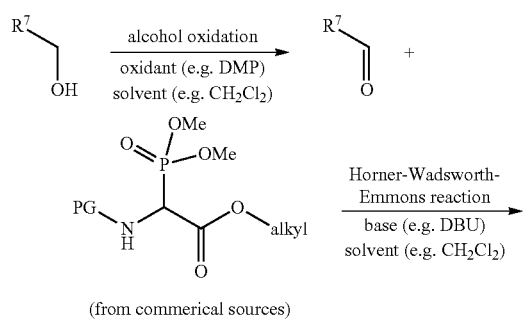
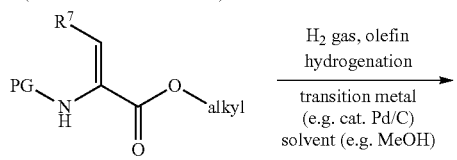

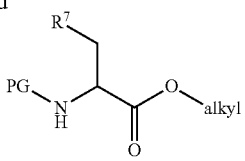

Method G: Oxidation of 2-Hydroxy Amides to Ketoamides

The 2-hydroxy-amide can be oxidized to the corresponding ketoamide under standard alcohol oxidation conditions, using oxidizing agents such as DMP or IBX. Representative conditions for the synthesis of ketoamides can be found within the recent review by Risi, Pollini and Zanirato in *Chem. Rev.*, 2016, 116, 3241-3305.

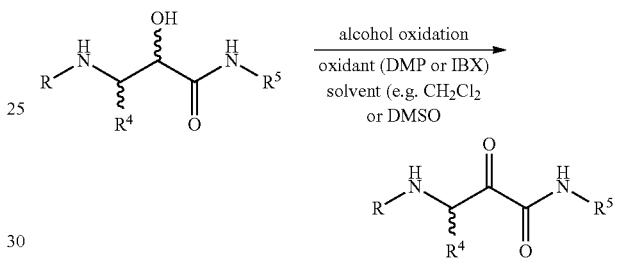

Preparation of Intermediates

Intermediate A: 3-Amino-2-hydroxy-4-methylpentanamide hydrochloride

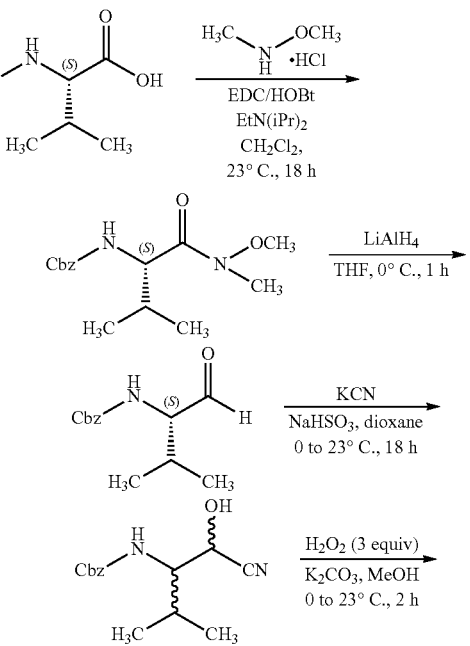

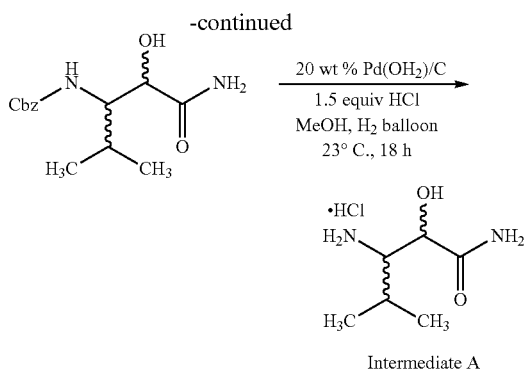

Intermediate A

Step 1: Preparation of benzyl (S)-(1-(methoxy(methyl)amino)-3-methyl-1-oxobutan-2-yl)carbamate Into a 500 mL round-bottom flask equipped with a magnetic stir bar and under nitrogen was added N-Cbz-L-valine (18.6 g, 74 mmol, 1.0 equiv), N,O-dimethylhydroxylamine hydrochloride (8.6 g, 88 mmol, 1.2 equiv), EDC (17 g, 88 mmol, 1.2 equiv), HOBt (1.2 g, 8.8 mmol, 0.1 equiv) and CH$_2$Cl$_2$ (200 mL). The reaction mixture was treated with EtN(iPr)$_2$ (31 mL, 177 mmol, 2.0 equiv) and stirred at room temperature for 18 h overnight. The reaction mixture was quenched with water (100 mL) and poured into a 500 mL separatory funnel containing water (100 mL) and extracted with CH$_2$Cl$_2$ (2×150 mL). The combined organic layers were washed with 1 M aqueous HCl solution (2×100 mL), brine (100 mL), dried over MgSO$_4$, filtered and concentrated to afford a yellow oil which was used directly in the next step (11.3 g).

Step 2: Preparation of benzyl (S)-(3-methyl-1-oxobutan-2-yl)carbamate

Into a flame-dried 500 mL round-bottom flask equipped with a magnetic stir bar and under nitrogen was added solid LiAlH$_4$ (3.6 g, 95 mmol, 1.5 equiv) and anhydrous THF (100 mL). The grey suspension was cooled to 0° C. in an ice bath and the flask was fitted with a 200 mL addition funnel. A solution of benzyl (S)-(1-(methoxy(methyl)amino)-3-methyl-1-oxobutan-2-yl)carbamate (18.8 g, 64 mmol, 1.0 equiv) in THF (100 mL) was prepared and added drop-wise via addition funnel to the grey suspension over 30 minutes. The reaction mixture was stirred at 0° C. for an additional 1 h and then cooled to −10° C. in an ice/brine bath. The reaction was quenched with drop-wise addition of an aqueous NaHSO$_4$ solution (11.4 g in 100 mL water, 83 mmol, 1.3 equiv) over 30 minutes and the thick suspension was allowed to warm to room temperature. The suspension was rinsed with EtOAc (3×100 mL) which was decanted from the solid and the combined organics were placed into a 500 mL separatory funnel. The organic layer was washed with sat. aqueous NaHCO$_3$ (100 mL), 1 M aqueous HCl solution (100 mL), water (100 mL), brine (100 mL), dried over MgSO$_4$, filtered and concentrated to afford a slightly opaque oil which was used directly without further purification.

Step 3: Preparation of benzyl (1-cyano-1-hydroxy-3-methylbutan-2-yl)carbamate Into a 500 mL round-bottom flask equipped with a magnetic stir bar and under nitrogen was added unpurified benzyl (S)-(3-methyl-1-oxobutan-2-yl)carbamate (64 mmol, 1.0 equiv) and 1,4-dioxane (66 mL). The solution was cooled to 0° C. and treated with 40% aqueous sodium bisulfite solution (33 mL, 128 mmol, 2 equiv) followed by KCN (8.3 g, 128 mmol, 2 equiv). The mixture was warmed to room temperature and stirred for 18 h overnight. The reaction mixture was quenched with water (200 mL) and poured into a 500 mL separatory funnel and extracted with EtOAc (3×100 mL). The combined organic layers were washed with brine (100 mL), dried over MgSO$_4$, filtered and concentrated under reduced pressure. Purification by column chromatography through silica gel (150 g) eluting with 100:0 to 50:50 Hexanes:EtOAc as a gradient afforded the desired compound as a clear oil (8.8 g).

Step 4: Preparation of benzyl (1-amino-2-hydroxy-4-methyl-1-oxopentan-3-yl)carbamate Into a 250 mL round-bottom flask equipped with a magnetic stir bar and under nitrogen was added benzyl (1-cyano-1-hydroxy-3-methylbutan-2-yl)carbamate (12.0 g, 46 mmol, 1.0 equiv), K$_2$CO$_3$ (7.0 g, 50 mmol, 1.1 equiv) and methanol (180 mL). The orange suspension was cooled to 0° C. and 35 wt % aqueous H$_2$O$_2$ (13.3 mL, 137 mmol, 3 equiv) was added. The reaction mixture was stirred at 0° C. for 1 h and then warmed to room temperature and stirred for an additional 1 h. TLC analysis at this time revealed conversion of starting material. The reaction was cooled to 0° C. and sodium thiosulfate (23 g, 146 mmol, 3.2 equiv) was added in 4 portions over 30 minutes and stirred at room temperature for an additional 30 minutes. The yellow mixture was poured into a 1 L separatory funnel containing water (600 mL) and extracted with EtOAc (3×150 mL). The combined organic layers were washed with brine (150 mL), dried over MgSO$_4$, filtered and concentrated to afford a yellow oil. Purification by column chromatography through silica gel (140 g) eluting with 100:0 to 90:10 CH$_2$Cl$_2$:MeOH as a gradient afford the title compound as an off-yellow solid (4.25 g).

Step 5: Preparation of 3-amino-2-hydroxy-4-methylpentanamide hydrochloride

Into a 100 mL round-bottom flask equipped with a magnetic stir bar and under nitrogen was added benzyl (1-amino-2-hydroxy-4-methyl-1-oxopentan-3-yl)carbamate (4.25 g, 1.5 mmol, 1.0 equiv) and methanol (20 mL). The contents of the flask were purged with a steady flow of N$_2$ for 10 minutes and then 20 wt % Pd(OH)$_2$ on carbon (1.0 g) was added and N$_2$ purging was continued for another 10 minutes after which the N$_2$ inlet was replaced with a balloon of H$_2$. Purging of the contents of the flask with H$_2$ was continued for 10 minutes, and then the bubbler outlet was removed and the reaction stirred under a balloon of H$_2$ for 18 h overnight. LCMS analysis revealed some starting material remaining, and so 10 M aqueous HCl solution was added (640 μL, 6.4 mmol, 1.5 equiv) and the mixture stirred under a balloon of H$_2$ for 4 h until all the starting material was consumed. The H$_2$ balloon was removed and the black suspension was filtered through a pad of celite on a sintered plastic funnel and the pad was washed with CH$_2$Cl$_2$ (3×10 mL). The slight yellow filtrate was concentrated under reduced pressure to afford the title compound as a yellow solid (2.23 g).

Intermediate B: (R)-2-(2-Naphthamido)-3-cyclohexylpropanoic acid

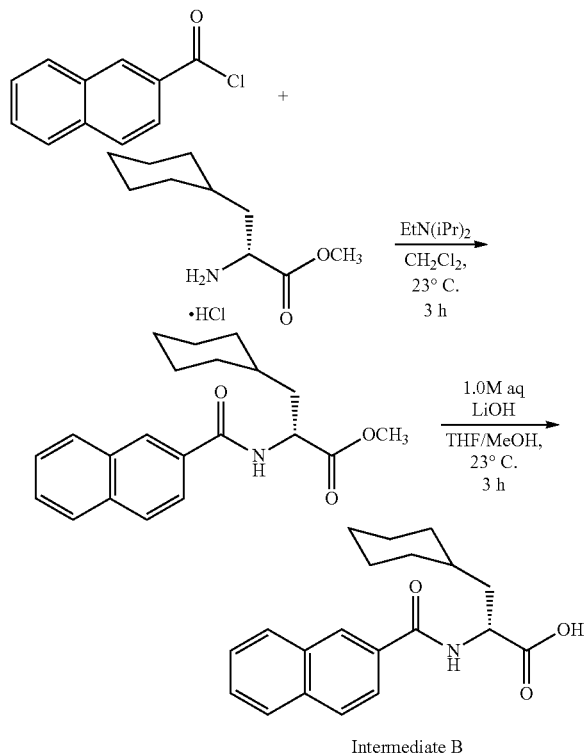

Step 1: Preparation of methyl (R)-2-(2-naphthamido)-3-cyclohexylpropanoate

Into a 100 mL round-bottom flask equipped with a magnetic stir bar and under a nitrogen atmosphere was added methyl (R)-2-amino-3-cyclohexylpropanoate hydrochloride (2.50 g, 11.3 mmol, 1.0 equiv) and $CH_2Cl_2$ (30 mL). The suspension was treated with 2-naphthoyl chloride (2.36 g, 12.4 mmol, 1.1 equiv) followed by $EtN(iPr)_2$ (4.1 mL, 23.7 mmol, 2.1 equiv). The slight yellow solution was stirred at room temperature for 3 h. TLC analysis revealed complete conversion of starting material. The reaction was quenched with water (25 mL) and poured into a 250 mL separatory funnel containing 1 M aqueous HCl solution (100 mL) and the aqueous layer was extracted with $CH_2Cl_2$ (2×75 mL). The combined organic layers were washed with brine (50 mL), dried over $MgSO_4$, filtered and concentrated under reduced pressure. The reaction mixture was purified by column chromatography on silica gel (40 g), eluting with 80:20 Hexanes:EtOAc to afford the indicated product as a white foam (2.36 g).

Step 2: Preparation of (R)-2-(2-naphthamido)-3-cyclohexylpropanoic acid

Into a 100 mL round-bottom flask equipped with a magnetic stir bar was added methyl (R)-2-(2-naphthamido)-3-cyclohexylpropanoate (2.35 g, 6.92 mmol, 1.0 equiv), THF (10 mL) and MeOH (10 mL). The solution was treated with 1 M aqueous LiOH solution (10.4 mL, 10.4 mmol, 1.5 equiv) and stirred at room temperature for 3 h. TLC analysis revealed complete conversion of starting material. The reaction mixture was concentrated under reduced pressure and the resulting solids were taken up in 5 mL of methanol and acidified to pH<2 with 1 M aqueous HCl solution (approx. 15 mL). The resulting white suspension was stirred at room temperature for 4 h and then filtered through a Buchner funnel containing Whatman #1 filter paper under vacuum. The filter cake was dried under vacuum to afford a white free flowing solid (2.07 g).

Intermediate C: (2S,4R)-1-((R)-2-(2-Naphthamido)-3-cyclohexylpropanoyl)-4-(piperidin-1-yl)pyrrolidine-2-carboxylic acid

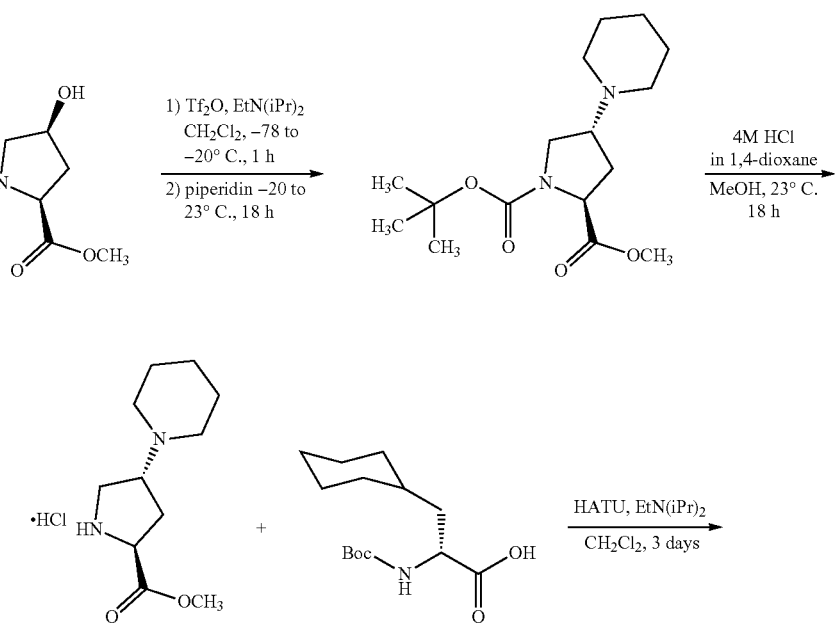

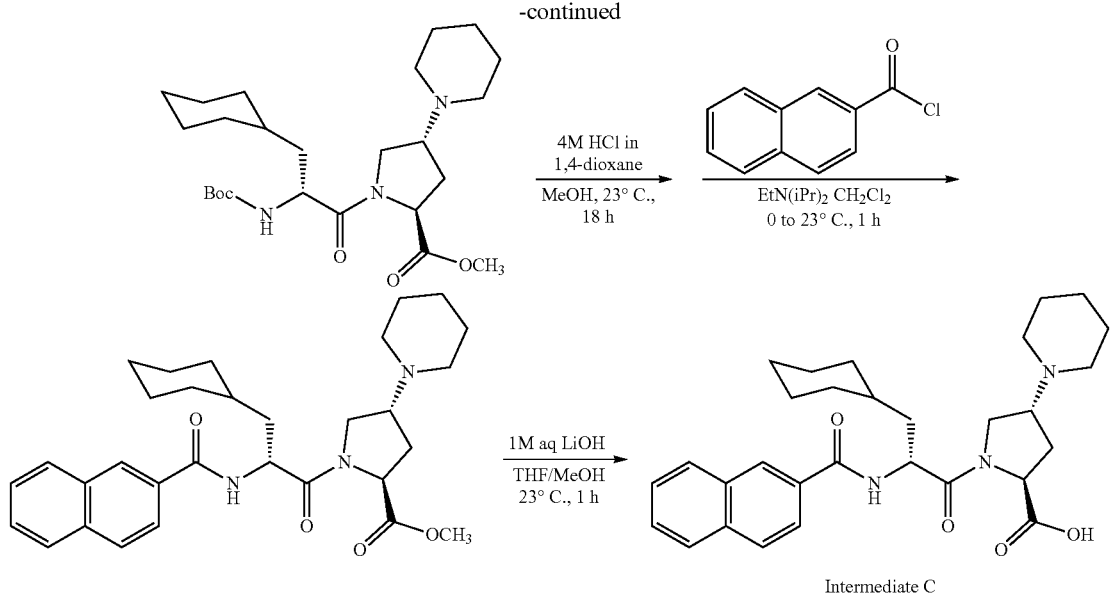

Step 1: Preparation of 1-(tert-butyl) 2-methyl (2S, 4R)-4-(piperidin-1-yl)pyrrolidine-1,2-dicarboxylate Into a 500 mL round-bottom flask equipped with a magnetic stir bar and under nitrogen was weighed 1-(tert-butyl) 2-methyl (2S,4S)-4-hydroxypyrrolidine-1,2-dicarboxylate (10.0 g, 41 mmol, 1.0 equiv). The solid was dissolved in CH$_2$Cl$_2$ (160 mL) and cooled to −78° C. in a dry ice/acetone Dewar. The cold solution was treated with EtN(iPr)$_2$ (8.6 mL, 49 mmol, 1.2 equiv) and then trifluoromethanesulfonic anhydride (7.4 mL, 45 mmol, 1.1 equiv) was added drop-wise over 30 minutes. After stirring at −78° C. for 1 h, the mixture was warmed to −20° C. and piperidine (8.1 mL, 82 mmol, 2.0 equiv) was added drop-wise over 15 minutes. The reaction mixture was allowed to warm to room temperature with stirring for 18 h overnight. LCMS analysis revealed product formation. The reaction mixture was poured into a 500 mL separatory funnel containing water (100 mL) and extracted with EtOAc (3×100 mL). The combined organic layers were washed with brine (100 mL), dried over MgSO$_4$, filtered and concentrated. Purification by column chromatography through silica gel (120 g), eluting with 90:10 to 0:100 Hexanes:EtOAc as a gradient afforded the desired product (9.7 g).

Step 2: Preparation of methyl (2S,4R)-4-(piperidin-1-yl)pyrrolidine-2-carboxylate hydrochloride Into a 250 mL round-bottom flask, equipped with a magnetic stir bar and under nitrogen was charged 1-(tert-butyl) 2-methyl (2S,4R)-4-(piperidin-1-yl)pyrrolidine-1,2-dicarboxylate (9.7 g, 31 mmol, 1.0 equiv) and methanol (20 mL). The solution was treated with 4 M HCl in dioxane (19 mL, 78 mmol, 2.5 equiv) and the reaction was stirred at room temperature for 18 h. The reaction mixture was filtered through Whatman #1 paper on a Hirsch funnel, washing with dioxane (20 mL). The resulting white filter cake was further washed with diethyl ether (40 mL) and dried under vacuum to afford a white solid (8.2 g).

Step 3: Preparation of methyl (2S,4R)-1-((R)-2-((tert-butoxycarbonyl)amino)-3-cyclohexylpropanoyl)-4-(piperidin-1-yl)pyrrolidine-2-carboxylate Into a 250 mL round-bottom flask equipped with a magnetic stir bar and under nitrogen was charged (R)-2-((tert-butoxycarbonyl)amino)-3-cyclohexylpropanoic acid (7.75 g, 29 mmol, 1.0 equiv), HATU (16.3 g, 43 mmol, 1.5 equiv) and CH$_2$Cl$_2$ (50 mL). The suspension was stirred at room temperature for 30 minutes and then treated with methyl (2S,4R)-4-(piperidin-1-yl)pyrrolidine-2-carboxylate hydrochloride (8.2 g, 29 mmol, 1.0 equiv), followed by EtN(iPr)$_2$ (15 mL, 86 mmol, 3.0 equiv) and the reaction was stirred at room temperature for 3 days. The reaction mixture was diluted with water (100 mL) and poured into a 500 mL separatory funnel and extracted with CH$_2$Cl$_2$ (2×100 mL). The combined organics were washed with sat. aqueous NaHCO$_3$ solution (100 mL), brine (100 mL), dried over MgSO$_4$, filtered and concentrated under reduced pressure. Purification by column chromatography through silica gel (120 g), eluting with 75:25 to 0:100 Hexanes:EtOAc as a gradient afforded the title compound as a foam (12.5 g).

Step 4: Preparation of methyl (2S,4R)-1-((R)-2-(2-naphthamido)-3-cyclohexylpropanoyl)-4-(piperidin-1-yl)pyrrolidine-2-carboxylate Into a 200 mL round-bottom flask equipped with a magnetic stir bar and under nitrogen was added methyl (2S,4R)-1-((R)-2-((tert-butoxycarbonyl)amino)-3-cyclohexylpropanoyl)-4-(piperidin-1-yl)pyrrolidine-2-carboxylate (10.2 g, 22 mmol, 1.0 equiv), 1,4-dioxane (15 mL) and methanol (15 mL). The solution was treated with 4 M HCl in dioxane (13.7 mL, 55 mmol, 2.5 equiv) and the mixture stirred at room temperature for 18 h overnight. The reaction mixture was concentrated under reduced pressure, re-suspended in methanol (5 mL) and EtOAc (40 mL) and concentrated under reduced pressure to afford an oil (7.8 g).

A portion of the oil obtained above (5.7 g, 13 mmol, 1.0 equiv) was dissolved in CH$_2$Cl$_2$ and cooled to 0° C. in an ice bath. To this was added 2-naphthoyl chloride (3.7 g, 20 mmol, 1.5 equiv) followed by EtN (iPr)$_2$ (6.8 mL, 39 mmol, 3 equiv) and stirred at room temperature for 1 h. LCMS analysis at this time reveals product formation. The reaction mixture was quenched with water (100 mL) and poured into a 500 mL separatory funnel and extracted with CH$_2$Cl$_2$ (2×100 mL). The combined organic layers were washed with sat. aqueous NaHCO$_3$ solution (100 mL), dried over MgSO$_4$, filtered and concentrated under reduced pressure. Purification by column chromatography through silica gel (120 g), eluting with 100:0 to 93:7 CH$_2$Cl$_2$:MeOH as a gradient afforded the title compound (5.96 g).

Step 5: Preparation of (2S,4R)-1-((R)-2-(2-naphthamido)-3-cyclohexylpropanoyl)-4-(piperidin-1-yl)pyrrolidine-2-carboxylic acid Into a 250 mL round-bottom flask equipped with a magnetic stir bar and under nitrogen was added methyl (2S,4R)-1-((R)-2-(2-naphthamido)-3-cyclohexylpropanoyl)-4-(piperidin-1-yl)pyrrolidine-2-carboxylate (5.9 g, 11.5 mmol, 1.0 equiv), methanol (30 mL) and THF (30 mL). The solution was treated with 1 M aqueous LiOH solution (28.7 mL, 28.7 mmol, 2.5 equiv) and stirred at room temperature for 1 h. LCMS analysis after this time revealed complete conversion to product. The reaction mixture was concentrated under reduced pressure to approx. half the original volume and diluted with 100 mL of CH$_2$Cl$_2$. The mixture was treated drop-wise with 1 M aqueous HCl solution (29 mL) over a 20 minute period and the mixture was poured into a 250 mL separatory funnel. The organic layer was removed and the aqueous layer was extracted with CH$_2$Cl$_2$ (100 mL). The combined organic layers were washed with water (40 mL), dried over MgSO$_4$, filtered and concentrated under reduced pressure to afford an off-white solid (5.95 g).

Intermediate D: (2S,4S)-1-((R)-2-(2-Naphthamido)-3-cyclohexylpropanoyl)-4-(piperidin-1-yl)pyrrolidine-2-carboxylic acid Intermediate D

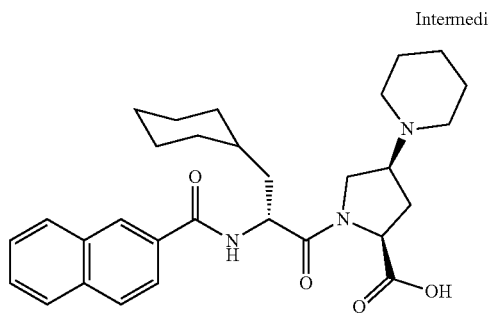

This compound was prepared in a similar manner to Intermediate C, except 1-(tert-butyl) 2-methyl (2S,4R)-4-hydroxypyrrolidine-1,2-dicarboxylate was used in place of 1-(tert-butyl) 2-methyl (2S,4S)-4-hydroxypyrrolidine-1,2-dicarboxylate in Step 1 of the reaction sequence.

Intermediate E: Benzyl (5,7-diamino-6-hydroxy-7-oxoheptyl)carbamate hydrochloride

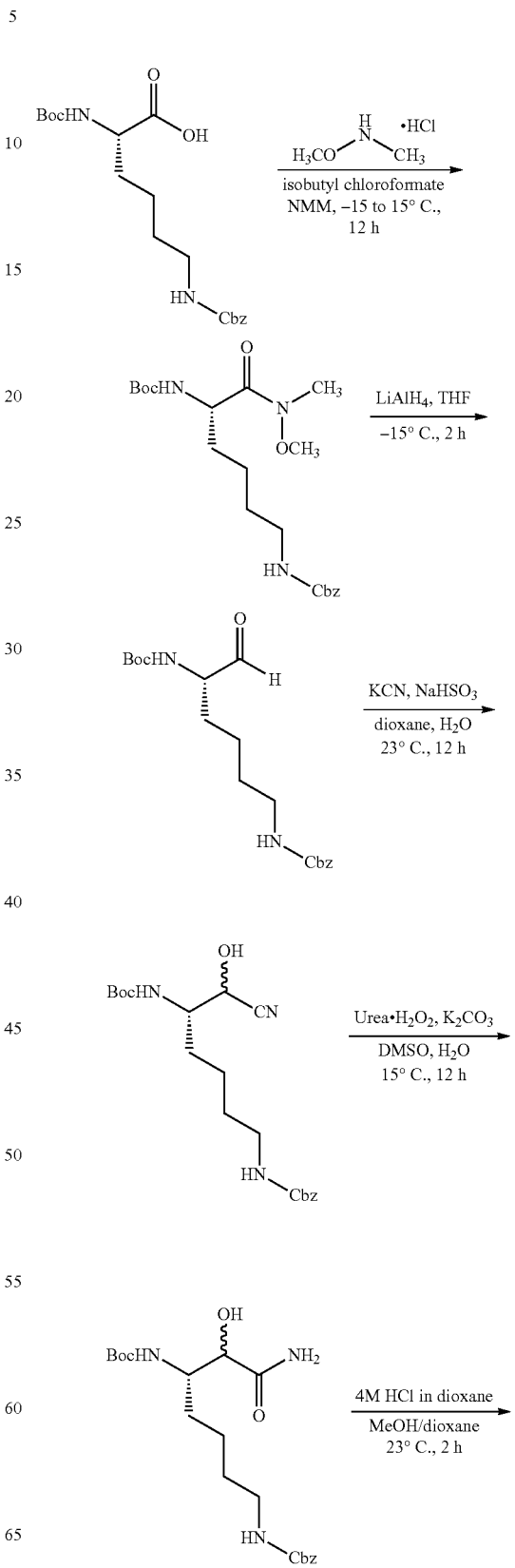

-continued

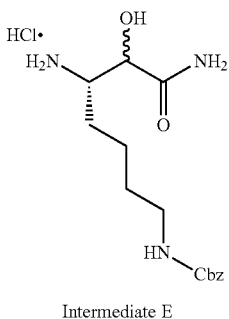

Intermediate E

Step 1: Preparation of benzyl tert-butyl (6-(methoxy(methyl)amino)-6-oxohexane-1,5-diyl)(S)-dicarbamate To a solution of $N^6$-((benzyloxy)carbonyl)-$N^2$-(tert-butoxycarbonyl)-L-lysine (300 g, 0.78 mol, 1.0 equiv) and N,O-dimethylhydroxylamine hydrochloride (159 g, 1.6 mol, 2.0 equiv) and NMM (176 mL, 1.6 mol, 2.0 equiv) in $CH_2Cl_2$ (3.0 L) was added isobutyl chloroformate (108 g, 0.8 mol, 1.0 equiv) at −15° C. The mixture was stirred at 15° C. for 12 hours. TLC analysis revealed conversion of starting material. The reaction mixture was quenched by addition of water (2 L) at 15° C., poured into a large separatory funnel and extracted with $CH_2Cl_2$ (3×1 L). The combined organic layers were washed with 1 M aqueous HCl solution (1 L), dried over $Na_2SO_4$, filtered and concentrated under reduced pressure to give a residue. The crude product was purified by column chromatography on silica gel eluting with 95:5 to 90:10 petroleum ether:EtOAc to afford the title compound as a yellow oil (268 g).

Step 2: Preparation of benzyl tert-butyl (6-oxohexane-1,5-diyl)(S)-dicarbamate To a solution of $LiAlH_4$ (17.9 g, 472 mmol, 2.0 equiv) in THF (1.0 L) was added drop-wise benzyl tert-butyl (6-(methoxy(methyl)amino)-6-oxohexane-1,5-diyl)(S)-dicarbamate (100 g, 236.1 mmol, 1.0 equiv) at −15° C. over a 1 h period. After the addition was complete, the mixture was stirred at this temperature for 1 h. LCMS analysis revealed complete consumption of starting material. The reaction mixture was quenched with slow addition of a sat. aqueous $KHSO_4$ solution (41.8 g, 306 mmol, 1.3 equiv) in water (200 mL) at such a rate to keep the reaction temperature below 0° C. while maintaining the bath temperature below −10° C. After addition was completed, the cooling bath was removed and the reaction was warmed up to room temperature over 1 h. After this time, this suspension was poured into a large separatory funnel and extracted with EtOAc (2×500 mL). The combined organic layers were washed with 1 M aqueous HCl solution (500 mL), sat. aqueous $NaHCO_3$ (500 mL), dried over $MgSO_4$, filtered and the solvent removed under reduced pressure to give a colorless oil. The material (90 g) was used directly in the next step without further purification.

Step 3: Preparation of benzyl tert-butyl ((5S)-6-cyano-6-hydroxyhexane-1,5-diyl)dicarbamate Into a 2 L round-bottom flask, equipped with a magnetic stir bar and under nitrogen was added benzyl tert-butyl (6-oxohexane-1,5-diyl)(S)-dicarbamate (90 g, 247 mmol, 1.0 equiv) and 1,4-dioxane (500 mL). The solution was cooled in an ice bath to 0° C. To this solution was added, via an addition funnel, a solution of 40% aqueous $NaHSO_3$ (194 g, 745 mmol, 3.0 equiv) over 10 minutes. This mixture was stirred another 30 minutes over the ice bath and then a solution of KCN (48.4 g, 742.9 mmol, 3.0 equiv) in $H_2O$ (200 mL) was added via an addition funnel over 10 minutes. The reaction mixture was stirred at room temperature for 12 h. After this time, EtOAc (2 L) and sat. aqueous $NaHCO_3$ (500 mL) were added and the layers were partitioned in a large separatory funnel. The aqueous layer was extracted with EtOAc (1 L) and the combined organic layers were washed with sat. aqueous $NaHCO_3$ (2×500 mL), dried over $MgSO_4$, filtered and concentrated under reduced pressure. The residue was purified by column chromatography through silica gel, eluting with 100:0 to 95:5 $CH_2Cl_2$:MeOH as a gradient to afford the title compound as a colourless oil (59 g).

Step 4: Preparation of benzyl tert-butyl ((5S)-7-amino-6-hydroxy-7-oxoheptane-1,5-diyl)dicarbamate To a 1 L round-bottom flask, equipped with a magnetic stir bar and under nitrogen was added benzyl tert-butyl ((5S)-6-cyano-6-hydroxyhexane-1,5-diyl)dicarbamate (59 g, 150 mmol, 1.0 equiv), $K_2CO_3$ (10.4 g, 75 mmol, 0.5 equiv), $H_2O$ (150 mL) and DMSO (450 mL). The suspension was cooled to 0° C. and treated with portion-wise addition of urea hydrogen peroxide (71 g, 753 mmol, 5.0 equiv). After addition was complete, the mixture was stirred at 15° C. for 12 h. The reaction mixture was quenched by addition of water (400 mL) at 15° C., and the mixture was poured into a large separatory funnel and extracted with $CH_2Cl_2$ (3×500 mL). The combined organic layers were washed with a 10% aqueous solution of $Na_2S_2O_3$ (200 mL), dried over $Na_2SO_4$, filtered and concentrated under reduced pressure. The residue was purified by recrystallization from EtOAc (150 mL) and the resulting filter cake washed with warm water (150 mL) and dried. Further purification by column chromatography through silica gel, eluting with 100:0 to 95:5 $CH_2Cl_2$:MeOH as a gradient, afforded the desired product as a white solid (25.5 g).

Step 5: Preparation of benzyl (5,7-diamino-6-hydroxy-7-oxoheptyl)carbamate hydrochloride Into a 250 mL round-bottom flask equipped with a magnetic stir bar and under nitrogen was added benzyl tert-butyl ((5S)-7-amino-6-hydroxy-7-oxoheptane-1,5-diyl)dicarbamate (10.0 g, 24.4 mmol, 1.0 equiv), 1,4-dioxane (25 mL) and methanol (25 mL). The solution was treated with 4 M HCl in dioxane (25 mL, 98 mmol, 4 equiv) and the resulting suspension was stirred at room temperature for 2 h. The mixture was diluted with EtOAc (100 mL) and stirred at room temperature for 20 minutes. The thick suspension was filtered under vacuum through Whatman #1 filter paper on a Hirsch funnel and the resulting filter cake was washed with EtOAc (2×25 mL), $Et_2O$ (2×25 mL) and hexanes (25 mL). The white solid was dried under high vacuum for 18 h to afford an off-white solid (8.3 g).

Intermediate F: (2S,4S)-1-((R)-2-(2-Naphthamido)-3-cyclohexylpropanoyl)-4-azidopyrrolidine-2-carboxylic acid

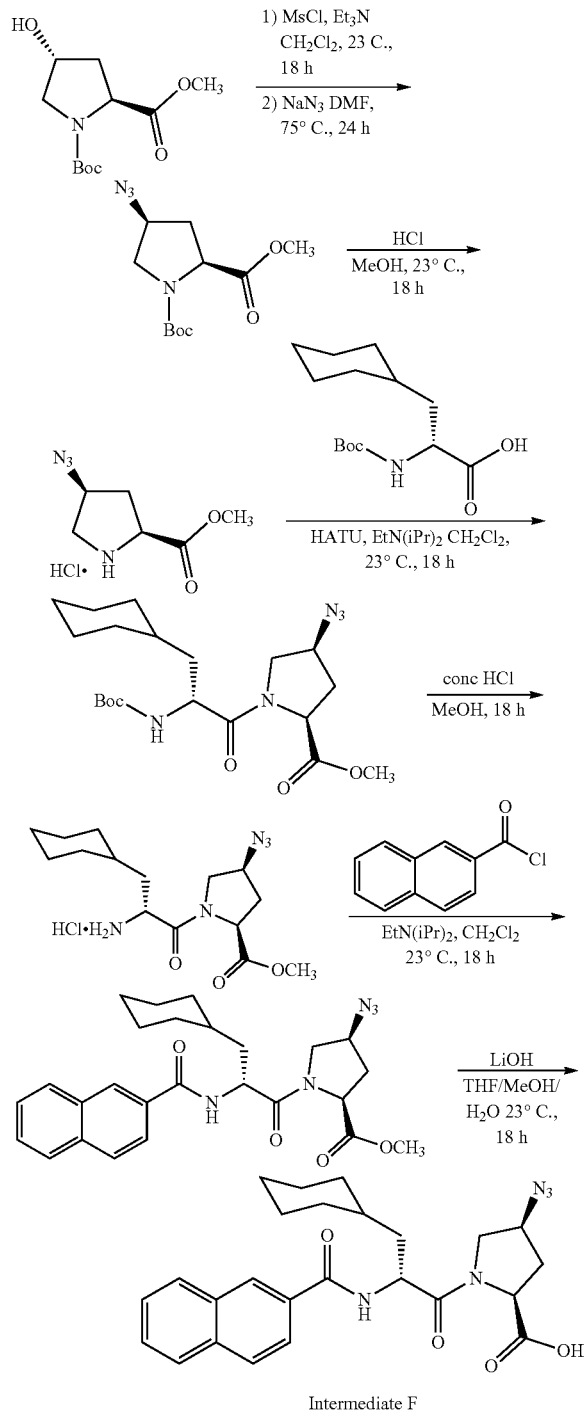

Intermediate F

Step 1: Preparation of 1-(tert-butyl) 2-methyl (2S, 4S)-4-azidopyrrolidine-1,2-dicarboxylate A solution of 1-(tert-butyl) 2-methyl (2S,4R)-4-hydroxypyrrolidine-1,2-dicarboxylate (33.8 g, 138 mmol, 1.0 equiv) in CH$_2$Cl$_2$ (280 mL) was cooled in an ice bath and Et$_3$N (44 mL, 606 mmol, 4.4 equiv) and methanesulfonyl chloride (23.5 mL, 303 mmol, 2.2 equiv) were added sequentially at 0° C. The reaction was allowed to warm to room temperature and stirred for 18 h overnight. After this time, the reaction mixture was diluted with CH$_2$Cl$_2$ (200 mL) and washed with sat. aqueous NaHCO$_3$ solution (200 mL), water (200 mL) and finally brine (100 mL). The combined organic layers were dried over MgSO$_4$, filtered and concentrated under reduced pressure to afford the title compound as an oil. To the resulting oil was added NaN$_3$ (18.0 g, 276 mmol, 2.0 equiv) in DMF (270 mL) and the mixture was stirred at 75° C. in an oil bath under nitrogen. After 24 h, the mixture was allowed to cool to room temperature, diluted with water (100 mL) and extracted with EtOAc (3×200 mL) using a separatory funnel. The combined organic layers were washed with brine (100 mL), dried over MgSO$_4$, filtered and the solvent was concentrated under reduced pressure. Purification by column chromatography through silica gel (660 g) eluting with 100:0 to 70:30 Hexanes:EtOAc as a gradient provided the title compound (34.7 g).

Step 2: Preparation of methyl (2S,4S)-4-azidopyrrolidine-2-carboxylate hydrochloride To a solution of 1-(tert-butyl) 2-methyl (2S,4S)-4-azidopyrrolidine-1,2-dicarboxylate (28.4 g, 105 mmol, 1.0 equiv) in MeOH (250 mL) was added 36% aqueous HCl solution (38 mL, 456 mmol, 4.3 equiv) and the mixture was stirred at room temperature for 18 h overnight. The solvent was removed under reduced pressure and the resulting residue was co-evaporated with MeOH (4×100 mL) to remove any water and excess HCl. The resulting solid was dried under vacuum to afford the desired product (21.9 g).

Step 3: Preparation of methyl (2S,4S)-4-azido-1-((R)-2-((tert-butoxycarbonyl)amino)-3-cyclohexylpropanoyl)pyrrolidine-2-carboxylate A suspension of (R)-2-((tert-butoxycarbonyl)amino)-3-cyclohexylpropanoic acid (34.2 g, 126 mmol, 1.2 equiv) and HATU (48 g, 126 mmol, 1.2 equiv) in CH$_2$Cl$_2$ (280 mL) was stirred for 10 minutes and then methyl (2S,4S)-4-azidopyrrolidine-2-carboxylate hydrochloride (21.7 g, 105 mmol, 1.0 equiv) and EtN(iPr)$_2$ (46 mL, 262 mmol, 2.5 equiv) were added and the reaction mixture was stirred at room temperature for 18 h overnight. The reaction mixture was cooled to 0° C. in an ice bath and quenched with 1 M aqueous HCl solution (500 mL). The mixture was transferred to a 1 L separatory funnel and extracted with CH$_2$Cl$_2$ (3×200 mL). The combined organic layers were washed with sat. aqueous NaHCO$_3$ solution (100 mL), brine (100 mL), dried over MgSO$_4$, filtered and concentrated under reduced pressure. This residue was purified by column chromatography through silica gel (660 g) eluting with 100:0 to 50:50 Hexanes:EtOAc as a gradient. The fractions were monitored by TLC (7:3 Hexanes:EtOAc, visualized by ninhydrin staining). The desired fractions were combined and the solvent was removed on the rotary evaporator to provide the title compound (24.4 g).

Step 4: Preparation of methyl (2S,4S)-1-((R)-2-amino-3-cyclohexylpropanoyl)-4-azidopyrrolidine-2-carboxylate hydrochloride Into a 250 mL round-bottom flask equipped with a magnetic stir bar and under nitrogen was added methyl (2S,4S)-

4-azido-1-((R)-2-((tert-butoxycarbonyl)amino)-3-cyclohexylpropanoyl)pyrrolidine-2-carboxylate (24.4 g, 57.5 mmol, 1.0 equiv) and MeOH (150 mL). The solution was treated with 36% aqueous HCl solution (42 mL, 402 mmol, 6.5 equiv) and the mixture was stirred at room temperature for 3 days, becoming a thick suspension. The reaction mixture was concentrated under reduced pressure, using additional MeOH (4×100 mL) to co-evaporate water and excess HCl. The resulting off-white solid was dried under vacuum to afford the desired compound (20.5 g).

Step 5: Preparation of methyl (2S,4S)-1-((R)-2-(2-naphthamido)-3-cyclohexylpropanoyl)-4-azidopyrrolidine-2-carboxylate To a suspension of methyl (2S,4S)-1-((R)-2-amino-3-cyclohexylpropanoyl)-4-azidopyrrolidine-2-carboxylate hydrochloride (20.5 g, 57 mmol, 1.0 equiv) and 2-naphthoyl chloride (11.9 g, 62.6 mmol, 1.1 equiv) in CH$_2$Cl$_2$ (300 mL) was added EtN(iPr)$_2$ (25 mL, 142 mmol, 2.5 equiv) and the reaction mixture was stirred at room temperature for 18 h overnight. The mixture was quenched with water (100 mL) and partitioned between 1 M aqueous HCl solution (300 mL) and CH$_2$Cl$_2$ (3×200 mL). The combined organic layers were washed with brine (150 mL), dried over MgSO$_4$, filtered and the solvent was removed under reduced pressure. This residue was purified by column chromatography through silica gel (330 g), eluting with a 100:0 to 50:50 Hexanes:EtOAc as a gradient. The desired fractions were combined and the solvent was removed under reduced pressure to provide the title compound (22.2 g).

Step 6: Preparation of (2S,4S)-1-((R)-2-(2-naphthamido)-3-cyclohexylpropanoyl)-4-azidopyrrolidine-2-carboxylic acid To a solution of methyl (2S,4S)-1-((R)-2-(2-naphthamido)-3-cyclohexylpropanoyl)-4-azidopyrrolidine-2-carboxylate (22.2 g, 46.5 mmol, 1.0 equiv) in MeOH (75 mL) and THF (75 mL) was added 1 M aqueous LiOH solution (70 mL, 70 mmol, 1.5 equiv) and the mixture was stirred at room temperature for 18 h overnight. The reaction mixture was concentrated under reduced pressure and the residue was diluted in EtOAc (70 mL) and acidified to pH<2 with 1 M aqueous HCl solution (z 90 mL). The reaction mixture was poured into a 250 mL separatory funnel containing water (100 mL) and the aqueous layer extracted with EtOAc (4×100 mL). The combined organic layers were washed with brine (100 mL), dried over MgSO$_4$, filtered and concentrated under reduced pressure to afford the title compound as a white solid (20.4 g).

Intermediate G: (2S,4S)-1-((R)-2-(2-Naphthamido)-3-cyclohexylpropanoyl)-N-(1,7-diamino-2-hydroxy-1-oxoheptan-3-yl)-4-(5-(2-hydroxypropan-2-yl)-1H-1,2,3-triazol-1-yl)pyrrolidine-2-carboxamide

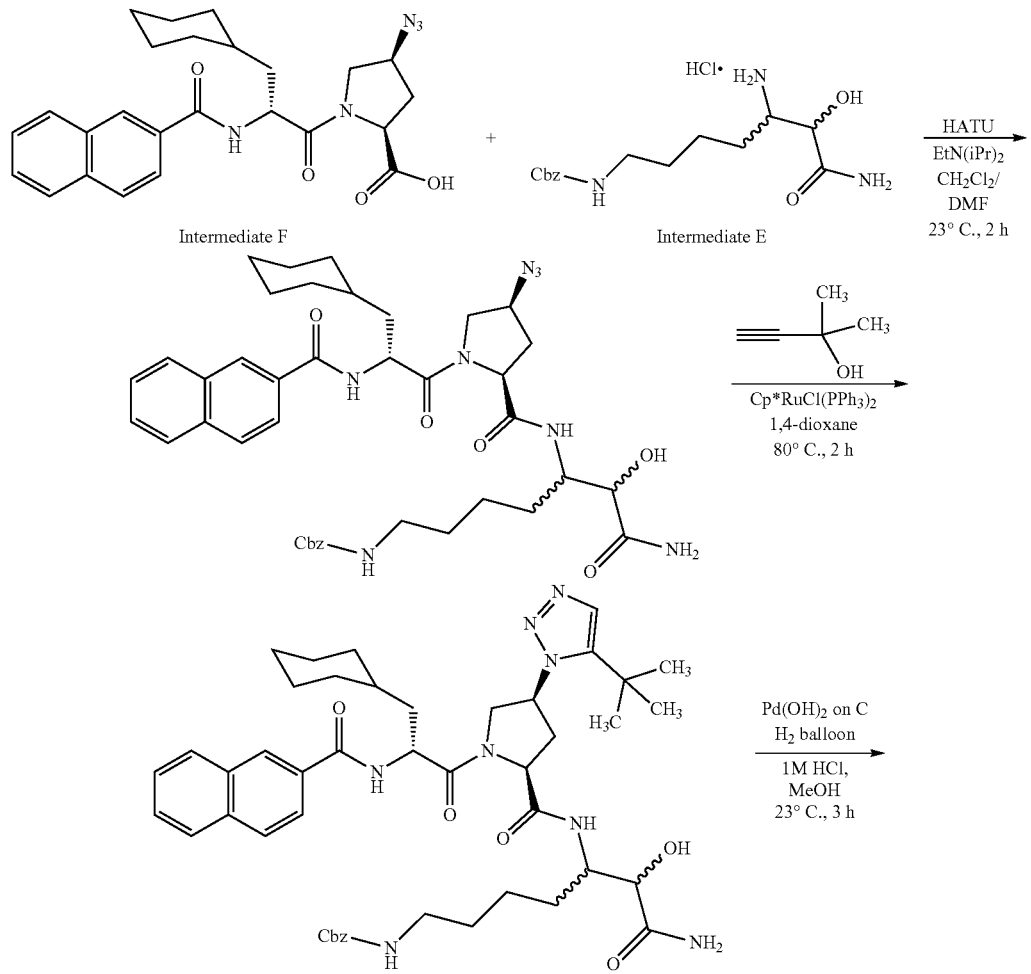

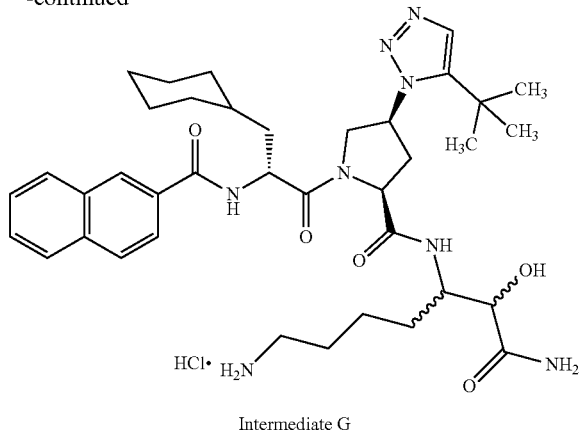

Intermediate G

Step 1: Preparation of benzyl (5-((2S,4S)-1-((R)-2-(2-naphthamido)-3-cyclohexylpropanoyl)-4-azidopyrrolidine-2-carboxamido)-7-amino-6-hydroxy-7-oxoheptyl)carbamate Into a 250 m round-bottom flask equipped with a magnetic stir bar and under nitrogen was added (2S,4S)-1-((R)-2-(2-naphthamido)-3-cyclohexylpropanoyl)-4-azidopyrrolidine-2-carboxylic acid (Intermediate F, 6.0 g, 13.0 mmol, 1.0 equiv), benzyl (5,7-diamino-6-hydroxy-7-oxoheptyl)carbamate hydrochloride (Intermediate E, 4.5 g, 13.0 mmol, 1.0 equiv), HATU (5.9 g, 15.5 mmol, 1.2 equiv), CH$_2$Cl$_2$ (26 mL) and DMF (3 mL). The reaction mixture was treated with EtN(iPr)$_2$ (9.1 mL, 51.9 mmol, 4.0 equiv) and the reaction mixture was stirred at room temperature for 2 h. LCMS analysis revealed complete conversion of starting material. The reaction mixture was quenched with water (500 mL) and poured into a 1 L separatory funnel and extracted with EtOAc (3×200 mL). The combined organic layers were washed with 1 M aqueous HCl solution (250 mL), brine (200 mL), dried over MgSO$_4$, filtered and concentrated under reduced pressure. Purification by column chromatography through silica gel (330 g), eluting with 100:0 to 85:15 CH$_2$Cl$_2$:MeOH as a gradient afforded the title compound as a beige foam (9.96 g).

Step 2: Preparation of benzyl (5-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-7-amino-6-hydroxy-7-oxoheptyl)carbamate Into a 250 mL round-bottom flask equipped with a magnetic stir bar and under nitrogen was added benzyl (5-((2S,4S)-1-((R)-2-(2-naphthamido)-3-cyclohexylpropanoyl)-4-azidopyrrolidine-2-carboxamido)-7-amino-6-hydroxy-7-oxoheptyl)carbamate (9.96 g, 13.2 mmol, 1.0 equiv), 2-methylbut-3-yn-2-ol (5.12 mL, 53 mmol, 4.0 equiv) and 1,4-dioxane (66 mL). The contents of the flask were purged with a steady flow of N$_2$ for 10 minutes, and then Cp*RuCl(PPh$_3$)$_2$ (526 mg, 0.66 mmol, 0.05 equiv) was added and purging was continued for another 15 minutes. The nitrogen outlet was removed and the contents of the flask were heated in an oil bath at 80° C. for 2 h, becoming a darkly coloured mixture. The cooled reaction mixture was concentrated under reduced pressure and loaded directly onto silica gel. Purification by column chromatography through silica gel (330 g), eluting with 100:0 to 90:10 EtOAc:MeOH as a gradient afforded the title compound as a slight orange foam (9.9 g).

Step 3: Preparation of (2S,4S)-1-((R)-2-(2-naphthamido)-3-cyclohexylpropanoyl)-N-(1,7-diamino-2-hydroxy-1-oxoheptan-3-yl)-4-(5-(2-hydroxypropan-2-yl)-1H-1,2,3-triazol-1-yl)pyrrolidine-2-carboxamide hydrochloride A solution of benzyl (5-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-7-amino-6-hydroxy-7-oxoheptyl)carbamate (9.9 g, 11.9 mmol, 1.0 equiv), MeOH (225 mL) and 1 M aqueous HCl solution (13.1 mL, 13.1 mmol, 1.1 equiv) was degassed with a steady flow of N$_2$ for 15 minutes. After this time, 20 wt % Pd(OH)$_2$ on carbon (997 mg) was added and degassing with a flow of N$_2$ was continued for another 15 minutes. The N$_2$ inlet was replaced with a balloon of H$_2$ and the contents of the flask were purged for an additional 15 minutes after which the outlet was removed. The black suspension was stirred under an atmosphere of H$_2$ for 3 h at room temperature. The reaction mixture was filtered through a pad of celite on a sintered plastic funnel, and the contents of the flask and the filter cake were washed with CH$_2$Cl$_2$ (3×50 mL). The clear filtrate was concentrated under reduced pressure and the title compound was isolated as a hydrochloride salt (8.32 g).

Intermediate H: Benzyl (5-((2S,4R)-1-((R)-2-(2-naphthamido)-3-cyclohexylpropanoyl)-4-azidopyrrolidine-2-carboxamido)-7-amino-6-hydroxy-7-oxoheptyl)carbamate

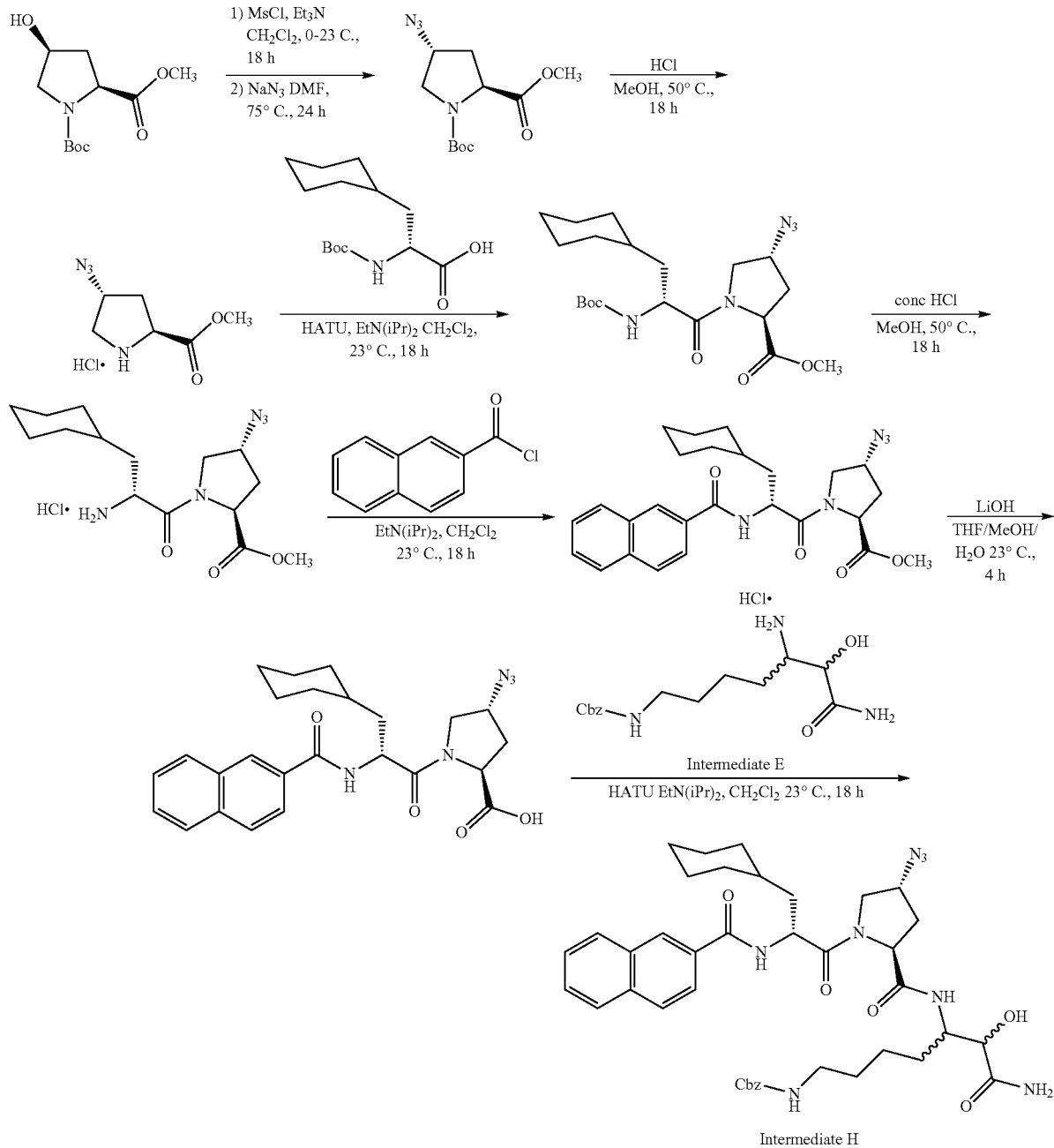

Intermediate H

Step 1: Preparation of 1-(tert-butyl) 2-methyl (2S, 4R)-4-azidopyrrolidine-1,2-dicarboxylate Into a 250 mL round-bottom flask equipped with a magnetic stir bar and under $N_2$ was added 1-(tert-butyl) 2-methyl (2S,4S)-4-hydroxypyrrolidine-1,2-dicarboxylate (5.0 g, 20.4 mmol, 1.0 equiv) and $CH_2Cl_2$ (50 mL). The solution was cooled to 0° C. in an ice bath and $Et_3N$ (12.5 mL, 90 mmol, 4.4 equiv) was added followed by methanesulfonyl chloride (3.5 mL, 45 mmol, 2.2 equiv). The resulting yellow-orange solution was stirred at 0° C. for 1 h and allowed to warm to room temperature over 18 h. The mixture was quenched with sat. aqueous $NaHCO_3$ solution (50 mL) and poured into a 250 mL separatory funnel containing water (50 mL). The mixture was extracted with $CH_2Cl_2$ (3×50 mL) and the combined organic layers were washed with brine (50 mL), dried over $MgSO_4$, filtered and concentrated under reduced pressure. The resulting oil was used directly without further purification Into a 250 mL round-bottom flask equipped with a magnetic stir bar and under $N_2$ was added the mesylate prepared above, $NaN_3$ (2.6 g, 41 mmol, 2.0 equiv) and DMF (40 mL). The suspension was stirred at 75° C. in an oil bath for 18 h overnight. The reaction mixture was cooled to room temperature and quenched with water (100 mL) and poured into a 250 mL separatory funnel. The reaction mixture was extracted with Et$_2$O (3×75 mL) and the combined organic layers were washed with brine (50 mL), dried over MgSO$_4$, filtered and concentrated under reduced pressure. Purification by column chromatography through silica gel (80 g), eluting with 100:0 to 50:50 Hexanes:EtOAc as a gradient afforded the title compound as a slight yellow oil (3.08 g).

Step 2: Preparation of methyl (2S,4R)-4-azidopyrrolidine-2-carboxylate hydrochloride Into a 100 mL round-bottom flask equipped with a magnetic stir bar and under N$_2$ was added 1-(tert-butyl) 2-methyl (2S,4R)-4-azidopyrrolidine-1,2-dicarboxylate (3.0 g, 11.1 mmol, 1.0 equiv) and methanol (15 mL). The solution was treated with 37% aqueous HCl solution (3.0 mL) and the reaction mixture was heated to 50° C. in an oil bath for 18 h overnight. LCMS analysis of the reaction mixture revealed complete conversion of starting material. The reaction was cooled to room temperature and concentrated under reduced pressure. The resulting yellow oil was dried under vacuum for 4 h and used directly in the next step without further purification (2.3 g).

Step 3: Preparation of methyl (2S,4R)-4-azido-1-((R)-2-((tert-butoxycarbonyl)amino)-3-cyclohexylpropanoyl)pyrrolidine-2-carboxylate Into a 100 mL round-bottom flask equipped with a magnetic stir bar and under N$_2$ was added (R)-2-((tert-butoxycarbonyl)amino)-3-cyclohexylpropanoic acid (2.5 g, 9.3 mmol, 1.0 equiv), HATU (4.22 g, 11.1 mmol, 1.2 equiv) and CH$_2$Cl$_2$ (20 mL). The reaction mixture was stirred at room temperature for 20 minutes and then methyl (2S,4R)-4-azidopyrrolidine-2-carboxylate hydrochloride (2.3 g, 11.1 mmol, 1.2 equiv) was added followed by EtN(iPr)$_2$ (3.2 mL, 18.6 mmol, 2.0 equiv). The reaction mixture was stirred at room temperature for 18 h overnight. The reaction mixture was quenched with 1 M aqueous HCl solution (100 mL) and poured into a 250 mL separatory funnel containing water (50 mL). The mixture was extracted with CH$_2$Cl$_2$ (3×50 mL) and the combined organic layers were washed with brine (50 mL), dried over MgSO$_4$, filtered and concentrated under reduced pressure. Purification by column chromatography through silica gel (80 g), eluting with 90:10 to 40:60 Hexanes:EtOAc as a gradient afforded the title compound as a white foam (2.52 g).

Step 4: Preparation of methyl (2S,4R)-1-((R)-2-amino-3-cyclohexylpropanoyl)-4-azidopyrrolidine-2-carboxylate hydrochloride Into a 100 mL round-bottom flask equipped with a magnetic stir bar and under N$_2$ was added methyl (2S,4R)-4-azido-1-((R)-2-((tert-butoxycarbonyl)amino)-3-cyclohexylpropanoyl)pyrrolidine-2-carboxylate (2.5 g, 5.9 mmol, 1.0 equiv), MeOH (20 mL) and 37% aqueous HCl (2.5 mL). The reaction mixture was heated to 50° C. in an oil bath for 18 h overnight. The reaction mixture was cooled to room temperature and concentrated under reduced pressure. An additional aliquot of MeOH (2×10 mL) was used to help drive off any excess water or HCl. The resulting solid was dried under vacuum and used directly in the next step (1.9 g).

Step 5: Preparation of methyl (2S,4R)-1-((R)-2-(2-naphthamido)-3-cyclohexylpropanoyl)-4-azidopyrrolidine-2-carboxylate Into a 100 mL round-bottom flask equipped with a magnetic stir bar and under N$_2$ was added methyl (2S,4R)-1-((R)-2-amino-3-cyclohexylpropanoyl)-4-azidopyrrolidine-2-carboxylate hydrochloride (1.9 g, 5.9 mmol, 1.0 equiv), 2-naphthoyl chloride (1.35 g, 7.1 mmol, 1.2 equiv) and CH$_2$Cl$_2$ (20 mL). The mixture was treated with EtN(iPr)$_2$ (2.1 mL, 11.8 mmol, 2 equiv) and the reaction was stirred at room temperature for 18 h overnight. The reaction was quenched with sat. aqueous NH$_4$Cl solution (100 mL) and poured into a 250 mL separatory funnel. The aqueous layer was extracted with CH$_2$Cl$_2$ (3×50 mL) and the combined organic layers were washed with brine (50 mL), dried over MgSO$_4$, filtered and concentrated under reduced pressure. The residue was purified by column chromatography through silica gel (80 g), eluting with 90:10 to 40:60 Hexanes:EtOAc as a gradient. The title compound was obtained as an off-white solid (1.65 g).

Step 6: Preparation of (2S,4R)-1-((R)-2-(2-naphthamido)-3-cyclohexylpropanoyl)-4-azidopyrrolidine-2-carboxylic acid Into a 100 mL round-bottom flask equipped with a magnetic stir bar and under N$_2$ was added methyl (2S,4R)-1-((R)-2-(2-naphthamido)-3-cyclohexylpropanoyl)-4-azidopyrrolidine-2-carboxylate (1.65 g, 3.45 mmol, 1.0 equiv), THF (10 mL) and MeOH (10 mL). The solution was treated with 1 M aqueous LiOH solution (8.6 mL, 8.6 mmol, 2.5 equiv) and the mixture was stirred at room temperature for 4 h. LCMS revealed no remaining starting material at this time. The reaction mixture was concentrated under reduced pressure and the residue was taken up in water (10 mL) and acidified to pH<2 with 1 M aqueous HCl solution. The mixture was poured into a 125 mL separatory funnel and extracted with CH$_2$Cl$_2$ (3×30 mL). The combined organics were washed with brine (50 mL), dried over MgSO$_4$, filtered and concentrated under reduced pressure. The resulting white foam was dried under vacuum to afford the title compound (1.32 g).

Step 7: Preparation of benzyl (5-((2S,4R)-1-((R)-2-(2-naphthamido)-3-cyclohexylpropanoyl)-4-azidopyrrolidine-2-carboxamido)-7-amino-6-hydroxy-7-oxoheptyl)carbamate Into a 100 mL round-bottom flask equipped with a magnetic stir bar and under nitrogen was added (2S,4R)-1-((R)-2-(2-naphthamido)-3-cyclohexylpropanoyl)-4-azidopyrrolidine-2-carboxylic acid (458 mg, 0.99 mmol, 1.1 equiv), benzyl (5,7-diamino-6-hydroxy-7-oxoheptyl)carbamate hydrochloride (Intermediate E, 310 mg, 0.90 mmol, 1.0 equiv), HATU (444 mg, 1.17 mmol, 1.3 equiv) and CH$_2$Cl$_2$ (5 mL). The reaction mixture was treated with EtN(iPr)$_2$ (480 µL, 2.7 mmol, 3 equiv) and the reaction mixture was stirred at room temperature for 18 h overnight. The reaction mixture was quenched with 1 M aqueous HCl solution (30 mL) and poured into a 125 mL separatory funnel and extracted with EtOAc (4×50 mL). The combined organic layers were washed with brine (20 mL), dried over MgSO$_4$, filtered and concentrated under reduced pressure. Purification by column chromatography through silica gel (24 g), eluting with 100:0 to 85:15 CH$_2$Cl$_2$:MeOH as a gradient afforded the title compound (523 mg).

Intermediate I: 3-Amino-2-hydroxyhex-5-enamide hydrochloride

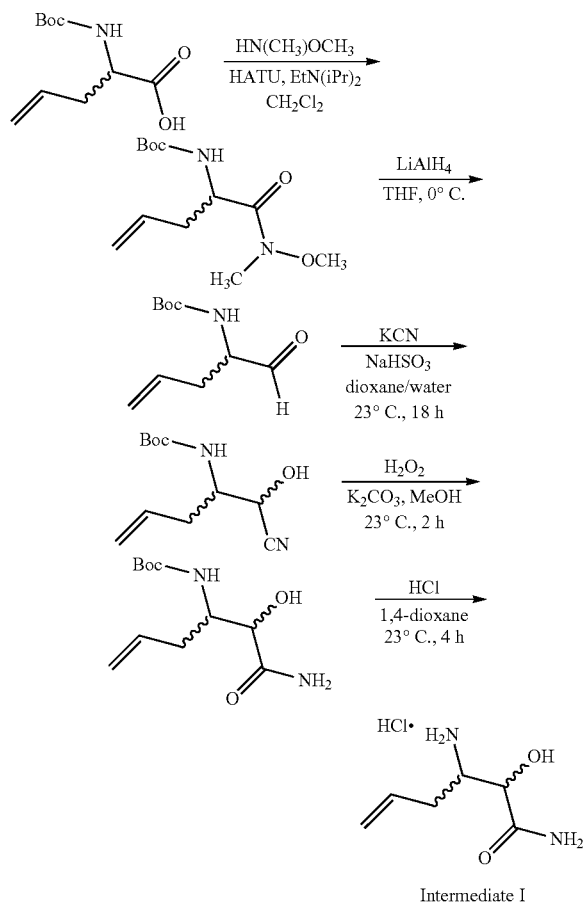

Intermediate I

Step 1: Preparation of tert-butyl (1-(methoxy (methyl)amino)-1-oxopent-4-en-2-yl)carbamate Into a 250 mL round-bottom flask equipped with a magnetic stir bar and under N$_2$ was added 2-((tert-butoxycarbonyl)amino)pent-4-enoic acid (5.00 g, 23.2 mmol, 1.0 equiv), N,O-dimethylhydroxylamine hydrochloride (2.49 g, 25.5 mmol, 1.1 equiv), HATU (10.6 g, 27.8 mmol, 1.2 equiv) and CH$_2$Cl$_2$ (50 mL). The reaction mixture was treated with EtN(iPr)$_2$ (8.1 mL, 46.4 mmol, 2 equiv) and the suspension was stirred at room temperature for 18 h overnight. The reaction mixture was quenched with 1 M aqueous HCl solution (50 mL), and poured into a 250 mL separatory funnel containing water (50 mL). The mixture was extracted with CH$_2$Cl$_2$ (3×50 mL) and the combined organic layers were washed with brine (50 mL), dried over MgSO$_4$, filtered and concentrated under reduced pressure. Purification by recrystallization from hot Et$_2$O afforded a slight yellow solid, which was dried under vacuum (5.18 g).

Step 2: Preparation of tert-butyl (1-oxopent-4-en-2-yl)carbamate

Into a flame-dried 250 mL round-bottom flask equipped with a magnetic stir bar and under N$_2$ was added solid LiAlH$_4$ (1.4 g, 38 mmol, 1.9 equiv) and anhydrous THF (25 mL). The grey suspension was cooled to 0° C. in an ice bath. To the grey suspension was added a solution of tert-butyl (1-(methoxy(methyl)amino)-1-oxopent-4-en-2-yl)carbamate (5.18 g, 20 mmol, 1.0 equiv) in anhydrous THF (25 mL) drop-wise over 20 minutes. The reaction mixture was stirred at 0° C. for 1 h and quenched with drop-wise addition of an aqueous NaHSO$_4$ solution (3.6 g, 26 mmol, 1.3 equiv in 20 mL of water) over a 20 minute period. The mixture was stirred at room temperature for 1 h and then poured into a 250 mL separatory funnel containing water (50 mL) and extracted with EtOAc (3×40 mL). The combined organic layers were washed with 1 M aqueous HCl solution (50 mL), water (50 mL), dried over MgSO$_4$, filtered and concentrated under reduced pressure to afford the desired compound, which was used directly without purification in the next step.

Step 3: Preparation of tert-butyl (1-cyano-1-hydroxypent-4-en-2-yl)carbamate

Into a 250 mL round-bottom flask equipped with a magnetic stir bar and under N$_2$ was charged tert-butyl (1-oxopent-4-en-2-yl)carbamate (20 mmol, 1.0 equiv), 1,4-dioxane (50 mL), 40% aqueous NaHSO$_3$ solution (21 mL, 80 mmol, 4 equiv) and KCN (5.2 g, 80 mmol, 4 equiv). The mixture was stirred at 0° C. in an ice bath for 1 h and allowed to warm to room temperature with stirring over 18 h overnight. The reaction mixture was quenched with sat. aqueous NaHCO$_3$ solution (20 mL) and poured into a 250 mL separatory funnel containing water (50 mL). The mixture was extracted with EtOAc (3×30 mL) and the combined organic layers were washed with brine (50 mL), dried over MgSO$_4$, filtered and concentrated under reduced pressure. Purification by column chromatography through silica gel (60 g), eluting with 100:0 to 50:50 Hexanes:EtOAc as a gradient afforded the title compound as a colourless oil (1.15 g).

Step 4: Preparation of tert-butyl (1-amino-2-hydroxy-1-oxohex-5-en-3-yl)carbamate Into a 250 mL round-bottom flask equipped with a magnetic stir bar and under N$_2$ was placed tert-butyl (1-cyano-1-hydroxypent-4-en-2-yl)carbamate (1.15 g, 5.1 mmol, 1.0 equiv), K$_2$CO$_3$ (770 mg, 5.6 mmol, 1.1 equiv) and MeOH (20 mL). The reaction mixture was treated with drop-wise addition of 30% aqueous H$_2$O$_2$ (1.5 mL, 15.2 mmol, 3 equiv) and the resulting suspension was stirred at room temperature for 2 h. The reaction mixture was cooled to 0° C. in an ice bath and quenched with 10% aqueous Na$_2$S$_2$O$_8$ solution added drop-wise over 10 minutes. The reaction mixture was warmed to room temperature and stirred for 1 h at this temperature. The mixture was poured into a 250 mL separatory funnel containing water (100 mL) and extracted with EtOAc (3×30 mL). The combined organic layers were washed with brine (50 mL), dried over MgSO$_4$, filtered and concentrated under reduced pressure. Purification by column chromatography through silica gel (24 g), eluting with 80:20 to 20:80 Hexanes:EtOAc as a gradient afforded the desired compound (345 mg).

Step 5: Preparation of 3-amino-2-hydroxyhex-5-enamide hydrochloride

Into a 25 mL round-bottom flask equipped with a magnetic stir bar and under N$_2$ was added tert-butyl (1-amino-2-hydroxy-1-oxohex-5-en-3-yl)carbamate (345 mg, 1.4 mmol, 1.0 equiv) and 1,4-dioxane (1 mL). The solution was treated with 4 M HCl in dioxane (880 µL, 3.5 mmol, 2.5 equiv) and stirred at room temperature for 4 h. TLC analysis at this time revealed no further starting material remained. The reaction mixture was concentrated under reduced pressure to afford an off-white solid which was dried under vacuum for 4 h (180 mg).

Intermediate J: (2S,4S)—N-(7-(3-Propargylureido)-1-amino-2-hydroxy-1-oxoheptan-3-yl)-1-((R)-2-amino-3-cyclohexylpropanoyl)-4-(5-(2-hydroxypropan-2-yl)-1H-1,2,3-triazol-1-yl)pyrrolidine-2-carboxamide hydrochloride

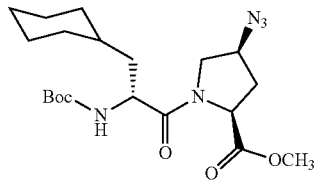

Intermediate F, Step 3

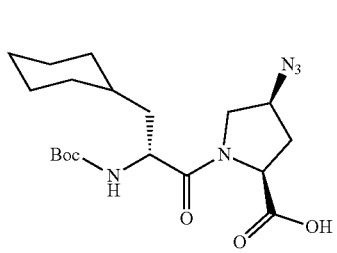

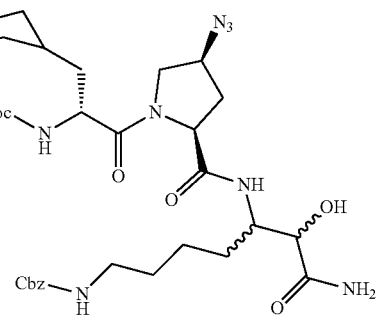

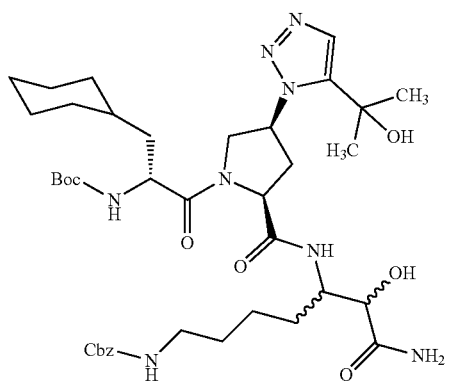

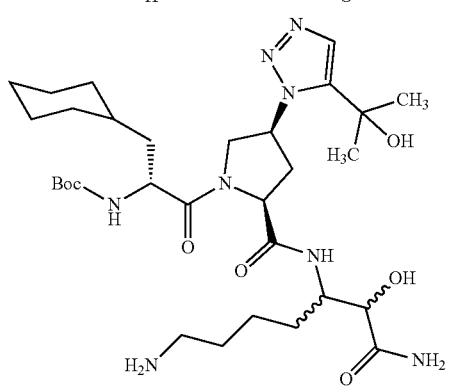

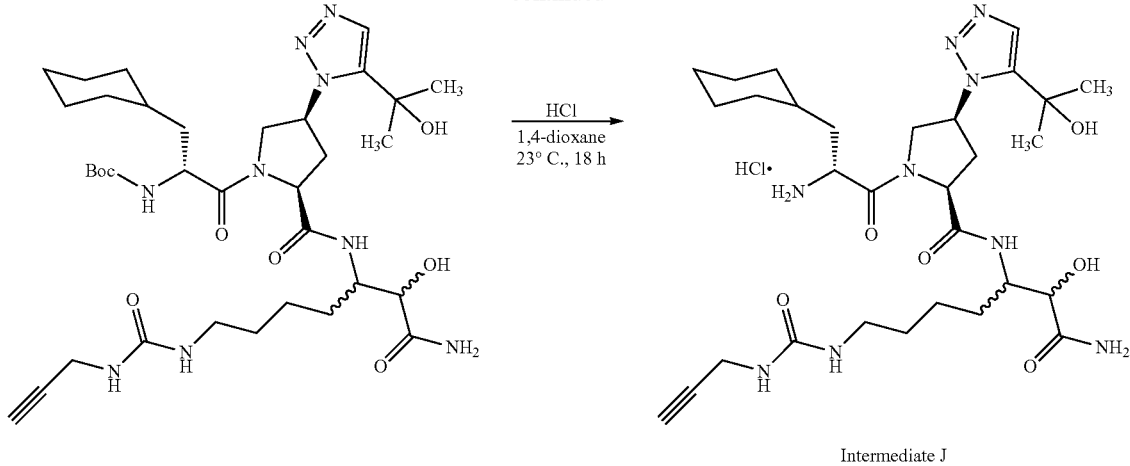

Intermediate J

Step 1: Preparation of (2S,4S)-4-azido-1-((R)-2-((tert-butoxycarbonyl)amino)-3-cyclohexylpropanoyl)pyrrolidine-2-carboxylic acid Into a 250 mL round-bottom flask equipped with a magnetic stir bar and under $N_2$ was added methyl (2S,4S)-4-azido-1-((R)-2-((tert-butoxycarbonyl)amino)-3-cyclohexylpropanoyl)pyrrolidine-2-carboxylate (Intermediate F, step 3, 7.0 g, 16.5 mmol, 1.0 equiv), MeOH (40 mL) and THF (40 mL). The solution was treated with 1 M aqueous LiOH solution (41 mL, 41 mmol, 2.5 equiv) and the reaction mixture was stirred at room temperature for 2 h. LCMS analysis at this time revealed complete conversion of starting material. The reaction mixture was concentrated under reduced pressure, diluted with water (25 mL) and cooled to 0° C. in an ice bath. Acidification with dropwise addition of 1 M aqueous HCl solution (approx. 50 mL) resulted in the formation of a white precipitate. The solid was collected by vacuum filtration through Whatman #1 filter paper on a Hirsch funnel, washing with water (2×20 mL) and hexanes (2×20 mL). The resulting white filter cake was dried under vacuum overnight to afford the title compound (5.4 g).

Step 2: Preparation of tert-butyl ((2R)-1-((2S,4S)-2-((1-amino-7-(((benzyloxy)carbonyl)amino)-2-hydroxy-1-oxoheptan-3-yl)carbamoyl)-4-azidopyrrolidin-1-yl)-3-cyclohexyl-1-oxopropan-2-yl)carbamate A mixture of (2S,4S)-4-azido-1-((R)-2-((tert-butoxycarbonyl)amino)-3-cyclohexylpropanoyl)pyrrolidine-2-carboxylic acid (992 mg, 2.43 mmol, 1.1 equiv), benzyl (5,7-diamino-6-hydroxy-7-oxoheptyl)carbamate hydrochloride (Intermediate E, 761 mg, 2.20 mmol, 1.0 equiv), HATU (1.1 g, 2.87 mmol, 1.3 equiv) and $CH_2Cl_2$ (11 mL) were stirred under $N_2$. The mixture was treated with $EtN(iPr)_2$ (1.2 mL, 6.62 mmol, 3 equiv) and stirred at room temperature for 2 days. The reaction mixture was quenched with 1 M aqueous HCl solution (20 mL) and poured into a 125 mL separatory funnel containing water (20 ml). The mixture was extracted with $CH_2Cl_2$ (3×20 mL) and the combined organic layers were washed with brine (20 mL), dried over $MgSO_4$, filtered and concentrated under reduced pressure. Purification by column chromatography through silica gel (50 g), eluting with 100:0 to 75:25 MeOH:$CH_2Cl_2$ as a gradient afforded the desired compound (1.54 g).

Step 3: Preparation of tert-butyl ((2R)-1-((2S,4S)-2-((1-amino-7-(((benzyloxy)carbonyl)amino)-2-hydroxy-1-oxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate A 100 mL round-bottom flask was charged with tert-butyl ((2R)-1-((2S,4S)-2-((1-amino-7-(((benzyloxy)carbonyl)amino)-2-hydroxy-1-oxoheptan-3-yl)carbamoyl)-4-azidopyrrolidin-1-yl)-3-cyclohexyl-1-oxopropan-2-yl)carbamate (1.54 µg, 2.21 mmol, 1.0 equiv), 2-methyl-3-butyn-2-ol (860 µL, 8.84 mmol, 4 equiv), Cp*RuCl(PPh_3)_2 (88 mg, 0.11 mmol, 0.05 equiv) and 1,4-dioxane (10 mL). The light brown solution was degassed with a steady flow of $N_2$ for 10 minutes and the mixture heated to 60° C. in an oil bath for 18 h overnight. The resulting dark brown reaction was concentrated under reduced pressure and loaded directly onto silica gel. Purification by column chromatography through silica gel (40 g) eluting with 100:0 to 85:15 $CH_2Cl_2$:MeOH as a gradient afforded the desired compound of approx. 80% purity. Repurification of the material (≈1 g) by column chromatography through silica gel (24 g), eluting with 100:0 to 85:15 $CH_2Cl_2$:MeOH as a gradient afforded the desired compound of sufficient purity for use in the subsequent step (560 mg).

Step 4: Preparation of tert-butyl ((2R)-3-cyclohexyl-1-((2S,4S)-2-((1,7-diamino-2-hydroxy-1-oxoheptan-3-yl)carbamoyl)-4-(5-(2-hydroxypropan-2-yl)-1H-1,2,3-triazol-1-yl)pyrrolidin-1-yl)-1-oxopropan-2-yl)carbamate Into a 100 mL round-bottom flask equipped with a magnetic stir bar and under $N_2$ was added tert-butyl ((2R)-1-((2S,4S)-2-((1-amino-7-(((benzyloxy)carbonyl)amino)-2-hydroxy-1-oxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate (560 mg, 0.71 mmol, 1.0 equiv) and MeOH (14 mL). The solution was purged with a steady flow of $N_2$ through the solution with a needle for 10 minutes. At this time, 10 wt % palladium on carbon (60 mg) was added to the flask and $N_2$ purging was continued for another 10 minutes at which stage the $N_2$ inlet was replaced with a balloon of $H_2$. Purging of the suspension with $H_2$ was continued for 10 minutes as which stage the outlet was removed and the reaction mixture was stirred under an atmosphere of H$_2$ for 1 h. LCMS analysis at this time revealed complete conversion of starting material. The reaction mixture was filtered through a pad of celite on a sintered plastic funnel, washing with MeOH (2×10 mL) and the resulting filtrate was concentrated under reduced pressure to afford the title compound (430 mg).

Step 5: Preparation of tert-butyl ((2R)-1-((2S,4S)-2-((7-(3-propargylureido)-1-amino-2-hydroxy-1-oxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate Into a dried 25 mL round-bottom flask equipped with a magnetic stir bar and under N$_2$ was added propargyl amine (127 µL, 1.3 mmol, 3 equiv) and THF (8 mL). The solution was cooled to −78° C. in a dry ice/acetone bath and a solution of triphosgene (219 mg, 0.73 mmol, 0.6 equiv) in THF (2 mL) was added. At this stage, EtN(iPr)$_2$ (453 µL, 2.6 mmol, 6 equiv) was added and the −78° C. bath was replaced with a 0° C. ice bath and the mixture was stirred at this temperature for 20 minutes.

Into a separate 25 mL round-bottom flask equipped with a magnetic stir bar and under N$_2$ was added tert-butyl ((2R)-3-cyclohexyl-1-((2S,4S)-2-((1,7-diamino-2-hydroxy-1-oxoheptan-3-yl)carbamoyl)-4-(5-(2-hydroxypropan-2-yl)-1H-1,2,3-triazol-1-yl)pyrrolidin-1-yl)-1-oxopropan-2-yl)carbamate (430 mg, 0.66 mmol, 1.0 equiv) and THF (2 mL). The solution was cooled to 0° C. in an ice bath and 4.6 mL of the isocyanate prepared above (0.75 mmol, 1.1 equiv based on the propargyl amine limiting reagent) was added dropwise at 0° C. and the mixture stirred at this temperature for 1 h. The reaction mixture was quenched with sat. aqueous NH$_4$Cl solution (10 mL) and warmed to room temperature. The mixture was extracted with EtOAc (3×10 mL) using a 50 mL separatory funnel and the combined organic layers were washed with brine (10 mL), dried over MgSO$_4$, filtered and concentrated under reduced pressure. This compound was used directly in the next reaction without further purification (498 mg).

Step 6: Preparation of (2S,4S)—N-(7-(3-propargylureido)-1-amino-2-hydroxy-1-oxoheptan-3-yl)-1-((R)-2-amino-3-cyclohexylpropanoyl)-4-(5-(2-hydroxypropan-2-yl)-1H-1,2,3-triazol-1-yl)pyrrolidine-2-carboxamide hydrochloride Into a round-bottom flask equipped with a magnetic stir bar and under N$_2$ was added tert-butyl ((2R)-1-((2S,4S)-2-((7-(3-propargylureido)-1-amino-2-hydroxy-1-oxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate (484 mg, 0.66 mmol, 1.0 equiv) and 1,4-dioxane (2 mL). The solution was treated with 4 M HCl in dioxane (700 µL, 2.7 mmol, 4 equiv) and the reaction mixture was stirred at room temperature for 18 h overnight. The reaction mixture was concentrated under reduced pressure, with MeOH (2×5 mL) being used to drive off any excess HCl or water. The resulting pale yellow solid was dried under vacuum (480 mg).

Intermediate K: Methyl (2S,4S)-1-((R)-2-((tert-butoxycarbonyl)amino)-3-cyclohexylpropanoyl)-4-(5-(2-hydroxypropan-2-yl)-1H-1,2,3-triazol-1-yl)pyrrolidine-2-carboxylate

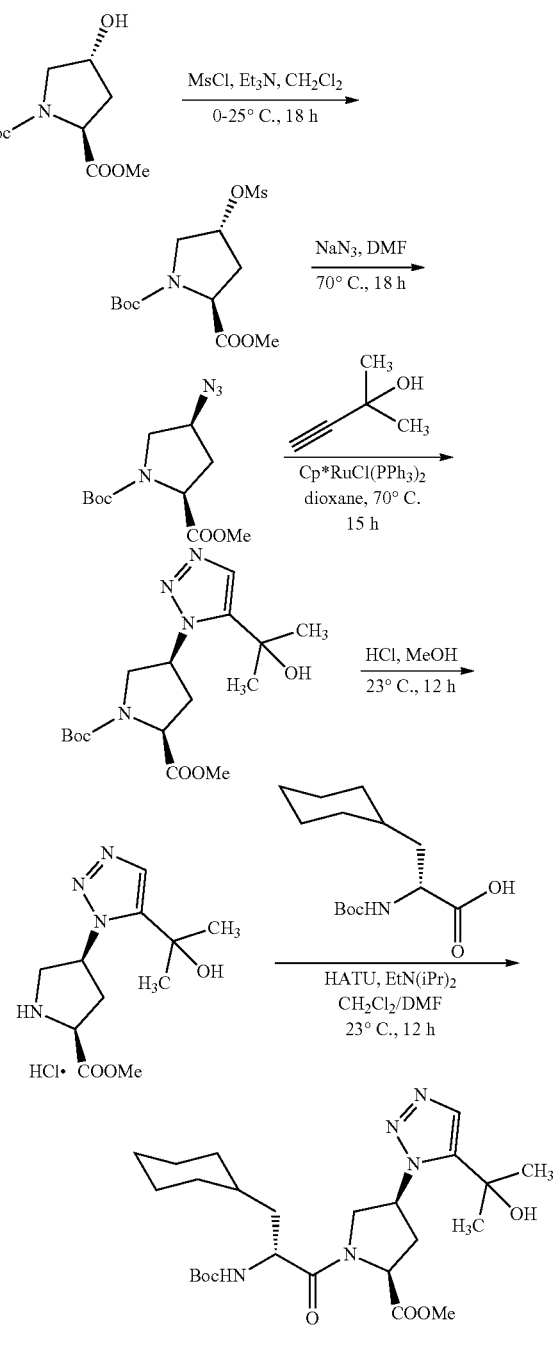

Intermediate K

Step 1: Preparation of 1-(tert-butyl) 2-methyl (2S,4R)-4-((methylsulfonyl)oxy)pyrrolidine-1,2-dicarboxylate Into a 2 L round-bottom flask equipped with a large stir bar and under nitrogen was added 1-(tert-butyl) 2-methyl (2S,4R)-4-hydroxypyrrolidine-1,2-dicarboxylate (100.0 g, 0.4 mol, 1.0 equiv) and CH$_2$Cl$_2$ (800 mL). The solution was cooled to 0° C. in an ice bath and triethylamine (182 g, 1.8 mol, 4.5 equiv) was added in a single portion, followed by drop-wise addition of methanesulfonyl chloride (103 g, 0.9 mol, 2.3 equiv). The resulting mixture was stirred at 0° C. for 1 h and then warmed to room temperature and stirred for 18 h overnight. TLC analysis revealed complete conversion of the alcohol starting material. The reaction was quenched by pouring the mixture into water (2.0 L) and the mixture transferred to a large separatory funnel. The aqueous layer was extracted with CH$_2$Cl$_2$ (3×1.0 L) and the combined organic layers were washed with saturated aqueous NaHCO$_3$ solution (1.0 L), water (1.0 L) and brine (1.0 L), dried over MgSO$_4$, filtered and concentrated under reduced pressure. The resulting yellow oil (130 g) was used directly in the next step without further purification.

Step 2: Preparation of 1-(tert-butyl) 2-methyl (2S, 4S)-4-azidopyrrolidine-1,2-dicarboxylate Into a 3 L round-bottom flask equipped with a magnetic stir bar and under nitrogen was added 1-(tert-butyl) 2-methyl (2S,4R)-4-((methylsulfonyl)oxy)pyrrolidine-1,2-dicarboxylate (143 g, 442 mmol, 1.0 equiv), sodium azide (53 g, 804 mmol, 1.8 equiv) and DMF (900 mL). The solution was heated to 70° C. for 18 h overnight. The reaction mixture was cooled to room temperature and poured into water (2.0 L). The mixture was transferred to a large separatory funnel and the aqueous layer was extracted with MTBE (3×1.0 L). The combined organic layers were washed with water (5×1.0 L), brine (2×1.0 L), dried over MgSO$_4$, filtered and concentrated under reduced pressure. The title compound was obtained as an oil (98 g).

Step 3: Preparation of 1-(tert-butyl) 2-methyl (2S, 4S)-4-(5-(2-hydroxypropan-2-yl)-1H-1,2,3-triazol-1-yl)pyrrolidine-1,2-dicarboxylate A solution of 1-(tert-butyl) 2-methyl (2S,4S)-4-azidopyrrolidine-1,2-dicarboxylate (Intermediate F, Step 1, 60 g, 220 mmol, 1.0 equiv), 2-methylbut-3-yn-2-ol (43 mL, 440 mmol, 2.0 equiv), Cp*RuCl(PPh$_3$)$_2$ (8.8 g, 11 mmol, 0.05 equiv) and 1,4-dioxane (500 mL) were charged into a 1 L round-bottom flask. The solution was bubbled with a steady flow of nitrogen for 1 h, and the reaction mixture changed colour from yellow to deep brown. The reaction mixture was heated to 70° C. for 15 h and then cooled to room temperature. The mixture was concentrated under reduced pressure to remove the bulk of the dioxane and the resulting oil was loaded directly onto a silica gel column (1 kg) and purified by column chromatography, eluting with 98:2 to 96:4 CH$_2$Cl$_2$:MeOH as a gradient. The title compound was obtained as a brown oil (67 g).

Step 4: Preparation of methyl (2S,4S)-4-(5-(2-hydroxypropan-2-yl)-1H-1,2,3-triazol-1-yl)pyrrolidine-2-carboxylate hydrochloride 1-(tert-Butyl) 2-methyl (2S,4S)-4-(5-(2-hydroxypropan-2-yl)-1H-1,2,3-triazol-1-yl)pyrrolidine-1,2-dicarboxylate (98 g, 277 mmol, 1.0 equiv), MeOH (400 mL) and methanolic HCl solution (approx. 3.0 M, 800 mL) were added to a 3 L round-bottom flask equipped with a magnetic stir bar. The reaction mixture was stirred at room temperature for 12 h at which point TLC analysis revealed complete conversion of starting material. The reaction mixture was concentrated under reduced pressure and dried under vacuum to remove any trace methanol or HCl residues. The resulting brown solid was used directly in the next step without further purification (90 g).

Step 5: Preparation of methyl (2S,4S)-1-((R)-2-((tert-butoxycarbonyl)amino)-3-cyclohexylpropanoyl)-4-(5-(2-hydroxypropan-2-yl)-1H-1,2,3-triazol-1-yl)pyrrolidine-2-carboxylate Into a 3 L round-bottom flask equipped with a magnetic stir bar was added methyl (2S,4S)-4-(5-(2-hydroxypropan-2-yl)-1H-1,2,3-triazol-1-yl)pyrrolidine-2-carboxylate hydrochloride (70 g, 241 mmol, 1.0 equiv), (R)-2-((tert-butoxycarbonyl)amino)-3-cyclohexylpropanoic acid (70 g, 258 mmol, 1.07 equiv), HATU (110 g, 289 mmol, 1.2 equiv), CH$_2$Cl$_2$ (600 mL) and DMF (400 mL). The reaction mixture was treated with EtN(iPr)$_2$ (126 g, 973 mmol, 4.0 equiv) drop-wise over 30 minutes and the mixture was stirred at room temperature for 12 h affording a deep brown solution. The reaction mixture was diluted with EtOAc (1.0 L) and poured into a large separatory funnel. The organic layers were washed with 1 M aqueous HCl solution (3×400 mL), brine (3×300 mL), dried over Na$_2$SO$_4$ and concentrated under reduced pressure to afford an oil. Purification by column chromatography through silica gel (1 kg), eluting with 98:2 to 96:4 CH$_2$Cl$_2$:MeOH as a gradient afforded the title compound as a light brown solid (77 g).

Intermediate L: Benzyl (7-amino-5-((2S,4S)-1-((R)-2-amino-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate hydrochloride

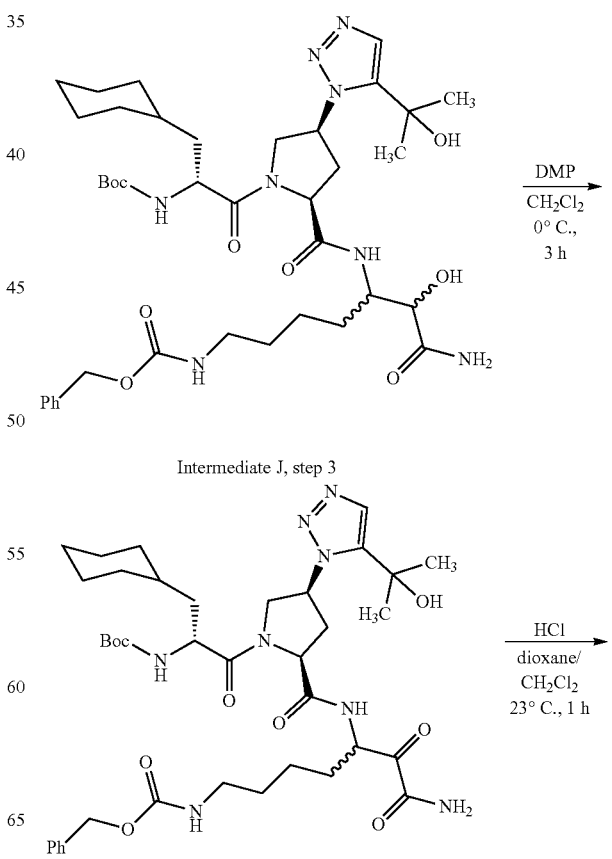

Intermediate J, step 3

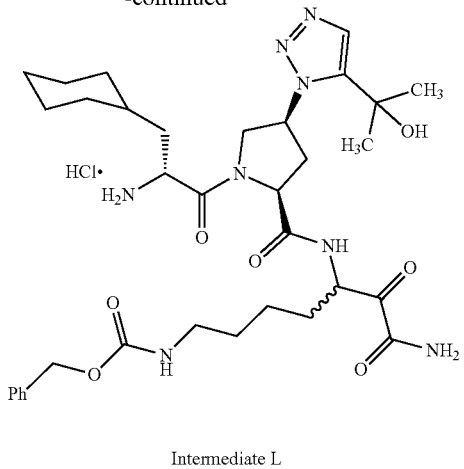

Intermediate L

Step 1: Preparation of benzyl (7-amino-5-((2S,4S)-1-((R)-2-((tert-butoxycarbonyl)amino)-3-cyclohexyl-propanoyl)-4-(5-(2-hydroxypropan-2-yl)-1H-1,2,3-triazol-1-yl)pyrrolidine-2-carboxamido)-6,7-dioxoheptyl)carbamate Into a 200 mL round-bottom flask equipped with a magnetic stir bar and under $N_2$ was added benzyl (7-amino-5-((2S,4S)-1-((R)-2-((tert-butoxycarbonyl)amino)-3-cyclohexylpropanoyl)-4-(5-(2-hydroxypropan-2-yl)-1H-1,2,3-triazol-1-yl)pyrrolidine-2-carboxamido)-6-hydroxy-7-oxoheptyl)carbamate (Intermediate J, step 3, 2.8 g, 3.6 mmol, 1.0 equiv) and $CH_2Cl_2$ (50 mL). The resulting solution was cooled to 0° C. in an ice bath and treated with Dess-Martin Periodinane (2.12 g, 5.0 mmol, 1.4 equiv) and the suspension was stirred at 0° C. for 3 h. The resulting mixture was diluted with $CH_2Cl_2$ (50 mL) and quenched with 10% aqueous $Na_2S_2O_3$ solution (20 mL). The mixture was poured into a 250 mL separatory funnel containing sat. aqueous $NaHCO_3$ solution (30 mL) and the organic layer was removed. The remaining aqueous layer was extracted with $CH_2Cl_2$ (50 mL) and the combined organic layers were dried over $MgSO_4$, filtered and concentrated under reduced pressure. Purification by column chromatography through silica gel (120 g), eluting with 100:0 to 80:20 $CH_2Cl_2$:MeOH as a gradient. The desired product containing fractions were concentrated under reduced pressure and dried under vacuum to afford an off-white foam (2.3 g).

Step 2: Preparation of benzyl (7-amino-5-((2S,4S)-1-((R)-2-amino-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate hydrochloride Into a 100 mL round-bottom flask equipped with a magnetic stir bar and under $N_2$ was added benzyl (7-amino-5-((2S,4S)-1-((R)-2-((tert-butoxycarbonyl)amino)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate (2.3 g, 2.9 mmol, 1.0 equiv) and $CH_2Cl_2$ (20 mL). The solution was treated with 4 M HCl in dioxane (2.9 mL, 11.8 mmol, 4 equiv) and stirred at room temperature for 1 h. The suspension was diluted with $CH_2Cl_2$ (10 mL) and filtered under vacuum through Whatman #1 filter paper on a Hirsch funnel, washing with $CH_2Cl_2$ (2×5 mL). The corresponding solid was dried under vacuum to afford the title compound (2.0 g).

Intermediate M: (2S,4S)-1-((R)-2-Amino-3-cyclohexylpropanoyl)-N-(1-amino-7-(3-cyclopropylureido)-1,2-dioxoheptan-3-yl)-4-(5-(2-hydroxypropan-2-yl)-1H-1,2,3-triazol-1-yl)pyrrolidine-2-carboxamide

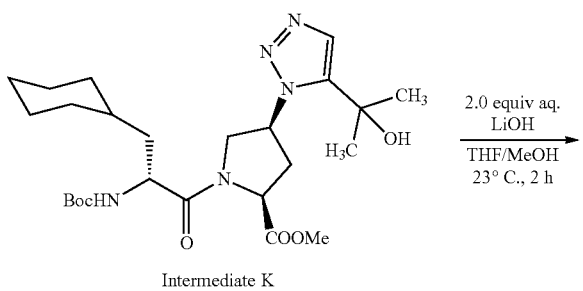

Intermediate K

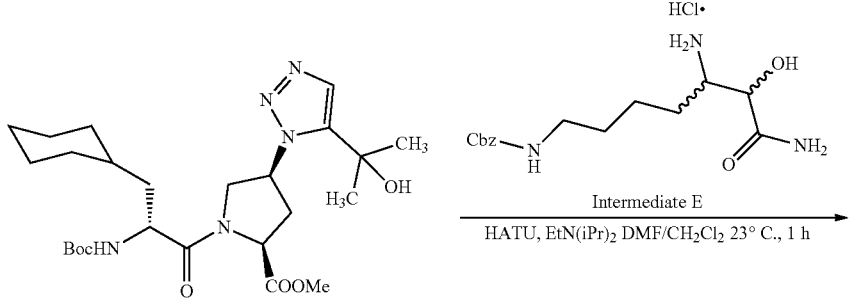

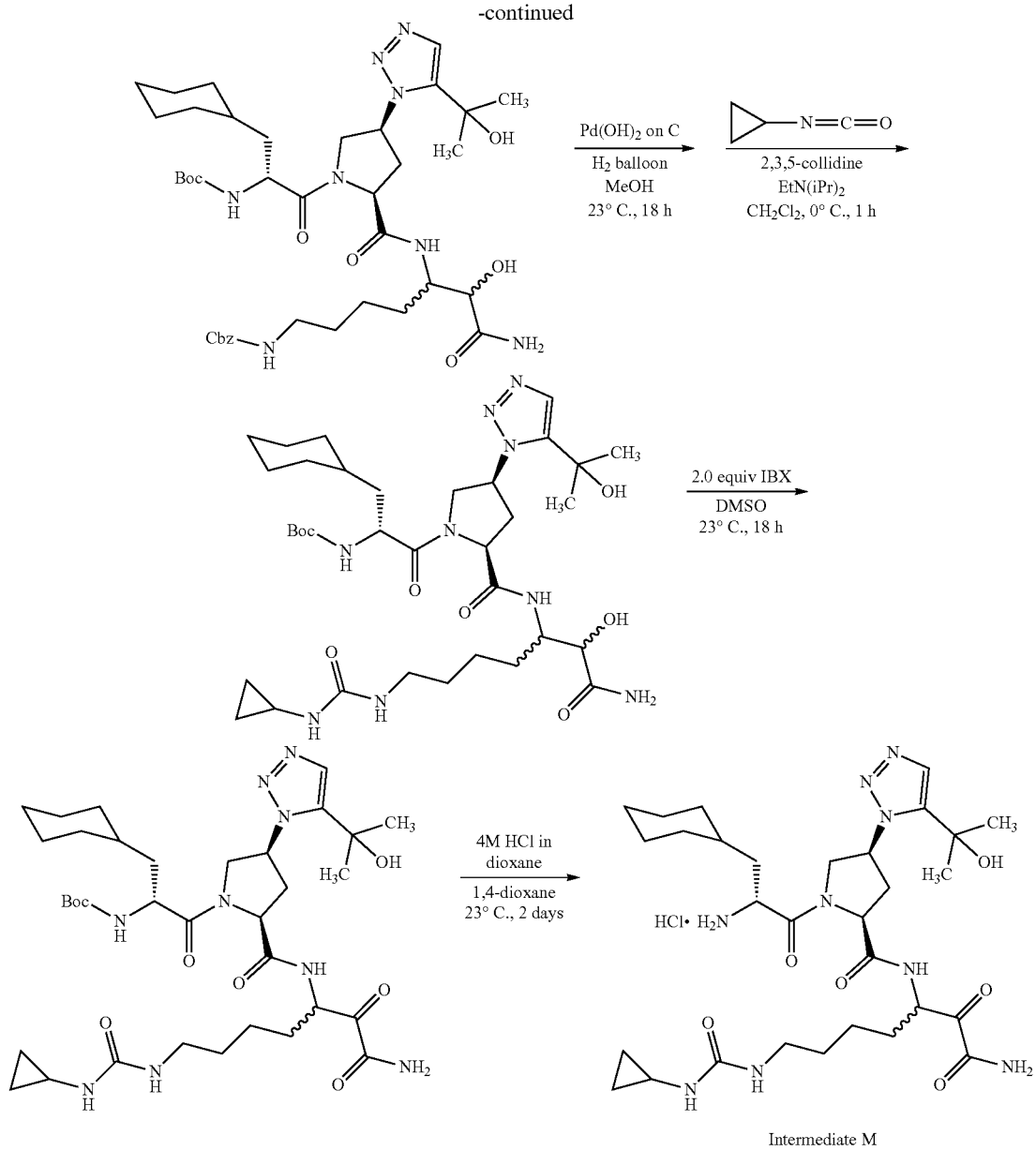

Intermediate M

Step 1: Preparation of (2S,4S)-1-((R)-2-((tert-butoxycarbonyl)amino)-3-cyclohexylpropanoyl)-4-(5-(2-hydroxypropan-2-yl)-1H-1,2,3-triazol-1-yl)pyrrolidine-2-carboxylic acid Into a 500 mL round-bottom flask equipped with a magnetic stir bar and under nitrogen was added methyl (2S,4S)-1-((R)-2-((tert-butoxycarbonyl)amino)-3-cyclohexylpropanoyl)-4-(5-(2-hydroxypropan-2-yl)-1H-1,2,3-triazol-1-yl)pyrrolidine-2-carboxylate (Intermediate K, 15.0 g, 29.6 mmol, 1.0 equiv), THF (50 mL) and methanol (50 mL). The solution was treated with 1.0 M aqueous LiOH solution (59 mL, 59 mmol, 2.0 equiv) and the mixture was stirred at room temperature for 2 h at which point LCMS analysis revealed complete conversion to product. The reaction mixture was concentrated under reduced pressure and the resulting mixture was diluted with water (50 mL) and acidified to pH, 4.0 with concentrated formic acid. Another 2 mL of 1.0 M aqueous HCl solution was added to drive full protonation. The reaction mixture was poured into a 250 mL separatory funnel and extracted with EtOAc (3×50 mL). The combined organic layers were washed with brine (50 mL), dried over MgSO$_4$, filtered and concentrated under reduced pressure to afford a beige foam (14.3 g).

Step 2: Preparation of tert-butyl ((2R)-1-((2S,4S)-2-((1-amino-7-(((benzyloxy)carbonyl)amino)-2-hydroxy-1-oxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate Into a 100 mL round-bottom flask equipped with a magnetic stir bar and under nitrogen was added (2S,4S)-1-((R)-2-((tert-butoxycarbonyl)amino)-3-cyclohexylpropanoyl)-4-(5-(2-hydroxypropan-2-yl)-1H-1,2,3-triazol-1-yl)pyrrolidine-2-carboxylic acid (2.76 g, 5.6 mmol, 1.0 equiv), benzyl (5,7-diamino-6-hydroxy-7-oxoheptyl)carbamate (Intermediate E, 1.94 g, 5.62 mmol, 1.0 equiv), HATU (2.74 g, 7.1 mmol, 1.3 equiv), CH$_2$Cl$_2$ (28 mL) and DMF (2 mL). The reaction mixture was treated with EtN(iPr)$_2$ (3.9 mL, 22.5 mmol, 4.0 equiv) and stirred at room temperature for 1 h. The reaction mixture was quenched with water (30 mL) and extracted with CH$_2$Cl$_2$ (3×30 mL) using a phase-separatory cartridge and the combined organic layers were concentrated under reduced pressure. Purification by column chromatography through silica gel (120 g) eluting with 100:0 to 90:10 CH$_2$Cl$_2$:MeOH as a gradient afforded the title compound (4.48 g).

Step 3: Preparation of tert-butyl ((2R)-1-((2S,4S)-2-((1-amino-7-(3-cyclopropylureido)-2-hydroxy-1-oxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate A solution of tert-butyl ((2R)-1-((2S,4S)-2-((1-amino-7-(((benzyloxy)carbonyl)amino)-2-hydroxy-1-oxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate (5.84 g, 5.62 mmol, 1.0 equiv) in methanol (50 mL) in a 100 mL round-bottom flask containing a stir bar was purged with nitrogen for 10 minutes. The solution was then treated with 20 wt % Pd(OH)$_2$ on carbon (800 mg) and nitrogen purging was continued for another 10 minutes. The nitrogen inlet was replaced with a balloon of H$_2$ gas, and purging was continued for 10 minutes after which the bubbler outlet was removed. The dark suspension was stirred under an atmosphere of hydrogen for 18 h overnight. LCMS analysis at this time reveals complete conversion of starting material. The balloon was removed and the suspension filtered through a pad of celite on a sintered plastic funnel, washing with CH$_2$Cl$_2$ (3×30 mL) and the filtrate was concentrated under reduced pressure to afford the free amine.

The free amine obtained above (5.62 mmol) was placed into a 100 mL round-bottom flask containing CH$_2$Cl$_2$ (50 mL), 2,3,5-collidine (1.4 mL, 11.2 mmol, 2.0 equiv) and EtN(iPr)$_2$ (1.9 mL, 11.2 mmol, 2.0 equiv). The solution was cooled to 0° C. in an ice batch and isocyanatocyclopropane (467 μL, 5.6 mmol, 1.1 equiv) was added. The solution was stirred at 0° C. for 1 h, at which stage LCMS analysis revealed complete conversion of starting material. The reaction mixture was quenched with the addition of methanol (10 mL) and the mixture concentrated under reduced pressure. The reaction mixture was loaded onto silica gel and purified by column chromatography through silica gel (100 g), eluting with 100:0 to 85:15 CH$_2$Cl$_2$:MeOH as a gradient afforded the title compound as an off-white foam (2.58 g).

Step 4: Preparation of tert-butyl ((2R)-1-((2S,4S)-2-((1-amino-7-(3-cyclopropylureido)-1,2-dioxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate A 100 mL round-bottom flask equipped with a magnetic stir bar and under nitrogen was charged with tert-butyl ((2R)-1-((2S,4S)-2-((1-amino-7-(3-cyclopropylureido)-2-hydroxy-1-oxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate (2.58 g, 3.5 mmol, 1.0 equiv) and DMSO (30 mL). The solution was treated with IBX (45 wt %, 4.5 g, 7.0 mmol, 2.0 equiv) and the suspension was stirred at room temperature for 18 h overnight. The reaction mixture was quenched with a 10% aqueous Na$_2$S$_2$O$_3$ solution (100 mL) and extracted with CH$_2$Cl$_2$ (3×30 mL) using a separatory funnel. The combined organics were washed with brine (30 mL), dried over MgSO$_4$, filtered and concentrated under reduced pressure. Purification by column chromatography through silica gel (100 g) eluting with 100:0 to 85:15 CH$_2$Cl$_2$:MeOH as a gradient afforded the title compound as an off-white foam (2.03 g).

Step 5: Preparation of (2S,4S)-1-((R)-2-amino-3-cyclohexylpropanoyl)-N-(1-amino-7-(3-cyclopropylureido)-1,2-dioxoheptan-3-yl)-4-(5-(2-hydroxypropan-2-yl)-1H-1,2,3-triazol-1-yl)pyrrolidine-2-carboxamide Into a 100 mL round-bottom flask equipped with a magnetic stir bar and under nitrogen was added tert-butyl ((2R)-1-((2S,4S)-2-((1-amino-7-(3-cyclopropylureido)-1,2-dioxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate (2.03 g, 2.78 mmol, 1.0 equiv) and 1,4-dioxane (4 mL). The solution was treated with 4 M HCl in dioxane (1.8 mL, 7.0 mmol, 2.5 equiv) and the reaction mixture was stirred at room temperature for 18 h overnight. LCMS reveals about 15% remaining starting material and so another portion of 4 M HCl in dioxane was added (1.0 mL) and the mixture stirred at room temperature for another day. LCMS revealed complete conversion of starting material. The reaction mixture was concentrated under reduced pressure to remove the dioxane and excess HCl and the mixture and dried under vacuum. The resulting off-white foam was used directly without further purification (2.03 g).

Intermediate N:
3-Amino-2-hydroxy-4-(4-nitrophenyl)butanamide hydrochloride

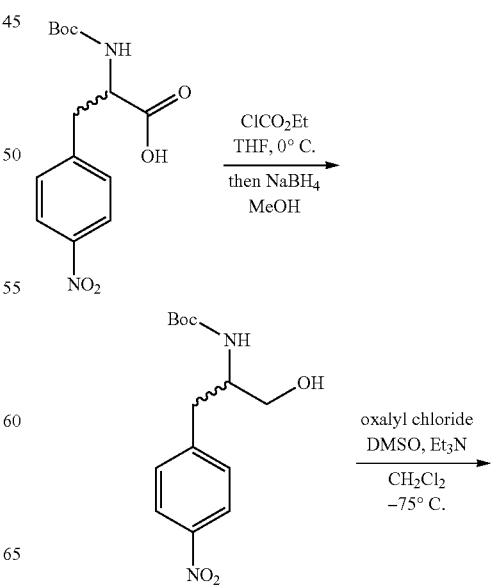

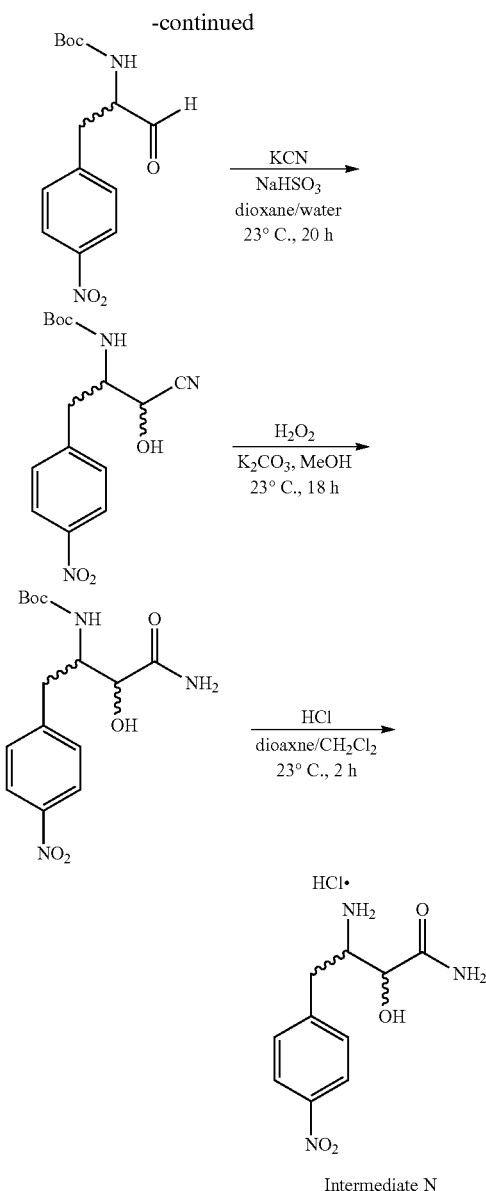

Intermediate N

Step 1: Preparation of tert-butyl (1-hydroxy-3-(4-nitrophenyl)propan-2-yl)carbamate Into a 500 mL flask equipped with a magnetic stir bar was added 2-((tert-butoxycarbonyl)amino)-3-(4-nitrophenyl)propanoic acid (10.0 g, 32.2 mmol, 1.0 equiv) and THF (80 mL). The solution was stirred at 0° C. for 30 minutes, and ethyl chloroformate (3.1 mL, 32.2 mmol, 1.0 equiv) was added drop-wise over 10 minutes. After the reaction mixture was stirred at 0° C. for 30 minutes, solid sodium borohydride (3.67 g, 96.6 mmol, 3 equiv) was added in a single addition. While keeping the reaction mixture at 0° C., MeOH (60 mL) was added slowly over a 1 h period. The ice bath was removed after addition was complete, and the mixture stirred at room temperature for an additional 30 minutes and then concentrated under reduced pressure. The residue was quenched with 1 M aqueous HCl solution (100 mL), poured into a separatory funnel and extracted with EtOAc (2×100 mL). The combined organic layers were dried over MgSO₄, filtered and concentrated under reduced pressure. Purification by column chromatography through silica gel (80 g), eluting with 100:0 to 50:50 Hexanes:EtOAc as a gradient afforded the title compound (5.2 g).

Step 2: Preparation of tert-butyl (1-(4-nitrophenyl)-3-oxopropan-2-yl)carbamate

Into a 500 mL flask equipped with a magnetic stir bar was added oxalyl chloride (1.27 g, 10 mmol, 1.5 equiv) and CH₂Cl₂ (10 mL). The solution was cooled to −78° C. in a dry ice/acetone bath and DMSO (0.95 mL, 13.4 mmol, 2 equiv) was added drop-wise at this temperature. After 40 minutes at below −70° C., a solution of tert-butyl (1-hydroxy-3-(4-nitrophenyl)propan-2-yl)carbamate (2.0 g, 6.7 mmol, 1.0 equiv) in CH₂Cl₂ (15 mL) was added drop-wise, while maintaining the reaction temperature below −65° C. After 30 minutes at this temperature, Et₃N (3.9 mL, 26.8 mmol, 4 equiv) was added. The reaction mixture was stirred at −78° C. for 2 h. At this time, the reaction mixture was quenched with drop-wise addition of water (300 mL). The solution was warmed to room temperature, poured into a separatory funnel and the organic layer isolated and washed with 1 M aqueous HCl solution (2×200 mL), sat. aqueous NaHCO₃ solution (200 mL), dried over MgSO₄, filtered and concentrated under reduced pressure. The obtained aldehyde (1.9 g) was used directly in the next step without further purification.

Step 3: Preparation of tert-butyl (1-cyano-1-hydroxy-3-(4-nitrophenyl)propan-2-yl)carbamate Into a 100 mL flask equipped with a magnetic stir bar was added tert-butyl (1-(4-nitrophenyl)-3-oxopropan-2-yl)carbamate (1.9 g, 6.5 mmol, 1.0 equiv) in 1,4-dioxane (60 mL). The solution was cooled to below 4° C. and a 40% aqueous solution of NaHSO₃ (6 mL, 23 mmol, 3.5 equiv) was added while maintaining the reaction temperature below 7° C. After stirring at this temperature for 10 minutes, a solution of KCN (1.5 g, 24 mmol, 3.7 equiv) in water (5 mL) was added to the reaction mixture drop-wise, while maintaining the temperature of the flask contents below 10° C. The solution was allowed to warm to room temperature and stirred for 20 h overnight. The solution was concentrated under reduced pressure, poured into a separatory funnel and extracted with EtOAc (400 mL). The organic layer was dried over MgSO₄, filtered and concentrated under reduced pressure. Purification by column chromatography through silica gel (80 g), eluting with 100:0 to 0:100 hexanes:EtOAc+10% MeOH as a gradient afforded the title compound (1.6 g).

Step 4: Preparation of tert-butyl (4-amino-3-hydroxy-1-(4-nitrophenyl)-4-oxobutan-2-yl)carbamate Into a 100 mL flask equipped with a magnetic stir bar was added tert-butyl (1-cyano-1-hydroxy-3-(4-nitrophenyl)propan-2-yl)carbamate (1.6 g, 5.0 mmol, 1.0 equiv), K₂CO₃ (757 mg, 5.5 mmol, 1.1 equiv) and MeOH (10 mL). The solution was cooled to below 4° C. in an ice bath and 35% aqueous hydrogen peroxide (1.5 g, 15 mmol, 3 equiv) was added. The solution was warmed to room temperature and stirred for 18 h overnight. The reaction was quenched with addition of solid Na₂S₂O₃ (3.5 g, 22.5 mmol, 4.5 equiv) and the reaction mixture was stirred for 1 h at this temperature. The reaction mixture was poured into a separatory funnel and extracted with CH₂Cl₂ (100 mL). The organic layer was dried over MgSO₄, filtered and concentrated under reduced pressure. Purification by column chromatography through silica gel (80 g), eluting with 100:0 to 0:100 hexanes:EtOAc+10% MeOH as a gradient afforded the title compound (1.0 g).

Step 5: Preparation of 3-amino-2-hydroxy-4-(4-nitrophenyl)butanamide hydrochloride Into a 100 mL flask equipped with a magnetic stir bar was added tert-butyl (4-amino-3-hydroxy-1-(4-nitrophenyl)-4-oxobutan-2-yl)carbamate (170 mg, 0.5 mmol, 1.0 equiv) and CH$_2$Cl$_2$ (5 mL). The solution was treated with 4 M HCl in dioxane (4.0 mL, 16 mmol, 32 equiv) and stirred at room temperature for 2 h. The reaction mixture was concentrated under reduced pressure, the resulting solid was used directly without further purification (138 mg).

Intermediate O: Benzyl (2,4-diamino-3-hydroxy-4-oxobutyl)carbamate

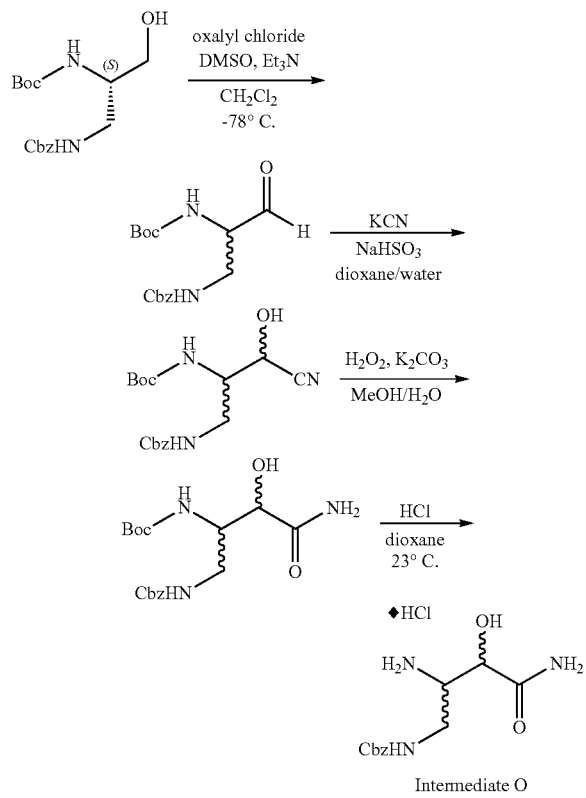

Intermediate O

Step 1: Preparation of benzyl tert-butyl (3-oxopropane-1,2-diyl)dicarbamate

Into a 100 mL round-bottom flask equipped with a magnetic stir bar and under N$_2$ was added CH$_2$Cl$_2$ (30 mL) and oxalyl chloride (1.9 mL, 22.7 mmol, 1.5 equiv). The solution was cooled to −78° C. in a dry ice/acetone bath and DMSO (2.1 mL, 30.2 mmol, 2 equiv) was added. After stirring at −78° C. for 10 minutes, a solution of benzyl tert-butyl (3-hydroxypropane-1,2-diyl)(S)-dicarbamate (4.9 g, 15.1 mmol, 1.0 equiv) in CH$_2$Cl$_2$ (10 mL) was added and the mixture was stirred at −78° C. for 20 minutes. At this time, Et$_3$N (8.5 mL, 60.4 mmol, 4 equiv) was added and the solution was stirred at −78° C. for another 20 minutes. The reaction was quenched with addition of water (10 mL) to the solution at −78° C. and the mixture was warmed to room temperature and poured into a 125 mL separatory funnel. The organic layer was washed with 1 M aqueous HCl solution (2×10 mL), sat. aqueous NaHCO$_3$ solution (10 mL), dried over MgSO$_4$, filtered and concentrated under reduced pressure. The aldehyde was used directly in the next reaction without further purification (4.3 g).

Step 2: Preparation of benzyl tert-butyl (3-cyano-3-hydroxypropane-1,2-diyl)dicarbamate Into a 100 mL round-bottom flask equipped with a magnetic stir bar and under N$_2$ was added benzyl tert-butyl (3-oxopropane-1,2-diyl)dicarbamate (3.9 g, 12 mmol, 1.0 equiv), 1,4-dioxane (20 mL) and 40% aqueous NaHSO$_3$ solution (12 mL). The mixture was cooled to 0° C. and solid KCN (2.8 g, 45 mmol, 3.7 equiv) was added. The reaction mixture was stirred at 0° C. for 1 h and allowed to warm to room temperature for 18 h overnight. The reaction mixture was diluted with EtOAc (150 mL) and poured into a 250 mL separatory funnel and washed with sat. aqueous NaHCO$_3$ solution (3×15 mL) The combined organic layers were dried over MgSO$_4$, filtered and concentrated under reduced pressure. Purification by column chromatography through silica gel (40 g), eluting with 100:0 to 50:50 Hexanes:EtOAc as a gradient afforded the desired compound (3.6 g).

Step 3: Preparation of benzyl tert-butyl (4-amino-3-hydroxy-4-oxobutane-1,2-diyl)dicarbamate A solution of benzyl tert-butyl (3-cyano-3-hydroxypropane-1,2-diyl)dicarbamate (3.6 g, 10.3 mmol, 1.0 equiv), K$_2$CO$_3$ (1.6 g, 11.3 mmol, 1.1 equiv) in MeOH (40 mL) was placed into a 250 mL round bottom flask containing a magnetic stir bar and stirred under N$_2$. The solution was treated with drop-wise addition of 30% aqueous H$_2$O$_2$ solution (3.5 mL, 31 mmol, 3 equiv). The reaction mixture was stirred at room temperature for 2 h, at which stage LCMS analysis revealed complete conversion of starting material. The reaction mixture was quenched with a 20% aqueous Na$_2$S$_2$O$_3$ solution (10 mL) and concentrated under reduced pressure. The residue was taken up in MeCN (20 mL) and filtered under vacuum through a sintered plastic funnel and the resulting filtrate was concentrated under reduced pressure. The reaction mixture was purified by column chromatography through silica gel (80 g), eluting with 100:0 to 40:60 Hexanes:EtOAc as a gradient to afford the title compound (800 mg).

Step 4: Preparation of benzyl (2,4-diamino-3-hydroxy-4-oxobutyl)carbamate

Into a 100 mL round-bottom flask equipped with a magnetic stir bar and under N$_2$ was added benzyl tert-butyl (4-amino-3-hydroxy-4-oxobutane-1,2-diyl)dicarbamate (800 mg, 2.2 mmol, 1.0 equiv) and CH$_2$Cl$_2$ (5 mL). The resulting solution was treated with 4 M HCl in dioxane (1 mL, 4.0 mmol, 1.8 equiv) and stirred at room temperature for 18 h overnight. The resulting mixture was concentrated under reduced pressure and dried under vacuum to afford an oil which was used directly without further purification (650 mg).

Intermediate P: (2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxylic acid

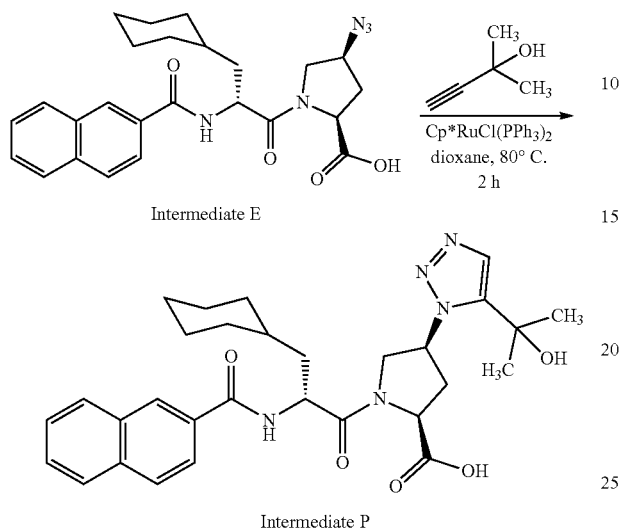

Into a 100 mL round-bottom flask equipped with a magnetic stir bar and under N₂ was added (2S,4S)-1-((R)-2-(2-naphthamido)-3-cyclohexylpropanoyl)-4-azidopyrrolidine-2-carboxylic acid (Intermediate F, 2.0 g, 4.32 mmol, 1.0 equiv), 2-methyl-3-butyn-2-ol (857 µL, 8.64 mmol, 2.0 equiv), Cp*RuCl(PPh₃)₂ (342 mg, 0.43 mmol, 0.1 equiv) and 1,4-dioxane (20 mL). The contents of the flask were purged with a steady flow of N₂ via a needle into the light orange solution for 20 minutes. At this stage the reaction mixture was heated in an oil bath at 80° C. for 2 h. The reaction mixture was cooled to room temperature and quenched with 1 M aqueous HCl solution (50 mL) and poured into a 250 mL separatory funnel containing water (50 mL). The mixture was extracted with EtOAc (3×30 mL). The combined organic layers were washed with brine (25 mL), dried over MgSO₄, filtered and concentrated under reduced pressure. Purification by column chromatography through silica gel (50 g), eluting with 100:0 to 90:10 CH₂Cl₂:MeOH+1% AcOH as a gradient afforded the desired product as a beige foam (1.13 g).

Intermediate Q: Benzyl (7-amino-6-hydroxy-5-((2S,4S)-4-(5-(2-hydroxypropan-2-yl)-1H-1,2,3-triazol-1-yl)pyrrolidine-2-carboxamido)-7-oxoheptyl)carbamate hydrochloride

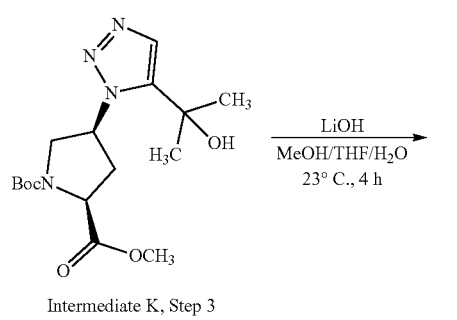

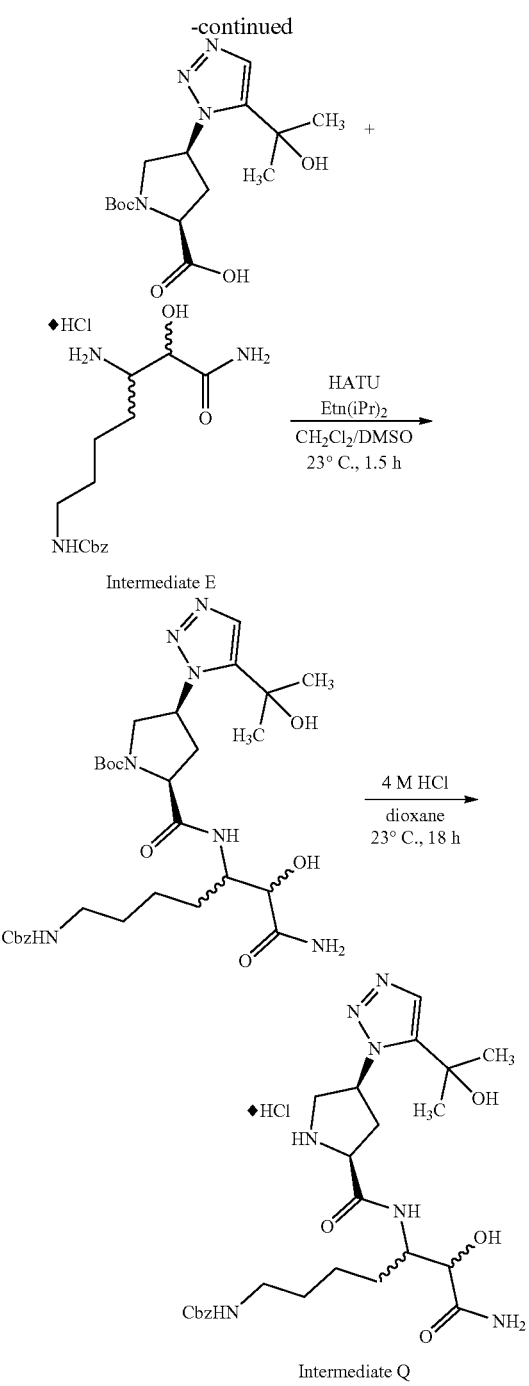

Step 1: Preparation of (2S,4S)-1-(tert-butoxycarbonyl)-4-(5-(2-hydroxypropan-2-yl)-1H-1,2,3-triazol-1-yl)pyrrolidine-2-carboxylic acid To a solution of 1-(tert-butyl) 2-methyl (2S,4S)-4-(5-(2-hydroxypropan-2-yl)-1H-1,2,3-triazol-1-yl)pyrrolidine-1,2-dicarboxylate (3.7 g, 10.5 mmol, 1.0 equiv) in MeOH (26 mL) and THF (26 mL) was added 1 M aqueous LiOH solution (26 mL, 26 mmol, 2.5 equiv) and the mixture was stirred at 23° C. for 4 hours. The solvent was removed under reduced pressure and the resulting residue was dissolved in THF (30 mL) and acidified with 1 M aqueous HCl solution to pH z 1. This mixture was further diluted with water (50 mL) and extracted with EtOAc (3×40 mL) using a separatory funnel. The combined organic extracts were dried over MgSO$_4$, filtered and the solvent was removed under reduced pressure to provide the title compound (2.5 g).

Step 2: Preparation of tert-butyl (2S,4S)-2-((1-amino-7-(((benzyloxy)carbonyl)amino)-2-hydroxy-1-oxoheptan-3-yl)carbamoyl)-4-(5-(2-hydroxypropan-2-yl)-1H-1,2,3-triazol-1-yl)pyrrolidine-1-carboxylate Into a 100 mL round-bottom flask equipped with a magnetic stir bar and under nitrogen was added (2S,4S)-1-(tert-butoxycarbonyl)-4-(5-(2-hydroxypropan-2-yl)-1H-1,2,3-triazol-1-yl)pyrrolidine-2-carboxylic acid (2.0 g, 6.0 mmol, 1.0 equiv), HATU (2.7 g, 7.2 mmol, 1.2 equiv) and CH$_2$Cl$_2$ (30 mL). The resulting suspension was treated with benzyl (5,7-diamino-6-hydroxy-7-oxoheptyl)carbamate hydrochloride (Intermediate E, 2.2 g, 7.2 mmol, 1.2 equiv) in DMSO (2 mL). To the mixture was added EtN(iPr)$_2$ (3.3 mL, 18.6 mmol, 2.0 equiv) and the yellow suspension was stirred at room temperature for 1.5 h. LCMS analysis revealed conversion to product. The reaction was quenched with sat. aqueous NH$_4$Cl (50 mL) and extracted with CH$_2$Cl$_2$ (3×50 mL) using a 250 mL separatory funnel. The combined organic layers were washed with brine (50 mL), dried over MgSO$_4$, filtered and concentrated under reduced pressure. The resulting yellow oil was loaded onto a 5 g C18 precartridge. Purification by reverse-phase column chromatography (40 g C18 column) eluting with 100:0 to 60:40 H$_2$O:MeCN+0.1% HCOOH as a gradient afforded the title compound as a white solid (1.9 g).

Step 3: Preparation of benzyl (7-amino-6-hydroxy-5-((2S,4S)-4-(5-(2-hydroxypropan-2-yl)-1H-1,2,3-triazol-1-yl)pyrrolidine-2-carboxamido)-7-oxoheptyl)carbamate hydrochloride Into a 100 mL round-bottom flask, equipped with a magnetic stir bar and under nitrogen was charged tert-butyl (2S,4S)-2-((1-amino-7-(((benzyloxy)carbonyl)amino)-2-hydroxy-1-oxoheptan-3-yl)carbamoyl)-4-(5-(2-hydroxypropan-2-yl)-1H-1,2,3-triazol-1-yl)pyrrolidine-1-carboxylate (1.9 g, 3.1 mmol, 1.0 equiv) and 1,4-dioxane (5.7 mL). The solution was treated with 4 M HCl in dioxane (1.9 mL, 7.7 mmol, 2.5 equiv) and the reaction was stirred at room temperature for 18 h. The reaction mixture was concentrated under reduced pressure to afford the title product which was used directly without further purification (1.5 g).

Intermediate R: 2-((tert-Butoxycarbonyl)amino)-3-(tetrahydro-2H-pyran-4-yl)propanoic acid

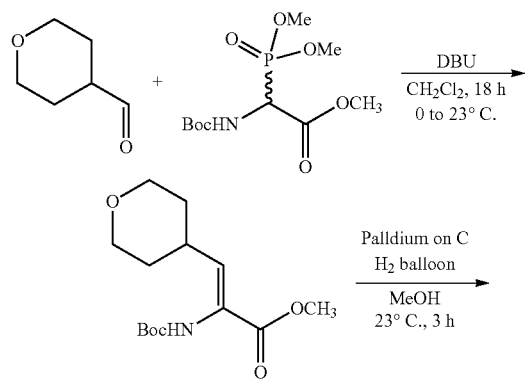

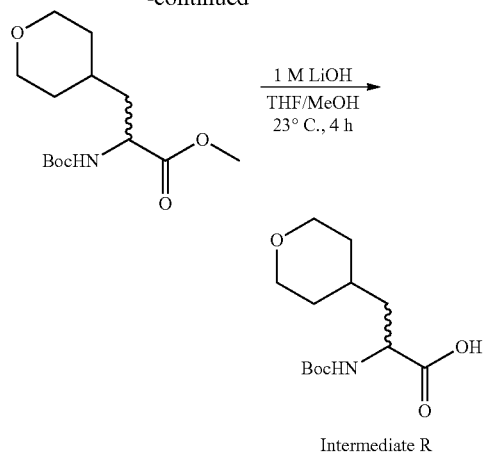

Intermediate R

Step 1: Preparation of methyl (Z)-2-((tert-butoxycarbonyl)amino)-3-(tetrahydro-2H-pyran-4-yl)acrylate A mixture of tetrahydro-2H-pyran-4-carbaldehyde (1.0 g, 8.8 mmol, 1.2 equiv), methyl 2-((tert-butoxycarbonyl)amino)-2-(dimethoxyphosphoryl)acetate (2.2 g, 7.3 mmol, 1.0 equiv) and CH$_2$Cl$_2$ (20 mL) were added into a flame-dried round-bottom flask containing a magnetic stir bar and stirred under N$_2$. The solution was cooled to 0° C. in an ice bath. To this was added DBU (1.1 mL, 7.3 mmol, 1.0 equiv) drop-wise while maintaining the reaction temperature around 0° C. The reaction mixture was allowed to warm to room temperature overnight for 18 h. The reaction was quenched by adding sat. aqueous NH$_4$Cl solution (40 mL) and extracted with CH$_2$Cl$_2$ (3×15 mL) using a phase-separatory cartridge. The combined organic layers were concentrated under reduced pressure and purified by column chromatography through silica gel (80 g), eluting with 95:5 to 50:50 Hexanes:EtOAc as a gradient to afford the desired compound (2.43 g).

Step 2: Preparation of methyl 2-((tert-butoxycarbonyl)amino)-3-(tetrahydro-2H-pyran-4-yl)propanoate Into a 100 mL round-bottom flask equipped with a magnetic stir bar and under N$_2$ was added methyl (Z)-2-((tert-butoxycarbonyl)amino)-3-(tetrahydro-2H-pyran-4-yl)acrylate (2.43 g, 8.76 mmol, 1.0 equiv) and MeOH (25 mL). The reaction mixture was purged with a steady flow of N$_2$ for 15 minutes at which stage 10 wt % palladium on carbon (354 mg) was added and the flask was purged with N$_2$ for 15 minutes. The N$_2$ inlet was replaced with a balloon of H$_2$ and purging was continued for 15 minutes, at which stage the outlet was removed and the reaction mixture was stirred at room temperature under a H$_2$ atmosphere for 3 h. LCMS analysis at this time revealed complete conversion of starting material. The reaction mixture was filtered through a pad of celite on a sintered plastic funnel, washing with MeOH (3×10 mL). The clear filtrate was concentrated under reduced pressure and used directly in the next step (≈2.4 g).

Step 4: Preparation of 2-((tert-butoxycarbonyl)amino)-3-(tetrahydro-2H-pyran-4-yl)propanoic acid Into a 20 mL sample vial equipped with a magnetic stir bar and under N$_2$ was added methyl 2-((tert-butoxycarbonyl)

amino)-3-(tetrahydro-2H-pyran-4-yl)propanoate (2.4 g, 8.7 mmol, 1.0 equiv), THF (22 mL), MeOH (22 mL) and 1 M aqueous LiOH solution (22 mL, 22 mmol, 2.5 equiv). The reaction mixture was stirred at room temperature for 4 h after which LCMS analysis revealed complete conversion of starting material. The reaction mixture was concentrated under reduced pressure and the resulting oil was diluted with CH$_2$Cl$_2$ (25 mL) and acidified to pH z 2 with 1 M aqueous HCl solution (approx. 25 mL). The mixture was poured into a 125 mL separatory funnel containing water (40 mL) and extracted with CH$_2$Cl$_2$ (3×25 mL). The combined organic layers were washed with brine (40 mL), dried over MgSO$_4$, filtered and concentrated to afford a brown oil which was used directly without further purification (≈2.0 g).

Intermediate S: 3-(Adamantan-1-yl)-2-((tert-butoxycarbonyl)amino)propanoic acid

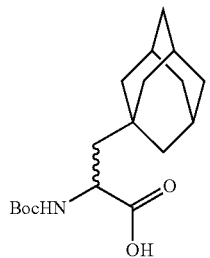

Intermediate S

This compound was prepared in an analogous manner as Intermediate R, using (adamantan-1-yl)carbaldehyde in place of tetrahydro-2H-pyran-4-carbaldehyde in Step 1.

Intermediate T: 2-((tert-Butoxycarbonyl)amino)-3-((1S,2R,5S)-6,6-dimethylbicyclo[3.1.1]heptan-2-yl)propanoic acid

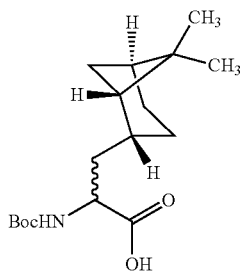

Intermediate T

This compound was prepared in an analogous manner as Intermediate R, using ((1S,2S,5S)-6,6-dimethylbicyclo[3.1.1]heptan-2-yl)carbaldehyde in place of tetrahydro-2H-pyran-4-carbaldehyde in Step 1.

Intermediate U: 2-((tert-Butoxycarbonyl)amino)-3-(3-methyloxetan-3-yl)propanoic acid

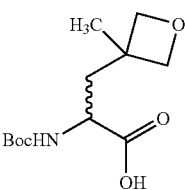

Intermediate U

This compound was prepared in an analogous manner as Intermediate R, using (3-methyloxetan-3-yl)carbaldehyde in place of tetrahydro-2H-pyran-4-carbaldehyde in Step 1.

Intermediate V: 2-(2-Naphthamido)-4-((1S,4R)-bicyclo[2.2.1]heptan-2-yl)butanoic acid -continued

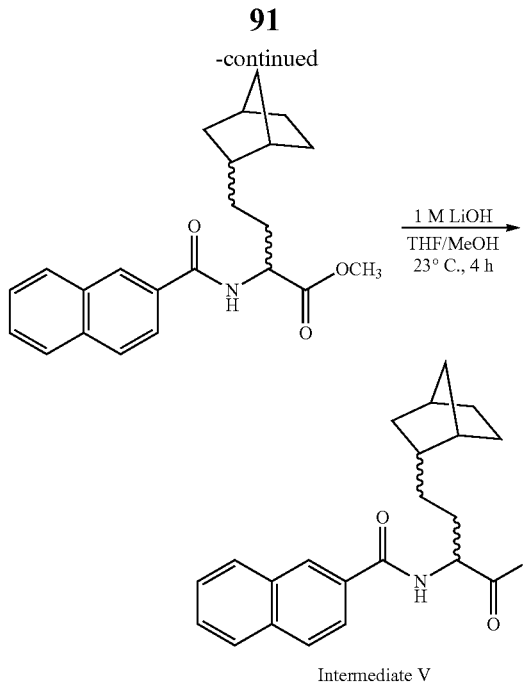

Intermediate V

Step 1: Preparation of 2-((1S,4R)-bicyclo[2.2.1]heptan-2-yl)ethan-1-ol

Into a flamed-dried 250 mL round-bottom flask equipped with a magnetic stir bar and under nitrogen was added LiAlH$_4$ powder (2.4 g, 64.8 mmol, 4.0 equiv). The solid was diluted with anhydrous Et$_2$O (32 mL) and cooled to 0° C. in an ice bath. Into a 200 mL beaker was added the commercially available 2-norbornaneacetic acid (2.5 g, 16.2 mmol, 1.0 equiv) and anhydrous THF (32 mL). The mixture was sonicated to give a solution, which was added drop-wise to the LiAlH$_4$/Et$_2$O slurry via an additional funnel over 1 h. The grey suspension was stirred at 0° C. for 1 h and then carefully quenched by sequential dropwise addition of H$_2$O (2.5 mL), 15% aqueous NaOH solution (2.5 mL) and H$_2$O (7.5 mL). The resulting grey-white suspension was stirred at 0° C. for 20 minutes and then filtered under vacuum through a pad of celite on a sintered glass funnel, washing with EtOAc (3×50 mL). The filtrate was dried over MgSO$_4$, filtered and concentrated under reduced pressure. The crude oil was dried under vacuum for 2 h and used directly without further purification (840 mg).

Step 2: Preparation of 2-((1S,4R)-bicyclo[2.2.1]heptan-2-yl)acetaldehyde

Into a 100 mL round-bottom flask equipped with a magnetic stir bar and under nitrogen was added 2-((1S,4R)-bicyclo[2.2.1]heptan-2-yl)ethan-1-ol (840 mg, 6.0 mmol, 1.0 equiv), CH$_2$Cl$_2$ (12 mL) and NaHCO$_3$ (1.0 g, 12.0 mmol, 2 equiv). The suspension was cooled to 0° C. in an ice bath and Dess-Martin Periodinane (3.8 g, 9.0 mmol, 1.5 equiv) was added portion-wise over 20 minutes. The reaction mixture was stirred at 0° C. for 40 minutes at which time TLC analysis revealed complete conversion of starting material. The reaction was quenched with drop-wise addition of 10% aqueous sodium thiosulfate solution (10 mL) and poured into a 125 mL separatory funnel containing water (20 mL). The mixture was extracted with CH$_2$Cl$_2$ (3×20 mL) and the combined organic layers were washed with brine (20 mL), dried over MgSO$_4$, filtered and concentrated under reduced pressure. Purification by column chromatography through silica gel (45 g), eluting with 98:2 to 70:30 Hexane:EtOAc as a gradient afforded the title product as a yellow oil (434 mg).

Step 3: Preparation of methyl (Z)-2-(((benzyloxy)carbonyl)amino)-4-((1S,4R)-bicyclo[2.2.1]heptan-2-yl)but-2-enoate Into a 25 mL flame-dried round bottom flask equipped with magnetic stir bar under nitrogen was added methyl 2-(((benzyloxy)carbonyl)amino)-2-(diethoxyphosphoryl)acetate (691 mg, 2.1 mmol, 1.0 equiv) and anhydrous CH$_2$Cl$_2$ (2 mL). The solution was cooled to 0° C. in an ice bath. To this mixture was added slowly DBU (312 ρL, 2.1 mmol, 1.0 equiv). The mixture was stirred at 0° C. for 20 minutes, then treated with a solution of 2-((1S,4R)-bicyclo[2.2.1]heptan-2-yl)acetaldehyde (434 mg, 3.1 mmol, 1.5 equiv) in CH$_2$Cl$_2$ (2 mL). The reaction was allowed to warm to room temperature over 18 h overnight. LCMS analysis revealed the formation of product. The reaction was quenched with sat. aqueous NH$_4$Cl solution (20 mL) and poured into a 125 mL separatory funnel and extracted with CH$_2$Cl$_2$ (3×15 mL). The combined organic layers were washed with brine (25 mL), dried over MgSO$_4$, filtered and concentrated under reduced pressure. Purification by column chromatography through silica gel (30 g), eluting with 100:0 to 70:30 Hexanes:EtOAc as a gradient afforded the title compound (720 mg).

Step 4: Preparation of methyl 2-amino-4-((1S,4R)-bicyclo[2.2.1]heptan-2-yl)butanoate Into a 25 mL round bottom flask equipped with a magnetic stir bar and under nitrogen was added methyl (Z)-2-(((benzyloxy)carbonyl)amino)-4-((1S,4R)-bicyclo[2.2.1]heptan-2-yl)but-2-enoate (720 mg, 2.1 mmol, 1.0 equiv) and MeOH (6 mL). The solution was purged under a steady stream of N$_2$ through a long needle for 30 minutes. To the flask was added 10 wt % palladium on carbon (85 mg) and purging with N$_2$ was continued for 10 minutes. At this time, the nitrogen source was then replaced with a hydrogen balloon. The contents of the flask were purged with hydrogen, followed by removing the outlet bubbler. The reaction was stirred at room temperature for 3 h under an atmosphere of H$_2$. LCMS analysis at this time revealed completion of reaction. The reaction mixture was filtered through a pad of celite on plastic sintered funnel, washing with CH$_2$Cl$_2$ (3×15 mL). The clear filtrate was concentrated and used directly in the next step without further purification.

Step 5: Preparation of methyl 2-(2-naphthamido)-4-((1S,4R)-bicyclo[2.2.1]heptan-2-yl)butanoate Into a 100 mL round-bottom flask equipped with a magnetic stir bar and under N$_2$ was added 2-naphthoic acid (359 mg, 2.1 mmol, 1.0 equiv), HATU (950 mg, 2.5 mmol, 1.2 equiv) and CH$_2$Cl$_2$ (10 mL). The solution was stirred at room temperature for 15 minutes and then methyl 2-amino-4-((1S,4R)-bicyclo[2.2.1]heptan-2-yl)butanoate (approx. 440 mg, 2.1 mmol, 1.0 equiv) was added followed by EtN(iPr)$_2$ (365 μL, 2.1 mmol, 1.0 equiv) and DMSO (2 mL). The reaction mixture was stirred at room temperature for 18 h overnight. The reaction mixture was diluted with water (10 mL) and extracted with CH$_2$Cl$_2$ (3×10 mL) using a separatory funnel. The combined organic layers were washed with brine (10 mL), dried over MgSO₄, filtered and concentrated under reduced pressure. Purification by column chromatography through silica gel (25 g), eluting with 95:5 to 50:50 Hexanes:EtOAc as a gradient afforded the title compound (518 mg).

Step 6: Preparation of 2-(2-naphthamido)-4-((1S, 4R)-bicyclo[2.2.1]heptan-2-yl)butanoic acid To a solution of methyl 2-(2-naphthamido)-4-((1S,4R)-bicyclo[2.2.1]heptan-2-yl)butanoate (518 mg, 1.4 mmol, 1.0 equiv) in MeOH (3.6 mL) and THF (3.6 mL) was added 1 M aqueous LiOH solution (3.6 mL, 3.6 mmol, 2.5 equiv) and the mixture was stirred at room temperature for 4 h. At this time, the solvent was removed under reduced pressure and the resulting residue was dissolved in THF (30 mL) and acidified to pH<2 with 1 M aqueous HCl solution. The mixture was further diluted with water (20 mL), poured into a 125 mL separatory funnel and extracted with EtOAc (3×20 mL). The combined organic layers were dried over MgSO₄, filtered and the solvent was removed under reduced pressure to provide the title compound (459 mg).

PREPARATION OF EXAMPLES

Example 1: (2S)-1-((R)-2-(2-Naphthamido)-3-cyclohexylpropanoyl)-N-(1-amino-4-methyl-1,2-dioxopentan-3-yl)pyrrolidine-2-carboxamide

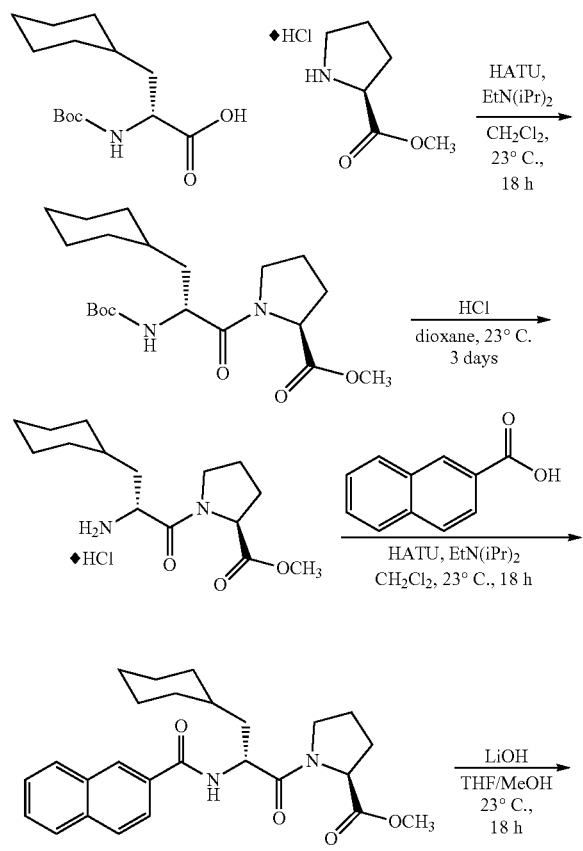

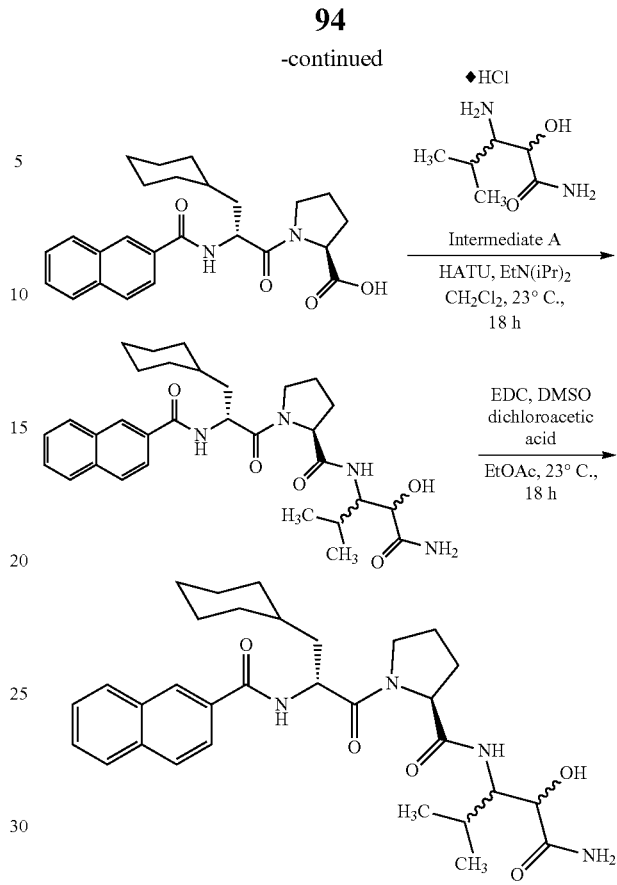

Example 1

Step 1: Preparation of methyl ((R)-2-((tert-butoxycarbonyl)amino)-3-cyclohexylpropanoyl)-L-prolinate Into a 100 mL round-bottom flask, equipped with a magnetic stir bar and under nitrogen was added (R)-2-((tert-butoxycarbonyl)amino)-3-cyclohexylpropanoic acid (2.05 g, 7.6 mmol, 1.0 equiv), HATU (4.31 g, 11.3 mmol, 1.5 equiv) and CH₂Cl₂ (20 mL). The suspension was stirred at room temperature for 30 minutes and then L-proline methyl ester hydrochloride (1.50 g, 9.1 mmol, 1.2 equiv) was added followed by EtN(iPr)₂ (2.6 mL, 15.1 mmol, 2 equiv). The resulting light yellow solution was stirred at room temperature for 18 h overnight. The reaction mixture was poured into a 250 mL separatory funnel containing 1 M aqueous HCl solution (100 mL) and extracted with CH₂Cl₂ (3×40 mL). The combined organic layers were washed with brine (50 mL), dried over MgSO₄, filtered and concentrated under reduced pressure. Purification by column chromatography through silica gel (65 g), eluting with 95:5 to 40:60 Hexanes:EtOAc as a gradient over 25 minutes afforded the title compound as a solid (2.62 g).

Step 2: Preparation of methyl ((R)-2-amino-3-cyclohexylpropanoyl)-L-prolinate hydrochloride Into a 100 mL round-bottom flask equipped with a magnetic stir bar and under nitrogen was added methyl ((R)-2-((tert-butoxycarbonyl)amino)-3-cyclohexylpropanoyl)-L-prolinate (2.5 g, 6.6 mmol, 1.0 equiv) and 1,4-dioxane (8 mL). The solution was treated with 4 M HCl in dioxane (4.0 mL, 16 mmol, 2.5 equiv) and the mixture stirred at room temperature for 1 h. At this stage, the mixture became very thick, and so MeOH (5 mL) was added. After stirring at room temperature for 3 days, the reaction mixture was concentrated under reduced pressure and the resulting compound was dried under vacuum to afford the desired compound as a yellow solid (2.1 g).

Step 3: Preparation of methyl ((R)-2-(2-naphthamido)-3-cyclohexylpropanoyl)-L-prolinate Into a 100 mL round-bottom flask equipped with a magnetic stir bar and under nitrogen was added 2-naphthoic acid (533 mg, 3.1 mmol, 1.0 equiv), HATU (1.41 g, 3.7 mmol, 1.2 equiv) and CH$_2$Cl$_2$ (10 mL). The mixture was stirred at room temperature for 30 minutes and then methyl ((R)-2-amino-3-cyclohexylpropanoyl)-L-prolinate hydrochloride (1.18 g, 3.7 mmol, 1.2 equiv) was added followed by EtN(iPr)$_2$ (810 μL, 4.6 mmol, 1.5 equiv). The reaction mixture was stirred at room temperature for 18 h overnight. The reaction was quenched with 1 M aqueous HCl solution (50 mL) and extracted with CH$_2$Cl$_2$ (3×30 mL) using a phase-separatory cartridge. The combined organic layers were concentrated. Purification by column chromatography through silica gel (65 g) eluting with 80:20 to 20:80 Hexanes:EtOAc as a gradient afforded the title compound as a white foam (1.1 g)

Step 4: Preparation of ((R)-2-(2-naphthamido)-3-cyclohexylpropanoyl)-L-proline

Into a 100 mL round-bottom flask equipped with a magnetic stir bar and under nitrogen was added methyl ((R)-2-(2-naphthamido)-3-cyclohexylpropanoyl)-L-prolinate (1.0 g, 2.3 mmol, 1.0 equiv), THF (5 mL) and methanol (5 mL). The solution was treated with 1 M aqueous LiOH solution (5.8 mL, 5.8 mmol, 2.5 equiv) and the solution stirred at room temperature for 18 h overnight. The reaction mixture was concentrated under reduced pressure and the resulting oil was diluted with water (50 mL) and acidified to pH<2 with 1 M aqueous HCl solution (=6 mL). The aqueous layer was extracted with CH$_2$Cl$_2$ (3×30 mL) using a phase-separatory cartridge and the combined organics were concentrated under reduced pressure to afford a white foam (810 mg).

Step 5: Preparation of (2S)-1-((R)-2-(2-naphthamido)-3-cyclohexylpropanoyl)-N-(1-amino-2-hydroxy-4-methyl-1-oxopentan-3-yl)pyrrolidine-2-carboxamide Into a 100 mL round-bottom flask equipped with a magnetic stir bar and under nitrogen was added ((R)-2-(2-naphthamido)-3-cyclohexylpropanoyl)-L-proline (134 mg, 0.32 mmol, 1.0 equiv), 3-amino-2-hydroxy-4-methylpentanamide hydrochloride (Intermediate A, 87 mg, 0.48 mmol, 1.5 equiv), HATU (180 mg, 0.48 mmol, 1.5 equiv) and CH$_2$Cl$_2$ (2 mL). The reaction mixture was treated with EtN(iPr)$_2$ (166 μL, 0.95 mmol, 3.0 equiv) and stirred at room temperature for 18 h overnight. The reaction was quenched with sat. aqueous NH$_4$Cl solution (10 mL) and extracted with CH$_2$Cl$_2$ (3×15 mL) using a phase-separatory cartridge. The combined organics were concentrated under reduced pressure. Purification by column chromatography through silica gel (29 g) eluting with 100:0 to 90:10 CH$_2$Cl$_2$:MeOH as a gradient afforded the title compound as a tan foam (150 mg).

Step 6: Preparation of (2S)-1-((R)-2-(2-naphthamido)-3-cyclohexylpropanoyl)-N-(1-amino-4-methyl-1,2-dioxopentan-3-yl)pyrrolidine-2-carboxamide Into a 20 mL sample vial equipped with a magnetic stir bar and under nitrogen was added (2S)-1-((R)-2-(2-naphthamido)-3-cyclohexylpropanoyl)-N-(1-amino-2-hydroxy-4-methyl-1-oxopentan-3-yl)pyrrolidine-2-carboxamide (200 mg, 0.36 mmol, 1.0 equiv) and EtOAc (2 mL). The solution was treated with DMSO (258 μL, 3.64 mmol, 10 equiv) and cooled to 0° C. in an ice bath. The solution was charged with EDC (350 mg, 1.82 mmol, 5 equiv) followed by dichloroacetic acid (150 μL, 1.82 mmol, 5 equiv) and the solution was stirred at 0° C. for 10 minutes then warmed to room temperature for 1 h. LCMS analysis at this time reveals approx. 20% remaining starting material, so another 5 equiv of EDC was added followed by 5 equiv of dichloroacetic acid and the mixture allowed to stir for 18 h overnight. The reaction was quenched with water (20 mL) and extracted with EtOAc (3×15 mL) using a phase-separatory cartridge. The combined organic layers were concentrated under reduced pressure. Purification by column chromatography through silica gel (15 g) eluting with 100:0 to 90:10 EtOAc:MeOH as a gradient afforded the title compound as a white solid (67 mg). MS (ESI+) 549 (M+1)$^\oplus$ 1H NMR (CDCl3, 300 MHz): δ 8.37 (1H, d, J=9.2 Hz), 7.96-7.89 (3H, m), 7.72-7.58 (3H, m), 7.08-7.06 (1H, m), 6.52-6.37 (1H, m), 5.41-5.28 (1H, m), 5.06-4.99 (2H, m), 4.72-4.64 (1H, m), 4.14-4.08 (2H, m), 3.62-3.57 (1H, m), 2.42-2.21 (1H, m), 1.99-0.72 (23H, m) ppm.

Example 2: Methyl (3-((S)-1-((R)-2-(2-naphthamido)-3-cyclohexylpropanoyl)pyrrolidine-2-carboxamido)-4-methyl-2-oxopentanoyl)glycinate

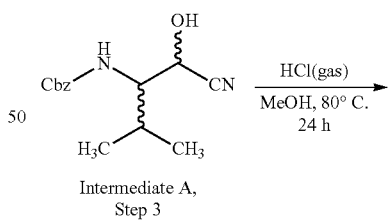

Intermediate A, Step 3

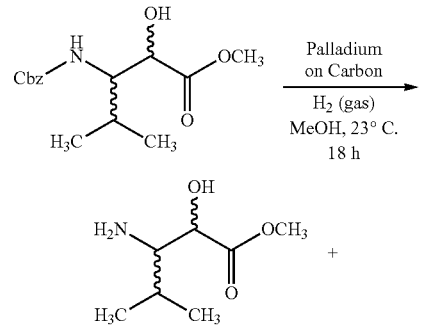

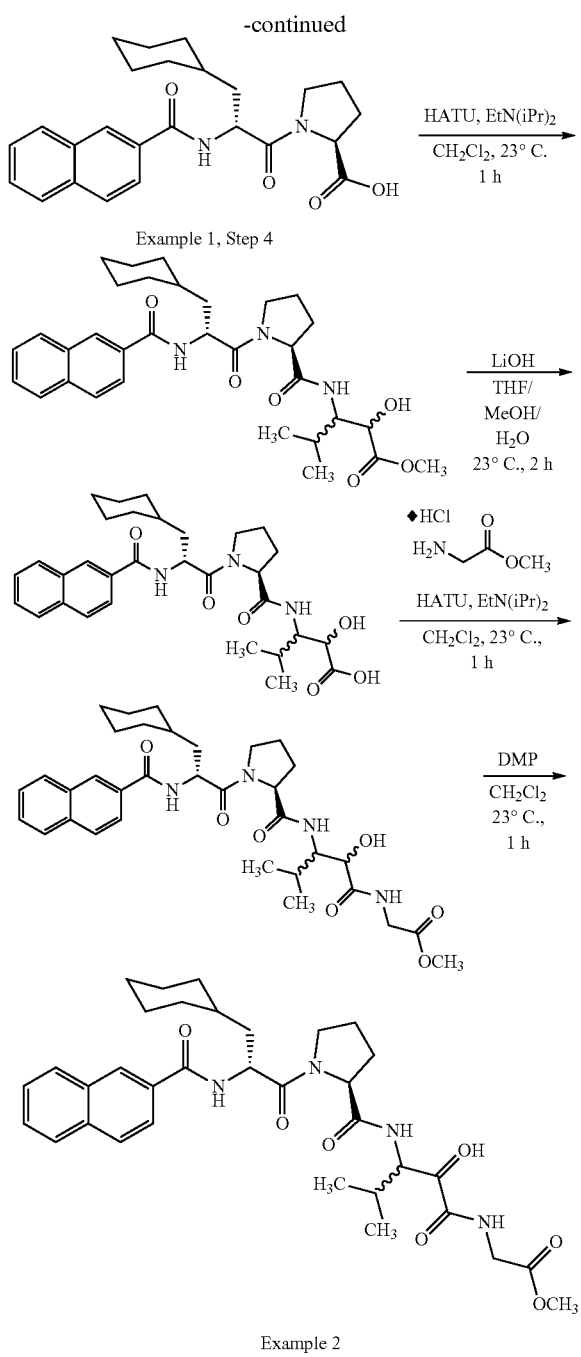

Example 2

Step 1: Preparation of methyl 3-(((benzyloxy)carbonyl)amino)-2-hydroxy-4-methylpentanoate Into a 200 mL round-bottom flask equipped with a magnetic stir bar and reflux condenser was added benzyl (1-cyano-1-hydroxy-3-methylbutan-2-yl)carbamate (Intermediate A, Step 3, 2.6 g, 10.0 mmol, 1.0 equiv) and MeOH (50 mL). Into the reaction mixture was bubbled in HCl (gas) via a fritted glass tube. The mixture was kept under an atmosphere of HCl (gas) and heated to reflux for 24 h. At this time, LCMS analysis revealed no remaining starting material. The reaction mixture was cooled to room temperature and concentrated under reduced pressure to afford a yellow oil which was used directly in the next step without further purification.

Step 2: Preparation of methyl 3-amino-2-hydroxy-4-methylpentanoate

Into a 100 mL round-bottom flask equipped with a magnetic stir bar and under $N_2$ was added methyl 3-(((benzyloxy)carbonyl)amino)-2-hydroxy-4-methylpentanoate (5.0 g, 17 mmol, 1.0 equiv) and methanol (25 mL). The contents of the flask were purged under a steady flow of $N_2$ for 10 minutes and then 10 wt % palladium on carbon (250 mg) was added and $N_2$ purging was continued for an additional 10 minutes. At this time, the $N_2$ inlet was replaced with a balloon of $H_2$ and $H_2$ purging was conducted for 10 minutes at which stage, the outlet was removed. The reaction mixture was stirred at room temperature under a $H_2$ atmosphere for 18 h overnight. The reaction mixture was filtered through a pad of celite on a sintered plastic funnel, washing with $CH_2Cl_2$ (25 mL). The resulting filtrate was concentrated under reduced pressure and utilized directly without further purification.

Step 3: Preparation of methyl 3-((S)-1-((R)-2-(2-naphthamido)-3-cyclohexylpropanoyl)pyrrolidine-2-carboxamido)-2-hydroxy-4-methylpentanoate A round-bottom flask equipped with a magnetic stir bar and under $N_2$ was charged with ((R)-2-(2-naphthamido)-3-cyclohexylpropanoyl)-L-proline (Example 1, Step 4, 106 mg, 0.25 mmol, 1.0 equiv), HATU (114 mg, 0.3 mmol, 1.2 equiv) and $CH_2Cl_2$ (5 mL). The reagents were treated with methyl 3-amino-2-hydroxy-4-methylpentanoate (48 mg, 0.3 mmol, 1.2 equiv) and EtN(iPr)$_2$ (82 µL, 0.6 mmol, 2.4 equiv) and the mixture was stirred at room temperature for 1 h. The resulting mixture was quenched with water (10 mL) and extracted with $CH_2Cl_2$ (3×5 mL) using a 25 mL separatory funnel. The combined organic layers were washed with brine (10 mL), dried over $MgSO_4$, filtered and concentrated. The compound was used directly in the next step without further purification (≈140 mg).

Step 4: Preparation of 3-((S)-1-((R)-2-(2-naphthamido)-3-cyclohexylpropanoyl)pyrrolidine-2-carboxamido)-2-hydroxy-4-methylpentanoic acid A solution of methyl 3-((S)-1-((R)-2-(2-naphthamido)-3-cyclohexylpropanoyl)pyrrolidine-2-carboxamido)-2-hydroxy-4-methylpentanoate (≈140 mg, 0.25 mmol, 1.0 equiv) in THF (2 mL) and MeOH (2 mL) was treated with 1 M aqueous LiOH solution (630 µL, 0.63 mmol, 2.5 equiv). The reaction mixture was stirred at room temperature for 2 h and then concentrated under reduced pressure. The residue was taken up in water (5 mL) and acidified to pH<2 with 1 M aqueous HCl solution. The reaction mixture was extracted with $CH_2Cl_2$ (3×5 mL) using a 25 mL separatory funnel. The combined organic layers were washed with brine (10 mL), dried over $MgSO_4$, filtered and concentrated. The compound was used directly in the next step without further purification (≈100 mg).

Step 5: Preparation of methyl (3-((S)-1-((R)-2-(2-naphthamido)-3-cyclohexylpropanoyl)pyrrolidine-2-carboxamido)-2-hydroxy-4-methylpentanoyl)glycinate Into a 25 mL round-bottom flask equipped with a magnetic stir bar and under N₂ was added 3-((S)-1-((R)-2-(2-naphthamido)-3-cyclohexylpropanoyl)pyrrolidine-2-carboxamido)-2-hydroxy-4-methylpentanoic acid (50 mg, 0.09 mmol, 1.0 equiv), HATU (38 mg, 0.1 mmol, 1.1 equiv) and CH₂Cl₂ (3 mL). The reaction mixture was stirred at room temperature for 5 minutes and then methyl glycinate hydrochloride (12 mg, 0.1 mmol, 1.1 equiv) and EtN(iPr)₂ (41 µL, 0.23 mmol, 2.5 equiv) were added and the reaction mixture was stirred at room temperature for 1 h. The reaction mixture was concentrated under reduced pressure. Purification by reverse-phase column chromatography (12 g, C18 column), eluting with 90:10 to 0:100 H₂O:MeCN+0.1% HCO₂H as a gradient afforded the title compound (50 mg).

Step 6: Preparation of methyl (3-((S)-1-((R)-2-(2-naphthamido)-3-cyclohexylpropanoyl)pyrrolidine-2-carboxamido)-4-methyl-2-oxopentanoyl)glycinate A solution of methyl (3-((S)-1-((R)-2-(2-naphthamido)-3-cyclohexylpropanoyl)pyrrolidine-2-carboxamido)-2-hydroxy-4-methylpentanoyl)glycinate (50 mg, 0.08 mmol, 1.0 equiv) in CH₂Cl₂ (3 mL) was treated with Dess-Martin Periodinane (37 mg, 0.09 mmol, 1.1 equiv). The reaction mixture was stirred at room temperature for 1 h and then concentrated under reduced pressure. Purification by reverse-phase column chromatography (12 g, C18 column), eluting with 90:10 to 10:90 H₂O:MeCN+0.1% HCO₂H as a gradient afforded the title compound (40 mg). MS (ESI+) 621 (M+1)$^{\oplus}$ Example 3 was prepared in a similar manner to Example 2, wherein methyl glycinate hydrochloride in Step 5 was replaced with 2-methoxyethan-1-amine.

Example 4: (2S,4R)-1-((R)-2-(2-naphthamido)-3-cyclohexylpropanoyl)-N-(1-amino-4-methyl-1,2-dioxopentan-3-yl)-4-phenylpyrrolidine-2-carboxamide

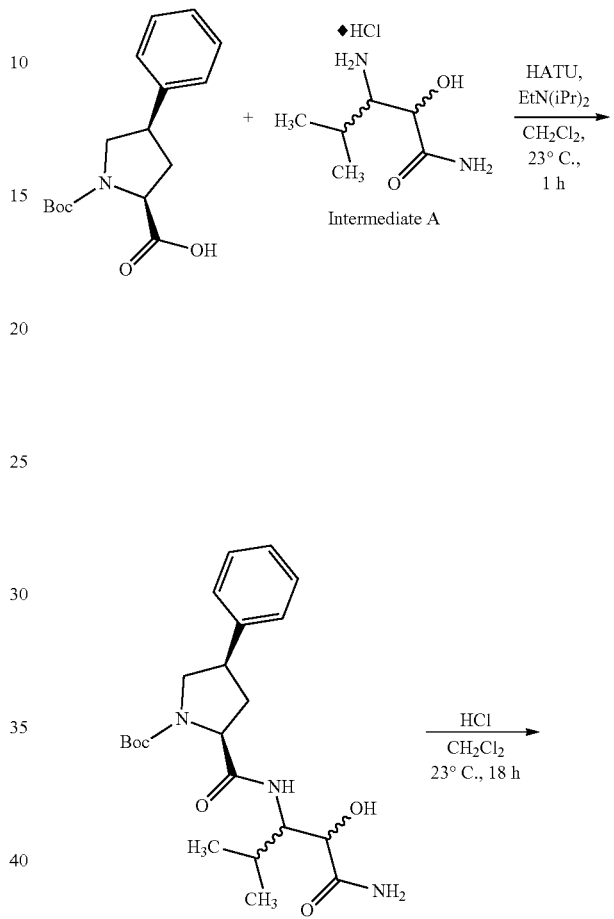

| Example | Structure | MW | MS (ESI+) |
|---|---|---|---|
| 3 | 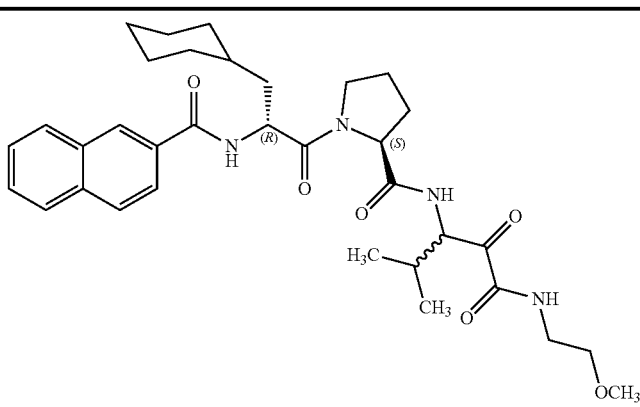 (2S)-1-((R)-2-(2-naphthamido)-3-cyclohexylpropanoyl)-N-(1-((2-methoxyethyl)amino)-4-methyl-1,2-dioxopentan-3-yl)pyrrolidine-2-carboxamide | 606.76 | 607 (M + 1)$^{\oplus}$ |

M aqueous HCl solution (25 mL), sat. aqueous NaHCO$_3$ solution (25 mL), brine (25 mL), dried over MgSO$_4$, filtered and concentrated under reduced pressure. Purification by column chromatography through silica gel, eluting with 100:0 to 0:100 Hexanes:10% MeOH in EtOAc as a gradient afforded the title compound which was used directly in the next step.

Step 2: Preparation of (2S,4R)—N-(1-amino-2-hydroxy-4-methyl-1-oxopentan-3-yl)-4-phenylpyrrolidine-2-carboxamide hydrochloride A solution of tert-butyl (2S,4R)-2-((1-amino-2-hydroxy-4-methyl-1-oxopentan-3-yl)carbamoyl)-4-phenylpyrrolidine-1-carboxylate (0.3 mmol, 1.0 equiv) in CH$_2$Cl$_2$ (5 mL) was treated with 4 M HCl in dioxane (0.5 mL, 0.8 mmol, 2.6 mmol). The reaction mixture was stirred at room temperature for 18 h overnight. The reaction mixture was concentrated under reduced pressure and dried under vacuum to afford an off-white solid (136 mg).

Step 3: Preparation of (2S,4R)-1-((R)-2-(2-naphthamido)-3-cyclohexylpropanoyl)-N-(1-amino-2-hydroxy-4-methyl-1-oxopentan-3-yl)-4-phenylpyrrolidine-2-carboxamide A mixture of (2S,4R)—N-(1-amino-2-hydroxy-4-methyl-1-oxopentan-3-yl)-4-phenylpyrrolidine-2-carboxamide hydrochloride (136 mg, 0.3 mmol, 1.0 equiv) and (R)-2-(2-naphthamido)-3-cyclohexylpropanoic acid (Intermediate B, 117 mg, 0.36 mmol, 1.2 equiv) in CH$_2$Cl$_2$ (5 mL) was treated with HATU (125 mg, 0.33 mmol, 1.1 equiv) followed by EtN(iPr)$_2$ (156 µL, 0.9 mmol, 3 equiv). The reaction mixture was stirred at room temperature for 18 h overnight. The reaction was poured into a separatory funnel containing CH$_2$Cl$_2$ (100 mL) and washed with 0.5 M aqueous HCl (25 mL), water (2×25 mL), brine (25 mL), dried over MgSO$_4$, filtered and concentrated under reduced pressure. The obtained material (230 mg) was used directly in the next step without further purification.

Step 4: Preparation of (2S,4R)-1-((R)-2-(2-naphthamido)-3-cyclohexylpropanoyl)-N-(1-amino-4-methyl-1,2-dioxopentan-3-yl)-4-phenylpyrrolidine-2-carboxamide A solution of (2S,4R)-1-((R)-2-(2-naphthamido)-3-cyclohexylpropanoyl)-N-(1-amino-2-hydroxy-4-methyl-1-oxopentan-3-yl)-4-phenylpyrrolidine-2-carboxamide (225 mg, 0.3 mmol, 1.0 equiv) in CH$_2$Cl$_2$ (4 mL) was treated with Dess-Martin Periodinane (153 mg, 0.36 mmol, 1.2 equiv). The reaction mixture was stirred at room temperature for 1 h and then quenched with water (5 mL). The mixture was extracted with CH$_2$Cl$_2$ (3×10 mL) dried over MgSO$_4$, filtered and concentrated under reduced pressure. Purification by reverse-phase column chromatography on a C18 column, eluting with 90:10 to 0:100 H$_2$O:MeCN+0.1% HCO$_2$H as a gradient afforded the desired compound as a mixture of diastereomers (52 mg). MS (ESI+) 625 (M+1)$^{\oplus}$

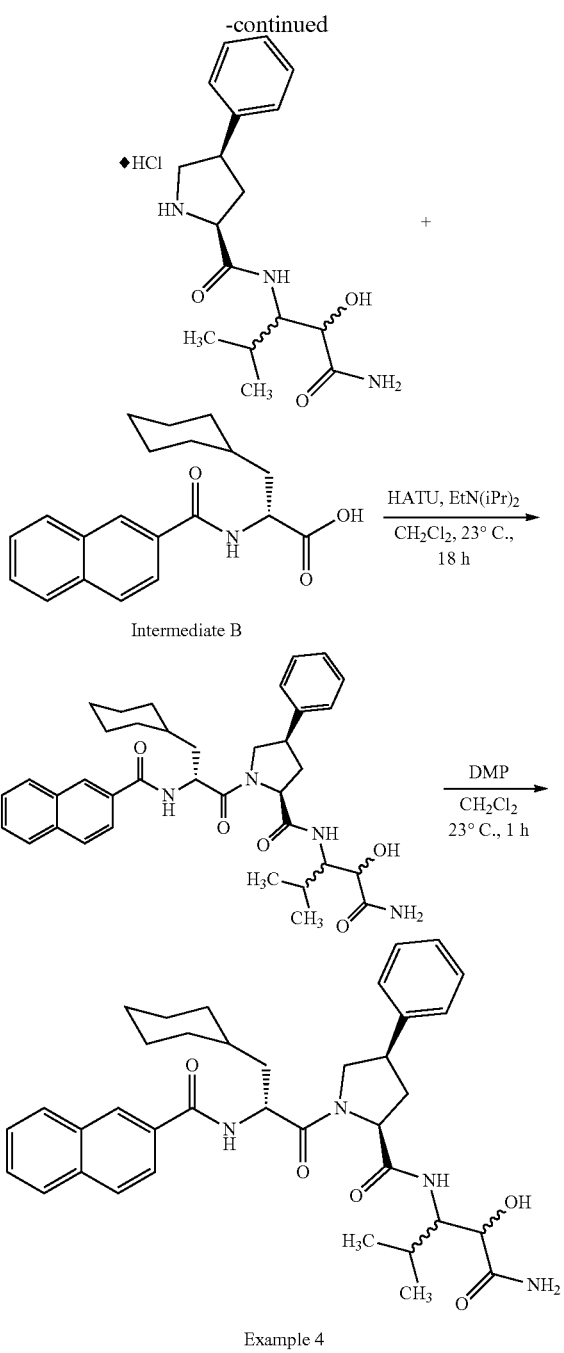

Intermediate B

Example 4

Step 1: Preparation of tert-butyl (2S,4R)-2-((1-amino-2-hydroxy-4-methyl-1-oxopentan-3-yl)carbamoyl)-4-phenylpyrrolidine-1-carboxylate A round-bottom flask was charged with (2S,4R)-1-(tert-butoxycarbonyl)-4-phenylpyrrolidine-2-carboxylic acid (88 mg, 0.3 mmol, 1.0 equiv), 3-amino-2-hydroxy-4-methylpentanamide hydrochloride (Intermediate A, 44 mg, 0.3 mmol, 1.0 equiv), HATU (125 mg, 0.33 mmol, 1.1 equiv) and CH$_2$Cl$_2$ (3 mL). The reaction was treated with EtN(iPr)$_2$ (104 µL, 0.6 mmol, 2.0 equiv) and stirred at room temperature for 1 h. The reaction was diluted with CH$_2$Cl$_2$ and poured into a 125 mL separatory funnel and washed with 0.5

Example 5: (2S,4R)-1-((R)-2-(2-Naphthamido)-3-cyclohexylpropanoyl)-N-(1-amino-4-methyl-1,2-dioxopentan-3-yl)-4-(piperidin-1-yl)pyrrolidine-2-carboxamide

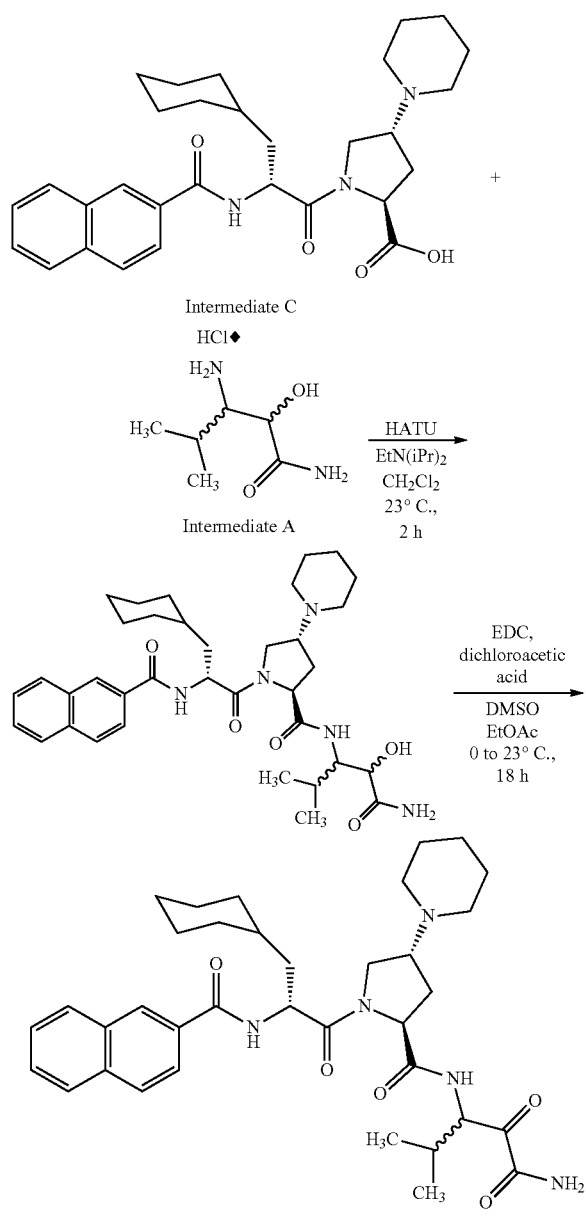

Example 5

Step 1: Preparation of (2S,4R)-1-((R)-2-(2-naphthamido)-3-cyclohexylpropanoyl)-N-(1-amino-2-hydroxy-4-methyl-1-oxopentan-3-yl)-4-(piperidin-1-yl)pyrrolidine-2-carboxamide Into a 25 mL round-bottom flask equipped with a magnetic stir bar and under nitrogen was added (2S,4R)-1-((R)-2-(2-naphthamido)-3-cyclohexylpropanoyl)-4-(piperidin-1-yl)pyrrolidine-2-carboxylic acid (Intermediate C, 466 mg, 0.9 mmol, 1.0 equiv), 3-amino-2-hydroxy-4-methylpentanamide hydrochloride (Intermediate A, 253 mg, 1.4 mmol, 1.5 equiv), HATU (456 mg, 1.2 mmol, 1.3 equiv) and CH$_2$Cl$_2$ (5 mL). The mixture was treated with EtN(iPr)$_2$ (322 μL, 1.8 mmol, 2 equiv) and stirred at room temperature for 2 h. The reaction was quenched with water (10 mL) and extracted with CH$_2$Cl$_2$ (2×20 mL). The combined organic layers were washed with sat. aqueous NaHCO$_3$ solution (5 mL), dried over MgSO$_4$, filtered and concentrated under reduced pressure. Purification by column chromatography through silica gel (40 g), eluting with 100:0 to 80:20 CH$_2$Cl$_2$:MeOH as a gradient afforded the desired compound as a mixture of diastereomers (544 mg).

Step 2: Preparation of (2S,4R)-1-((R)-2-(2-naphthamido)-3-cyclohexylpropanoyl)-N-(1-amino-4-methyl-1,2-dioxopentan-3-yl)-4-(piperidin-1-yl)pyrrolidine-2-carboxamide A solution of (2S,4R)-1-((R)-2-(2-naphthamido)-3-cyclohexylpropanoyl)-N-(1-amino-2-hydroxy-4-methyl-1-oxopentan-3-yl)-4-(piperidin-1-yl)pyrrolidine-2-carboxamide (544 mg, 0.86 mmol, 1.0 equiv) in EtOAc (5 mL) was treated with DMSO (609 L, 8.6 mmol, 10 equiv) and cooled to 0° C. in an ice bath. The solution was treated with EDC (821 mg, 4.3 mmol, 5 equiv), stirred for 10 minutes and then treated with dichloroacetic acid (353 μL, 4.3 mmol, 5 equiv) and stirred at 0° for another 10 minutes. The reaction mixture was allowed to warm to room temperature and stirred at this temperature for 18 h overnight. The reaction mixture was quenched with water (10 mL) and extracted with EtOAc (2×10 mL). The combined organic layers were washed with sat. aqueous NaHCO$_3$ solution (10 mL), dried over MgSO$_4$, filtered and concentrated under reduced pressure. Purification by column chromatography through silica gel (40 g), eluting with 100:0 to 80:20 CH$_2$Cl$_2$:MeOH as a gradient afforded the desired compound as a mixture of diastereomers (351 mg). MS (ESI+) 632 (M+1)$^{\oplus}$ 1H NMR (CDCl3, 300 MHz): δ 8.33-8.30 (1H, m), 7.91-7.77 (4H, m), 7.57-7.52 (2H, m), 7.25-7.20 (2H, m), 6.80-6.78 (1H, bs), 6.06-6.05 (1H, bs), 5.08-5.04 (2H, m), 4.79-4.76 (1H, m), 4.40-4.36 (1H, m), 3.89-3.85 (1H, m), 3.70-3.65 (1H, m), 2.80-2.61 (4H, m), 2.21-2.16 (2H, m), 1.81-1.75 (1H, m), 1.69-0.63 (25H, m) ppm.

Example 6: (2S,4R)-1-((R)-2-(2-Naphthamido)-3-cyclohexylpropanoyl)-N-(1-amino-7-(3-cyclohexylureido)-2-hydroxy-1-oxoheptan-3-yl)-4-(piperidin-1-yl)pyrrolidine-2-carboxamide

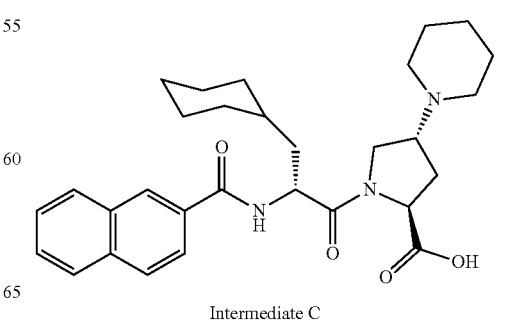

Intermediate C

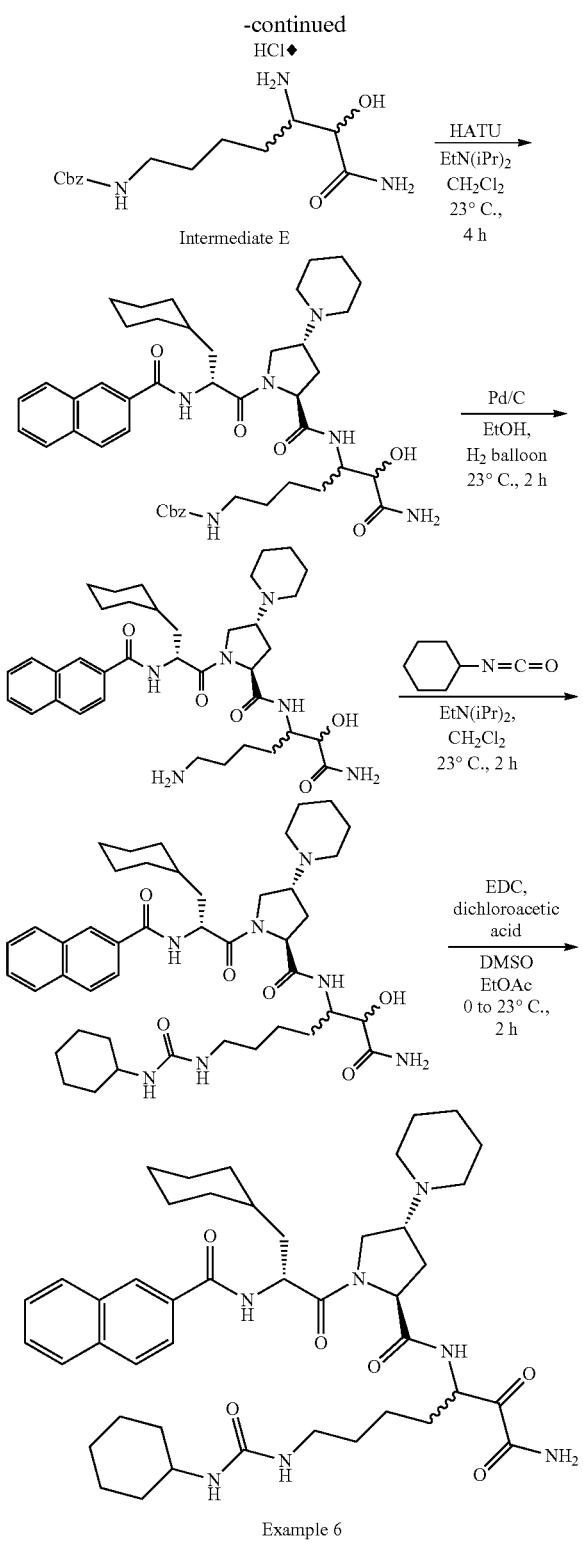

Example 6

Step 1: Preparation of benzyl (5-((2S,4R)-1-((R)-2-(2-naphthamido)-3-cyclohexylpropanoyl)-4-(piperidin-1-yl)pyrrolidine-2-carboxamido)-7-amino-6-hydroxy-7-oxoheptyl)carbamate Into a 50 mL round-bottom flask equipped with a magnetic stir bar and under nitrogen were added (2S,4R)-1-((R)-2-(2-naphthamido)-3-cyclohexylpropanoyl)-4-(piperidin-1-yl)pyrrolidine-2-carboxylic acid (Intermediate C, 226 mg, 0.47 mmol, 1.0 equiv), benzyl (5,7-diamino-6-hydroxy-7-oxoheptyl)carbamate hydrochloride (Intermediate E, 232 mg, 0.67 mmol, 1.4 equiv), HATU (255 mg, 0.47 mmol, 1.4 equiv) and $CH_2Cl_2$. The mixture was treated with $EtN(iPr)_2$ (3 mL, 1.34 mmol, 2.9 equiv) and stirred at room temperature for 4 h. The reaction mixture was quenched with water (5 mL) and extracted with $CH_2Cl_2$ (2×5 mL) using a separatory funnel. The combined organic layers were washed with sat. aqueous $NaHCO_3$ (5 mL), dried over $MgSO_4$ and concentrated under reduced pressure. Purification by column chromatography through silica gel (40 g), eluting with 100:0 to 80:20 $CH_2Cl_2$:MeOH as a gradient afforded the title compound (280 mg).

Step 2: Preparation of (2S,4R)-1-((R)-2-(2-naphthamido)-3-cyclohexylpropanoyl)-N-(1,7-diamino-2-hydroxy-1-oxoheptan-3-yl)-4-(piperidin-1-yl)pyrrolidine-2-carboxamide A solution of benzyl (5-((2S,4R)-1-((R)-2-(2-naphthamido)-3-cyclohexylpropanoyl)-4-(piperidin-1-yl)pyrrolidine-2-carboxamido)-7-amino-6-hydroxy-7-oxoheptyl)carbamate (279 mg, 0.35 mmol, 1.0 equiv) in ethanol (10 mL) was prepared. The solution was added to a 100 mL round-bottom, nitrogen purged flask containing 10 wt % palladium on carbon (140 mg) and the contents of the flask were purged with a steady stream of nitrogen. The nitrogen inlet was replaced with a balloon of $H_2$ and the reaction mixture stirred under a $H_2$ atmosphere at room temperature for 2 h. LCMS analysis revealed complete conversion of starting material. The reaction mixture was filtered through a pad of celite on a plastic sintered funnel, washing with MeOH (2×10 mL). The filtrate was concentrated under reduced pressure and used directly in the next reaction (200 mg).

Step 3: Preparation of (2S,4R)-1-((R)-2-(2-naphthamido)-3-cyclohexylpropanoyl)-N-(1-amino-7-(3-cyclohexylureido)-2-hydroxy-1-oxoheptan-3-yl)-4-(piperidin-1-yl)pyrrolidine-2-carboxamide Into a 25 mL round-bottom flask equipped with a magnetic stir bar and under nitrogen was added (2S,4R)-1-((R)-2-(2-naphthamido)-3-cyclohexylpropanoyl)-N-(1,7-diamino-2-hydroxy-1-oxoheptan-3-yl)-4-(piperidin-1-yl)pyrrolidine-2-carboxamide (200 mg, 0.3 mmol, 1.0 equiv) and $CH_2Cl_2$ (2 mL). The solution was treated with cyclohexyl isocyanate (43 µL, 0.338 mmol, 1.12 equiv) followed by $EtN(iPr)_2$ (59 µL, 0.338 mmol, 1.12 equiv) and the mixture was stirred at room temperature for 2 h. The reaction was quenched with sat. aqueous $NaHCO_3$ solution (5 mL) and extracted with $CH_2Cl_2$ (2×5 mL) using a phase-separatory cartridge. The combined organics were concentrated under reduced pressure and purified by column chromatography through silica gel (12 g), eluting with 100:0 to 80:20 $CH_2Cl_2$:MeOH as a gradient afforded the desired compound as an off-white foam (181 mg).

Step 4: Preparation of (2S,4R)-1-((R)-2-(2-naphthamido)-3-cyclohexylpropanoyl)-N-(1-amino-7-(3-cyclohexylureido)-2-hydroxy-1-oxoheptan-3-yl)-4-(piperidin-1-yl)pyrrolidine-2-carboxamide A solution of (2S,4R)-1-((R)-2-(2-naphthamido)-3-cyclohexylpropanoyl)-N-(1-amino-7-(3-cyclohexylureido)-2-hydroxy-1-oxoheptan-3-yl)-4-(piperidin-1-yl)pyrrolidine-2- carboxamide (181 mg, 0.23 mmol, 1.0 equiv) in EtOAc (1.5 mL) and DMSO (163 µL, 2.3 mmol, 10 equiv) was cooled to 0° C. in an ice bath. The solution was treated with EDC (221 mg, 1.15 mmol, 5 equiv) and stirred at 0° for 15 minutes. After this time, dichloroacetic acid (95 µL, 1.15 mmol, 5 equiv) was added and the mixture stirred at 0° for 30 minutes and then warmed to room temperature for 2 h with stirring. LCMS analysis reveals complete conversion of starting material. The reaction mixture was diluted with EtOAc (10 mL) and water (5 mL) and poured into a 50 mL separatory funnel. The organic layer was removed and further washed with sat. aqueous NaHCO$_3$ solution (2 mL). The aqueous layers were combined and further extracted with EtOAc (2×4 mL) and the combined organic layers were dried over MgSO$_4$, filtered and concentrated under reduced pressure. Purification by column chromatography through silica gel (12 g), eluting with 100:0 to 80:20 CH$_2$Cl$_2$:MeOH as a gradient afforded the desired compound as an off-white foam (100 mg). MS (ESI+) 787 (M+1)$^{\oplus}$ Example 7: (2S,4R)-1-((R)-2-(2-Naphthamido)-3-cyclohexylpropanoyl)-N-(4-amino-1-cyclobutyl-3,4-dioxobutan-2-yl)-4-(piperidin-1-yl)pyrrolidine-2-carboxamide

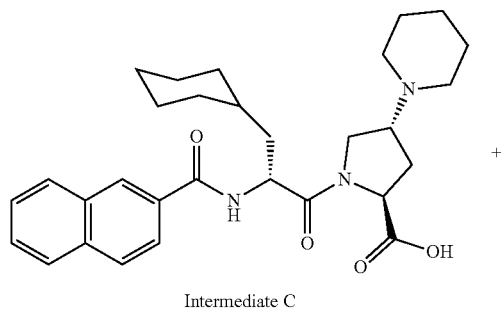

Intermediate C

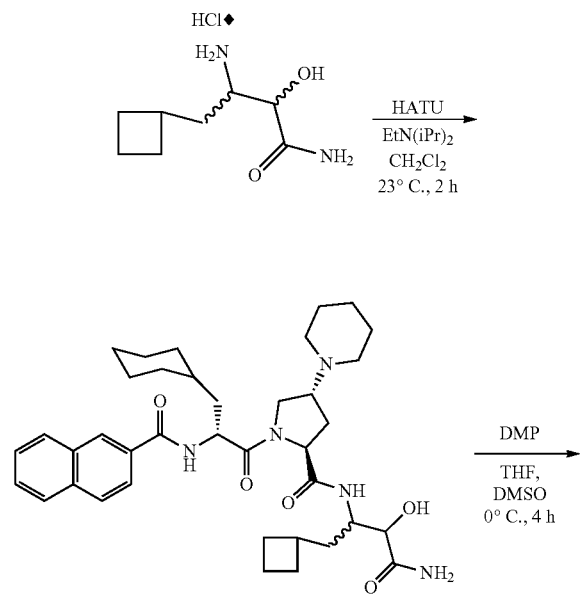

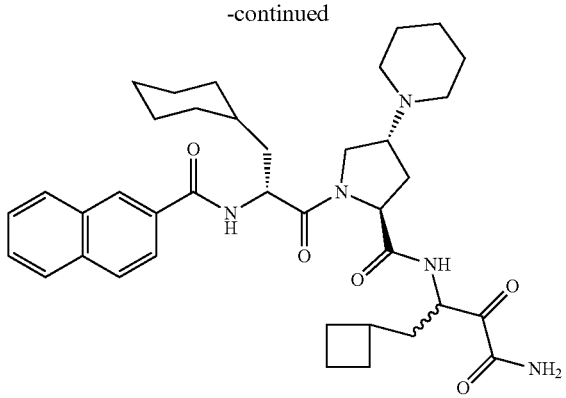

Example 7

Step 1: Preparation of (2S,4R)-1-((R)-2-(2-naphthamido)-3-cyclohexylpropanoyl)-N-(4-amino-1-cyclobutyl-3-hydroxy-4-oxobutan-2-yl)-4-(piperidin-1-yl)pyrrolidine-2-carboxamide Into a 50 mL round-bottom flask equipped with a magnetic stir bar and under nitrogen was added (2S,4R)-1-((R)-2-(2-naphthamido)-3-cyclohexylpropanoyl)-4-(piperidin-1-yl)pyrrolidine-2-carboxylic acid (Intermediate C, 200 mg, 0.40 mol, 1.0 equiv), 3-amino-4-cyclobutyl-2-hydroxybutanamide hydrochloride (99 mg, 0.48 mmol, 1.2 equiv), HATU (183 mg, 0.59 mmol, 1.5 equiv) and CH$_2$Cl$_2$ (2 mL). The reaction mixture was stirred at room temperature for 2 h and then quenched with sat. aqueous NaHCO$_3$ (5 mL). The mixture was extracted with CH$_2$Cl$_2$ (2×5 mL) using a phase-separatory cartridge. The combined organic layers were concentrated under reduced pressure. Purification by column chromatography through silica gel (12 g), eluting with 100:0 to 80:20 CH$_2$Cl$_2$:MeOH as a gradient afforded the title compound as a beige foam (268 mg).

Step 2: Preparation of (2S,4R)-1-((R)-2-(2-naphthamido)-3-cyclohexylpropanoyl)-N-(4-amino-1-cyclobutyl-3,4-dioxobutan-2-yl)-4-(piperidin-1-yl)pyrrolidine-2-carboxamide A flask was charged with (2S,4R)-1-((R)-2-(2-naphthamido)-3-cyclohexylpropanoyl)-N-(4-amino-1-cyclobutyl-3-hydroxy-4-oxobutan-2-yl)-4-(piperidin-1-yl)pyrrolidine-2-carboxamide (268 mg, 0.41 mmol, 1.0 equiv), THF (5 mL) and DMSO (500 L). The reaction mixture was cooled to 0° C. in an ice bath and treated with Dess-Martin Periodinane (516 mg, 1.22 mmol, 3 equiv). The reaction mixture was stirred at 0° C. for 4 h until LCMS analysis revealed complete conversion of starting material. The reaction mixture was quenched with 10% aqueous Na$_2$S$_2$O$_8$ solution (5 mL) and extracted with EtOAc (30 mL). The organic layer was further washed with sat. aqueous NaHCO$_3$ solution (10 mL), dried over MgSO$_4$, filtered and concentrated under reduced pressure. Purification by column chromatography through silica gel (24 g), eluting with 100:0 to 80:20 CH$_2$Cl$_2$:MeOH as a gradient afforded the title compound as a beige foam (85 mg). MS (ESI+) 658 (M+1)$^{\oplus}$ Examples 8 and 9 were prepared in a similar fashion as Example 7, using 3-amino-2-hydroxy-4-methylhexanamide (Example 8—see WO 2008106139 A1 for a similar preparation) or 3-amino-2-hydroxy-4-phenylbutanamide (Example 9—commercial reagent) in place of 3-amino-4-cyclobutyl-2-hydroxybutanamide hydrochloride in step 1.

| Example | Structure | MW | MS (ESI+) |
|---|---|---|---|
| 8 | (2S,4R)-1-((R)-2-(2-naphthamido)-3-cyclohexylpropanoyl)-N-(1-amino-4-methyl-1,2-dioxohexan-3-yl)-4-(piperidin-1-yl)pyrrolidine-2-carboxamide | 645.85 | 646 (M + 1)⊕ |
| 9 | (2S,4R)-1-((R)-2-(2-naphthamido)-3-cyclohexylpropanoyl)-N-(4-amino-3,4-dioxo-1-phenylbutan-2-yl)-4-(piperidin-1-yl)pyrrolidine-2-carboxamide | 679.86 | 680 (M + 1)⊕ |

Example 10: (2S,4S)-1-((R)-2-(2-Naphthamido)-3-cyclohexylpropanoyl)-N-(4-amino-1-cyclobutyl-3,4-dioxobutan-2-yl)-4-(piperidin-1-yl)pyrrolidine-2-carboxamide

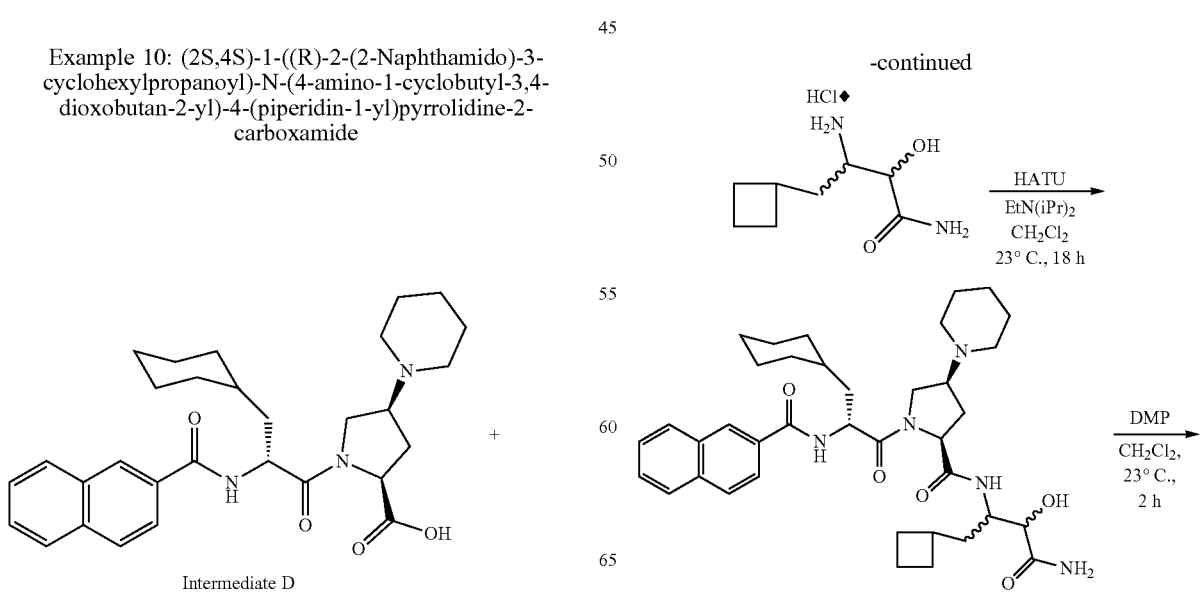

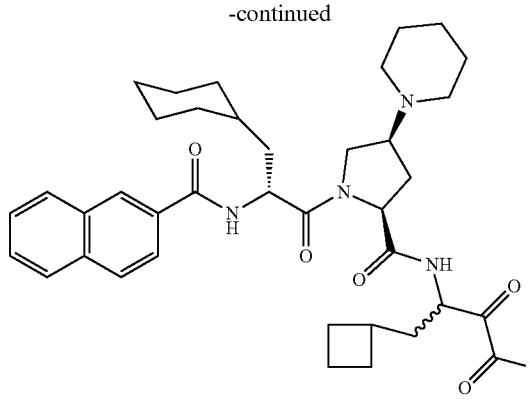

Example 10

Step 1: Preparation of (2S,4S)-1-((R)-2-(2-naphthamido)-3-cyclohexylpropanoyl)-N-(4-amino-1-cyclobutyl-3-hydroxy-4-oxobutan-2-yl)-4-(piperidin-1-yl)pyrrolidine-2-carboxamide Into a 20 mL vial equipped with a teflon septa, a magnetic stir bar and under nitrogen was added (2S,4S)-1-((R)-2-(2-naphthamido)-3-cyclohexylpropanoyl)-4-(piperidin-1-yl)pyrrolidine-2-carboxylic acid (Intermediate D, 1.0 g, 1.98 mmol, 1.0 equiv), 3-amino-4-cyclobutyl-2-hydroxybutanamide hydrochloride (417 mg, 1.98 mmol, 1.0 equiv), HATU (1.13 g, 2.97 mmol, 1.5 equiv) and CH$_2$Cl$_2$ (5 mL). The reaction mixture was treated with EtN(iPr)$_2$ (700 µL, 4.0 mmol, 2.0 equiv) and stirred at room temperature for 18 h overnight. The reaction mixture was quenched with sat. aqueous NaHCO$_3$ (40 mL) and extracted with CH$_2$Cl$_2$ (3×25 mL) using a phase-separatory cartridge. The combined organic layers were concentrated under reduced pressure. Purification by column chromatography through silica gel (50 g), eluting with 100:0 to 85:15 CH$_2$Cl$_2$:MeOH as a gradient afforded the desired product as a beige film (129 mg).

Step 2: Preparation of (2S,4S)-1-((R)-2-(2-naphthamido)-3-cyclohexylpropanoyl)-N-(4-amino-1-cyclobutyl-3,4-dioxobutan-2-yl)-4-(piperidin-1-yl)pyrrolidine-2-carboxamide Into a 25 mL round-bottom flask equipped with a magnetic stir bar and under nitrogen was added (2S,4S)-1-((R)-2-(2-naphthamido)-3-cyclohexylpropanoyl)-N-(4-amino-1-cyclobutyl-3-hydroxy-4-oxobutan-2-yl)-4-(piperidin-1-yl)pyrrolidine-2-carboxamide (120 mg, 0.182 mmol, 1.0 equiv) and CH$_2$Cl$_2$ (2 mL). The solution was treated with Dess-Martin Periodinane (93 mg, 0.22 mmol, 1.2 equiv) and stirred at room temperature for 2 h. The reaction mixture was quenched with sat. aqueous NaHCO$_3$ solution (5 mL) and 10% aqueous Na$_2$S$_2$O$_8$ solution (5 mL). The reaction mixture was extracted with CH$_2$Cl$_2$ (3×5 mL) using a phase-separatory cartridge and the combined organic layers were concentrated under reduced pressure. Purification by reverse-phase column chromatography (13 g C18 column) eluting with 90:10 to 20:80 H$_2$O:MeCN+0.1% HCO$_2$H as a gradient. The desired fractions were concentrated, dissolved in CH$_2$Cl$_2$ (5 mL) and washed with sat. aqueous NaHCO$_3$ solution (2×5 mL). The organic layer was concentrated under reduced pressure to afford the title compound as a foam (18 mg). MS (ESI+) 659 (M+1)$^{\oplus}$ Example 11: (2S,4S)-1-((R)-2-(2-Naphthamido)-3-cyclohexylpropanoyl)-N-(1-amino-7-(3-cyclopropylureido)-1,2-dioxoheptan-3-yl)-4-(5-(2-hydroxypropan-2-yl)-1H-1,2,3-triazol-1-yl)pyrrolidine-2-carboxamide

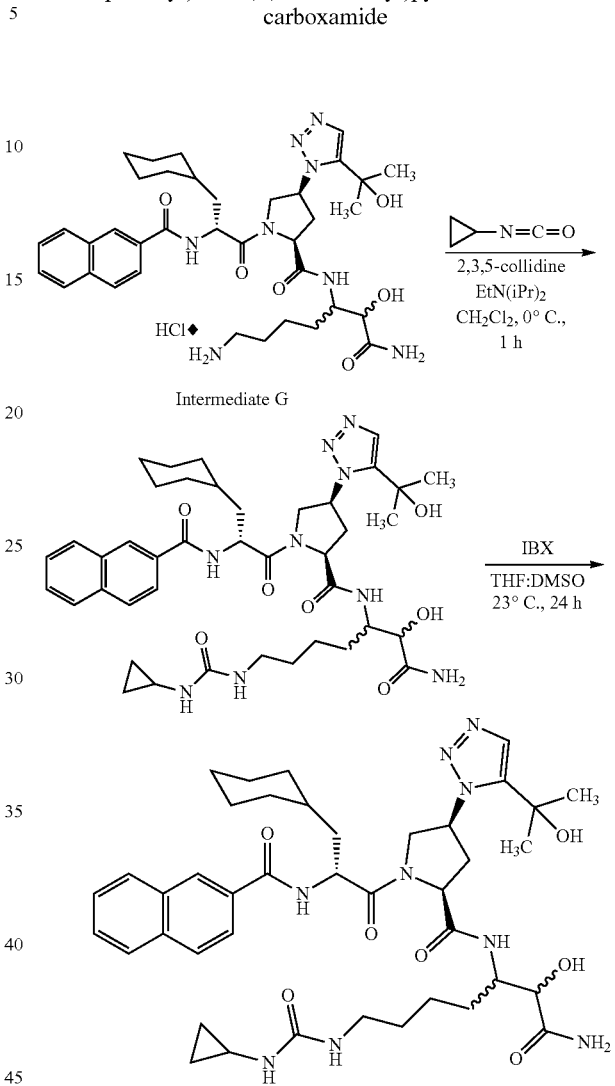

Example 11

Step 1: Preparation of (2S,4S)-1-((R)-2-(2-naphthamido)-3-cyclohexylpropanoyl)-N-(1-amino-7-(3-cyclopropylureido)-2-hydroxy-1-oxoheptan-3-yl)-4-(5-(2-hydroxypropan-2-yl)-1H-1,2,3-triazol-1-yl)pyrrolidine-2-carboxamide Into a 100 mL round-bottom flask equipped with a magnetic stir bar and under nitrogen was added (2S,4S)-1-((R)-2-(2-naphthamido)-3-cyclohexylpropanoyl)-N-(1,7-diamino-2-hydroxy-1-oxoheptan-3-yl)-4-(5-(2-hydroxypropan-2-yl)-1H-1,2,3-triazol-1-yl)pyrrolidine-2-carboxamide hydrochloride (Intermediate G, 8.22 g, 11.2 mmol, 1.0 equiv) and CH$_2$Cl$_2$ (140 mL). The solution was cooled to 0° C. and 2,3,5-collidine (2.93 mL, 22.5 mmol, 2 equiv) and EtN(iPr)$_2$ (3.93 mL, 22.5 mmol, 2 equiv) were added followed by isocyanotocyclopropane (1.03 mL, 12.4 mmol, 1.1 equiv). The solution was stirred at 0° C. for 1 h and then quenched with 0.5 M aqueous HCl solution (200 mL) and extracted with CH$_2$Cl$_2$ (6×100 mL) using a 500 mL separatory funnel. The combined organic layers were washed with brine (100 mL), dried over MgSO$_4$, filtered and concentrated under reduced pressure. Purification by column chromatography through silica gel (330 g), eluting with 100:0 to 85:15 CH$_2$Cl$_2$:MeOH as a gradient afforded the title compound as a foam (6.44 g).

Step 2: Preparation of (2S,4S)-1-((R)-2-(2-naphthamido)-3-cyclohexylpropanoyl)-N-(1-amino-7-(3-cyclopropylureido)-1,2-dioxoheptan-3-yl)-4-(5-(2-hydroxypropan-2-yl)-1H-1,2,3-triazol-1-yl)pyrrolidine-2-carboxamide Into a 100 mL round-bottom flask equipped with a magnetic stir bar and under nitrogen was added (2S,4S)-1-((R)-2-(2-naphthamido)-3-cyclohexylpropanoyl)-N-(1-amino-7-(3-cyclopropylureido)-2-hydroxy-1-oxoheptan-3-yl)-4-(5-(2-hydroxypropan-2-yl)-1H-1,2,3-triazol-1-yl)pyrrolidine-2-carboxamide (1.50 g, 1.9 mmol, 1.0 equiv), THF (8 mL) and DMSO (2 mL). The solution was treated with 45 wt % IBX (2.37 g, 3.8 mmol, 2.0 equiv) and the white suspension was stirred at room temperature for 18 h overnight. The reaction mixture was quenched with 10% aqueous Na$_2$S$_2$O$_8$ solution (50 mL) and poured into a 250 mL separatory funnel containing water (75 mL) and extracted with CH$_2$Cl$_2$ (3×50 mL). The combined organic layers were washed with brine (50 mL), dried over MgSO$_4$, filtered and concentrated under reduced pressure. Purification by column chromatography through silica gel (120 g), eluting with 100:0 to 85:15 EtOAc:MeOH as a gradient afforded the title compound as a white foam (584 mg). MS (ESI+) 786 (M+1)$^⊕$ 1H NMR (CD3OD, 300 MHz): δ 8.23-8.19 (1H, m), 8.00-7.89 (4H, m), 7.62-7.45 (3H, m), 5.84-5.78 (1H, m), 5.28-5.18 (1H, m), 4.66-4.43 (1H, m), 4.40-4.06 (2H, m), 3.18-2.97 (4H, m), 2.40-2.19 (1H, m), 1.97-0.36 (30H, m) ppm.

Example 12: (2S,4S)-1-((R)-2-(2-naphthamido)-3-cyclohexylpropanoyl)-N-(1-amino-7-(3-isobutylureido)-1,2-dioxoheptan-3-yl)-4-(5-(2-hydroxypropan-2-yl)-1H-1,2,3-triazol-1-yl)pyrrolidine-2-carboxamide

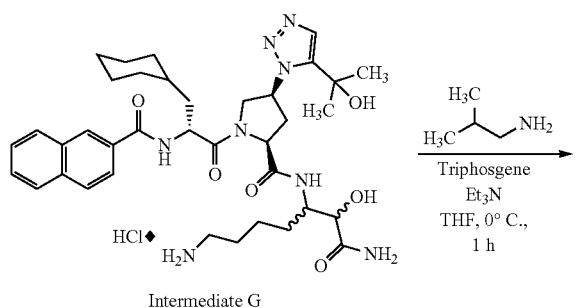

Intermediate G

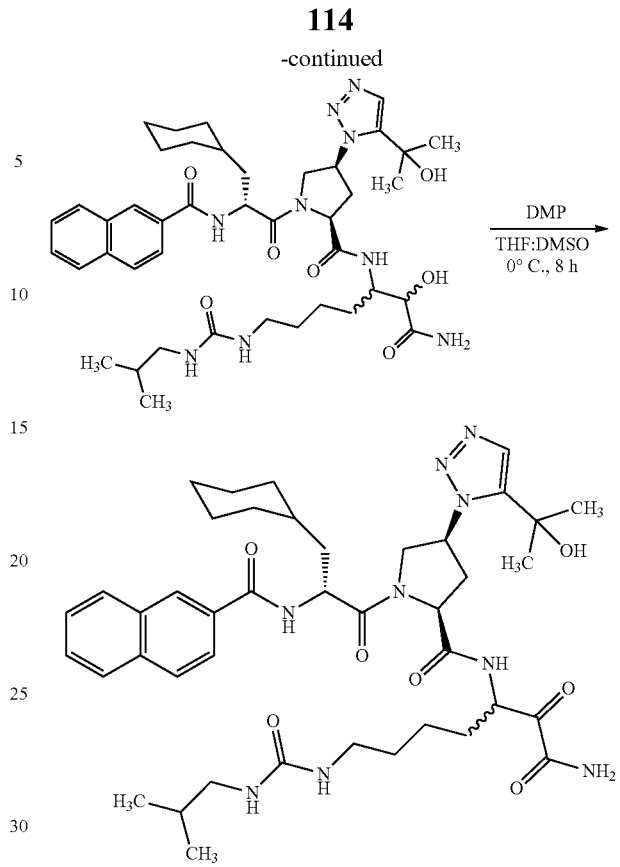

Example 12

Step 1: Preparation of (2S,4S)-1-((R)-2-(2-naphthamido)-3-cyclohexylpropanoyl)-N-(1-amino-2-hydroxy-7-(3-isobutylureido)-1-oxoheptan-3-yl)-4-(5-(2-hydroxypropan-2-yl)-1H-1,2,3-triazol-1-yl)pyrrolidine-2-carboxamide Into a 20 mL sample vial equipped with a magnetic stir bar and under nitrogen was added isobutyl amine (36.9 mg, 0.5 mmol, 11 equiv) and THF (10 mL). The solution was cooled to 0° C. in an ice bath and triphosgene (45.3 mg, 0.17 mmol, 3 equiv) was added followed by Et$_3$N (200 μL, 1.4 mmol, 2.8 equiv). The solution was stirred at 0° C. for 1 h to afford the unpurified isocyanate.

A separate 20 mL sample vial containing (2S,4S)-1-((R)-2-(2-naphthamido)-3-cyclohexylpropanoyl)-N-(1,7-diamino-2-hydroxy-1-oxoheptan-3-yl)-4-(5-(2-hydroxypropan-2-yl)-1H-1,2,3-triazol-1-yl)pyrrolidine-2-carboxamide (Intermediate G, 34 mg, 0.046 mmol, 1.0 equiv), Et$_3$N (20 μL, 0.138 mmol, 3 equiv) and THF (2 mL) was cooled to 0° C. in an ice bath. A 1.0 mL portion of the isocyanate prepared above (1.0 mL=0.050 mmol, 1.1 equiv) was added to the vial and the mixture was stirred at 0° C. for 1 h. The reaction was quenched with water (10 mL) and extracted with EtOAc (2×30 mL). The combined organic layers were dried over MgSO$_4$, filtered and concentrated under reduced pressure. Purification by column chromatography through silica gel (10 g), eluting with 100:0 to 80:20 EtOAc:MeOH as a gradient afforded the title compound (17 mg).

Step 2: Preparation of (2S,4S)-1-((R)-2-(2-naph-thamido)-3-cyclohexylpropanoyl)-N-(1-amino-7-(3-isobutylureido)-1,2-dioxoheptan-3-yl)-4-(5-(2-hydroxypropan-2-yl)-1H-1,2,3-triazol-1-yl)pyrrolidine-2-carboxamide Into a 20 mL sample vial equipped with a magnetic stir bar and under nitrogen was added (2S,4S)-1-((R)-2-(2-naphthamido)-3-cyclohexylpropanoyl)-N-(1-amino-2-hydroxy-7-(3-isobutylureido)-1-oxoheptan-3-yl)-4-(5-(2-hydroxypropan-2-yl)-1H-1,2,3-triazol-1-yl)pyrrolidine-2-carboxamide (17 mg, 0.021 mmol, 1.0 equiv), THF (4 mL) and DMSO (0.5 mL). The solution was treated with Dess-Martin Periodinane (54 mg, 0.126 mmol, 6.0 equiv) and the reaction was stirred at 0° C. for 8 h. The reaction was quenched with 10% aqueous $Na_2S_2O_3$ solution (2 mL) and stirred at room temperature for 30 minutes. The reaction mixture was diluted with water (5 mL) and extracted with EtOAc (25 mL). The organic layer was washed with water (5 mL), dried over $MgSO_4$, filtered and concentrated under reduced pressure. Purification by column chromatography through silica gel (10 g), eluting with 100:0 to 75:25 EtOAc:MeOH as a gradient afforded the title compound as an off-white foam (6.1 mg). MS (ESI+) 802 (M+1)$^\oplus$ Examples 13-29 were prepared in a similar manner as Example 12, using the appropriate amine in Step 1 for formation of the isocyanate. In the case of Example 13, the corresponding cyclohexylisocyanate was purchased commercially. In the case of Example 15, the corresponding ethylisocyanate was purchased commercially. In the case of Example 20, tetrahydro-2H-thiopyran-4-amine was used as the amine in step 1, and oxidation to the sulfoxide occurred during the DMP oxidation of step 2. For Example 21, the DMP oxidation step reaction time was reduced to 1 h in order to isolate the sulfide. For Example 29, trifluoromethanesulfonyl chloride was used in place of an isocyanate.

| Example | Structure | MW | MS (ESI+) |
|---|---|---|---|
| 13 | (2S,4S)-1-((R)-2-(2-naphthamido)-3-cyclohexylpropanoyl)-N-(1-amino-7-(3-cyclohexylureido)-1,2-dioxoheptan-3-yl)-4-(5-(2-hydroxypropan-2-yl)-1H-1,2,3-triazol-1-yl)pyrrolidine-2-carboxamide | 828.03 | 829 (M + 1)$^\oplus$ |
| 14 | (2S,4S)-1-((R)-2-(2-naphthamido)-3-cyclohexylpropanoyl)-N-(1-amino-1,2-dioxo-7-(3-(pyridin-4-yl)ureido)heptan-3-yl)-4-(5-(2-hydroxypropan-2-yl)-1H-1,2,3-triazol-1-yl)pyrrolidine-2-carboxamide | 822.97 | 823 (M + 1)$^\oplus$ |

| Example | Structure | MW | MS (ESI+) |
|---|---|---|---|
| 15 | (2S,4S)-1-((R)-2-(2-naphthamido)-3-cyclohexylpropanoyl)-N-(1-amino-7-(3-ethylureido)-1,2-dioxoheptan-3-yl)-4-(5-(2-hydroxypropan-2-yl)-1H-1,2,3-triazol-1-yl)pyrrolidine-2-carboxamide | 773.94 | 774 $(M+1)^{\oplus}$ |
| 16 | (2S,4S)-1-((R)-2-(2-naphthamido)-3-cyclohexylpropanoyl)-N-(1-amino-7-(3-(1-methyl-1H-pyrazol-3-yl)ureido)-1,2-dioxoheptan-3-yl)-4-(5-(2-hydroxypropan-2-yl)-1H-1,2,3-triazol-1-yl)pyrrolidine-2-carboxamide | 825.97 | 826 $(M+1)^{\oplus}$ |
| 17 | (2S,4S)-1-((R)-2-(2-naphthamido)-3-cyclohexylpropanoyl)-N-(1-amino-7-(3-(isoxazol-3-yl)ureido)-1,2-dioxoheptan-3-yl)-4-(5-(2-hydroxypropan-2-yl)-1H-1,2,3-triazol-1-yl)pyrrolidine-2-carboxamide | 812.93 | 813 $(M+1)^{\oplus}$ |

| Example | Structure | MW | MS (ESI+) |
|---|---|---|---|
| 18 | 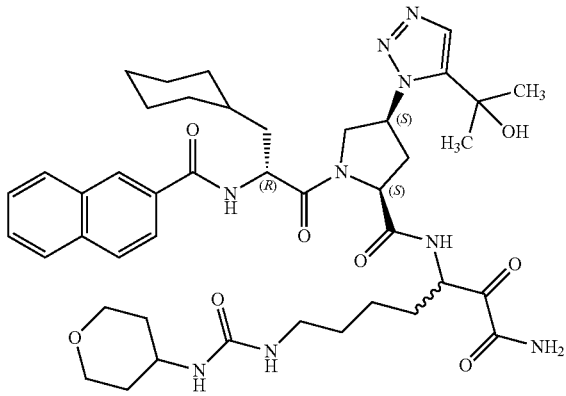<br>(2S,4S)-1-((R)-2-(2-naphthamido)-3-cyclohexylpropanoyl)-N-(1-amino-1,2-dioxo-7-(3-(tetrahydro-2H-pyran-4-yl)ureido)heptan-3-yl)-4-(5-(2-hydroxypropan-2-yl)-1H-1,2,3-triazol-1-yl)pyrrolidine-2-carboxamide | 830.00 | 830 $(M + 1)^{\oplus}$ |
| 19 | 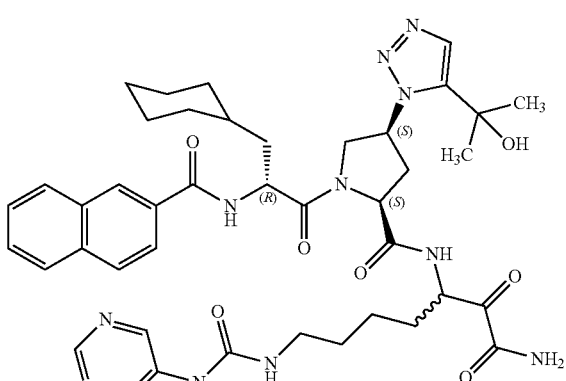<br>(2S,4S)-1-((R)-2-(2-naphthamido)-3-cyclohexylpropanoyl)-N-(1-amino-1,2-dioxo-7-(3-(pyrimidin-5-yl)ureido)heptan-3-yl)-4-(5-(2-hydroxypropan-2-yl)-1H-1,2,3-triazol-1-yl)pyrrolidine-2-carboxamide | 823.96 | 824 $(M + 1)^{\oplus}$ |
| 20 | 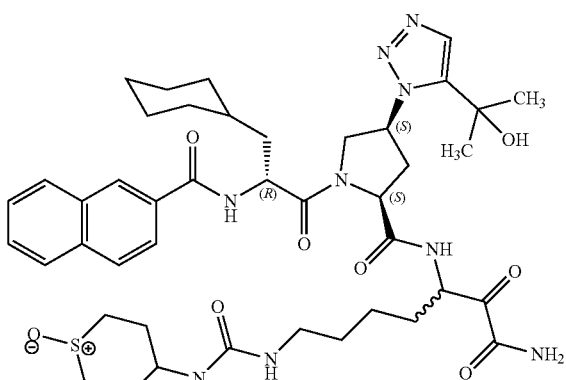<br>(2S,4S)-1-((R)-2-(2-naphthamido)-3-cyclohexylpropanoyl)-N-(1-amino-7-(3-(1-oxidotetrahydro-2H-thiopyran-4-yl)ureido)-1,2-dioxoheptan-3-yl)-4-(5-(2-hydroxypropan-2-yl)-1H-1,2,3-triazol-1-yl)pyrrolidine-2-carboxamide | 862.06 | 862 $(M + 1)^{\oplus}$ |

-continued

| Example | Structure | MW | MS (ESI+) |
|---|---|---|---|
| 21 | (2S,4S)-1-((R)-2-(2-naphthamido)-3-cyclohexylpropanoyl)-N-(1-amino-1,2-dioxo-7-(3-(tetrahydro-2H-thiopyran-4-yl)ureido)heptan-3-yl)-4-(5-(2-hydroxypropan-2-yl)-1H-1,2,3-triazol-1-yl)pyrrolidine-2-carboxamide | 846.06 | 846 $(M + 1)^\oplus$ |
| 22 | (2S,4S)-1-((R)-2-(2-naphthamido)-3-cyclohexylpropanoyl)-N-(1-amino-1,2-dioxo-7-(3-(pyridin-3-yl)ureido)heptan-3-yl)-4-(5-(2-hydroxypropan-2-yl)-1H-1,2,3-triazol-1-yl)pyrrolidine-2-carboxamide | 822.97 | 823 $(M + 1)^\oplus$ |
| 23 | (2S,4S)-1-((R)-2-(2-naphthamido)-3-cyclohexylpropanoyl)-N-(1-amino-1,2-dioxo-7-(3-(pyridin-2-yl)ureido)heptan-3-yl)-4-(5-(2-hydroxypropan-2-yl)-1H-1,2,3-triazol-1-yl)pyrrolidine-2-carboxamide | 822.97 | 823 $(M + 1)^\oplus$ |

-continued

| Example | Structure | MW | MS (ESI+) |
|---|---|---|---|
| 24 | (2S,4S)-1-((R)-2-(2-naphthamido)-3-cyclohexylpropanoyl)-N-(1-amino-1,2-dioxo-7-(3-(prop-2-yn-1-yl)ureido)heptan-3-yl)-4-(5-(2-hydroxypropan-2-yl)-1H-1,2,3-triazol-1-yl)pyrrolidine-2-carboxamide | 783.93 | 784 (M + 1)$^{\oplus}$ |
| 25 | (2S,4S)-1-((R)-2-(2-naphthamido)-3-cyclohexylpropanoyl)-N-(1-amino-7-(3-(5-(tert-butyl)isoxazol-3-yl)ureido)-1,2-dioxoheptan-3-yl)-4-(5-(2-hydroxypropan-2-yl)-1H-1,2,3-triazol-1-yl)pyrrolidine-2-carboxamide | 869.04 | 869 (M + 1)$^{\oplus}$ |
| 26 | (2S,4S)-1-((R)-2-(2-naphthamido)-3-cyclohexylpropanoyl)-N-(7-(3-allylureido)-1-amino-1,2-dioxoheptan-3-yl)-4-(5-(2-hydroxypropan-2-yl)-1H-1,2,3-triazol-1-yl)pyrrolidine-2-carboxamide | 785.95 | 787 (M + 1)$^{\oplus}$ |

-continued
| Example | Structure | MW | MS (ESI+) |
|---|---|---|---|
| 27 | 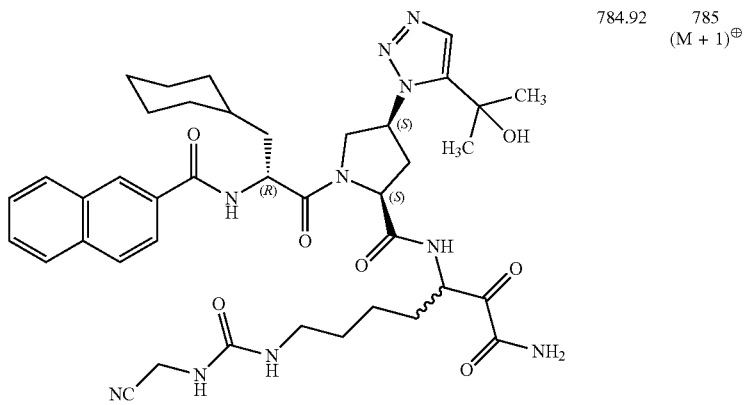<br>(2S,4S)-1-((R)-2-(2-naphthamido)-3-cyclohexylpropanoyl)-N-(1-amino-7-(3-(cyanomethyl)ureido)-1,2-dioxoheptan-3-yl)-4-(5-(2-hydroxypropan-2-yl)-1H-1,2,3-triazol-1-yl)pyrrolidine-2-carboxamide | 784.92 | 785 $(M + 1)^{\oplus}$ |
| 28 | 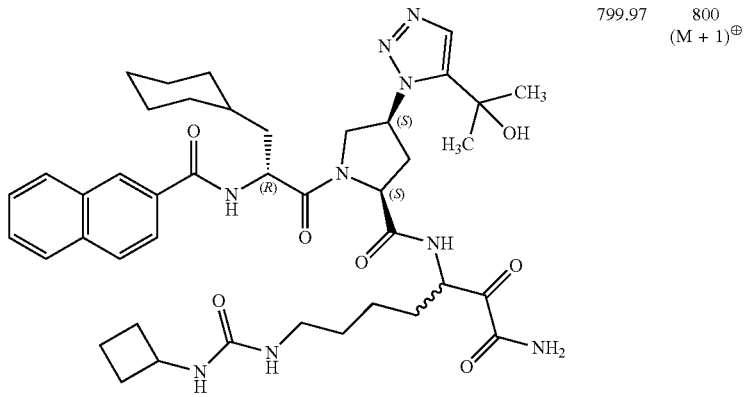<br>(2S,4S)-1-((R)-2-(2-naphthamido)-3-cyclohexylpropanoyl)-N-(1-amino-7-(3-cyclobutylureido)-1,2-dioxoheptan-3-yl)-4-(5-(2-hydroxypropan-2-yl)-1H-1,2,3-triazol-1-yl)pyrrolidine-2-carboxamide | 799.97 | 800 $(M + 1)^{\oplus}$ |

| Example | Structure | MW | MS (ESI+) |
|---|---|---|---|
| 29 | 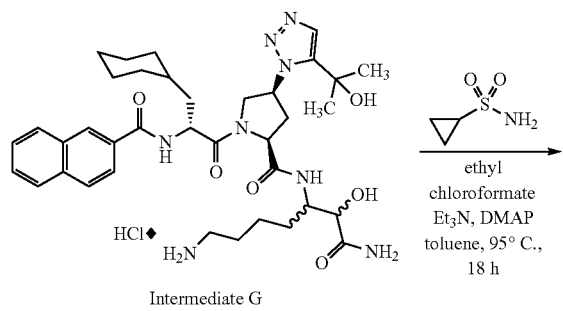 (2S,4S)-1-((R)-2-(2-naphthamido)-3-cyclohexylpropanoyl)-N-(1-amino-1,2-dioxo-7-((trifluoromethyl)sulfonamido)heptan-3-yl)-4-(5-(2-hydroxypropan-2-yl)-1H-1,2,3-triazol-1-yl)pyrrolidine-2-carboxamide | 834.91 | 835 $(M + 1)^{\oplus}$ |

Example 30: (2S,4S)-1-((R)-2-(2-Naphthamido)-3-cyclohexylpropanoyl)-N-(1-amino-7-(3-(cyclopropylsulfonyl)ureido)-1,2-dioxoheptan-3-yl)-4-(5-(2-hydroxypropan-2-yl)-1H-1,2,3-triazol-1-yl)pyrrolidine-2-carboxamide

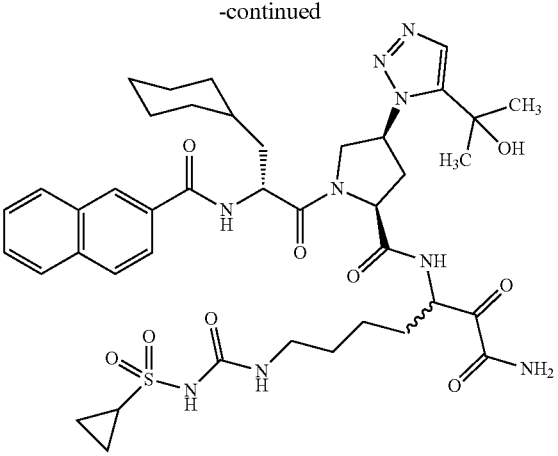

Example 30

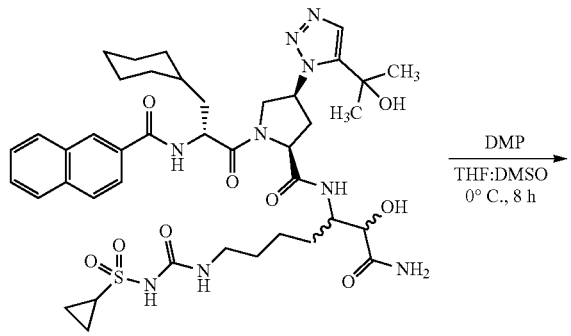

Step 1: Preparation of (2S,4S)-1-((R)-2-(2-naphthamido)-3-cyclohexylpropanoyl)-N-(1-amino-7-(3-(cyclopropylsulfonyl)ureido)-2-hydroxy-1-oxoheptan-3-yl)-4-(5-(2-hydroxypropan-2-yl)-1H-1,2,3-triazol-1-yl)pyrrolidine-2-carboxamide Into a 20 mL sample vial equipped with a magnetic stir bar and under nitrogen was added cyclopropyl sulfonamide (121 mg, 1.0 mmol, 15 equiv), Et₃N (430 μL, 3.0 mmol, 45 equiv) and CH₂Cl₂ (6 mL). The reaction mixture was cooled to 0° C. and ethyl chloroformate (170 μL, 1.7 mmol, 26 equiv) was added. The mixture was warmed to room temperature and stirred for 2 h. The reaction was quenched with water (5 mL) and acidified to pH z 4 with dropwise addition of glacial acetic acid. The organic layer was removed and concentrated under reduced pressure. The resulting oil was dissolved in toluene (3 mL) and to this was added (2S,4S)-1-((R)-2-(2-naphthamido)-3-cyclohexylpropanoyl)-N-(1,7-diamino-2-hydroxy-1-oxoheptan-3-yl)-4-(5-(2-hydroxypropan-2-yl)-1H-1,2,3-triazol-1-yl)pyrrolidine-2-carboxamide (Intermediate G, 50 mg, 0.07 mmol, 1.0 equiv), DMAP (200 mg) and the resulting mixture was heated to 95° C. in an oil bath for 18 h overnight. The reaction mixture was cooled to room temperature and quenched with water (5 mL). The aqueous layer was washed with EtOAc (2×2 mL). The resulting aqueous layer was acidified to pH<1 with 1 M aqueous HCl solution and extracted with CH$_2$Cl$_2$ (2×2 mL). The CH$_2$Cl$_2$ layers were concentrated under reduced pressure to provide the title compound (14 mg).

Step 2: Preparation of (2S,4S)-1-((R)-2-(2-naphthamido)-3-cyclohexylpropanoyl)-N-(1-amino-7-(3-(cyclopropylsulfonyl)ureido)-1,2-dioxoheptan-3-yl)-4-(5-(2-hydroxypropan-2-yl)-1H-1,2,3-triazol-1-yl)pyrrolidine-2-carboxamide Into a 20 mL sample vial equipped with a magnetic stir bar and under nitrogen was added (2S,4S)-1-((R)-2-(2-naphthamido)-3-cyclohexylpropanoyl)-N-(1-amino-7-(3-(cyclopropylsulfonyl)ureido)-2-hydroxy-1-oxoheptan-3-yl)-4-(5-(2-hydroxypropan-2-yl)-1H-1,2,3-triazol-1-yl)pyrrolidine-2-carboxamide (14 mg, 0.016 mmol, 1.0 equiv), THF (4 mL) and DMSO (0.5 mL). The solution was treated with Dess-Martin Periodinane (50 mg, 0.120 mmol, 7.5 equiv) and the reaction was stirred at 0° C. for 8 h. The reaction was quenched with 10% aqueous Na$_2$S$_2$O$_3$ solution (2 mL) and stirred at room temperature for 30 minutes. The reaction mixture was diluted with water (5 mL) and extracted with EtOAc (25 mL). The organic layer was washed with water (5 mL), dried over MgSO$_4$, filtered and concentrated under reduced pressure. Purification by column chromatography through silica gel (12 g), eluting with 100:0 to 75:25 CH$_2$Cl$_2$:MeOH as a gradient afforded the title compound as an off-white foam (2 mg). MS (ESI+) 851 (M+1)$^⊕$ Example 31: Benzyl (5-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate

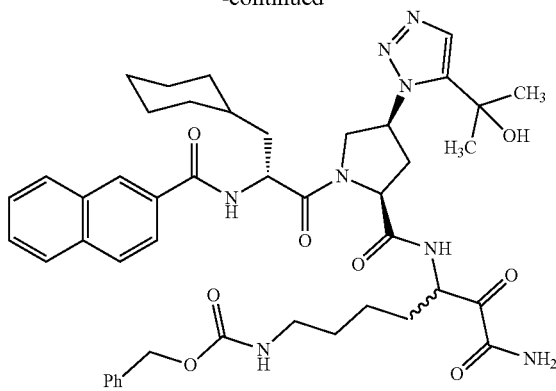

Example 31

Into a 20 mL sample vial equipped with a magnetic stir bar and under nitrogen was added benzyl (5-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-7-amino-6-hydroxy-7-oxoheptyl)carbamate (Intermediate G, Step 2, 60 mg, 0.070 mmol, 1.0 equiv), THF (4 mL) and DMSO (0.5 mL). The solution was treated with Dess-Martin Periodinane (180 mg, 0.42 mmol, 6 equiv) and the reaction was stirred at 0° C. for 8 h. The reaction was quenched with 10% aqueous Na$_2$S$_2$O$_3$ solution (2 mL) and stirred at room temperature for 30 minutes. The reaction mixture was diluted with water (5 mL) and extracted with EtOAc (25 mL). The organic layer was washed with water (5 mL), dried over MgSO$_4$, filtered and concentrated under reduced pressure. Purification by column chromatography through silica gel (12 g), eluting with 100:0 to 75:25 CH$_2$Cl$_2$:MeOH as a gradient afforded the title compound as an off-white foam (35 mg). MS (ESI+) 837 (M+1)$^⊕$ Example 32: Benzyl (5-((2S,4S)-1-((R)-2-(2-naphthamido)-3-cyclohexylpropanoyl)-4-(4-(2-hydroxypropan-2-yl)-1H-1,2,3-triazol-1-yl)pyrrolidine-2-carboxamido)-7-amino-6,7-dioxoheptyl)carbamate

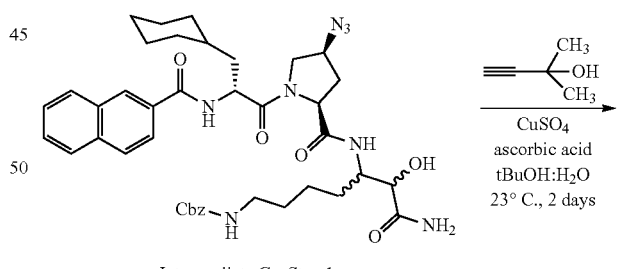

Intermediate G - Step 1

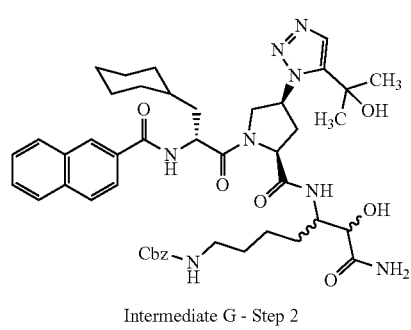

Intermediate G - Step 2

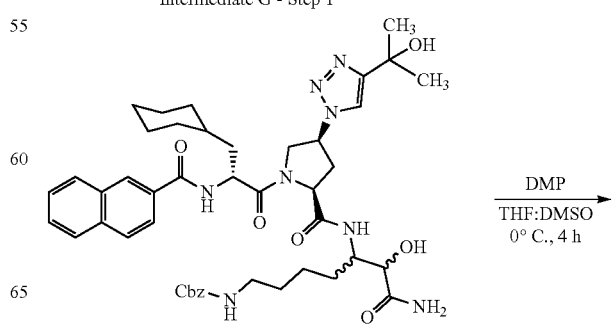

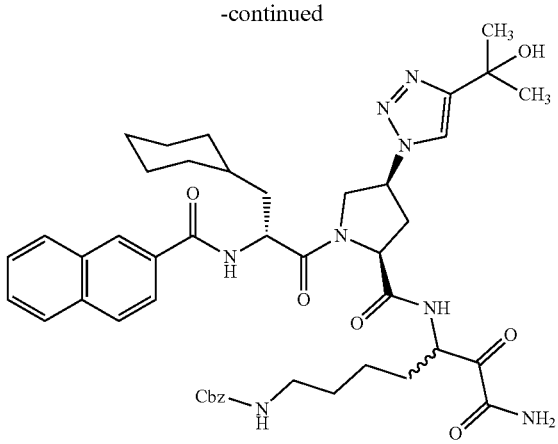

Example 32

Step 1: Preparation of benzyl (5-((2S,4S)-1-((R)-2-(2-naphthamido)-3-cyclohexylpropanoyl)-4-(4-(2-hydroxypropan-2-yl)-1H-1,2,3-triazol-1-yl)pyrrolidine-2-carboxamido)-7-amino-6-hydroxy-7-oxoheptyl)carbamate Into a 20 mL sample vial equipped with a magnetic stir bar and under nitrogen was added benzyl (5-((2S,4S)-1-((R)-2-(2-naphthamido)-3-cyclohexylpropanoyl)-4-azidopyrrolidine-2-carboxamido)-7-amino-6-hydroxy-7-oxoheptyl)carbamate (Intermediate G, Step 1, 242 mg, 0.32 mmol, 1.0 equiv), $CuSO_4$ (10 mg, 0.06 mmol, 0.2 equiv), L-ascorbic acid (56 mg, 0.32 mmol, 1 equiv), t-BuOH (2 mL) and water (2 mL). The mixture was treated with 2-methyl-3-butyn-2-ol (78 μL, 0.80 mmol, 2.5 equiv) and the suspension was stirred at room temperature for 2 days. The reaction was quenched with water (10 mL) and extracted with EtOAc (4×5 mL) using a separatory funnel. The combined organic layers were washed with brine (10 mL), dried over $MgSO_4$, filtered and concentrated under reduced pressure. Purification by column chromatography through silica gel (12 g), eluting with 100:0 to 90:10 $CH_2Cl_2$:MeOH as a gradient afforded the desired compound as a foam (128 mg).

Step 2: Preparation of benzyl (5-((2S,4S)-1-((R)-2-(2-naphthamido)-3-cyclohexylpropanoyl)-4-(4-(2-hydroxypropan-2-yl)-1H-1,2,3-triazol-1-yl)pyrrolidine-2-carboxamido)-7-amino-6,7-dioxoheptyl)carbamate Into a 20 mL sample vial equipped with a magnetic stir bar and under nitrogen was added benzyl (5-((2S,4S)-1-((R)-2-(2-naphthamido)-3-cyclohexylpropanoyl)-4-(4-(2-hydroxypropan-2-yl)-1H-1,2,3-triazol-1-yl)pyrrolidine-2-carboxamido)-7-amino-6-hydroxy-7-oxoheptyl)carbamate (128 mg, 0.15 mmol, 1.0 equiv), THF (4 mL) and DMSO (1 mL). The solution was treated with Dess-Martin Periodinane (390 mg, 0.92 mmol, 6 equiv) and the reaction was stirred at 0° C. for 4 h. The reaction was quenched with 10% aqueous $Na_2S_2O_3$ solution (5 mL) and stirred at room temperature for 30 minutes. The reaction mixture was diluted with water (5 mL) and extracted with EtOAc (4×10 mL). The organic layer was washed with brine (10 mL), dried over $MgSO_4$, filtered and concentrated under reduced pressure. Purification by column chromatography through silica gel (12 g), eluting with 100:0 to 75:25 $CH_2Cl_2$:MeOH as a gradient afforded the title compound as an off-white foam (32 mg). MS (ESI−) 835 (M−1)$^\ominus$

Example 33: Benzyl (5-((2S,4R)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate

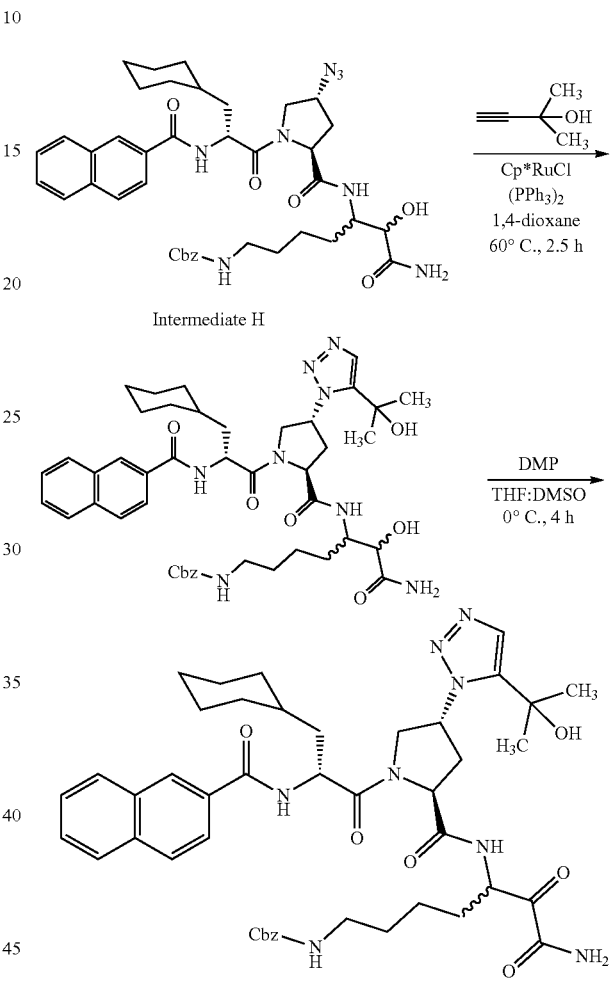

Example 33

Step 1: Preparation of benzyl (5-((2S,4R)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-7-amino-6-hydroxy-7-oxoheptyl)carbamate Into a 25 mL round-bottom flask equipped with a magnetic stir bar and under $N_2$ was added benzyl (5-((2S,4R)-1-((R)-2-(2-naphthamido)-3-cyclohexylpropanoyl)-4-azidopyrrolidine-2-carboxamido)-7-amino-6-hydroxy-7-oxoheptyl)carbamate (Intermediate H, 230 mg, 0.31 mmol, 1.0 equiv), 2-methyl-3-butyn-2-ol (118 μL, 1.22 mmol, 4 equiv) and Cp*RuCl(PPh$_3$)$_2$ (12 mg, 0.015 mmol, 0.05 equiv) in 1,4-dioxane (3 mL). The contents of the flask were purged with a steady flow of $N_2$ for 10 minutes and then the solution was heated to 60° C. in an oil bath for 2.5 h. The reaction was cooled to room temperature and loaded directly onto silica gel. Purification by column chromatography through silica gel (12 g), eluting with 100:0 to 90:10 CH₂Cl₂:MeOH as a gradient afforded the title compound as a tan foam (155 mg).

Step 2: Preparation of benzyl (5-((2S,4R)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate Into a 25 mL round-bottom flask equipped with a magnetic stir bar and under N₂ was added benzyl (5-((2S,4R)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-7-amino-6-hydroxy-7-oxoheptyl)carbamate (155 mg, 0.19 mmol, 1.0 equiv), THF (2 mL) and DMSO (0.6 mL). The solution was cooled to 0° C. in an ice bath and Dess-Martin Periodinane (470 mg, 1.1 mmol, 6 equiv) was added and the suspension stirred at 0° C. for 4 h. The reaction was quenched with 10% aqueous Na₂S₂O₃ solution (5 mL) and stirred at room temperature for 30 minutes. The reaction mixture was diluted with water (5 mL) and extracted with EtOAc (4×10 mL). The organic layer was washed with brine (10 mL), dried over MgSO₄, filtered and concentrated under reduced pressure. Purification by column chromatography through silica gel (12 g), eluting with 100:0 to 75:25 CH₂Cl₂:MeOH as a gradient afforded the title compound as an off-white foam (70 mg). MS (ESI+) 837 (M+1)⊕

Example 34: Benzyl (5-((2S,4R)-1-((R)-2-(2-naphthamido)-3-cyclohexylpropanoyl)-4-(4-(2-hydroxypropan-2-yl)-1H-1,2,3-triazol-1-yl)pyrrolidine-2-carboxamido)-7-amino-6,7-dioxoheptyl)carbamate

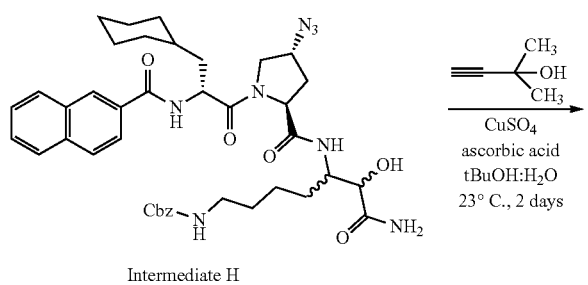

Intermediate H

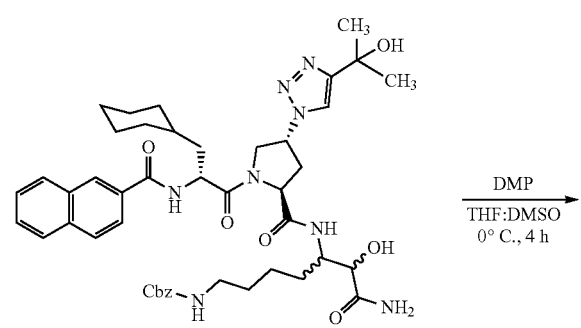

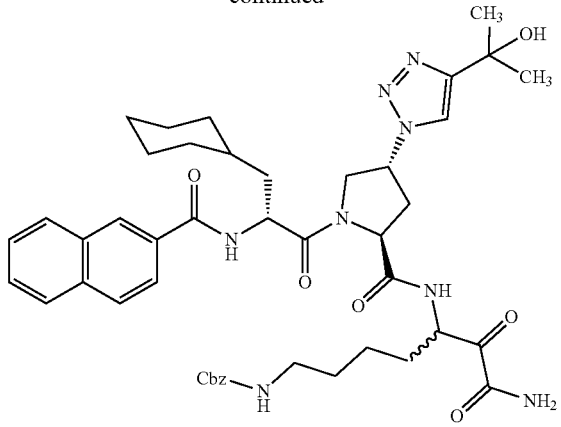

Example 34

Step 1: Preparation of benzyl (5-((2S,4R)-1-((R)-2-(2-naphthamido)-3-cyclohexylpropanoyl)-4-(4-(2-hydroxypropan-2-yl)-1H-1,2,3-triazol-1-yl)pyrrolidine-2-carboxamido)-7-amino-6-hydroxy-7-oxoheptyl)carbamate Into a 25 mL round-bottom flask equipped with a magnetic stir bar and under N₂ was added benzyl (5-((2S,4R)-1-((R)-2-(2-naphthamido)-3-cyclohexylpropanoyl)-4-azidopyrrolidine-2-carboxamido)-7-amino-6-hydroxy-7-oxoheptyl)carbamate (Intermediate H, 293 mg, 0.39 mmol, 1.0 equiv), 2-methyl-3-butyn-2-ol (90 μL, 0.97 mmol, 2.5 equiv), CuSO₄ (12 mg, 0.08 mmol, 0.2 equiv) and L-ascorbic acid (68 mg, 0.31 mmol, 0.8 equiv). The solids were taken up in t-BuOH (2 mL) and water (2 mL) and stirred at room temperature for 18 h overnight. LCMS revealed some starting material remained, so another portion of 2-methyl-3-butyn-2-ol (90 μL, 0.97 mmol, 2.5 equiv), CuSO₄ (12 mg, 0.08 mmol, 0.2 equiv) and L-ascorbic acid (68 mg, 0.31 mmol, 0.8 equiv) were added. The contents of the flask were stirred at room temperature for an additional 24 h. The reaction was quenched with water (10 mL) and extracted with EtOAc (4×10 mL) using a separatory funnel. The combined organic layers were washed with brine (10 mL), dried over MgSO₄, filtered and concentrated under reduced pressure. Purification by column chromatography through silica gel (12 g), eluting with 100:0 to 90:10 CH₂Cl₂:MeOH as a gradient afforded the desired compound as a foam (90 mg).

Step 2: Preparation of benzyl (5-((2S,4R)-1-((R)-2-(2-naphthamido)-3-cyclohexylpropanoyl)-4-(4-(2-hydroxypropan-2-yl)-1H-1,2,3-triazol-1-yl)pyrrolidine-2-carboxamido)-7-amino-6,7-dioxoheptyl)carbamate Into a 25 mL round-bottom flask equipped with a magnetic stir bar and under N₂ was added benzyl (5-((2S,4R)-1-((R)-2-(2-naphthamido)-3-cyclohexylpropanoyl)-4-(4-(2-hydroxypropan-2-yl)-1H-1,2,3-triazol-1-yl)pyrrolidine-2-carboxamido)-7-amino-6-hydroxy-7-oxoheptyl)carbamate (90 mg, 0.11 mmol, 1.0 equiv), THF (2.5 mL) and DMSO (1 mL). The solution was cooled to 0° C. in an ice bath and Dess-Martin Periodinane (273 mg, 0.64 mmol, 6 equiv) was added and the suspension stirred at 0° C. for 4 h. The reaction was quenched with 10% aqueous Na₂S₂O₃ solution (5 mL) and stirred at room temperature for 30 minutes. The reaction mixture was diluted with water (5 mL) and extracted with EtOAc (4×10 mL). The organic layer was washed with brine (10 mL), dried over MgSO$_4$, filtered and concentrated under reduced pressure. Purification by column chromatography through silica gel (12 g), eluting with 100:0 to 75:25 CH$_2$Cl$_2$:MeOH as a gradient afforded the title compound as an off-white foam (19 mg). MS (ESI−) 835 (M−1)$^{\ominus}$ Example 35: (2S,4S)-1-((R)-2-(2-Naphthamido)-3-cyclohexylpropanoyl)-N-(1-amino-1,2-dioxohex-5-en-3-yl)-4-(5-(2-hydroxypropan-2-yl)-1H-1,2,3-triazol-1-yl)pyrrolidine-2-carboxamide

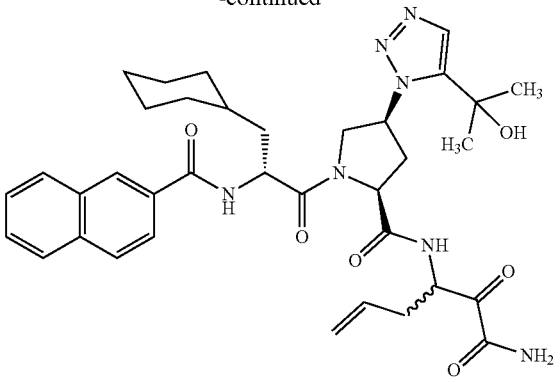

Example 35

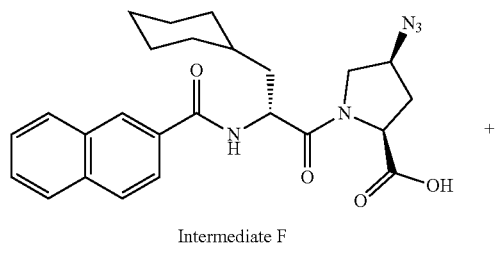

Intermediate F

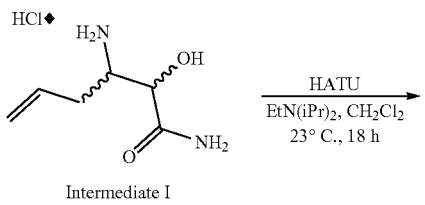

Intermediate I

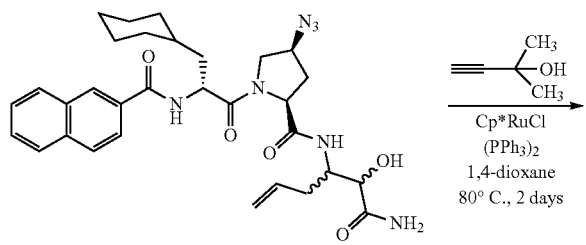

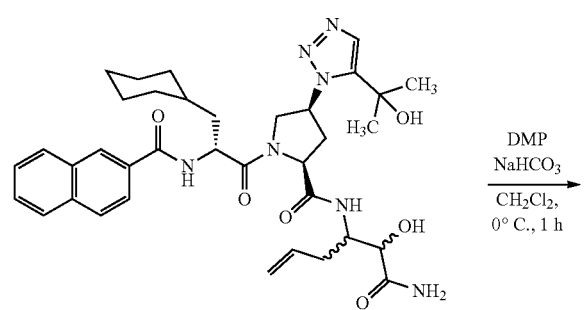

Step 1: Preparation of (2S,4S)-1-((R)-2-(2-naphthamido)-3-cyclohexylpropanoyl)-N-(1-amino-2-hydroxy-1-oxohex-5-en-3-yl)-4-azidopyrrolidine-2-carboxamide Into a 25 mL round-bottom flask equipped with a magnetic stir bar and under N$_2$ was added (2S,4S)-1-((R)-2-(2-naphthamido)-3-cyclohexylpropanoyl)-4-azidopyrrolidine-2-carboxylic acid (Intermediate F, 590 mg, 1.27 mmol, 1.0 equiv), 3-amino-2-hydroxyhex-5-enamide hydrochloride (Intermediate I, 203 mg, 1.40 mmol, 1.1 equiv), HATU (580 mg, 1.52 mmol, 1.2 equiv) and CH$_2$Cl$_2$ (3 mL). The reaction mixture was stirred at room temperature for 30 minutes and then EtN(iPr)$_2$ (666 µL, 3.81 mmol, 3 equiv) was added. The reaction mixture was stirred at room temperature for 18 h overnight. LCMS at this time revealed complete conversion to product. The reaction mixture was quenched with 1 M aqueous HCl solution (20 mL) and extracted with CH$_2$Cl$_2$ (3×10 mL) using a phase-separatory cartridge. The combined organic layers were concentrated under reduced pressure. Purification by column chromatography through silica gel (45 g), eluting with 100:0 to 90:10 CH$_2$Cl$_2$:MeOH as a gradient afforded the title compound as a white solid (740 mg).

Step 2: Preparation of (2S,4S)-1-((R)-2-(2-naphthamido)-3-cyclohexylpropanoyl)-N-(1-amino-2-hydroxy-1-oxohex-5-en-3-yl)-4-(5-(2-hydroxypropan-2-yl)-1H-1,2,3-triazol-1-yl)pyrrolidine-2-carboxamide Into a 50 mL round-bottom flask equipped with a magnetic stir bar and under N$_2$ was added (2S,4S)-1-((R)-2-(2-naphthamido)-3-cyclohexylpropanoyl)-N-(1-amino-2-hydroxy-1-oxohex-5-en-3-yl)-4-azidopyrrolidine-2-carboxamide (750 mg, 1.27 mmol, 1.0 equiv), 2-methyl-3-butyn-2-ol (185 µL, 1.91 mmol, 1.5 equiv), Cp*RuCl(PPh$_3$)$_2$ (101 mg, 0.13 mmol, 0.1 equiv) and 1,4-dioxane (5 mL). The reaction mixture was degassed with a steady flow of N$_2$ for 20 minutes and then heated to 80° C. in an oil bath for 2 days. The reaction mixture was concentrated under reduced pressure and loaded directly onto silica gel. Purification by column chromatography through silica gel (60 g), eluting with 100:0 to 90:10 CH$_2$Cl$_2$:MeOH as a gradient afforded the desired product as a brownish-tan foam (253 mg).

Step 3: Preparation of (2S,4S)-1-((R)-2-(2-naphthamido)-3-cyclohexylpropanoyl)-N-(1-amino-1,2-dioxohex-5-en-3-yl)-4-(5-(2-hydroxypropan-2-yl)-1H-1,2,3-triazol-1-yl)pyrrolidine-2-carboxamide Into a 25 mL round-bottom flask equipped with a magnetic stir bar and under $N_2$ was added (2S,4S)-1-((R)-2-(2-naphthamido)-3-cyclohexylpropanoyl)-N-(1-amino-2-hydroxy-1-oxohex-5-en-3-yl)-4-(5-(2-hydroxypropan-2-yl)-1H-1,2,3-triazol-1-yl)pyrrolidine-2-carboxamide (75 mg, 0.11 mmol, 1.0 equiv), $NaHCO_3$ (19 mg, 0.22 mmol, 2.0 equiv) and $CH_2Cl_2$ (2 mL). The suspension was cooled to 0° C. in an ice bath and Dess-Martin Periodinane (57 mg, 0.13 mmol, 1.2 equiv) was added. The mixture was stirred at 0° C. for 30 minutes at which stage LCMS analysis revealed about 30% conversion. Another 1.0 equiv of DMP was added and the reaction mixture stirred at 0° C. for 30 minutes. LCMS analysis now revealed 60% conversion, so another 1.0 equiv of DMP was added and the mixture was stirred at 0° C. for a further 30 minutes. LCMS analysis revealed complete conversion to product. The reaction mixture was quenched with 10% aqueous $Na_2S_2O_8$ solution (10 mL) and extracted with $CH_2Cl_2$ (3×10 mL) using a phase-separatory cartridge. The combined organic layers were concentrated under reduced pressure. Purification by reverse-phase column chromatography (15 g C18 column), eluting with 80:20 to 20:80 $H_2O$:MeCN+0.1% $HCO_2H$ as a gradient afforded the title compound as a white solid (15 mg). MS (ESI+) 672 (M+1)$^{\oplus}$ Example 36: N-((2R)-1-((2S,4S)-2-((7-(3-propargylureido)-1-amino-1,2-dioxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)isonicotinamide

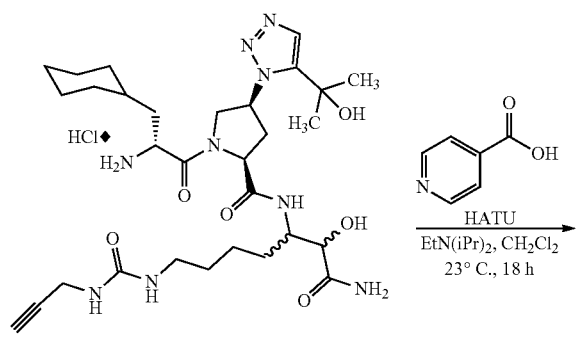

Intermediate J

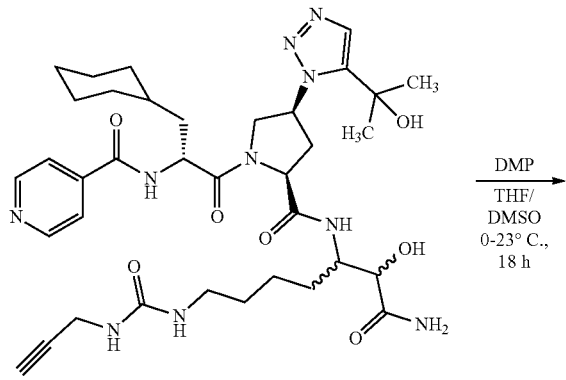

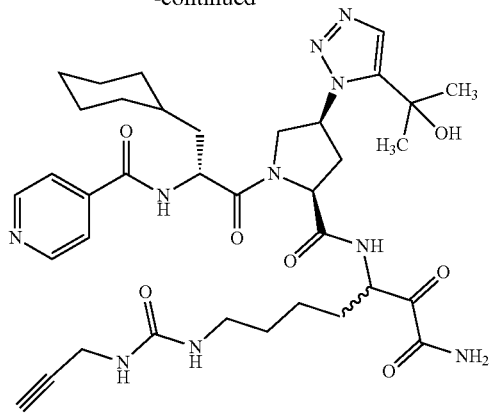

Example 36

Step 1: Preparation of N-((2R)-1-((2S,4S)-2-((7-(3-propargylureido)-1-amino-2-hydroxy-1-oxoheptan-3-yl)carbamoyl)-4-(5-(2-hydroxypropan-2-yl)-1H-1,2,3-triazol-1-yl)pyrrolidin-1l-yl)-3-cyclohexyl-1-oxopropan-2-yl)isonicotinamide To a 4 mL sample vial containing a magnetic stir bar and under $N_2$ was added isonicotinic acid (14 mg, 0.11 mmol, 1.5 equiv), HATU (42 mg, 0.11 mmol, 1.5 equiv) and $CH_2Cl_2$ (0.5 mL). The suspension was stirred at room temperature for 10 minutes and then (2S,4S)—N-(7-(3-propargylureido)-1-amino-2-hydroxy-1-oxoheptan-3-yl)-1-((R)-2-amino-3-cyclohexylpropanoyl)-4-(5-(2-hydroxypropan-2-yl)-1H-1,2,3-triazol-1-yl)pyrrolidine-2-carboxamide (Intermediate J, 49 mg, 0.07 mmol, 1.0 equiv) was added followed by $EtN(iPr)_2$ (38 μL, 0.22 mmol, 3 equiv). The reaction mixture was stirred at room temperature for 18 h overnight. The reaction was quenched with sat. aqueous $NH_4Cl$ solution (1 mL) and MeOH (2.5 mL). The mixture was concentrated under reduced pressure and the residue loaded directly onto silica gel. Purification by column chromatography through silica gel (8 g), eluting with 100:0 to 80:20 $CH_2Cl_2$:MeOH as a gradient afforded the title compound (47 mg).

Step 2: Preparation of N-((2R)-1-((2S,4S)-2-((7-(3-propargylureido)-1-amino-1,2-dioxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)isonicotinamide Into a 25 mL round-bottom flask equipped with a magnetic stir bar and under $N_2$ was added N-((2R)-1-((2S,4S)-2-((7-(3-propargylureido)-1-amino-2-hydroxy-1-oxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)isonicotinamide (47 mg, 0.06 mmol, 1.0 equiv), THF (2 mL) and DMSO (1 mL). The solution was cooled to 0° C. in an ice bath and treated with Dess-Martin Periodinane (162 mg, 0.38 mmol, 6 equiv). The reaction mixture was stirred at 0° C. for 4 h and allowed to warm to room temperature overnight. The reaction mixture was quenched with 10% aqueous $Na_2S_2O_8$ solution (2 mL) and stirred at room temperature for 30 minutes. The mixture was diluted with water (10 mL) and extracted with $CH_2Cl_2$ (3×5 mL) using a phase-separatory cartridge. The combined organic layers were concentrated under reduced pressure. Purification by reverse-phase column chromatography (C18, 4 g column), eluting with 90:10 to 30:70 H₂O:MeCN+0.1% HCO₂H as a gradient afforded the title compound (3 mg). MS (ESI+) 736 (M+1)⁺

Examples 37 and 38 were prepared in a similar manner to Example 36, where isonicotinic acid in Step 1 was substituted with 4-(methylsulfonyl)benzoic acid (for Example 37) or 4-(trifluoroacetyl)benzoic acid (for Example 38).

| Example | Structure | MW | MS (ESI+) |
|---|---|---|---|
| 37 | 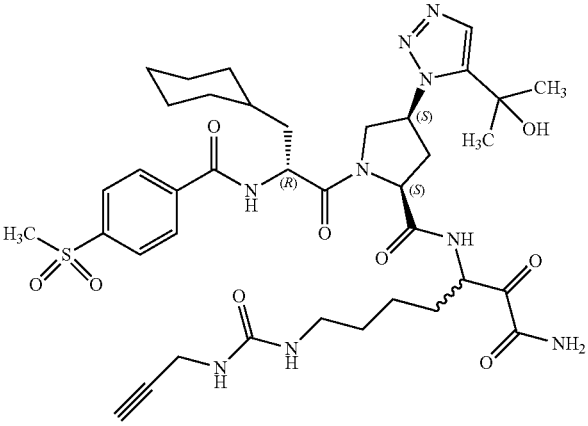 (2S,4S)-N-(7-(3-propargylureido)-1-amino-1,2-dioxoheptan-3-yl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide | 811.96 | 812 (M + 1)⁺ |
| 38 | 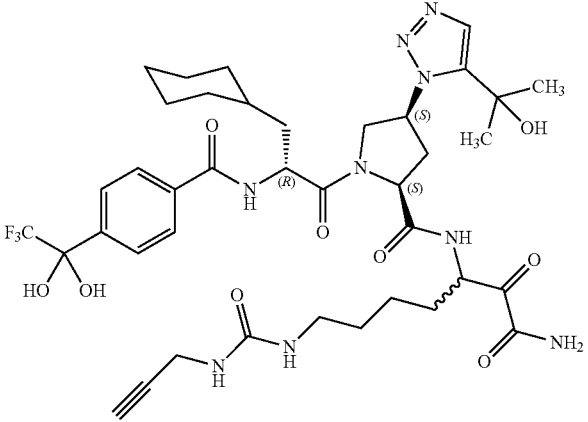 (2S,4S)-N-(1-amino-1,2-dioxo-7-(3-(prop-2-yn-1-yl)ureido)heptan-3-yl)-1-((R)-3-cyclohexyl-2-(4-(2,2,2-trifluoro-1,1-dihydroxyethyl)benzamido)propanoyl)-4-(5-(2-hydroxypropan-2-yl)-1H-1,2,3-triazol-1-yl)pyrrolidine-2-carboxamide | 847.89 | 848 (M + 1)⁺ |

Example 39: Benzyl (5-((2S,4S)-1-((R)-2-(1H-benzo[d]imidazole-2-carboxamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate

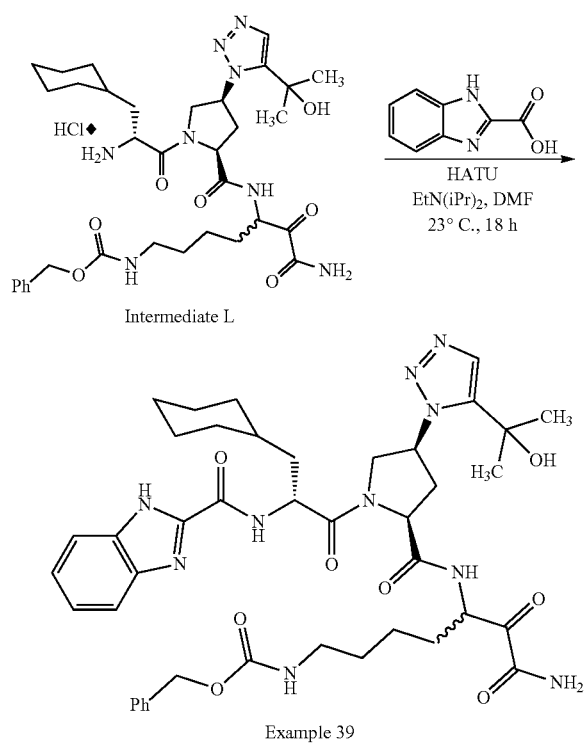

Intermediate L

Example 39

To a 4 mL sample vial equipped with a magnetic stir bar was placed benzyl (7-amino-5-((2S,4S)-1-((R)-2-amino-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate (Intermediate L, 20 mg, 0.028 mmol, 1.0 equiv), 1H-benzo[d]imidazole-2-carboxylic acid (10 mg, 0.062 mmol, 2.2 equiv), HATU (12.7 mg, 0.033 mmol, 1.2 equiv) and DMF (400 pL). The solution was treated with EtN(iPr)$_2$ (15 pL, 0.083 mmol, 3 equiv) and the mixture was stirred at room temperature for 18 h overnight. The reaction mixture was filtered through a 13 mm 0.45 μM PFTE syringe filter and the filtrate was collected. Purification of the filtrate by reverse-phase column chromatograph (Waters XSelect CSH Prep C18, 5 μm, 30×75 mm) using 60:40 to 35:65 H$_2$O:MeCN+0.1% HCO$_2$H as a gradient over 10 minutes afforded the title compound. MS (ESI+) 826 (M+1)$^\oplus$ Examples 40-111 were prepared in a similar manner as Example 39, substituting 1H-benzo[d]imidazole-2-carboxylic acid with the appropriate corresponding carboxylic acid. In some cases, a reverse-phase purification was conducted using a Phenomenex Gemini-NX C18 column (5 μm, 30×50 mm) or a Waters Xselect HSS PFP column (5 μm, 30×75 mm) and the gradient was within the 80:20 to 30:70 H$_2$O:MeCN+0.1% HCO$_2$H range.

| Example | Structure | MW | MS (ESI+) |
|---|---|---|---|
| 40 | benzyl (7-amino-5-((2S,4S)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamido)-6,7-dioxoheptyl)carbamate | 865.02 | 865 (M + 1)$^\oplus$ |

| Example | Structure | MW | MS (ESI+) |
|---|---|---|---|
| 41 | 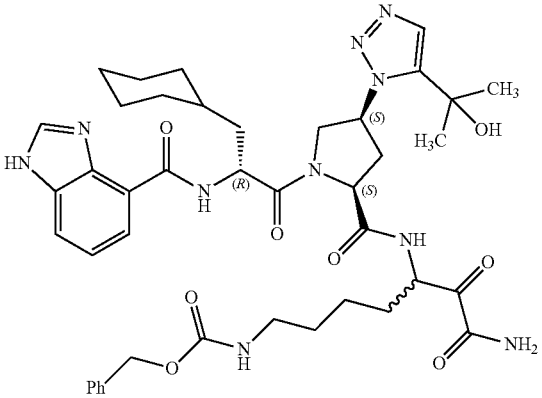<br>benzyl (5-((2S,4S)-1-((R)-2-(1H-benzo[d]imidazole-4-carboxamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate | 826.96 | 827 $(M + 1)^{\oplus}$ |
| 42 | 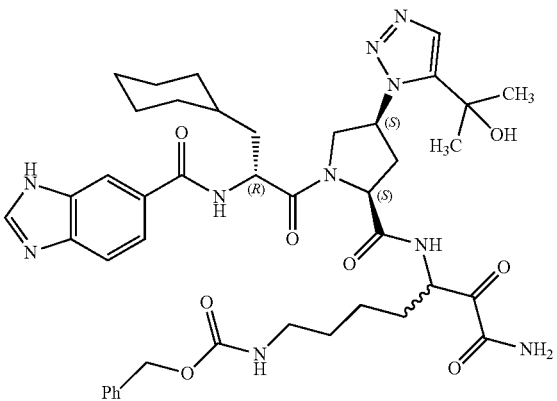<br>benzyl (5-((2S,4S)-1-((R)-2-(1H-benzo[d]imidazole-6-carboxamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate | 826.96 | 827 $(M + 1)^{\oplus}$ |
| 43 | 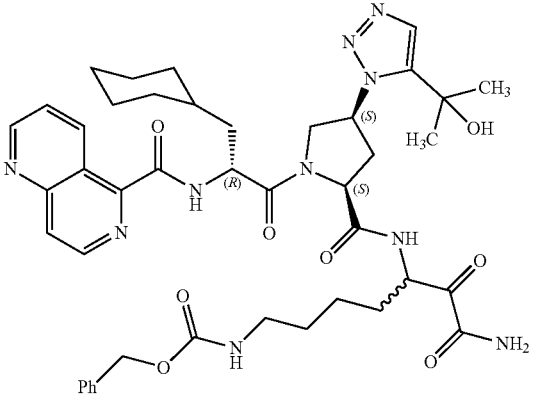<br>benzyl (7-amino-5-((2S,4S)-1-((R)-3-cyclohexyl-2-(1,6-naphthyridine-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 838.97 | 839 $(M + 1)^{\oplus}$ |

-continued

| Example | Structure | MW | MS (ESI+) |
|---|---|---|---|
| 44 | 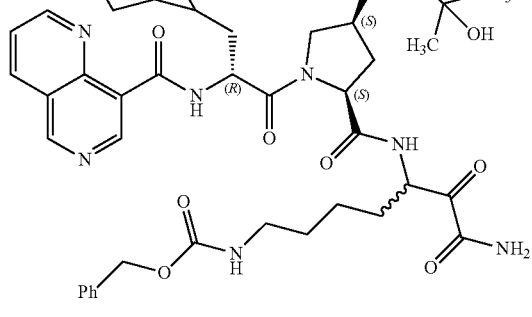 benzyl (7-amino-5-((2S,4S)-1-((R)-3-cyclohexyl-2-(1,6-naphthyridine-8-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 838.97 | 839 (M + 1)⁺ |
| 45 | 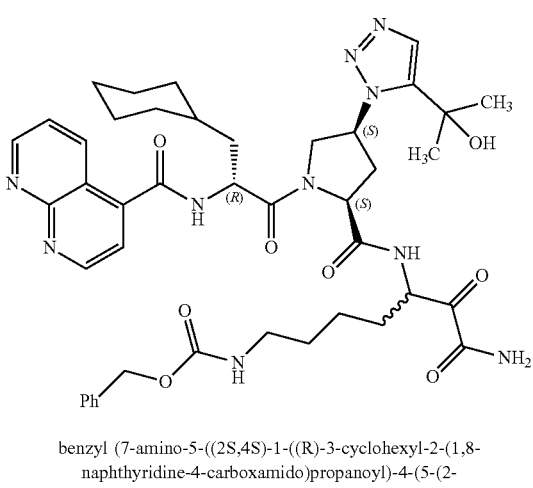 benzyl (7-amino-5-((2S,4S)-1-((R)-3-cyclohexyl-2-(1,8-naphthyridine-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 838.97 | 839 (M + 1)⁺ |
| 46 | 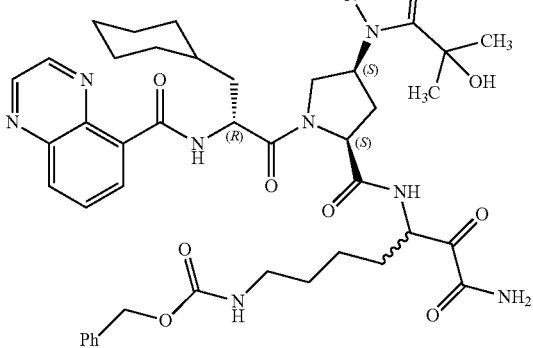 benzyl (7-amino-5-((2S,4S)-1-((R)-3-cyclohexyl-2-(quinoxaline-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 838.97 | 840 (M + 1)⁺ |

| Example | Structure | MW | MS (ESI+) |
|---|---|---|---|
| 47 | 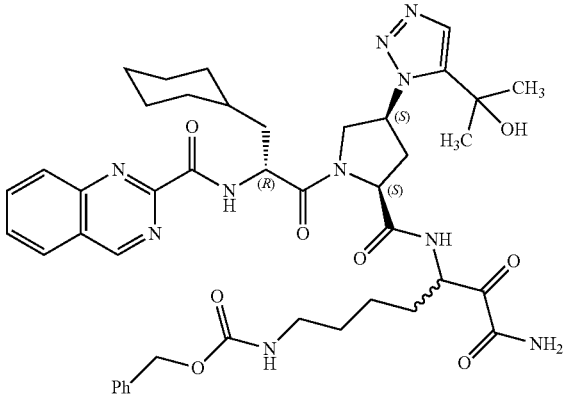<br>benzyl (7-amino-5-((2S,4S)-1-((R)-3-cyclohexyl-2-(quinazoline-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 838.97 | 840 $(M+1)^{\oplus}$ |
| 48 | 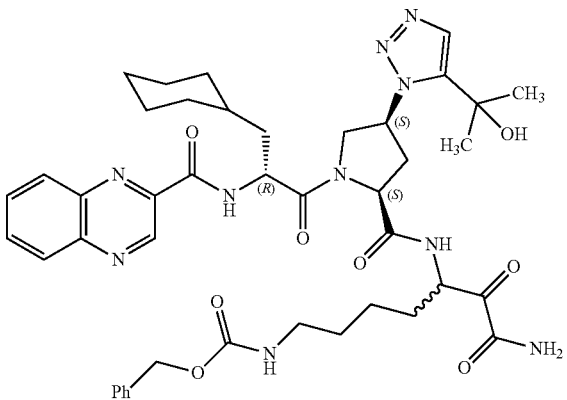<br>benzyl (7-amino-5-((2S,4S)-1-((R)-3-cyclohexyl-2-(quinoxaline-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 838.97 | 840 $(M+1)^{\oplus}$ |
| 49 | 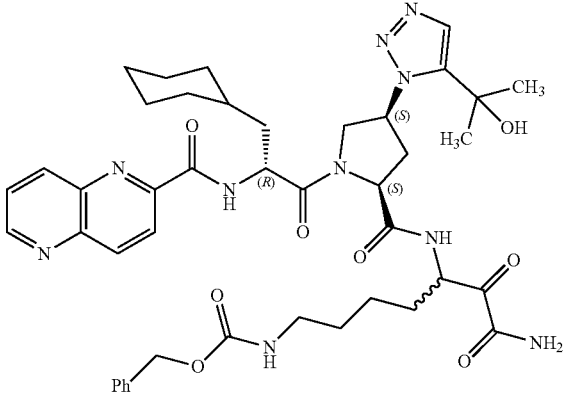<br>benzyl (7-amino-5-((2S,4S)-1-((R)-3-cyclohexyl-2-(1,5-naphthyridine-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 838.97 | 840 $(M+1)^{\oplus}$ |

-continued

| Example | Structure | MW | MS (ESI+) |
|---|---|---|---|
| 50 | benzyl (7-amino-5-((2S,4S)-1-((R)-3-cyclohexyl-2-(1,6-naphthyridine-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 838.97 | 840 (M + 1)⊕ |
| 51 | benzyl (7-amino-5-((2S,4S)-1-((R)-3-cyclohexyl-2-(1,8-naphthyridine-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 838.97 | 840 (M + 1)⊕ |
| 52 | benzyl (7-amino-5-((2S,4S)-1-((R)-3-cyclohexyl-2-(1,7-naphthyridine-3-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 838.97 | 840 (M + 1)⊕ |

| Example | Structure | MW | MS (ESI+) |
|---|---|---|---|
| 53 | 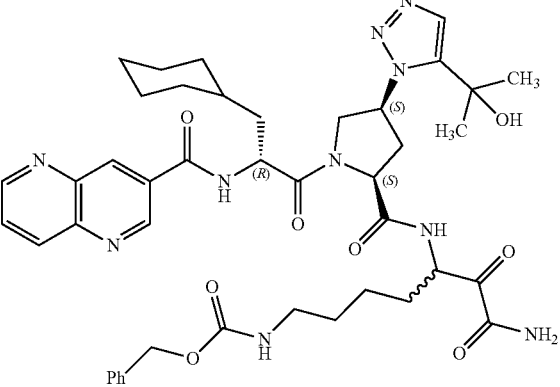<br>benzyl (7-amino-5-((2S,4S)-1-((R)-3-cyclohexyl-2-(1,5-naphthyridine-3-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 838.97 | 840 (M + 1)⊕ |
| 54 | 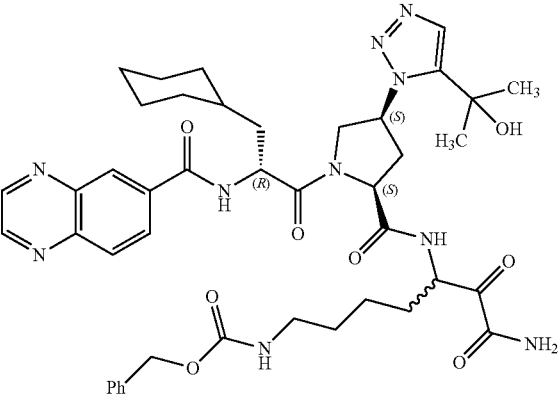<br>benzyl (7-amino-5-((2S,4S)-1-((R)-3-cyclohexyl-2-(quinoxaline-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 838.97 | 840 (M + 1)⊕ |
| 55 | 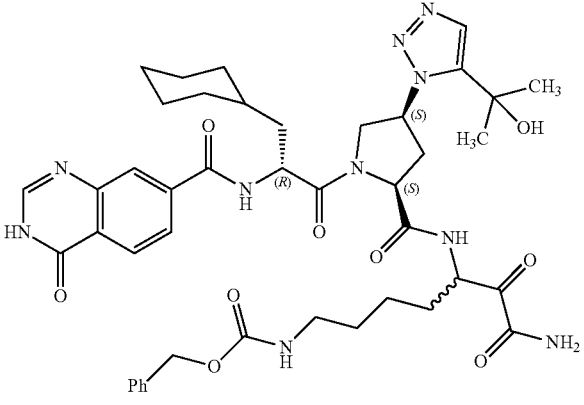<br>benzyl (7-amino-5-((2S,4S)-1-((R)-3-cyclohexyl-2-(4-oxo-3,4-dihydroquinazoline-7-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 854.97 | 855 (M + 1)⊕ |

| Example | Structure | MW | MS (ESI+) |
|---|---|---|---|
| 56 | 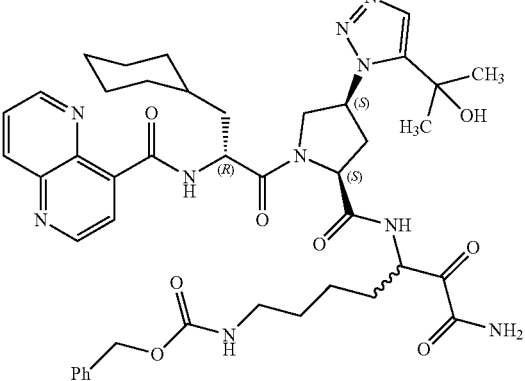 benzyl (7-amino-5-((2S,4S)-1-((R)-3-cyclohexyl-2-(1,5-naphthyridine-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 838.97 | 840 (M + 1)⁺ |
| 57 | 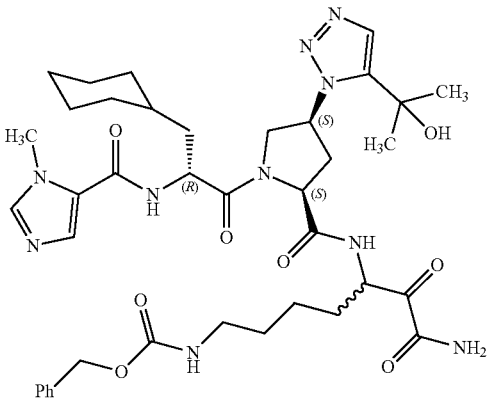 benzyl (7-amino-5-((2S,4S)-1-((R)-3-cyclohexyl-2-(1-methyl-1H-imidazole-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 790.92 | 791 (M + 1)⁺ |
| 58 | 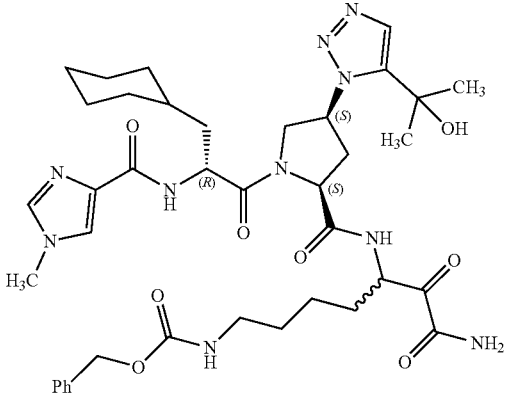 benzyl (7-amino-5-((2S,4S)-1-((R)-3-cyclohexyl-2-(1-methyl-1H-imidazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 790.92 | 791 (M + 1)⁺ |

| Example | Structure | MW | MS (ESI+) |
|---|---|---|---|
| 59 | benzyl (7-amino-5-((2S,4S)-1-((R)-3-cyclohexyl-2-(1-methyl-1H-imidazole-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 790.92 | 791 (M + 1)⊕ |
| 60 | benzyl (7-amino-5-((2S,4S)-1-((R)-3-cyclohexyl-2-(1H-pyrrolo[3,2-c]pyridine-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 826.96 | 827 (M + 1)⊕ |
| 61 | benzyl (7-amino-5-((2S,4S)-1-((R)-3-cyclohexyl-2-(1H-indole-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 825.97 | 827 (M + 1)⊕ |

| Example | Structure | MW | MS (ESI+) |
|---|---|---|---|
| 62 | 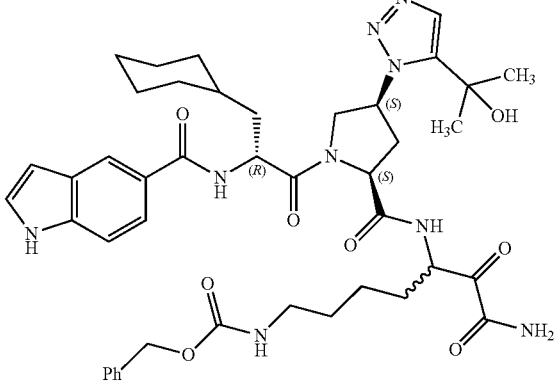 benzyl (7-amino-5-((2S,4S)-1-((R)-3-cyclohexyl-2-(1H-indole-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 825.97 | 827 (M + 1)$^⊕$ |
| 63 | 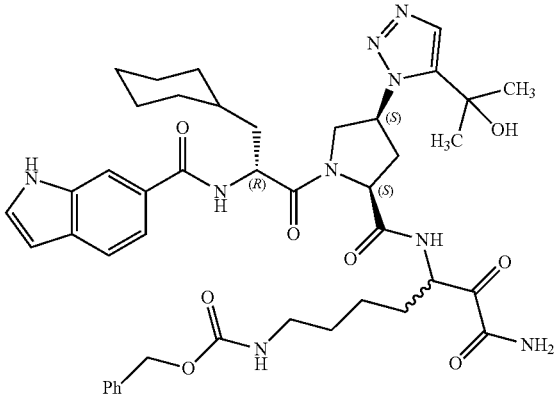 benzyl (7-amino-5-((2S,4S)-1-((R)-3-cyclohexyl-2-(1H-indole-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 825.97 | 827 (M + 1)$^⊕$ |
| 64 | 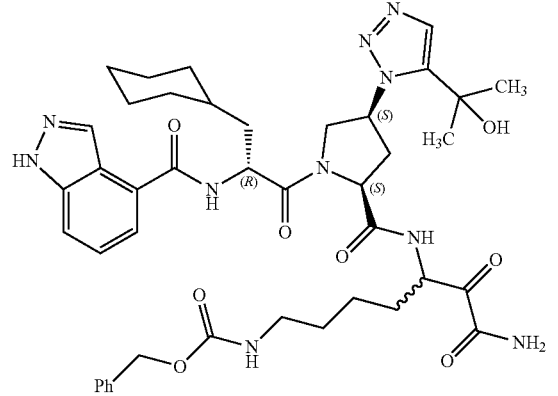 benzyl (7-amino-5-((2S,4S)-1-((R)-3-cyclohexyl-2-(1H-indazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 826.96 | 827 (M + 1)$^⊕$ |

-continued

| Example | Structure | MW | MS (ESI+) |
|---|---|---|---|
| 65 | 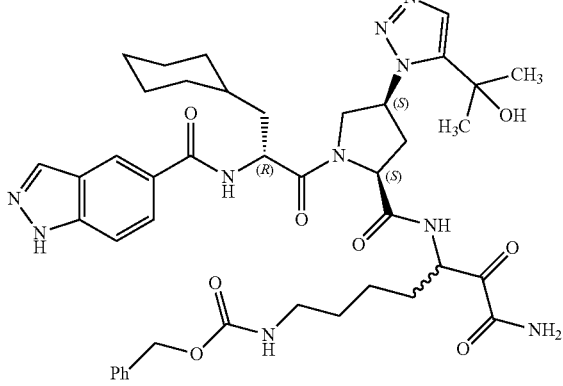 benzyl (7-amino-5-((2S,4S)-1-((R)-3-cyclohexyl-2-(1H-indazole-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 826.96 | 827 (M + 1)$^{\oplus}$ |
| 66 | 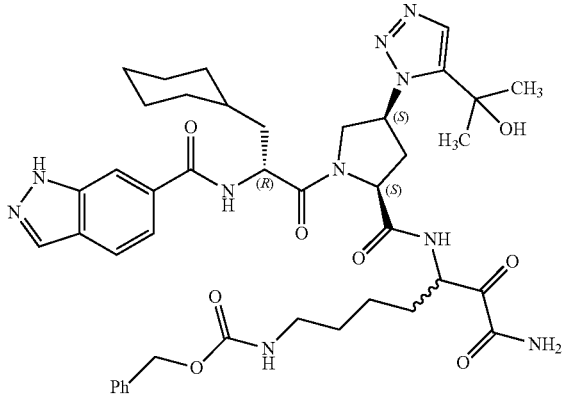 benzyl (7-amino-5-((2S,4S)-1-((R)-3-cyclohexyl-2-(1H-indazole-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 826.96 | 827 (M + 1)$^{\oplus}$ |
| 67 | 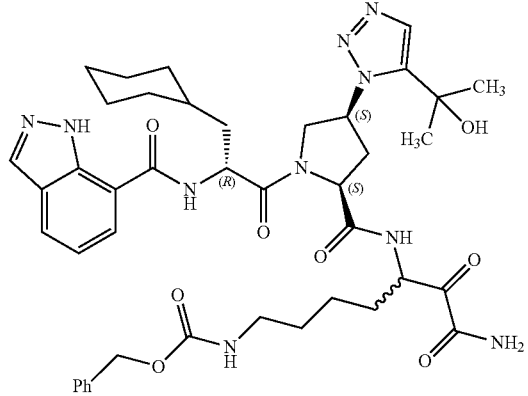 benzyl (7-amino-5-((2S,4S)-1-((R)-3-cyclohexyl-2-(1H-indazole-7-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 826.96 | 827 (M + 1)$^{\oplus}$ |

| Example | Structure | MW | MS (ESI+) |
|---|---|---|---|
| 68 | benzyl (5-((2S,4S)-1-((R)-2-(1-naphthamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate | 836.99 | 837 (M + 1)$^\oplus$ |
| 69 | benzyl (7-amino-5-((2S,4S)-1-((R)-3-cyclohexyl-2-(isoxazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 777.88 | 778 (M + 1)$^\oplus$ |
| 70 | benzyl (7-amino-5-((2S,4S)-1-((R)-3-cyclohexyl-2-(oxazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 777.88 | 778 (M + 1)$^\oplus$ |

-continued

| Example | Structure | MW | MS (ESI+) |
|---|---|---|---|
| 71 | 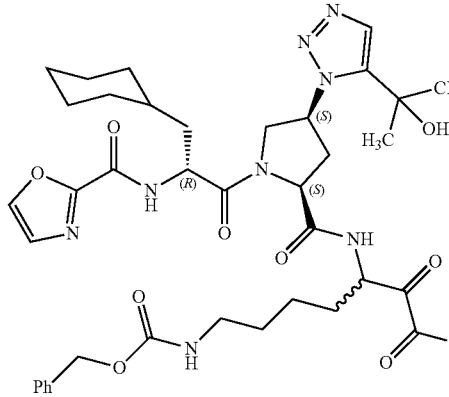 benzyl (7-amino-5-((2S,4S)-1-((R)-3-cyclohexyl-2-(oxazole-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 777.88 | 778 (M + 1)⊕ |
| 72 | 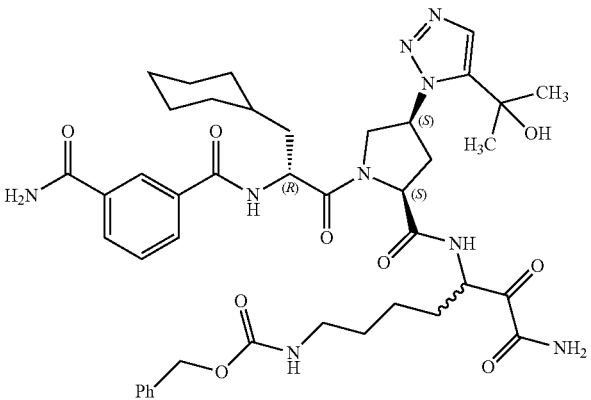 benzyl (7-amino-5-((2S,4S)-1-((R)-2-(3-carbamoylbenzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate | 829.96 | 830 (M + 1)⊕ |
| 73 | 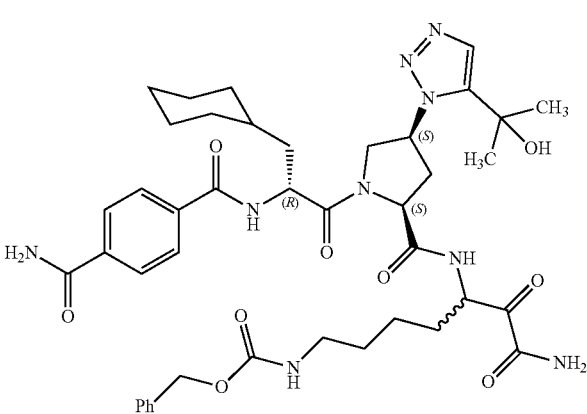 benzyl (7-amino-5-((2S,4S)-1-((R)-2-(4-carbamoylbenzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate | 829.96 | 830 (M + 1)⊕ |

| Example | Structure | MW | MS (ESI+) |
|---|---|---|---|
| 74 | 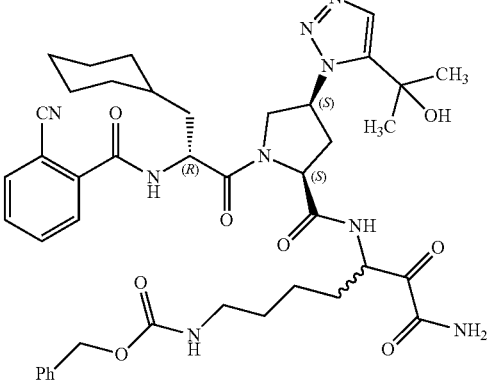<br>benzyl (7-amino-5-((2S,4S)-1-((R)-2-(2-cyanobenzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate | 811.94 | 812 (M + 1)⊕ |
| 75 | 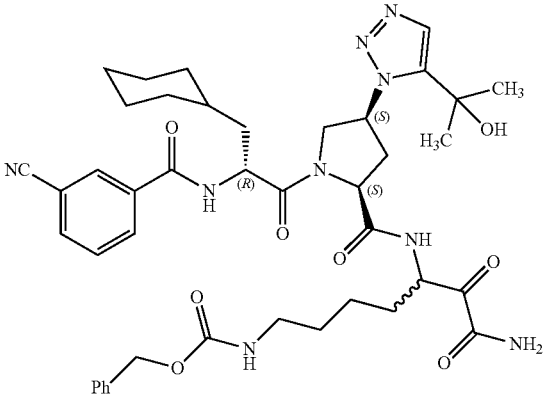<br>benzyl (7-amino-5-((2S,4S)-1-((R)-2-(3-cyanobenzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate | 811.94 | 812 (M + 1)⊕ |
| 76 | 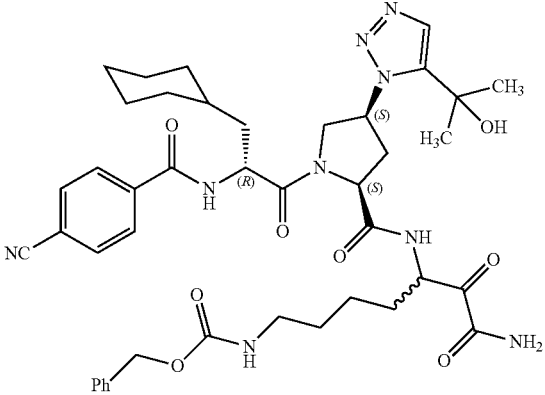<br>benzyl (7-amino-5-((2S,4S)-1-((R)-2-(4-cyanobenzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate | 811.94 | 812 (M + 1)⊕ |

| Example | Structure | MW | MS (ESI+) |
|---|---|---|---|
| 77 | benzyl (7-amino-5-((2S,4S)-1-((R)-3-cyclohexyl-2-(2-fluorobenzamido)propanoyl)-4-(5-(2-hydroxypropan-2-yl)-1H-1,2,3-triazol-1-yl)pyrrolidine-2-carboxamido)-6,7-dioxoheptyl)carbamate | 804.92 | 805 (M + 1)$^\oplus$ |
| 78 | benzyl (7-amino-5-((2S,4S)-1-((R)-3-cyclohexyl-2-(4-fluorobenzamido)propanoyl)-4-(5-(2-hydroxypropan-2-yl)-1H-1,2,3-triazol-1-yl)pyrrolidine-2-carboxamido)-6,7-dioxoheptyl)carbamate | 804.92 | 805 (M + 1)$^\oplus$ |
| 79 | benzyl (7-amino-5-((2S,4S)-1-((R)-3-cyclohexyl-2-(2-methoxybenzamido)propanoyl)-4-(5-(2-hydroxypropan-2-yl)-1H-1,2,3-triazol-1-yl)pyrrolidine-2-carboxamido)-6,7-dioxoheptyl)carbamate | 816.96 | 817 (M + 1)$^\oplus$ |

| Example | Structure | MW | MS (ESI+) |
|---|---|---|---|
| 80 | 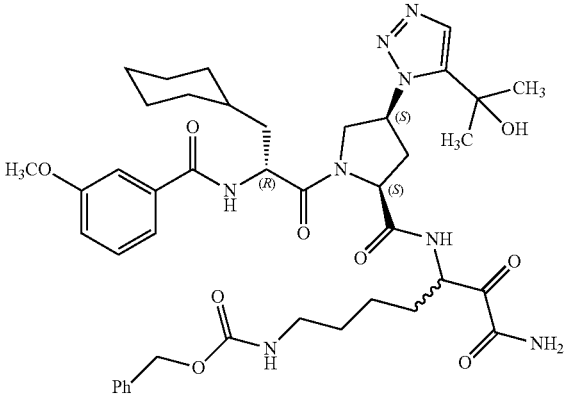<br>benzyl (7-amino-5-((2S,4S)-1-((R)-3-cyclohexyl-2-(3-methoxybenzamido)propanoyl)-4-(5-(2-hydroxypropan-2-yl)-1H-1,2,3-triazol-1-yl)pyrrolidine-2-carboxamido)-6,7-dioxoheptyl)carbamate | 816.96 | 817 (M + 1)$^{\oplus}$ |
| 81 | 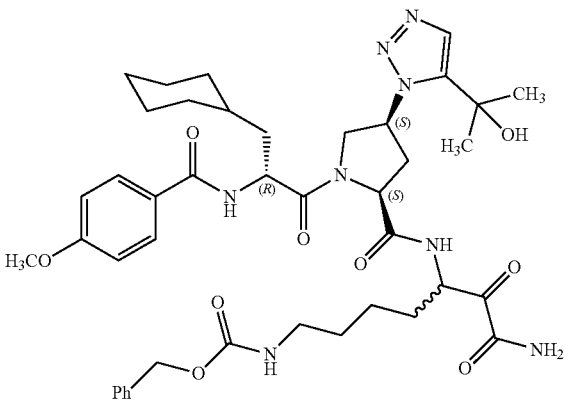<br>benzyl (7-amino-5-((2S,4S)-1-((R)-3-cyclohexyl-2-(4-methoxybenzamido)propanoyl)-4-(5-(2-hydroxypropan-2-yl)-1H-1,2,3-triazol-1-yl)pyrrolidine-2-carboxamido)-6,7-dioxoheptyl)carbamate | 816.96 | 817 (M + 1)$^{\oplus}$ |
| 82 | 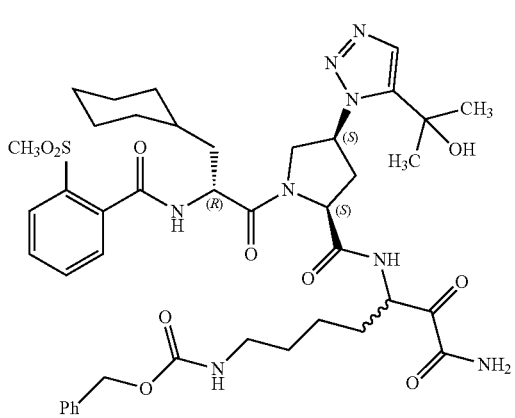<br>benzyl (7-amino-5-((2S,4S)-1-((R)-3-cyclohexyl-2-(2-((methylperoxy)thio)benzamido)propanoyl)-4-(5-(2-hydroxypropan-2-yl)-1H-1,2,3-triazol-1-yl)pyrrolidine-2-carboxamido)-6,7-dioxoheptyl)carbamate | 865.02 | 865 (M + 1)$^{\oplus}$ |

| Example | Structure | MW | MS (ESI+) |
|---|---|---|---|
| 83 | 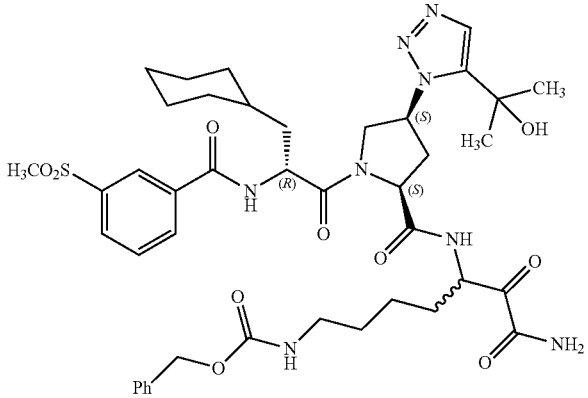 benzyl (7-amino-5-((2S,4S)-1-((R)-3-cyclohexyl-2-(3-((methylperoxy)thio)benzamido)propanoyl)-4-(5-(2-hydroxypropan-2-yl)-1H-1,2,3-triazol-1-yl)pyrrolidine-2-carboxamido)-6,7-dioxoheptyl)carbamate | 865.02 | 865 (M + 1)$^{\oplus}$ |
| 84 | 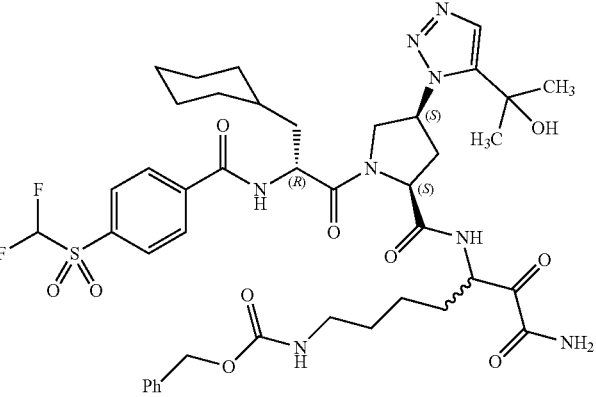 benzyl (7-amino-5-((2S,4S)-1-((R)-3-cyclohexyl-2-(4-((difluoromethyl)sulfonyl)benzamido)propanoyl)-4-(5-(2-hydroxypropan-2-yl)-1H-1,2,3-triazol-1-yl)pyrrolidine-2-carboxamido)-6,7-dioxoheptyl)carbamate | 901.00 | 901 (M + 1)$^{\oplus}$ |
| 85 | 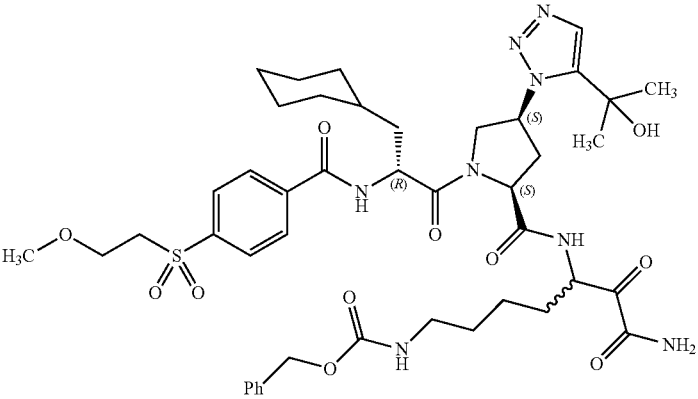 benzyl (7-amino-5-((2S,4S)-1-((R)-3-cyclohexyl-2-(4-((2-methoxyethyl)sulfonyl)benzamido)propanoyl)-4-(5-(2-hydroxypropan-2-yl)-1H-1,2,3-triazol-1-yl)pyrrolidine-2-carboxamido)-6,7-dioxoheptyl)carbamate | 909.07 | 909 (M + 1)$^{\oplus}$ |

| Example | Structure | MW | MS (ESI+) |
|---|---|---|---|
| 86 | 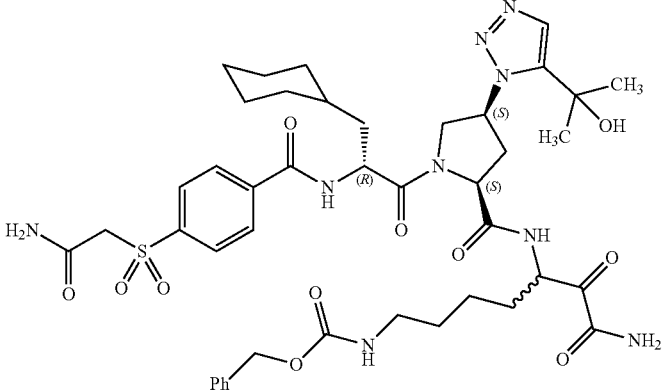 benzyl (7-amino-5-((2S,4S)-1-((R)-2-(4-((2-amino-2-oxoethyl)sulfonyl)benzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate | 908.04 | 908 $(M+1)^\oplus$ |
| 87 | 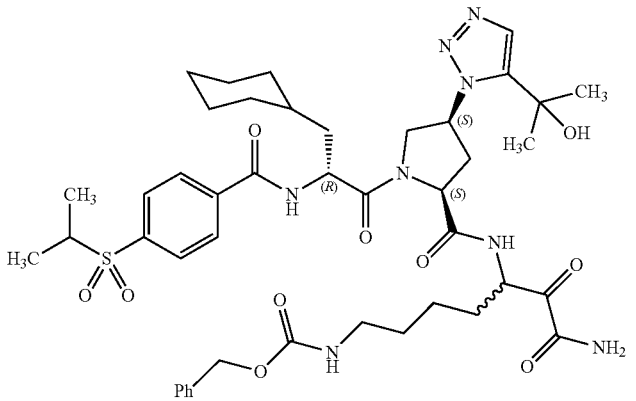 benzyl (7-amino-5-((2S,4S)-1-((R)-3-cyclohexyl-2-(4-(isopropylsulfonyl)benzamido)propanoyl)-4-(5-(2-hydroxypropan-2-yl)-1H-1,2,3-triazol-1-yl)pyrrolidine-2-carboxamido)-6,7-dioxoheptyl)carbamate | 893.07 | 893 $(M+1)^\oplus$ |
| 88 | 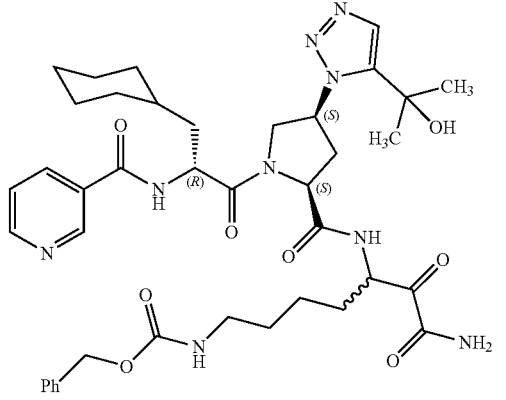 benzyl (7-amino-5-((2S,4S)-1-((R)-3-cyclohexyl-2-(nicotinamido)propanoyl)-4-(5-(2-hydroxypropan-2-yl)-1H-1,2,3-triazol-1-yl)pyrrolidine-2-carboxamido)-6,7-dioxoheptyl)carbamate | 787.92 | 788 $(M+1)^\oplus$ |

-continued

| Example | Structure | MW | MS (ESI+) |
|---|---|---|---|
| 89 | 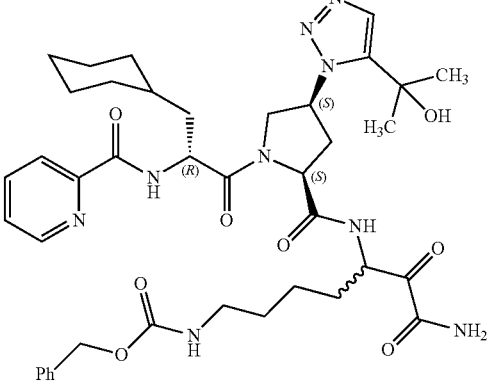 benzyl (7-amino-5-((2S,4S)-1-((R)-3-cyclohexyl-2-(picolinamido)propanoyl)-4-(5-(2-hydroxypropan-2-yl)-1H-1,2,3-triazol-1-yl)pyrrolidine-2-carboxamido)-6,7-dioxoheptyl)carbamate | 787.92 | 788 (M + 1)⊕ |
| 90 | 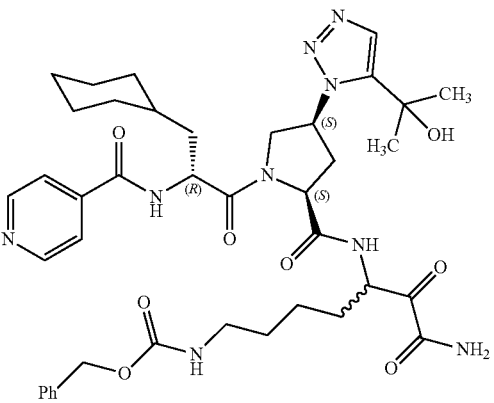 benzyl (7-amino-5-((2S,4S)-1-((R)-3-cyclohexyl-2-(isonicotinamido)propanoyl)-4-(5-(2-hydroxypropan-2-yl)-1H-1,2,3-triazol-1-yl)pyrrolidine-2-carboxamido)-6,7-dioxoheptyl)carbamate | 787.92 | 788 (M + 1)⊕ |
| 91 | 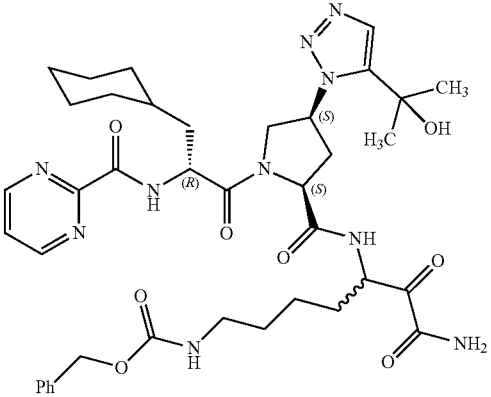 benzyl (7-amino-5-((2S,4S)-1-((R)-3-cyclohexyl-2-(pyrimidine-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 788.91 | 789 (M + 1)⊕ |

| Example | Structure | MW | MS (ESI+) |
|---|---|---|---|
| 92 | 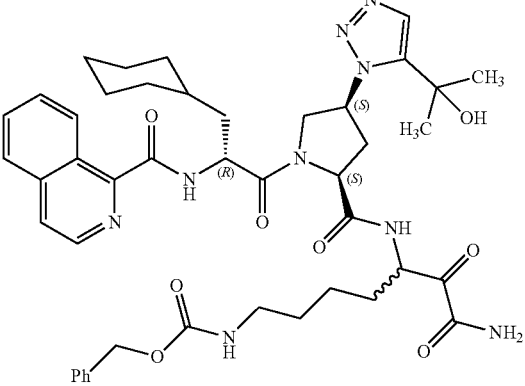 benzyl (7-amino-5-((2S,4S)-1-((R)-3-cyclohexyl-2-(isoquinoline-1-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 837.98 | 838 $(M+1)^{\oplus}$ |
| 93 | 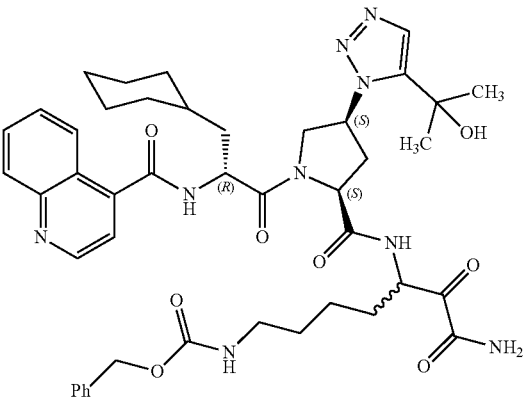 benzyl (7-amino-5-((2S,4S)-1-((R)-3-cyclohexyl-2-(quinoline-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 837.98 | 838 $(M+1)^{\oplus}$ |
| 94 | 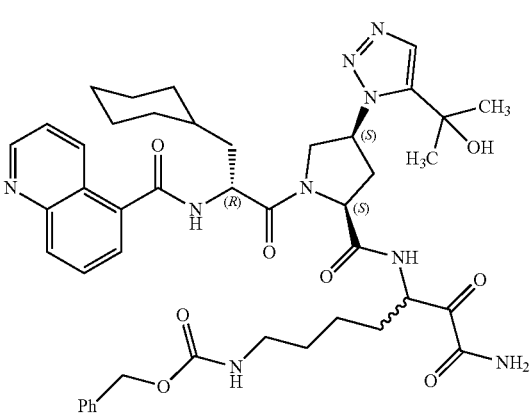 benzyl (7-amino-5-((2S,4S)-1-((R)-3-cyclohexyl-2-(quinoline-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 837.98 | 838 $(M+1)^{\oplus}$ |

-continued

| Example | Structure | MW | MS (ESI+) |
|---|---|---|---|
| 95 | benzyl (7-amino-5-((2S,4S5)-1-((R)-3-cyclohexyl-2-(isoquinoline-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 837.98 | 838 (M + 1)$^{\oplus}$ |
| 96 | benzyl (7-amino-5-((2S,4S)-1-((R)-3-cyclohexyl-2-(isoquinoline-8-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 837.98 | 838 (M + 1)$^{\oplus}$ |
| 97 | benzyl (7-amino-5-((2S,4S)-1-((R)-3-cyclohexyl-2-(quinoline-8-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 837.98 | 838 (M + 1)$^{\oplus}$ |

-continued

| Example | Structure | MW | MS (ESI+) |
|---|---|---|---|
| 98 | 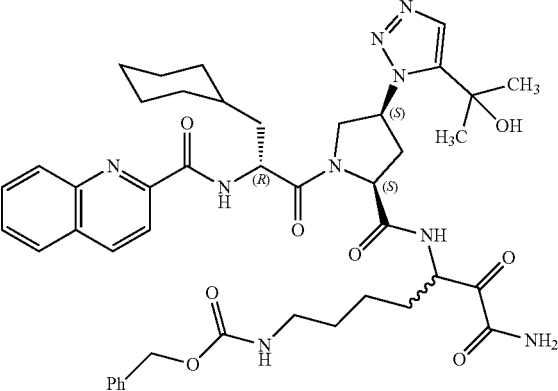 benzyl (7-amino-5-((2S,4S)-1-((R)-3-cyclohexyl-2-(quinoline-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 837.98 | 838 $(M + 1)^{\oplus}$ |
| 99 | 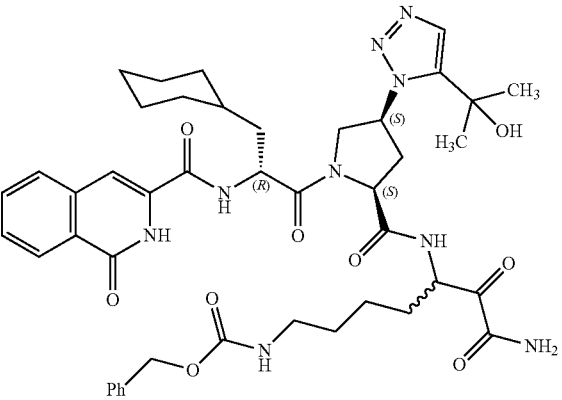 benzyl (7-amino-5-((2S,4S)-1-((R)-3-cyclohexyl-2-(1-oxo-1,2-dihydroisoquinoline-3-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 853.98 | 854 $(M + 1)^{\oplus}$ |
| 100 | 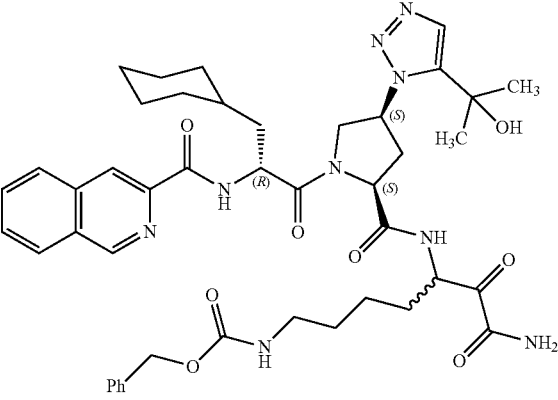 benzyl (7-amino-5-((2S,4S)-1-((R)-3-cyclohexyl-2-(isoquinoline-3-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 837.98 | 838 $(M + 1)^{\oplus}$ |

-continued

| Example | Structure | MW | MS (ESI+) |
|---|---|---|---|
| 101 | 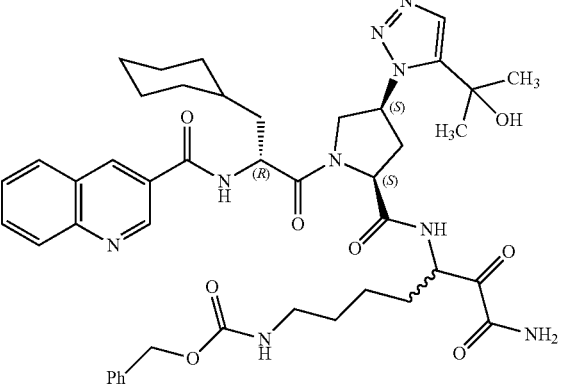 benzyl (7-amino-5-((2S,4S)-1-((R)-3-cyclohexyl-2-(quinoline-3-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 837.98 | 838 (M + 1)⊕ |
| 102 | 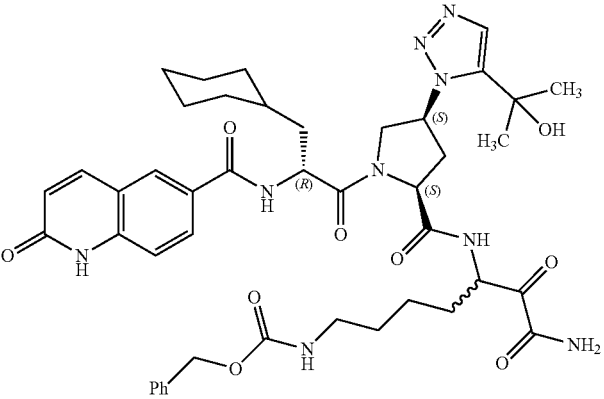 benzyl (7-amino-5-((2S,4S)-1-((R)-3-cyclohexyl-2-(2-oxo-1,2-dihydroquinoline-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 853.98 | 854 (M + 1)⊕ |
| 103 | 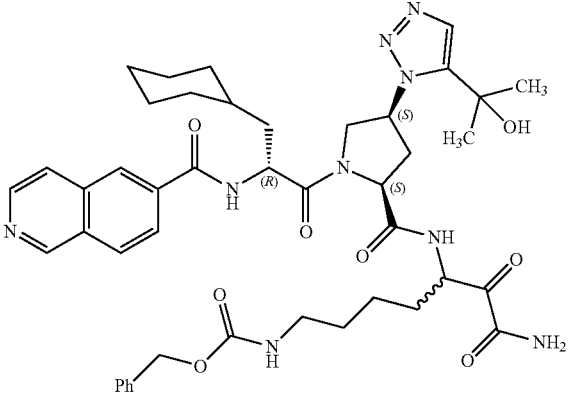 benzyl (7-amino-5-((2S,4S)-1-((R)-3-cyclohexyl-2-(isoquinoline-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 837.98 | 838 (M + 1)⊕ |

-continued

| Example | Structure | MW | MS (ESI+) |
|---|---|---|---|
| 104 | 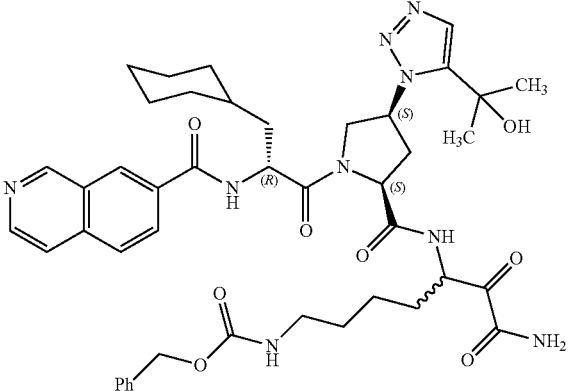<br>benzyl (7-amino-5-((2S,4S)-1-((R)-3-cyclohexyl-2-(isoquinoline-7-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 837.98 | 838 (M + 1)$^\oplus$ |
| 105 | 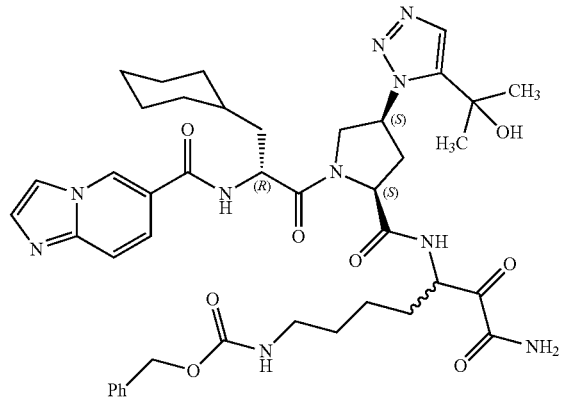<br>benzyl (7-amino-5-((2S,4S)-1-((R)-3-cyclohexyl-2-(imidazo[1,2-a]pyridine-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 826.96 | 827 (M + 1)$^\oplus$ |
| 106 | 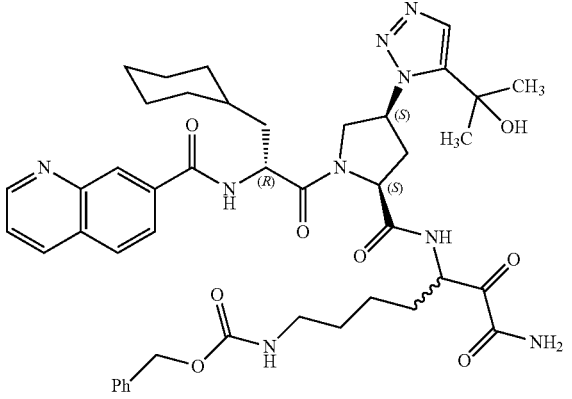<br>benzyl (7-amino-5-((2S,4S)-1-((R)-3-cyclohexyl-2-(quinoline-7-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 837.98 | 838 (M + 1)$^\oplus$ |

| Example | Structure | MW | MS (ESI+) |
|---|---|---|---|
| 107 | 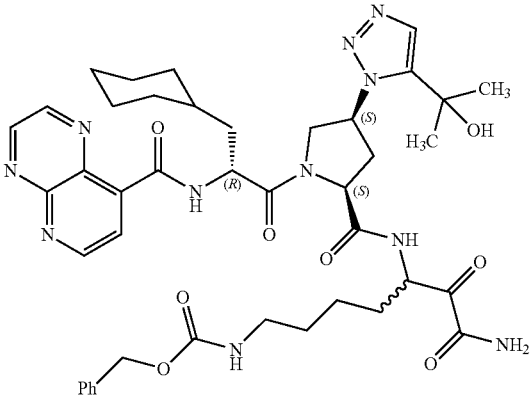 benzyl (7-amino-5-((2S,4S)-1-((R)-3-cyclohexyl-2-(pyrido[2,3-b]pyrazine-8-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 839.96 | 840 (M + 1)⊕ |
| 108 | 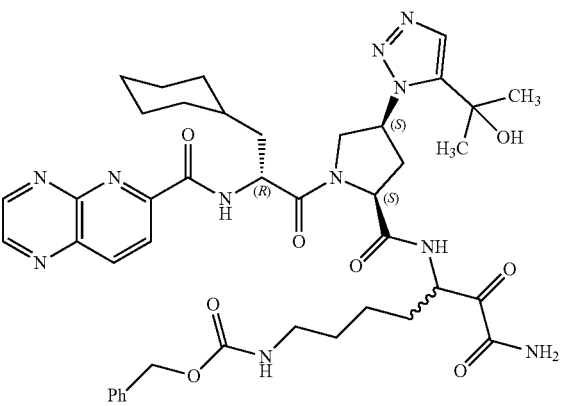 benzyl (7-amino-5-((2S,4S)-1-((R)-3-cyclohexyl-2-(pyrido[2,3-b]pyrazine-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 839.96 | 840 (M + 1)⊕ |
| 109 | 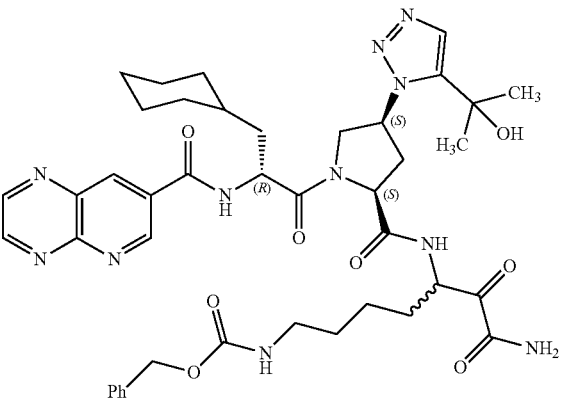 benzyl (7-amino-5-((2S,4S)-1-((R)-3-cyclohexyl-2-(pyrido[2,3-b]pyrazine-7-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 839.96 | 840 (M + 1)⊕ |

-continued

| Example | Structure | MW | MS (ESI+) |
|---|---|---|---|
| 110 | 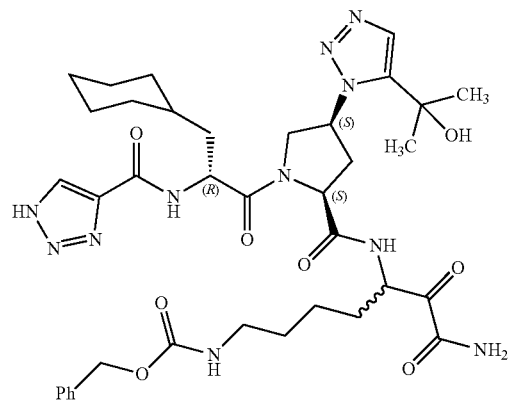 benzyl (7-amino-5-((2S,4S)-1-((R)-3-cyclohexyl-2-(1H-1,2,3-triazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 777.88 | 778 $(M + 1)^\oplus$ |
| 111 | 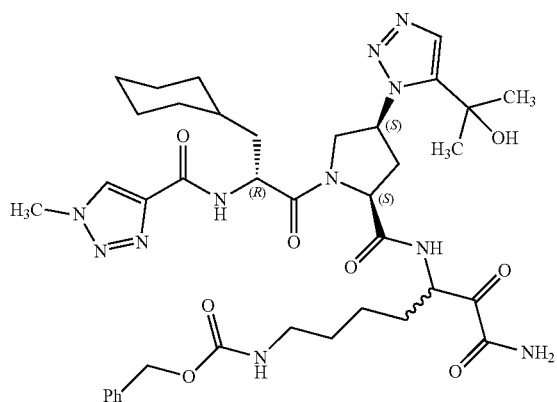 benzyl (7-amino-5-((2S,4S)-1-((R)-3-cyclohexyl-2-(1-methyl-1H-1,2,3-triazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate | 791.91 | 792 $(M + 1)^\oplus$ |

Example 112: (2S,4S)—N-(1-Amino-7-(3-cyclopropylureido)-1,2-dioxoheptan-3-yl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide

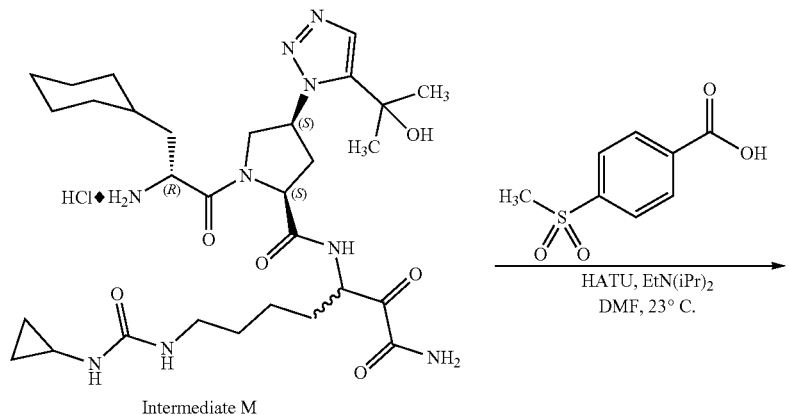

Intermediate M

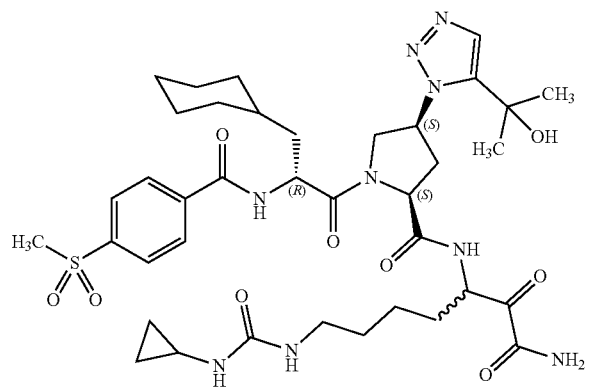

Example 112

To a round-bottom flask equipped with a magnetic stir bar and under nitrogen was prepared a solution of (2S,4S)-1-((R)-2-amino-3-cyclohexylpropanoyl)-N-(1-amino-7-(3-cyclopropylureido)-1,2-dioxoheptan-3-yl)-4-(5-(2-hydroxypropan-2-yl)-1H-1,2,3-triazol-1-yl)pyrrolidine-2-carboxamide hydrochloride (Intermediate M, 100 mg, 0.15 mmol, 1.0 equiv), 4-(methylsulfonyl)benzoic acid (30 mg, 0.15 mmol, 1.0 equiv), HATU (68 mg, 0.18 mmol, 1.2 equiv) and DMF (1.0 mL). The solution was treated with drop-wise addition of EtN(iPr)$_2$ (105 µL, 0.6 mmol, 4.0 equiv) and the mixture was stirred at room temperature for 18 h overnight. The reaction mixture was quenched with water (5 mL) and extracted with CH$_2$Cl$_2$ (3×5 mL) and the combined organic layers were concentrated under reduced pressure and loaded directly onto a 5 g C18 cartridge. Purification by reverse-phase column chromatography (15 g C18 column+5 g C18 precartridge), eluting with 100:0 to 60:40 H$_2$O:MeCN+0.1% HCO$_2$H as a gradient afforded the title compound (24 mg).

1H NMR (CD3OD, 300 MHz): δ 8.12-7.85 (4H, m), 7.48-7.45 (1H, m), 5.85-5.76 (1H, m), 5.11-5.03 (1H, m), 4.67-4.38 (1H, m), 4.20-4.05 (2H, m), 3.11 (3H, s), 3.15-2.86 (4H, m), 2.24-2.18 (1H, m), 1.98-0.34 (30H, m) ppm. MS (ESI+) 814 (M+1)$^⊕$ Examples 113-119 were prepared in a similar manner as Example 112, replacing 4-(methylsulfonyl)benzoic acid in the above procedure with the corresponding commercially available carboxylic acid derivatives.

| Example | Structure | MW | MS (ESI+) |
|---|---|---|---|
| 113 | (2S,4S)-N-(1-amino-7-(3-cyclopropylureido)-1,2-dioxoheptan-3-yl)-1-((R)-2-(4-cyanobenzamido)-3-cyclohexylpropanoyl)-4-(5-(2-hydroxypropan-2-yl)-1H-1,2,3-triazol-1-yl)pyrrolidine-2-carboxamide | 760.90 | 761 (M + 1)⊕ |
| 114 | N-((2R)-1-((2S,4S)-2-((1-amino-7-(3-cyclopropylureido)-1,2-dioxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)imidazo[1,2-a]pyridine-6-carboxamide | 775.91 | 776 (M + 1)⊕ |
| 115 | N-((2R)-1-((2S,4S)-2-((1-amino-7-(3-cyclopropylureido)-1,2-dioxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)quinoline-3-carboxamide | 786.94 | 787 (M + 1)⊕ |

-continued

| Example | Structure | MW | MS (ESI+) |
|---|---|---|---|
| 116 | (2S,4S)-1-((R)-2-(4-((2-amino-2-oxoethyl)sulfonyl)benzamido)-3-cyclohexylpropanoyl)-N-(1-amino-7-(3-cyclopropylureido)-1,2-dioxoheptan-3-yl)-4-(5-(2-hydroxypropan-2-yl)-1H-1,2,3-triazol-1-yl)pyrrolidine-2-carboxamide | 857.00 | 857 (M + 1)⁺ |
| 117 | (2S,4S)-N-(1-amino-7-(3-cyclopropylureido)-1,2-dioxoheptan-3-yl)-1-((R)-3-cyclohexyl-2-(4-((difluoromethyl)sulfonyl)benzamido)propanoyl)-4-(5-(2-hydroxypropan-2-yl)-1H-1,2,3-triazol-1-yl)pyrrolidine-2-carboxamide | 849.95 | 850 (M + 1)⁺ |
| 118 | N-((2R)-1-((2S,4S)-2-((1-amino-7-(3-cyclopropylureido)-1,2-dioxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)-1H-indazole-7-carboxamide | 775.91 | 776 (M + 1)⁺ |

| Example | Structure | MW | MS (ESI+) |
|---|---|---|---|
| 119 | 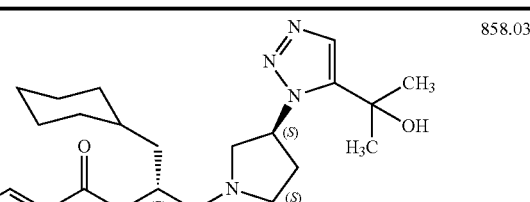<br>(2S,4S)-N-(1-amino-7-(3-cyclopropylureido)-1,2-dioxoheptan-3-yl)-1-((R)-3-cyclohexyl-2-(4-((2-methoxyethyl)sulfonyl)benzamido)propanoyl)-4-(5-(2-hydroxypropan-2-yl)-1H-1,2,3-triazol-1-yl)pyrrolidine-2-carboxamide | 858.03 | 858 (M + 1)⊕ |

Example 120: (2S,4S)-1-((R)-2-(2-Naphthamido)-3-cyclohexylpropanoyl)-N-(4-amino-1-(4-nitrophenyl)-3,4-dioxobutan-2-yl)-4-(5-(2-hydroxypropan-2-yl)-1H-1,2,3-triazol-1-yl)pyrrolidine-2-carboxamide

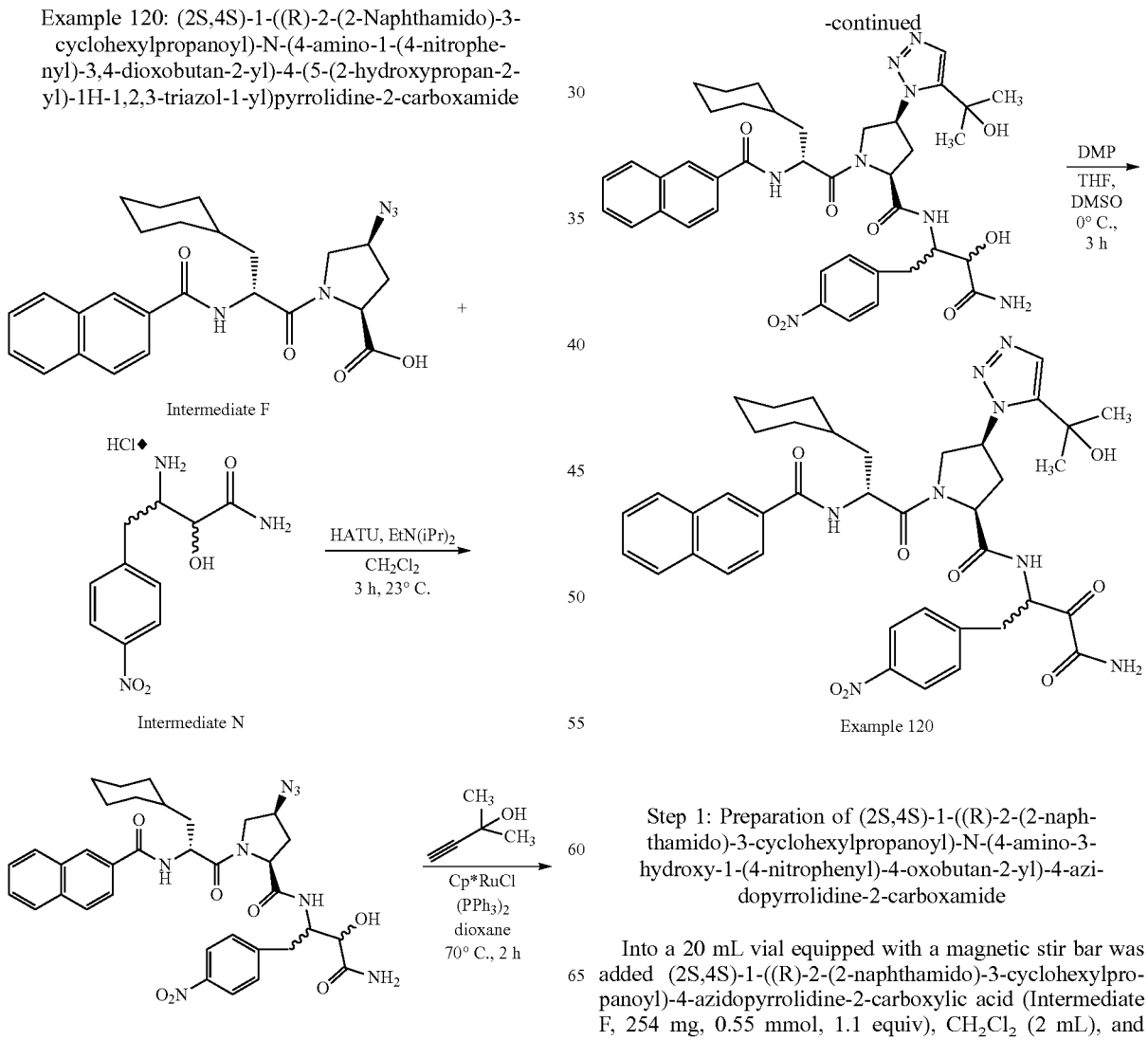

Step 1: Preparation of (2S,4S)-1-((R)-2-(2-naphthamido)-3-cyclohexylpropanoyl)-N-(4-amino-3-hydroxy-1-(4-nitrophenyl)-4-oxobutan-2-yl)-4-azidopyrrolidine-2-carboxamide Into a 20 mL vial equipped with a magnetic stir bar was added (2S,4S)-1-((R)-2-(2-naphthamido)-3-cyclohexylpropanoyl)-4-azidopyrrolidine-2-carboxylic acid (Intermediate F, 254 mg, 0.55 mmol, 1.1 equiv), $CH_2Cl_2$ (2 mL), and HATU (228 mg, 0.60 mmol, 1.2 equiv). The solution was stirred at room temperature for 10 minutes, then added to a suspension of 3-amino-2-hydroxy-4-(4-nitrophenyl)butanamide hydrochloride (Intermediate N, 138 mg, 0.50 mmol, 1.0 equiv), EtN(iPr)$_2$ (263 μL, 1.5 mmol, 3 equiv) and CH$_2$Cl$_2$ (2 mL). The solution was stirred at room temperature for 3 h. The reaction mixture was quenched with water (20 mL), poured into a 125 mL separatory funnel, and extracted with CH$_2$Cl$_2$ (3×10 mL). The combined organic layers were dried over MgSO$_4$, filtered and concentrated under reduced pressure. Purification by column chromatography through silica gel (24 g), eluting with 100:0 to 0:100 hexanes:EtOAc+20% MeOH as a gradient afforded the title compound (180 mg).

Step 2: Preparation of (2S,4S)-1-((R)-2-(2-naphthamido)-3-cyclohexylpropanoyl)-N-(4-amino-3-hydroxy-1-(4-nitrophenyl)-4-oxobutan-2-yl)-4-(5-(2-hydroxypropan-2-yl)-1H-1,2,3-triazol-1-yl)pyrrolidine-2-carboxamide Into a 20 mL vial equipped with a magnetic stir bar was added (2S,4S)-1-((R)-2-(2-naphthamido)-3-cyclohexylpropanoyl)-N-(4-amino-3-hydroxy-1-(4-nitrophenyl)-4-oxobutan-2-yl)-4-azidopyrrolidine-2-carboxamide (180 mg, 0.26 mmol, 1.0 equiv), Cp*RuCl(PPh$_3$)$_2$ (20 mg, 0.026 mmol, 0.1 equiv), 2-methylbut-3-yn-2-ol (84 mg, 1.0 mmol, 4 equiv) and 1,4-dioxane (4 mL). The solution was bubbled with a steady flow of nitrogen for 10 minutes then heated in an oil bath at 70° C. for 2 h. The mixture was concentrated under reduced pressure to remove the bulk of the dioxane and the resulting oil was loaded directly onto a silica gel and purified by column chromatography through silica gel (25 g), eluting with 98:2 to 80:20 CH$_2$Cl$_2$:MeOH as a gradient. The title compound was obtained as a brown oil (110 mg).

Step 3: Preparation of (2S,4S)-1-((R)-2-(2-naphthamido)-3-cyclohexylpropanoyl)-N-(4-amino-1-(4-nitrophenyl)-3,4-dioxobutan-2-yl)-4-(5-(2-hydroxypropan-2-yl)-1H-1,2,3-triazol-1-yl)pyrrolidine-2-carboxamide Into a 20 mL vial equipped with a magnetic stir bar was added (2S,4S)-1-((R)-2-(2-naphthamido)-3-cyclohexylpropanoyl)-N-(4-amino-3-hydroxy-1-(4-nitrophenyl)-4-oxobutan-2-yl)-4-(5-(2-hydroxypropan-2-yl)-1H-1,2,3-triazol-1-yl)pyrrolidine-2-carboxamide (110 mg, 0.14 mmol, 1.0 equiv), THF (10 mL) and DMSO (1 mL). The solution was cooled to 0° C. in an ice bath and treated with Dess-Martin Periodinane (182 mg, 0.42 mmol, 3.0 equiv) and stirred at 0° C. for 3 h. The reaction was quenched with 10% aqueous Na$_2$S$_2$O$_3$ solution (2 mL) and stirred at room temperature for 30 minutes. The reaction mixture was diluted with water (5 mL) and extracted with EtOAc (25 mL). The organic layer was washed with water (5 mL), dried over MgSO$_4$, filtered and concentrated under reduced pressure. Purification by column chromatography through silica gel (10 g), eluting with 100:0 to 75:25 EtOAc:MeOH as a gradient afforded the title compound as an off-white foam (91 mg). MS (ESI+) 767 (M+1)$^⊕$ Example 121: (2S,4S)-1-((R)-2-(2-Naphthamido)-3-cyclohexylpropanoyl)-N-(1-(4-acetamidophenyl)-4-amino-3,4-dioxobutan-2-yl)-4-(5-(2-hydroxypropan-2-yl)-1H-1,2,3-triazol-1-yl)pyrrolidine-2-carboxamide

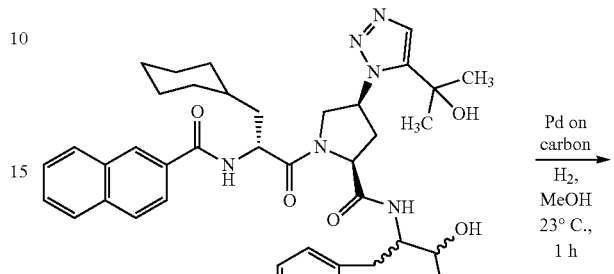

Example 120, Step 2

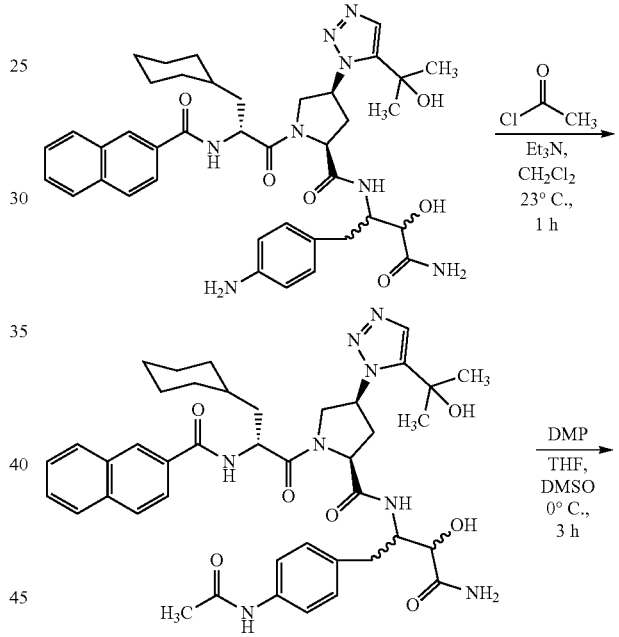

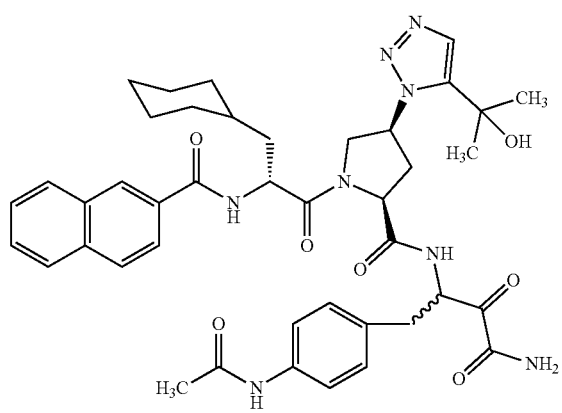

Example 121

Step 1: Preparation of (2S,4S)-1-((R)-2-(2-naphthamido)-3-cyclohexylpropanoyl)-N-(4-amino-1-(4-aminophenyl)-3-hydroxy-4-oxobutan-2-yl)-4-(5-(2-hydroxypropan-2-yl)-1H-1,2,3-triazol-1-yl)pyrrolidine-2-carboxamide Into a 100 mL flask equipped with a magnetic stir bar was added (2S,4S)-1-((R)-2-(2-naphthamido)-3-cyclohexylpropanoyl)-N-(4-amino-3-hydroxy-1-(4-nitrophenyl)-4-oxobutan-2-yl)-4-(5-(2-hydroxypropan-2-yl)-1H-1,2,3-triazol-1-yl)pyrrolidine-2-carboxamide (Example 120, Step 2, 120 mg, 0.16 mmol, 1.0 equiv) and MeOH (10 mL). The flask was purged with nitrogen for 10 minutes, after which 10 wt % palladium on carbon (30 mg) was added to the flask and $N_2$ purging continued for 10 minutes. The $N_2$ inlet was replaced with a $H_2$ balloon which was bubbled into the solution with vigorous stirring for 1 h. The suspension was filtered through a pad of celite on a sintered plastic funnel and the filtrate concentrated under reduced pressure to yield a white solid (60 mg).

Step 2: Preparation of (2S,4S)-1-((R)-2-(2-naphthamido)-3-cyclohexylpropanoyl)-N-(1-(4-acetamidophenyl)-4-amino-3-hydroxy-4-oxobutan-2-yl)-4-(5-(2-hydroxypropan-2-yl)-1H-1,2,3-triazol-1-yl)pyrrolidine-2-carboxamide Into a 20 mL vial equipped with a magnetic stir bar was added (2S,4S)-1-((R)-2-(2-naphthamido)-3-cyclohexylpropanoyl)-N-(4-amino-1-(4-aminophenyl)-3-hydroxy-4-oxobutan-2-yl)-4-(5-(2-hydroxypropan-2-yl)-1H-1,2,3-triazol-1-yl)pyrrolidine-2-carboxamide (15 mg, 0.019 mmol, 1.0 equiv), and $CH_2Cl_2$ (2 mL). To the reaction mixture was added $Et_3N$ (19 µL, 0.14 mmol, 7 equiv) followed by acetyl chloride (1.5 mg, 0.019 mmol, 1.0 equiv). The solution was stirred for 1 h at room temperature and concentrated under reduced pressure to afford a yellow oil which was used directly in the next step without purification.

Step 3: Preparation of (2S,4S)-1-((R)-2-(2-naphthamido)-3-cyclohexylpropanoyl)-N-(1-(4-acetamidophenyl)-4-amino-3,4-dioxobutan-2-yl)-4-(5-(2-hydroxypropan-2-yl)-1H-1,2,3-triazol-1-yl)pyrrolidine-2-carboxamide Into a 4 mL sample vial equipped with a magnetic stir bar and under $N_2$ was added (2S,4S)-1-((R)-2-(2-naphthamido)-3-cyclohexylpropanoyl)-N-(1-(4-acetamidophenyl)-4-amino-3-hydroxy-4-oxobutan-2-yl)-4-(5-(2-hydroxypropan-2-yl)-1H-1,2,3-triazol-1-yl)pyrrolidine-2-carboxamide (10 mg, 0.013 mmol, 1.0 equiv), THF (2 mL) and DMSO (0.4 mL). The solution was cooled to 0° C. in an ice bath and Dess-Martin Periodinane (30 mg, 0.07 mmol, 6 equiv) was added and the mixture was stirred at 0° C. for 3 h, monitoring with LCMS. After 3 h at 0° C., the reaction was quenched with 10% aqueous $Na_2S_2O_8$ solution (5 mL) and extracted with EtOAc (2×5 mL). The combined organic layers were concentrated under reduced pressure. Purification by reverse-phase column chromatography (12 g, C18 column), eluting with 90:10 to 20:80 $H_2O$:MeCN+0.1% $HCO_2H$ as a gradient afforded the desired compound (3 mg). MS (ESI+) 780 (M+1)$^\oplus$ Example 122: (2S,4S)-1-((R)-2-(2-Naphthamido)-3-cyclohexylpropanoyl)-N-(4-amino-1-(4-(3-cyclohexylureido)phenyl)-3,4-dioxobutan-2-yl)-4-(5-(2-hydroxypropan-2-yl)-H-1,2,3-triazol-1-yl)pyrrolidine-2-carboxamide

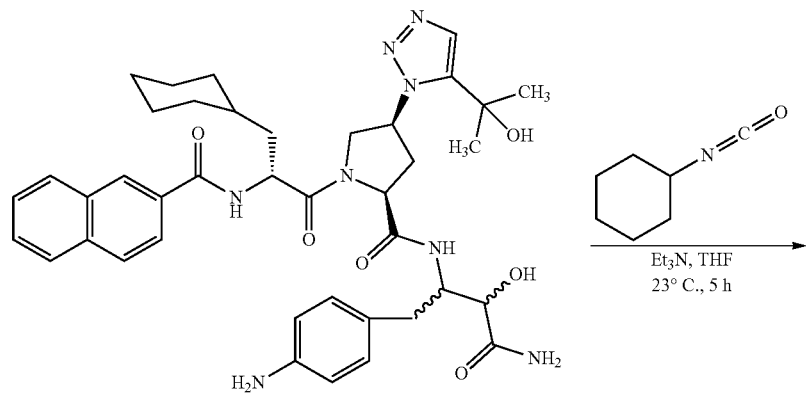

Example 121, Step 1

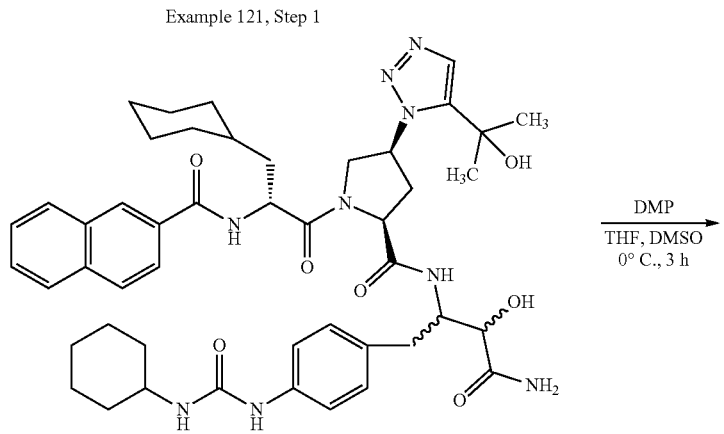

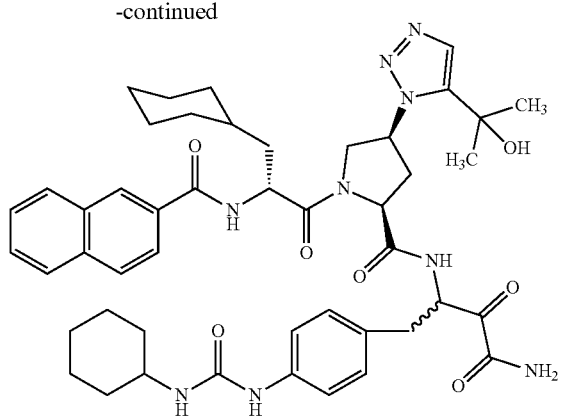

Example 122

Step 1: Preparation of (2S,4S)-1-((R)-2-(2-naph-thamido)-3-cyclohexylpropanoyl)-N-(4-amino-1-(4-(3-cyclohexylureido)phenyl)-3-hydroxy-4-oxobutan-2-yl)-4-(5-(2-hydroxypropan-2-yl)-1H-1,2,3-triazol-1-yl)pyrrolidine-2-carboxamide Into a 20 mL vial equipped with a magnetic stir bar was added (2S,4S)-1-((R)-2-(2-naphthamido)-3-cyclohexylpropanoyl)-N-(4-amino-1-(4-aminophenyl)-3-hydroxy-4-oxobutan-2-yl)-4-(5-(2-hydroxypropan-2-yl)-1H-1,2,3-triazol-1-yl)pyrrolidine-2-carboxamide (Example 121, Step 1, 10 mg, 0.014 mmol, 1.0 equiv), Et₃N (29 µL, 0.21 mmol, 15 equiv) and THF (2 mL). The solution was cooled to 0° C. in an ice bath and isocyanatocyclohexane (30 mg, 0.24 mmol, 17 equiv) was added. The reaction mixture was stirred at room temperature for 5 h. The reaction was quenched with water (5 mL) and poured into a 50 mL separatory funnel and extracted with EtOAc (20 mL). The organic layer was washed with water (5 mL), dried over MgSO₄, filtered and concentrated under reduced pressure. The resulting product was used directly in the next step without further purification.

Step 2: Preparation of (2S,4S)-1-((R)-2-(2-naph-thamido)-3-cyclohexylpropanoyl)-N-(4-amino-1-(4-(3-cyclohexylureido)phenyl)-3,4-dioxobutan-2-yl)-4-(5-(2-hydroxypropan-2-yl)-1H-1,2,3-triazol-1-yl)pyrrolidine-2-carboxamide Into a 4 mL sample vial equipped with a magnetic stir bar and under N₂ was added (2S,4S)-1-((R)-2-(2-naphthamido)-3-cyclohexylpropanoyl)-N-(4-amino-1-(4-(3-cyclohexylureido)phenyl)-3-hydroxy-4-oxobutan-2-yl)-4-(5-(2-hydroxypropan-2-yl)-1H-1,2,3-triazol-1-yl)pyrrolidine-2-carboxamide (10 mg, 0.012 mmol, 1.0 equiv), THF (2 mL) and DMSO (0.4 mL). The solution was cooled to 0° C. in an ice bath and Dess-Martin Periodinane (30 mg, 0.07 mmol, 6 equiv) was added and the mixture was stirred at 0° C. for 3 h, monitoring with LCMS. After 3 h at 0° C., the reaction was quenched with 10% aqueous Na₂S₂O₈ solution (5 mL) and extracted with EtOAc (2×5 mL). The combined organic layers were concentrated under reduced pressure. Purification by reverse-phase column chromatography (12 g, C18 column), eluting with 90:10 to 20:80 H₂O:MeCN+0.1% HCO₂H as a gradient afforded the desired compound (3 mg). MS (ESI+) 862 (M+1)$^{\oplus}$ Example 123: Benzyl (2-((2S,4S)-1-((R)-2-(2-naph-thamido)-3-cyclohexylpropanoyl)-4-(5-(2-hydroxy-propan-2-yl)-1H-1,2,3-triazol-1-yl)pyrrolidine-2-carboxamido)-4-amino-3,4-dioxobutyl)carbamate

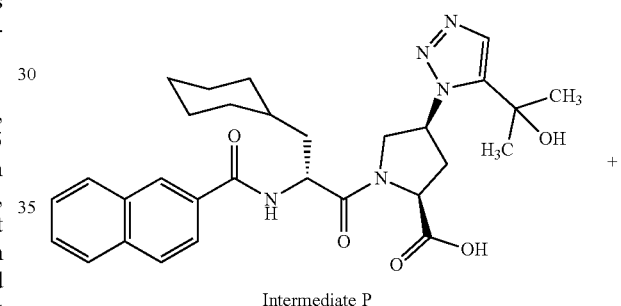

Intermediate P

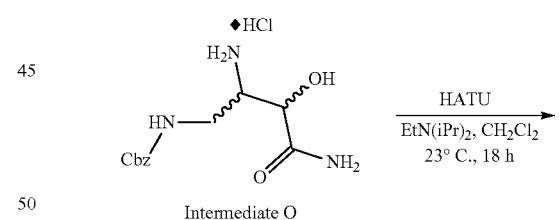

Intermediate O

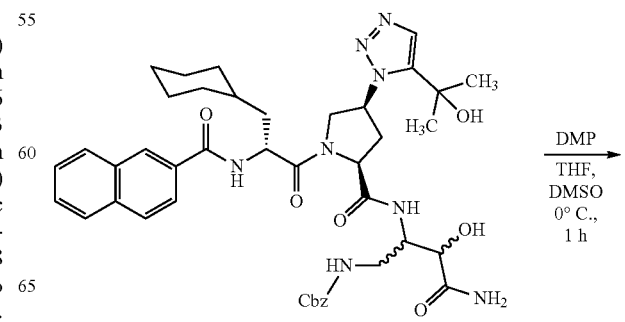

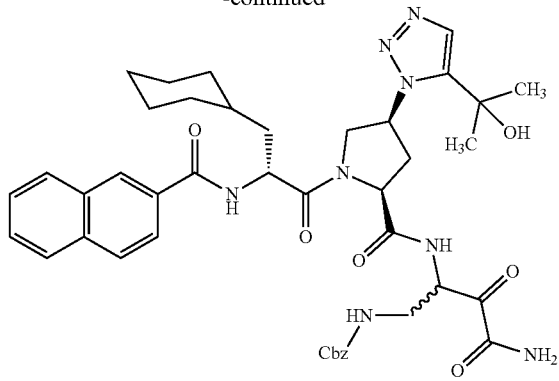

Example 123

Step 1: Preparation of benzyl (2-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-4-amino-3-hydroxy-4-oxobutyl)carbamate Into a 20 mL vial equipped with a magnetic stir bar and under N₂ was added (2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxylic acid (Intermediate P, 85 mg, 0.15 mmol, 1.0 equiv), HATU (75 mg, 0.20 mmol, 1.3 equiv), EtN(iPr)₂ (157 μL, 0.90 mmol, 6 equiv) and CH₂Cl₂ (2 mL). The solution was treated with benzyl (2,4-diamino-3-hydroxy-4-oxobutyl)carbamate hydrochloride (Intermediate O, 100 mg, 0.33 mmol, 2 equiv) and the mixture was stirred at room temperature for 18 h overnight.

The reaction mixture was concentrated under reduced pressure and loaded directly onto silica gel (5 g). Purification by column chromatography through silica gel (12 g), eluting with 100:0 to 70:30 CH₂Cl₂:iPrOH as a gradient afforded the desired compound (10 mg).

Step 2: Preparation of benzyl (2-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-4-amino-3,4-dioxobutyl)carbamate Into a 4 mL vial equipped with a magnetic stir bar and under N₂ was added benzyl (2-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-4-amino-3-hydroxy-4-oxobutyl)carbamate (5 mg, 0.006 mmol, 1.0 equiv) in THF (2 mL) and DMSO (0.4 mL) was cooled to 0° C. in an ice bath. The solution was treated with Dess-Martin Periodinane (16 mg, 0.036 mmol, 6 equiv) and stirred at 0° C. for 1 h, at which stage LCMS analysis revealed complete conversion of starting material. The reaction was quenched with 10% aqueous Na₂S₂O₃ solution (2 mL) and extracted with EtOAc (6 mL). The organic layer was concentrated under reduced pressure. Purification by reverse-phase column chromatography (12 g, C18 column), eluting with 90:10 to 10:90 H₂O:MeCN+0.1% HCO₂H as a gradient afforded the title compound (2 mg). MS (ESI+) 795 (M+1)⊕

Example 124: Benzyl (7-amino-5-((3S)-2-((R)-3-cyclohexyl-2-(4-(methylsulfonyl)benzamido)propanoyl)-2-azabicyclo[22.1]heptane-3-carboxamido)-6,7-dioxoheptyl)carbamate

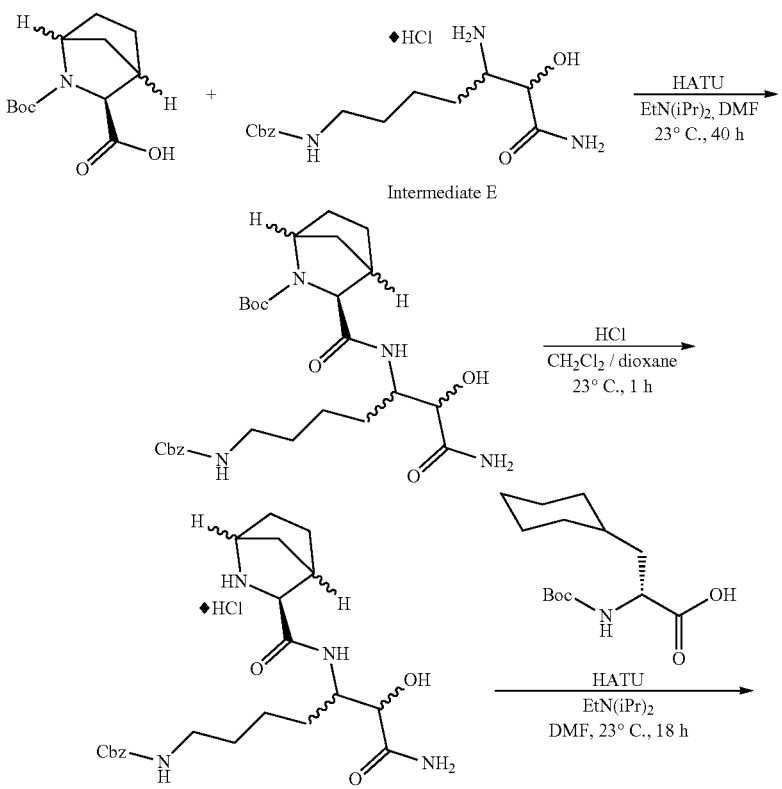

Intermediate E

-continued
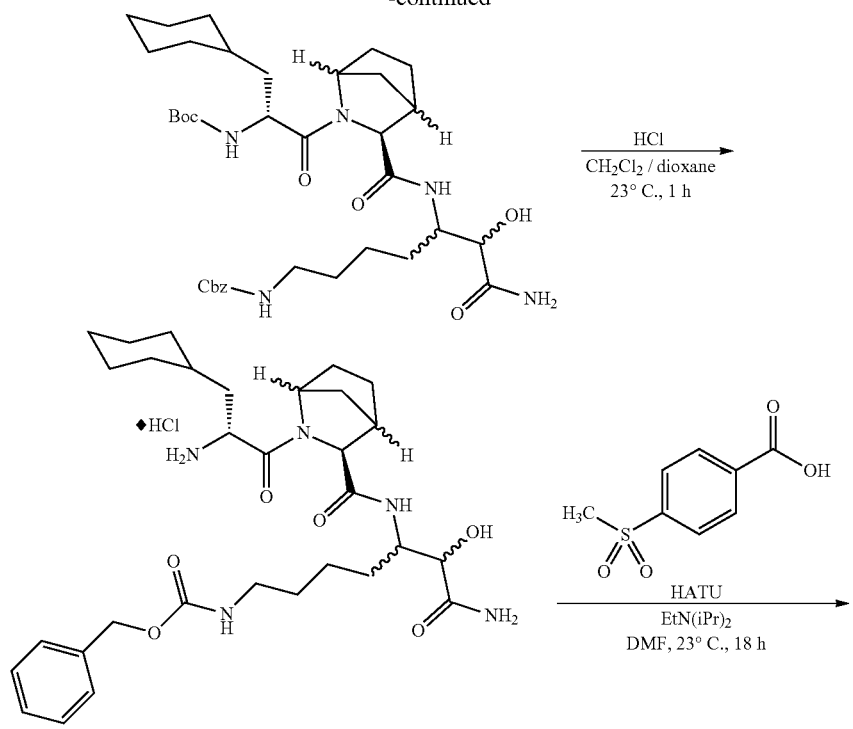
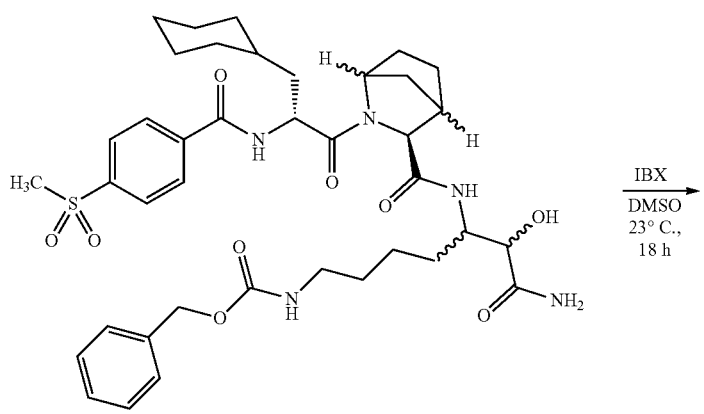
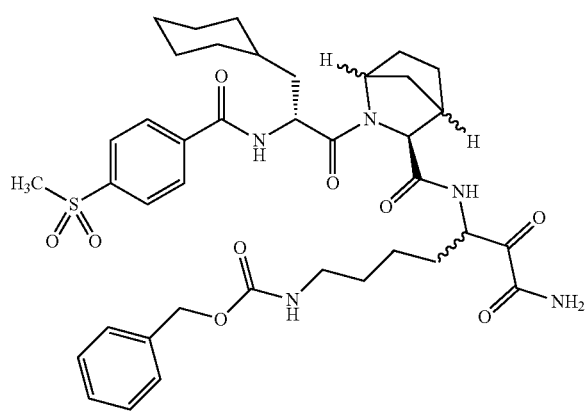
Example 124

Step 1: Preparation of tert-butyl (3S)-3-((1-amino-7-(((benzyloxy)carbonyl)amino)-2-hydroxy-1-oxoheptan-3-yl)carbamoyl)-2-azabicyclo[2.2.1]heptane-2-carboxylate Into a 20 mL sample vial equipped with a magnetic stir bar and under $N_2$ was added (3S)-2-(tert-butoxycarbonyl)-2-azabicyclo[2.2.1]heptane-3-carboxylic acid (420 mg, 1.7 mmol, 1.0 equiv), HATU (722 mg, 1.92 mmol, 1.1 equiv), EtN(iPr)$_2$ (591 µL, 6.8 mmol, 4 equiv) and DMF (3 mL). The mixture was stirred at 0° C. in an ice bath for 10 minutes at which stage benzyl (5,7-diamino-6-hydroxy-7-oxoheptyl)carbamate hydrochloride (Intermediate E, 661 mg, 1.92 mmol, 1.1 equiv) in DMF (2 mL) was added. The reaction mixture was stirred at room temperature for 40 h. The reaction mixture was quenched with water (10 mL) and extracted with EtOAc (2×20 mL). The combined organic layers were washed with brine (5 mL), dried over MgSO$_4$, filtered and concentrated under reduced pressure. Purification by column chromatography through silica gel (40 g), eluting with 100:0: to 70:30 CH$_2$Cl$_2$:iPrOH as a gradient afforded the title compound (470 mg).

Step 2: Preparation of benzyl (7-amino-5-((3S)-2-azabicyclo[2.2.1]heptane-3-carboxamido)-6-hydroxy-7-oxoheptyl)carbamate hydrochloride To a mixture of tert-butyl (3S)-3-((1-amino-7-(((benzyloxy)carbonyl)amino)-2-hydroxy-1-oxoheptan-3-yl)carbamoyl)-2-azabicyclo[2.2.1]heptane-2-carboxylate (470 mg, 0.88 mmol, 1.0 equiv) in CH$_2$Cl$_2$ (3 mL) was treated with 4 M HCl in dioxane (3 mL). The reaction mixture was stirred at room temperature for 1 h and then concentrated under reduced pressure and used directly in the next reaction without purification.

Step 3: Preparation of benzyl (7-amino-5-((3S)-2-((R)-2-((tert-butoxycarbonyl)amino)-3-cyclohexylpropanoyl)-2-azabicyclo[2.2.1]heptane-3-carboxamido)-6-hydroxy-7-oxoheptyl)carbamate Into a 20 mL sample vial equipped with a magnetic stir bar and under $N_2$ was added (R)-2-((tert-butoxycarbonyl)amino)-3-cyclohexylpropanoic acid (239 mg, 0.88 mmol, 1.0 equiv), HATU (334 mg, 0.88 mmol, 1.0 equiv), DMF (2 mL) and EtN(iPr)$_2$ (307 L, 3.5 mmol, 4 equiv). The mixture was stirred at 0° C. in an ice bath for 10 minutes at which stage benzyl (7-amino-5-((3S)-2-azabicyclo[2.2.1]heptane-3-carboxamido)-6-hydroxy-7-oxoheptyl)carbamate hydrochloride (380 mg, 0.88 mmol, 1.0 equiv) in DMF (2 mL) was added. The reaction mixture was stirred at room temperature for 18 h overnight. The reaction mixture was quenched with water (10 mL) and extracted with EtOAc (2×20 mL). The combined organic layers were washed with brine (5 mL), dried over MgSO$_4$, filtered and concentrated under reduced pressure. Purification by column chromatography through silica gel (24 g), eluting with 100:0:0 to 70:15:15 Hexanes:CH$_2$Cl$_2$:iPrOH as a gradient afforded the title compound (380 mg).

Step 4: Preparation of benzyl (7-amino-5-((3S)-2-((R)-2-amino-3-cyclohexylpropanoyl)-2-azabicyclo[2.2.1]heptane-3-carboxamido)-6-hydroxy-7-oxoheptyl)carbamate hydrochloride A mixture of benzyl (7-amino-5-((3S)-2-((R)-2-((tert-butoxycarbonyl)amino)-3-cyclohexylpropanoyl)-2-azabicyclo[2.2.1]heptane-3-carboxamido)-6-hydroxy-7-oxoheptyl)carbamate (100 mg, 0.23 mmol, 1.0 equiv) in CH$_2$Cl$_2$ (3 mL) was added 4 M HCl in dioxane (3 mL). The reaction mixture was stirred at room temperature for 1 h and then concentrated under reduced pressure and used directly in the next reaction without purification.

Step 5: Preparation of benzyl (7-amino-5-((3S)-2-((R)-3-cyclohexyl-2-(4-(methylsulfonyl)benzamido)propanoyl)-2-azabicyclo[2.2.1]heptane-3-carboxamido)-6-hydroxy-7-oxoheptyl)carbamate Into a 20 mL sample vial equipped with a magnetic stir bar and under $N_2$ was added 4-(methanesulfonyl)benzoic acid (46 mg, 0.23 mmol, 1.0 equiv), HATU (89 mg, 0.23 mmol, 1.0 equiv), EtN(iPr)$_2$ (161 µL, 0.92 mmol, 4 equiv) and DMF (2 mL). The reaction was stirred at room temperature for 10 minutes at which stage a solution of benzyl (7-amino-5-((3S)-2-((R)-2-amino-3-cyclohexylpropanoyl)-2-azabicyclo[2.2.1]heptane-3-carboxamido)-6-hydroxy-7-oxoheptyl)carbamate hydrochloride (140 mg, 0.23 mmol, 1.0 equiv) in DMF (2 mL) was added. The reaction mixture was stirred at room temperature for 18 h overnight. The reaction mixture was quenched with water (10 mL) and extracted with EtOAc (2×20 mL). The combined organic layers were washed with brine (5 mL), dried over MgSO$_4$, filtered and concentrated under reduced pressure. Purification by column chromatography through silica gel (24 µg), eluting with 100:0:0 to 70:15:15 Hexanes:CH$_2$Cl$_2$:iPrOH as a gradient afforded the title compound (90 mg).

Step 6: Preparation of benzyl (7-amino-5-((3S)-2-((R)-3-cyclohexyl-2-(4-(methylsulfonyl)benzamido)propanoyl)-2-azabicyclo[22.1]heptane-3-carboxamido)-6,7-dioxoheptyl)carbamate Into a 20 mL sample vial equipped with a magnetic stir bar and under $N_2$ was added benzyl (7-amino-5-((3S)-2-((R)-3-cyclohexyl-2-(4-(methylsulfonyl)benzamido)propanoyl)-2-azabicyclo[2.2.1]heptane-3-carboxamido)-6-hydroxy-7-oxoheptyl)carbamate (45 mg, 0.059 mmol, 1.0 equiv) and DMSO (2 mL). The solution was treated with 45 wt % IBX (73 mg, 0.117 mmol, 2 equiv) and the mixture was stirred at room temperature for 18 h overnight. The reaction was quenched with 10% aqueous Na$_2$S$_2$O$_8$ (10 mL) and extracted with EtOAc (2×20 mL) using a separatory funnel. The combined organic layers were washed with brine (5 mL), dried over MgSO$_4$, filtered and concentrated under reduced pressure. The reaction mixture was purified by column chromatography through silica gel (12 µg), eluting with 100:0 to 40:40:20 CH$_2$Cl$_2$:iPrOH:Hexanes as a gradient. The compound was further purified by reverse-phase column chromatography (16 g, C18 column), eluting with 100:0:0 to 20:40:40 H$_2$O:MeCN:MeOH+0.1% HCO$_2$H as a gradient to afford the title compound (9 mg). MS (ESI+) 766 (M+1)$^\oplus$

Example 125: Benzyl (5-((2S,4S)-1-(2-(2-naphthamido)-4-((1S,4R)-bicyclo[2.2.1]heptan-2-yl)butanoyl)-4-(5-(2-hydroxypropan-2-yl)-1H-1,2,3-triazol-1-yl)pyrrolidine-2-carboxamido)-7-amino-6,7-dioxoheptyl)carbamate

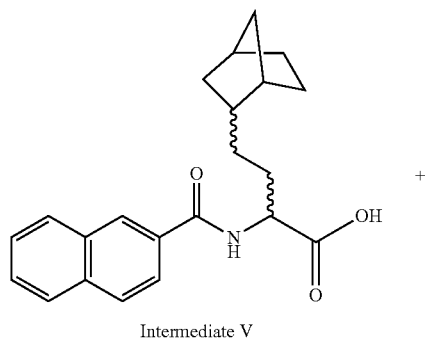

Intermediate V

+

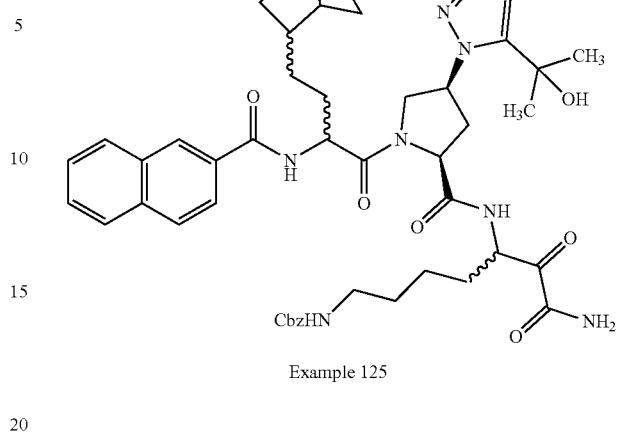

Example 125

Step 1: Preparation of benzyl (5-((2S,4S)-1-(2-(2-naphthamido)-4-((1S,4R)-bicyclo[2.2.1]heptan-2-yl)butanoyl)-4-(5-(2-hydroxypropan-2-yl)-1H-1,2,3-triazol-1-yl)pyrrolidine-2-carboxamido)-7-amino-6-hydroxy-7-oxoheptyl)carbamate Into a 25 mL round-bottom flask equipped with a magnetic stir bar and under $N_2$ was added 2-(2-naphthamido)-4-((1S,4R)-bicyclo[2.2.1]heptan-2-yl)butanoic acid (Intermediate V, 150 mg, 0.43 mmol, 1.0 equiv), benzyl (7-amino-6-hydroxy-5-((2S,4S)-4-(5-(2-hydroxypropan-2-yl)-1H-1,2,3-triazol-1-yl)pyrrolidine-2-carboxamido)-7-oxoheptyl)carbamate hydrochloride (Intermediate Q, 243 mg, 0.43 mmol, 1.0 equiv), HATU (195 mg, 0.51 mmol, 1.2 equiv) and DMF (2 mL). The reaction mixture was treated with $EtN(iPr)_2$ (300 μL, 1.71 mmol, 4 equiv) and stirred at room temperature for 18 h. The reaction mixture was loaded directly onto silica gel (5 g) and purified by column chromatography through silica gel (40 g), eluting with 100:0 to 85:15 $CH_2Cl_2$:MeOH as a gradient to afford the title compound (38 mg).

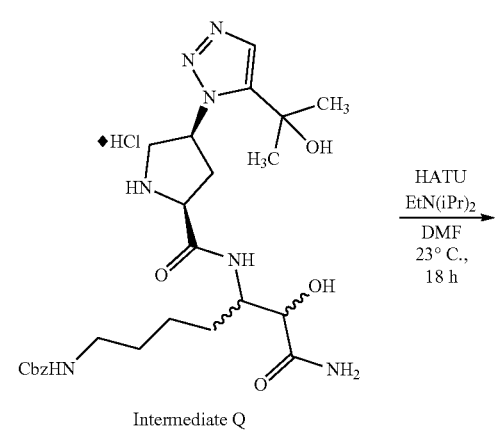

Intermediate Q

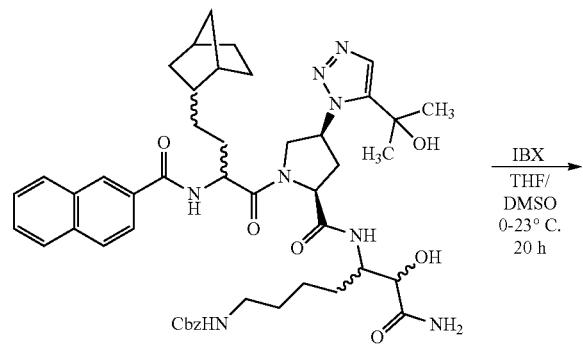

Step 2: Preparation of benzyl (5-((2S,4S)-1-(2-(2-naphthamido)-4-((1S,4R)-bicyclo[2.2.1]heptan-2-yl)butanoyl)-4-(5-(2-hydroxypropan-2-yl)-1H-1,2,3-triazol-1-yl)pyrrolidine-2-carboxamido)-7-amino-6,7-dioxoheptyl)carbamate Into a 10 mL round-bottom flask equipped with a magnetic stir bar and under $N_2$ was added benzyl (5-((2S,4S)-1-(2-(2-naphthamido)-4-((1S,4R)-bicyclo[2.2.1]heptan-2-yl)butanoyl)-4-(5-(2-hydroxypropan-2-yl)-1H-1,2,3-triazol-1-yl)pyrrolidine-2-carboxamido)-7-amino-6-hydroxy-7-oxoheptyl)carbamate (22 mg, 0.025 mmol, 1.0 equiv), THF (200 μL) and DMSO (200 μL). The reaction mixture was treated with 45 wt % IBX (31 mg, 0.05 mmol, 2 equiv) and stirred at 0° C. for 1 h after which another portion of IBX (47 mg, 0.075 mmol, 3 equiv) was added. The reaction was stirred at 0° C. for 1 h and then another portion of IBX added (78 mg, 0.125 mmol, 5 equiv) and the mixture stirred at 0° C. for 2 h. A final portion of IBX was added (78 mg, 0.125 mmol, 5 equiv) and the reaction mixture was stirred at room temperature for 16 h overnight. The reaction mixture was loaded onto a C18 column and purified by reverse-phase column chromatography (15 g, C18 column), eluting with 60:40 to 10:90 $H_2O$:MeCN+0.1% $HCO_2H$ as a gradient to afford the desired compound as a mixture of diastereomers (17 mg). MS (ESI+) 863 (M+1)⊕

Example 126: Benzyl (5-((2S,4S)-1-((R)-2-(2-naphthamido)-3-(((benzyloxy)carbonyl)amino)propanoyl)-4-(5-(2-hydroxypropan-2-yl)-1H-1,2,3-triazol-1-yl)pyrrolidine-2-carboxamido)-7-amino-6,7-dioxoheptyl)carbamate

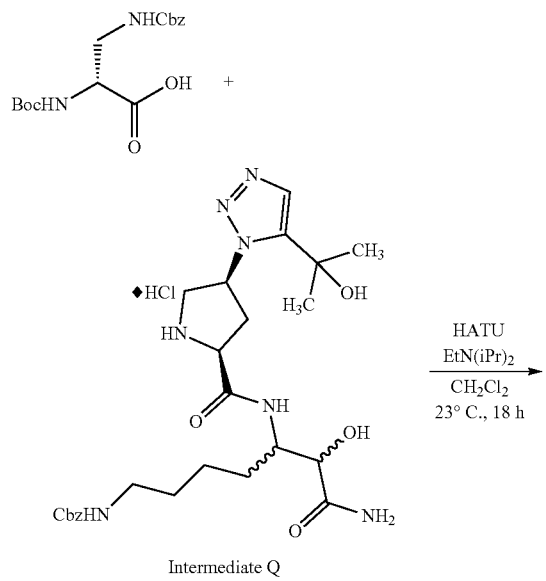

Intermediate Q

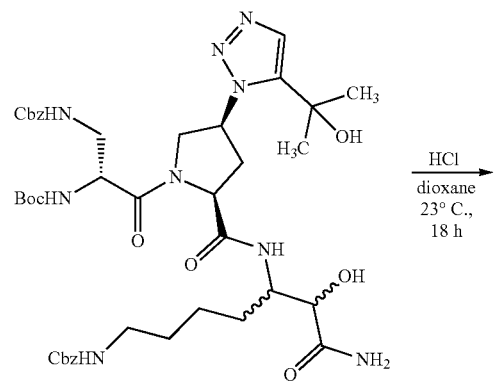

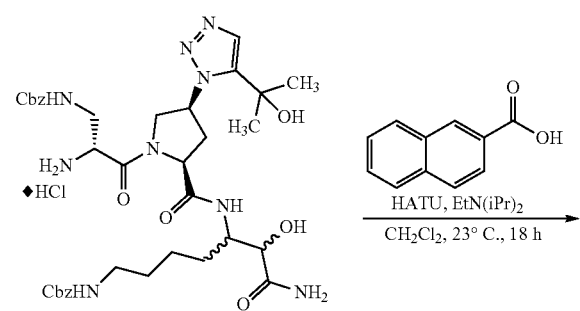

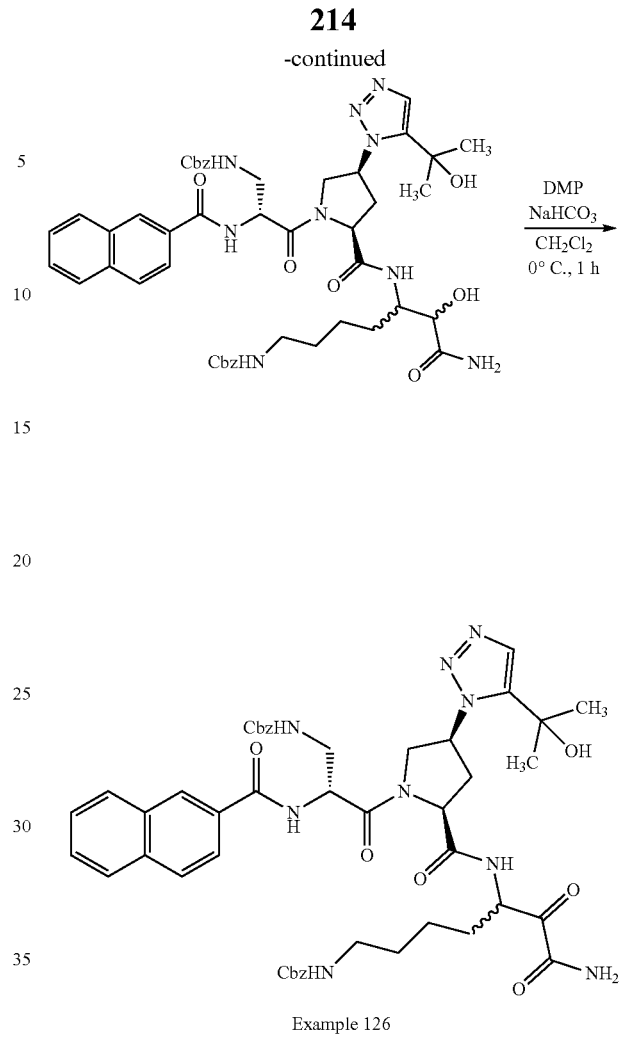

Example 126

Step 1: Preparation of benzyl tert-butyl ((2R)-3-((2S,4S)-2-((1-amino-7-(((benzyloxy)carbonyl)amino)-2-hydroxy-1-oxoheptan-3-yl)carbamoyl)-4-(5-(2-hydroxypropan-2-yl)-1H-1,2,3-triazol-1-yl)pyrrolidin-1-yl)-3-oxopropane-1,2-diyl)dicarbamate Into a 100 mL round-bottom flask equipped with a magnetic stir bar and under N₂ was added (R)-3-(((benzyloxy)carbonyl)amino)-2-((tert-butoxycarbonyl)amino)propanoic acid (135 mg, 0.4 mmol, 1.0 equiv), HATU (182 mg, 0.48 mmol, 1.2 equiv) and CH₂Cl₂ (3 mL). The reaction mixture was stirred at room temperature for 10 minutes before being treated with benzyl (7-amino-6-hydroxy-5-((2S,4S)-4-(5-(2-hydroxypropan-2-yl)-1H-1,2,3-triazol-1-yl)pyrrolidine-2-carboxamido)-7-oxoheptyl)carbamate hydrochloride (Intermediate Q, 227 mg, 0.4 mmol, 1.0 equiv), DMSO (500 L) and EtN(iPr)₂ (280 μL, 1.6 mmol, 4 equiv). The reaction mixture was stirred at room temperature for 18 h overnight. The reaction mixture was diluted with water (10 mL) and extracted with CH₂Cl₂ (3×10 mL) using a phase-separatory cartridge. The combined organic layers were concentrated under reduced pressure. Purification by column chromatography through silica gel (24 g), eluting with 100:0 to 80:20 CH₂Cl₂:MeOH as a gradient afforded the title compound (340 mg).

Step 2: Preparation of benzyl (7-amino-5-((2S,4S)-1-((R)-2-amino-3-(((benzyloxy)carbonyl)amino)propanoyl)-4-(5-(2-hydroxypropan-2-yl)-1H-1,2,3-triazol-1-yl)pyrrolidine-2-carboxamido)-6-hydroxy-7-oxoheptyl)carbamate A solution of benzyl tert-butyl ((2R)-3-((2S,4S)-2-((1-amino-7-(((benzyloxy)carbonyl)amino)-2-hydroxy-1-oxoheptan-3-yl)carbamoyl)-4-(5-(2-hydroxypropan-2-yl)-1H-1,2,3-triazol-1-yl)pyrrolidin-1-yl)-3-oxopropane-1,2-diyl)dicarbamate (340 mg, 0.4 mmol, 1.0 equiv) in 1,4-dioxane (4 mL) was treated with 4 M HCl in dioxane (250 µL, 1.0 mmol, 2.5 equiv). The reaction mixture was stirred at room temperature for 18 h overnight. The resulting mixture was concentrated under reduced pressure and dried under vacuum before being used directly in the next reaction.

Step 3: Preparation of benzyl (5-((2S,4S)-1-((R)-2-(2-naphthamido)-3-(((benzyloxy)carbonyl)amino)propanoyl)-4-(5-(2-hydroxypropan-2-yl)-1H-1,2,3-triazol-1-yl)pyrrolidine-2-carboxamido)-7-amino-6-hydroxy-7-oxoheptyl)carbamate Into a 100 mL round-bottom flask equipped with a magnetic stir bar and under N₂ was added benzyl (7-amino-5-((2S,4S)-1-((R)-2-amino-3-(((benzyloxy)carbonyl)amino)propanoyl)-4-(5-(2-hydroxypropan-2-yl)-1H-1,2,3-triazol-1-yl)pyrrolidine-2-carboxamido)-6-hydroxy-7-oxoheptyl)carbamate (280 mg, 0.36 mmol, 1.0 equiv), 2-naphthoic acid (62 mg, 0.36 mmol, 1.0 equiv) HATU (163 mg, 0.43 mmol, 1.2 equiv) and CH₂Cl₂ (5 mL). The reaction mixture was treated with EtN(iPr)₂ (252 µL, 1.44 mmol, 4 equiv) and stirred at room temperature for 18 h. The reaction mixture was quenched with water (10 mL) and extracted with CH₂Cl₂ (3×5 mL) and the combined organic layers were concentrated under reduced pressure. Purification by column chromatography through silica gel (29 g), eluting with 100:0 to 90:10 CH₂Cl₂:MeOH as a gradient afforded the title compound (480 mg).

Step 4: Preparation of benzyl (5-((2S,4S)-1-((R)-2-(2-naphthamido)-3-(((benzyloxy)carbonyl)amino)propanoyl)-4-(5-(2-hydroxypropan-2-yl)-1H-1,2,3-triazol-1-yl)pyrrolidine-2-carboxamido)-7-amino-6,7-dioxoheptyl)carbamate Into a 4 mL sample vial equipped with a magnetic stir bar and under N₂ was added benzyl (5-((2S,4S)-1-((R)-2-(2-naphthamido)-3-(((benzyloxy)carbonyl)amino)propanoyl)-4-(5-(2-hydroxypropan-2-yl)-1H-1,2,3-triazol-1-yl)pyrrolidine-2-carboxamido)-7-amino-6-hydroxy-7-oxoheptyl)carbamate (360 mg, 0.36 mmol, 1.0 equiv), NaHCO₃ (61 mg, 0.72 mmol, 2 equiv) and CH₂Cl₂ (1.2 mL). The suspension was cooled to 0° C., Dess-Martin Periodinane (182 mg, 0.43 mmol, 1.2 equiv) was added and the mixture was stirred at 0° C. for 1 h. The reaction was quenched with 10% aqueous Na₂S₂O₈ solution (5 mL) and extracted with CH₂Cl₂ (3×5 mL) using a phase-separatory cartridge. The combined organic layers were concentrated under reduced pressure. Purification by reverse-phase column chromatography (30 g, C18 column), eluting with 100:0 to 30:70 H₂O:MeCN+0.1% HCO₂H as a gradient afforded the title compound (8 mg). MS (ESI+) 904 (M+1)⊕

The following compounds were prepared in a similar manner to Example 126, where (R)-3-(((benzyloxy)carbonyl)amino)-2-((tert-butoxycarbonyl)amino)propanoic acid in Step 1 is replaced with: 2-((tert-butoxycarbonyl)amino)-3-(tetrahydro-2H-pyran-4-yl)propanoic acid (Intermediate R, Example 127); 3-(adamantan-1-yl)-2-((tert-butoxycarbonyl)amino)propanoic acid (Intermediate S, Example 128); 2-((tert-butoxycarbonyl)amino)-3-((1S,2R,5S)-6,6-dimethylbicyclo[3.1.1]heptan-2-yl)propanoic acid (Intermediate T, Example 129); 2-((tert-butoxycarbonyl)amino)-3-(3-methyloxetan-3-yl)propanoic acid (Intermediate U, Example 130).

| Example | Structure | MW | MS (ESI+) |
|---|---|---|---|
| 127 | 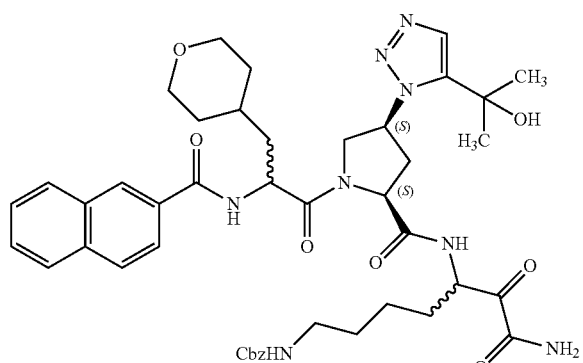 | 838.40 | 839 (M + 1)⊕ | benzyl (5-((2S,4S)-1-(2-(2-naphthamido)-3-(tetrahydro-2H-pyran-4-yl)propanoyl)-4-(5-(2-hydroxypropan-2-yl)-1H-1,2,3-triazol-1-yl)pyrrolidine-2-carboxamido)-7-amino-6,7-dioxoheptyl)carbamate -continued

| Example | Structure | MW | MS (ESI+) |
|---|---|---|---|
| 128 | 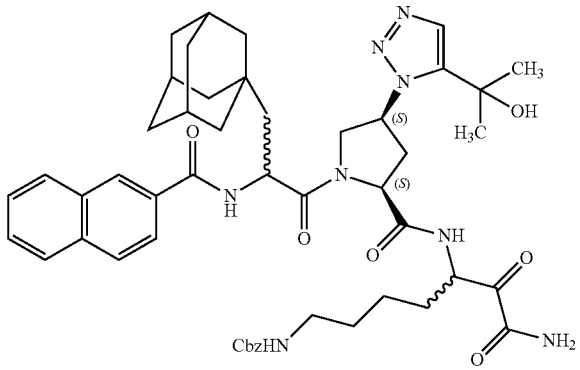 benzyl (5-((2S,4S)-1-(2-(2-naphthamido)-3-((3S,5S,7S)-adamantan-1-yl)propanoyl)-4-(5-(2-hydroxypropan-2-yl)-1H-1,2,3-triazol-1-yl)pyrrolidine-2-carboxamido)-7-amino-6,7-dioxoheptyl)carbamate | 888.45 | 889 (M + 1)⊕ |
| 129 | 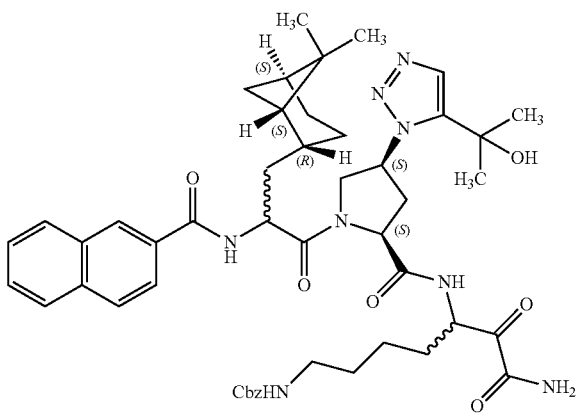 benzyl (5-((2S,4S)-1-(2-(2-naphthamido)-3-((1S,2R,5S)-6,6-dimethylbicyclo[3.1.1]heptan-2-yl)propanoyl)-4-(5-(2-hydroxypropan-2-yl)-1H-1,2,3-triazol-1-yl)pyrrolidine-2-carboxamido)-7-amino-6,7-dioxoheptyl)carbamate | 876.45 | 877 (M + 1)⊕ |
| 130 | 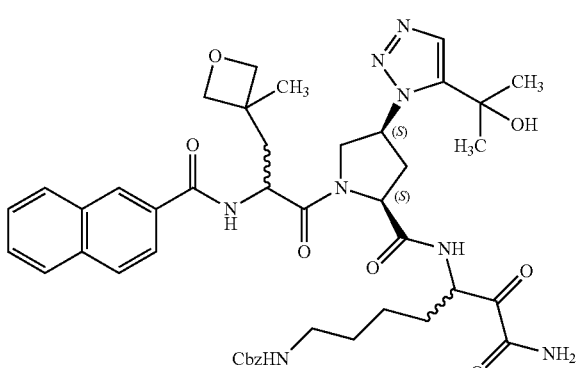 benzyl (5-((2S,4S)-1-(2-(2-naphthamido)-3-(3-methyloxetan-3-yl)propanoyl)-4-(5-(2-hydroxypropan-2-yl)-1H-1,2,3-triazol-1-yl)pyrrolidine-2-carboxamido)-7-amino-6,7-dioxoheptyl)carbamate | 824.39 | 825 (M + 1)⊕ |

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed in practicing the present disclosure. It is intended that the following claims define the scope of the present disclosure and that methods and structures within the scope of these claims and their equivalents be covered thereby.

What is claimed is:

1. A compound of Formula (I):

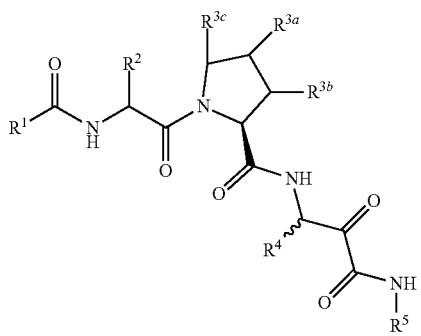

or a pharmaceutically acceptable salt, solvate, solvate of the salt or prodrug thereof wherein:

$R^1$ is selected from the group consisting of:
(a) -aryl and
(b) -heteroaryl;

wherein the aryl and heteroaryl of choices (a) and (b) are each optionally substituted with 1 to 3 substituents independently selected from the group consisting of:
(i) -halogen,
(ii) —CN,
(iii) —$C_{1-6}$alkyl,
(iv) —$C_{2-6}$alkenyl,
(v) —$C_{2-6}$alkynyl,
(vi) —C(O)$R^8$,
(vii) —CO$_2R^8$,
(viii) —CONR$^5R^6$,
(ix) —OH,
(x) —O—$C_{1-6}$alkyl,
(xi) —SH,
(xii) —S(O)$_p$—$C_{1-6}$alkyl,
(xiii) —S(O)$_2$NR$^5R^6$,
(xiv) —NO$_2$,
(xv) —NR$^5R^6$,
(xvi) —NHC(O)$R^8$,
(xvii) —NHC(O)O$R^8$,
(xviii) —NHC(O)NR$^5R^6$, and
(xix) —NHSO$_2C_{1-6}$alkyl, wherein each of the alkyl group of choices (iii), (x), (xii) and (xix) is optionally substituted with 1 to 5 substituents independently selected from -halogen, -halo$C_{1-4}$alkyl, —COR$^8$, —CO$_2R^8$, —CONR$^5R^6$, —NR$^5R^6$, —OH, —O—$C_{1-4}$alkyl, —SH and —S—$C_{1-4}$alkyl;

$R^2$ is selected from the group consisting of:
(a) —$C_{3-8}$alkyl,
(b) —$C_{0-6}$alkyl-$R^7$, and
(c) —(CH$_2$)$_{1-6}$—N(R$^{13}$)(R$^{13}$), wherein each of the alkyl group of choices (a) and (b) is optionally substituted with 1 to 5 substituents independently selected from:
(i) -halogen,
(ii) —$C_{1-4}$alkyl,
(iii) -halo$C_{1-4}$alkyl,
(iv) —OH,
(v) —O—$C_{1-4}$alkyl,
(vi) —SH, and
(vii) —S—$C_{1-4}$alkyl;

$R^{3b}$ and $R^{3c}$ together represent —(CH$_2$)$_{2-3}$—, and $R^{3a}$ is H; or $R^{3b}$ and $R^{3c}$ are each H, and $R^{3a}$ is selected from the group consisting of:

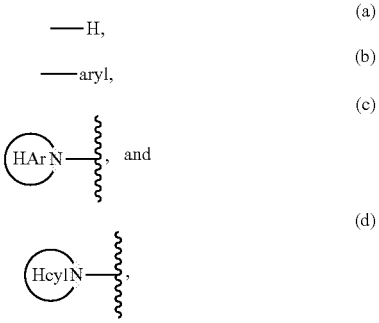

wherein HAr is heteroaryl and Hcyl is heterocycle, wherein each of the aryl of choice (b), HAr and Hcyl is optionally substituted with 1 to 3 groups independently selected from the group consisting of:
(i) -halogen,
(ii) —OH,
(iii) —CR$^{10}R^{11}R^{12}$,
(iv) —(CH$_2$)$_{0-3}$—NHSO$_2$—$C_{1-4}$alkyl, and
(v) —(CH$_2$)$_{0-3}$—SO$_2$—$C_{1-4}$alkyl;

$R^4$ is selected from the group consisting of:
(a) —$C_{1-6}$alkyl,
(b) -halo$C_{1-6}$alkyl,
(c) —$C_{2-6}$alkenyl,
(d) —$C_{2-6}$alkynyl,
(e) —$C_{1-6}$alkyl-$C_{3-6}$cycloalkyl,
(f) —$C_{1-6}$alkyl-aryl, wherein aryl is optionally substituted with nitro or —N(R$^{13}$)(R$^{13}$),
(g) —$C_{1-6}$alkyl-$R^9$, and
(h) -halo$C_{1-6}$alkyl-$R^9$;

each $R^5$ and each $R^6$ are independently selected from the group consisting of:
(a) —H,
(b) —$C_{1-6}$alkyl,
(c) —$C_{0-6}$alkyl-$C_{3-12}$cycloalkyl,
(d) —$C_{0-6}$alkyl-heterocyclyl,
(e) —$C_{0-6}$alkyl-heteroaryl, and
(f) —$C_{0-6}$alkyl-aryl, wherein the alkyl group of choices (b)-(f) is optionally substituted with 1 to 3 groups independently selected from:
(i) -halogen,
(ii) —C(O)$C_{1-4}$alkyl,
(iii) —C(O)O$C_{1-4}$alkyl,
(iv) —OH,
(v) —O$C_{1-4}$alkyl,
(vi) —SH,
(vii) —S$C_{1-4}$alkyl,
(viii) —NH$_2$,
(ix) —NH(C$_{1-4}$alkyl), and
(x) —N(C$_{1-4}$alkyl)(C$_{1-4}$alkyl); or $R^5$, $R^6$ and the nitrogen atom to which they are attached together form a 3- to 7-membered monocyclic or 6- to 11-membered bicyclic heterocycle optionally having an additional heteroatomic moiety selected from —O—, —S(O)$_p$—, and —NR$^{13}$—, and wherein said heterocycle is optionally substituted with 1 to 2 groups independently selected from halogen, -haloC$_{1-4}$alkyl, —OH, —O—C$_{1-4}$alkyl, —SH and —S—C$_{1-4}$alkyl;

R$^7$ is selected from the group consisting of:
(a) —C$_{3-10}$cycloalkyl, and
(b) —C$_{4-10}$heterocyclyl,
wherein each of choices (a) and (b) is optionally substituted with 1 to 3 substituents independently selected from the group consisting of:
(i) —C$_{1-4}$alkyl,
(ii) -halogen,
(iii) —OH,
(iv) —O—C$_{1-4}$alkyl,
(v) —SH, and
(vi) —S—C$_{1-4}$alkyl;

R$^8$ is selected from the group consisting of:
(a) —C$_{1-6}$alkyl,
(b) —C$_{0-6}$alkyl-C$_{3-12}$cycloalkyl,
(c) —C$_{0-6}$alkyl-heterocyclyl,
(d) —C$_{0-6}$alkyl-heteroaryl, and
(e) —C$_{0-6}$alkyl-aryl,
wherein each of the alkyl group of choices (a)-(e) is optionally substituted with 1 to 3 groups independently selected from:
(i) -halogen,
(ii) —OH,
(iii) —OC$_{1-4}$alkyl,
(iv) —SH, and
(v) —SC$_{1-4}$alkyl;

R$^9$ is selected from the group consisting of:
(a) —NH$_2$,
(b) —NH—C$_{1-4}$alkyl,
(c) —N(C$_{1-4}$alkyl)$_2$,
(d) —NH—C(=O)—NH$_2$,
(e) —NH—C(=O)—NH—C$_{1-4}$alkyl,
(f) —NH—C(=O)—N(C$_{1-4}$alkyl)$_2$,
(g) —NH—C(=O)—NH—C$_{3-5}$alkenyl,
(h) —NH—C(=O)—NH—C$_{3-5}$alkynyl,
(i) —NH—C(=O)—NH—C$_{3-6}$cycloalkyl,
(j) —NH—C(=O)—NH-aryl,
(k) —NH—C(=O)—NH-heterocycle,
(l) —NH—C(=O)—NH-heteroaryl,
(m) —NH—C(=O)—NH—SO$_2$—C$_{1-4}$alkyl,
(n) —NH—C(=O)—NH—SO$_2$—C$_{3-6}$cycloalkyl,
(o) —NH—C(=O)—O—C$_{1-4}$alkyl,
(p) —NH—C(=O)—O—C$_{1-4}$alkylaryl,
(q) —NH—C(=O)—C$_{1-4}$alkyl,
(r) —NH—C(=O)—C$_{3-6}$cycloalkyl,
(s) —NH—C(=O)-aryl,
(t) —NH—C(=O)-heterocycle,
(u) —NH—C(=O)-heteroaryl, and
(v) —NH—SO$_2$—C$_{1-4}$alkyl,
wherein each of choices (b) to (v) is optionally substituted with 1 to 3 substituents independently selected from the group consisting of:
(i) —C$_{1-4}$alkyl,
(ii) -halogen,
(iii) —OH,
(iv) —O—C$_{1-4}$alkyl,
(v) —SH,
(vi) —S—C$_{1-4}$alkyl;
(vii) —NO$_2$, and
(viii) —CN;

R$^{10}$, R$^{11}$, and R$^{12}$ are independently selected from the group consisting of: H, halogen, —OH and —C$_{1-6}$alkyl; or
R$^{10}$, R$^{11}$ and the carbon atom to which they are attached together form a C$_{3-12}$cycloalkyl or a heterocyclyl group;

R$^{13}$ is selected from the group consisting of:
(a) —H,
(b) —C$_{1-4}$alkyl,
(c) —C(O)—C$_{1-4}$alkyl,
(d) —C(O)NH$_2$,
(e) —C(O)—NH(C$_{1-4}$alkyl),
(f) —C(O)—NH(C$_{3-6}$cycloalkyl),
(g) —C(O)—N(C$_{1-4}$alkyl)$_2$,
(h) —C(O)O—C$_{1-4}$alkyl, and
(i) —C(O)O—C$_{1-4}$alkylaryl;

p is 0, 1 or 2.

2. A compound of claim 1 wherein R$^1$ is selected from the group consisting of:
(a) -aryl and
(b) -heteroaryl;
wherein the aryl and heteroaryl of choices (a) and (b) are each optionally substituted with 1 to 3 substituents independently selected from the group consisting of:
(i) -halogen,
(ii) —CN,
(iii) —C(O)R$^8$,
(iv) —CONR$^5$R$^6$,
(v) —OH,
(vi) —O—C$_{1-6}$alkyl,
(vii) —S(O)$_p$—C$_{1-6}$alkyl,
(viii) —S(O)$_2$NR$^5$R$^6$,
(ix) —NHC(O)R$^8$,
(x) —NHC(O)OR$^8$,
(xi) —NHSO$_2$C$_{1-6}$alkyl,
wherein each of the alkyl group of choices (iii), (x), (xii) and (xix) is optionally substituted with 1 to 5 substituents independently selected from -halogen, -haloC$_{1-4}$alkyl, —COR$^8$, —CO$_2$R$^8$, —CONR$^5$R$^6$, —NR$^5$R$^6$, —OH, —O—C$_{1-4}$alkyl, —SH and —S—C$_{1-4}$alkyl.

3. A compound of claim 1 wherein R$^2$ is selected from the group consisting of:
(a) —C$_{1-6}$alkyl-R$^7$, and
(b) —(CH$_2$)$_{1-6}$—N(R$^{13}$)(R$^{13}$),
wherein the alkyl group of choice (a) is optionally substituted with 1 to 5 substituents independently selected from:
(i) -halogen,
(ii) —C$_{1-4}$alkyl,
(iii) -haloC$_{1-4}$alkyl,
(iv) —OH,
(v) —O—C$_{1-4}$alkyl,
(vi) —SH, and
(vii) —S—C$_{1-4}$alkyl.

4. A compound of claim 1 wherein R$^2$ is selected from the group consisting of:
(a) —(CH$_2$)$_{1-6}$—R$^7$, and
(b) —(CH$_2$)$_{1-6}$—N(R$^{13}$)(R$^{13}$).

5. A compound of claim 1 wherein R$^{3b}$ and R$^{3c}$ are each H, and R$^{3a}$ is selected from the group consisting of:

(a)

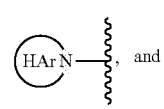, and

-continued

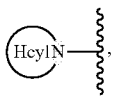
(b)

wherein HAr is heteroaryl and Hcyl is heterocycle, wherein each of HAr and Hcyl is optionally substituted with 1 to 3 groups independently selected from the group consisting of:
(i) -halogen,
(ii) —OH,
(iii) —CR$^{10}$R$^{11}$R$^{12}$,
(iv) —(CH$_2$)$_{0-3}$—NHSO$_2$—C$_{1-4}$alkyl, and
(v) —(CH$_2$)$_{0-3}$—SO$_2$—C$_{1-4}$alkyl.

6. A compound of claim 1 wherein R$^4$ is selected from the group consisting of:
(a) —C$_{1-6}$alkyl,
(b) —C$_{2-6}$alkenyl,
(c) —C$_{1-6}$alkyl-C$_{3-6}$cycloalkyl,
(d) —C$_{1-6}$alkyl-aryl, wherein aryl is optionally substituted with nitro or —N(R$^{13}$)(R$^{13}$), and
(e) —C$_{1-6}$alkyl-R$^9$.

7. A compound of claim 1 wherein R$^4$ is —C$_{1-6}$alkyl-R$^9$.

8. A compound of claim 1 having the Formula (Ia):

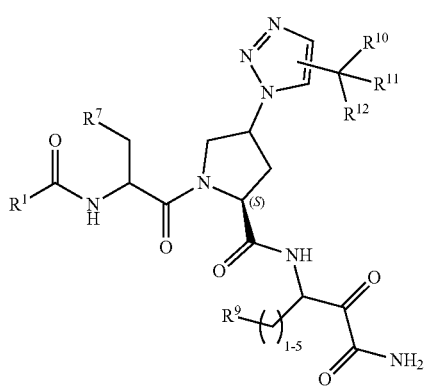
(Ia)

or a pharmaceutically acceptable salt, solvate, solvate of the salt or prodrug thereof; wherein
R$^1$ is selected from the group consisting of:
(a) -aryl and
(b) -heteroaryl;
wherein the aryl and heteroaryl of choices (a) and (b) are each optionally substituted with 1 to 3 substituents independently selected from the group consisting of:
(i) -halogen,
(ii) —CN,
(iii) —C$_{1-6}$alkyl,
(iv) —C$_{2-6}$alkenyl,
(v) —C$_{2-6}$alkynyl,
(vi) —C(O)R$^8$,
(vii) —CO$_2$R$^8$,
(viii) —CONR$^5$R$^6$,
(ix) —OH,
(x) —O—C$_{1-6}$alkyl,
(xi) —SH,
(xii) —S(O)$_p$—C$_{1-6}$alkyl,
(xiii) —S(O)$_2$NR$^5$R$^6$,
(xiv) —NO$_2$,
(xv) —NR$^5$R$^6$,
(xvi) —NHC(O)R$^8$,
(xvii) —NHC(O)OR$^8$,
(xviii) —NHC(O)NR$^5$R$^6$, and
(xix) —NHSO$_2$C$_{1-6}$alkyl,
wherein each of the alkyl group of choices (iii), (x), (xii) and (xix) is optionally substituted with 1 to 5 substituents independently selected from -halogen, -haloC$_{1-4}$alkyl, —COR$^8$, —CO$_2$R$^8$, —CONR$^5$R$^6$, —NR$^5$R$^6$, —OH, —O—C$_{1-4}$alkyl, —SH and —S—C$_{1-4}$alkyl;
each R$^5$ and each R$^6$ are independently selected from the group consisting of:
(a) —H,
(b) —C$_{1-6}$alkyl,
(c) —C$_{0-6}$alkyl-C$_{3-12}$cycloalkyl,
(d) —C$_{0-6}$alkyl-heterocyclyl,
(e) —C$_{0-6}$alkyl-heteroaryl, and
(f) —C$_{0-6}$alkyl-aryl,
wherein each of the alkyl groups of choices (b)-(f) is optionally substituted with 1 to 3 groups independently selected from:
(i) -halogen,
(ii) —C(O)C$_{1-4}$alkyl,
(iii) —C(O)OC$_{1-4}$alkyl,
(iv) —OH,
(v) —OC$_{1-4}$alkyl,
(vi) —SH,
(vii) —SC$_{1-4}$alkyl,
(viii) —NH$_2$,
(ix) —NH(C$_{1-4}$alkyl), and
(x) —N(C$_{1-4}$alkyl)(C$_{1-4}$alkyl); or
R$^5$, R$^6$ and the nitrogen atom to which they are attached together form a 3- to 7-membered monocyclic or 6- to 11-membered bicyclic heterocycle optionally having an additional heteroatomic moiety selected from —O—, —S(O)$_p$—, and —NR$^{13}$—, and wherein said heterocycle is optionally substituted with 1 to 2 groups independently selected from halogen, -haloC$_{1-4}$alkyl, —OH, —O—C$_{1-4}$alkyl, —SH and —S—C$_{1-4}$alkyl;
R$^7$ is selected from the group consisting of:
(a) —C$_{3-10}$cycloalkyl, and
(b) -heterocyclyl,
wherein each of choices (a) and (b) is optionally substituted with 1 to 3 substituents independently selected from the group consisting of:
(i) —C$_{1-4}$alkyl,
(ii) -halogen,
(iii) —OH,
(iv) —O—C$_{1-4}$alkyl,
(v) —SH, and
(vi) —S—C$_{1-4}$alkyl;
R$^8$ is selected from the group consisting of:
(a) —C$_{1-6}$alkyl,
(b) —C$_{0-6}$alkyl-C$_{3-12}$cycloalkyl,
(c) —C$_{0-6}$alkyl-heterocyclyl,
(d) —C$_{0-6}$alkyl-heteroaryl, and
(e) —C$_{0-6}$alkyl-aryl,
wherein the alkyl group of choices (a)-(e) is optionally substituted with 1 to 3 groups independently selected from:
(i) -halogen,
(ii) —OH,
(iii) —OC$_{1-4}$alkyl,
(iv) —SH, and
(v) —SC$_{1-4}$alkyl;

R⁹ is selected from the group consisting of:
(a) —NH₂,
(b) —NH—$C_{1-4}$alkyl,
(c) —N($C_{1-4}$alkyl)₂,
(d) —NH—C(=O)—NH₂,
(e) —NH—C(=O)—NH—$C_{1-4}$alkyl,
(f) —NH—C(=O)—N($C_{1-4}$alkyl)₂,
(g) —NH—C(=O)—NH—$C_{3-5}$alkenyl,
(h) —NH—C(=O)—NH—$C_{3-5}$alkynyl,
(i) —NH—C(=O)—NH—$C_{3-6}$cycloalkyl,
(j) —NH—C(=O)—NH-aryl,
(k) —NH—C(=O)—NH-heterocycle,
(l) —NH—C(=O)—NH-heteroaryl,
(m) —NH—C(=O)—NH—SO₂—$C_{1-4}$alkyl,
(n) —NH—C(=O)—NH—SO₂—$C_{3-6}$cycloalkyl,
(o) —NH—C(=O)—O—$C_{1-4}$alkyl,
(p) —NH—C(=O)—O—$C_{1-4}$alkylaryl,
(q) —NH—C(=O)—$C_{1-4}$alkyl,
(r) —NH—C(=O)—$C_{3-6}$cycloalkyl,
(s) —NH—C(=O)-aryl,
(t) —NH—C(=O)-heterocycle,
(u) —NH—C(=O)-heteroaryl, and
(v) —NH—SO₂—$C_{1-4}$alkyl,
wherein each of choices (b) to (v) is optionally substituted with 1 to 3 substituents independently selected from the group consisting of:
(i) —$C_{1-4}$alkyl,
(ii) -halogen,
(iii) —OH,
(iv) —O—$C_{1-4}$alkyl,
(v) —SH,
(vi) —S—$C_{1-4}$alkyl;
(vii) —NO₂, and
(viii) —CN;
$R^{10}$, $R^{11}$, and $R^{12}$ are independently selected from the group consisting of: H, halogen, —OH and —$C_{1-6}$alkyl; or
$R^{10}$, $R^{11}$ and the carbon atom to which they are attached together form a $C_{3-12}$cycloalkyl or a heterocyclyl group;
$R^{13}$ is selected from the group consisting of:
(a) —H,
(b) —$C_{1-4}$alkyl,
(c) —C(O)—$C_{1-4}$alkyl,
(d) —C(O)NH₂,
(e) —C(O)—NH($C_{1-4}$alkyl),
(f) —C(O)—NH($C_{3-6}$cycloalkyl),
(g) —C(O)—N($C_{1-4}$alkyl)₂,
(h) —C(O)O—$C_{1-4}$alkyl, and
(i) —C(O)O—$C_{1-4}$alkylaryl; and
p is 0, 1 or 2.

9. A compound of claim 8 wherein $R^1$ is selected from the group consisting of:
(a) -aryl, and
(b) -heteroaryl;
wherein the aryl and heteroaryl of choices (a) and (b) are each optionally substituted with 1 to 3 substituents independently selected from the group consisting of:
(i) -halogen,
(ii) —CN,
(iii) —C(O)R⁸,
(iv) —CONR⁵R⁶,
(v) —OH,
(vi) —O—$C_{1-6}$alkyl,
(vii) —S(O)$_p$—$C_{1-6}$alkyl,
(viii) —S(O)₂NR⁵R⁶,
(ix) —NHC(O)R⁸,
(x) —NHC(O)OR⁸, and
(xi) —NHSO₂$C_{1-6}$alkyl,
wherein each of the alkyl group of choices (vi), (vii), and (xi) is optionally substituted with 1 to 5 substituents independently selected from -halogen, -halo$C_{1-4}$alkyl, —COR⁸, —CO₂R⁸, —CONR⁵R⁶, —NR⁵R⁶, —OH, —O—$C_{1-4}$alkyl, —SH and —S—$C_{1-4}$alkyl;
$R^7$ is —$C_{3-10}$cycloalkyl;
$R^9$ is selected from the group consisting of:
(a) —NH—C(=O)—NH—$C_{1-4}$alkyl,
(b) —NH—C(=O)—N($C_{1-4}$alkyl)₂,
(c) —NH—C(=O)—NH—$C_{3-5}$alkenyl,
(d) —NH—C(=O)—NH—$C_{3-5}$alkynyl,
(e) —NH—C(=O)—NH—$C_{3-6}$cycloalkyl,
(f) —NH—C(=O)—NH-aryl,
(g) —NH—C(=O)—NH-heterocycle,
(h) —NH—C(=O)—NH-heteroaryl,
(i) —NH—C(=O)—NH—SO₂—$C_{1-4}$alkyl,
(j) —NH—C(=O)—NH—SO₂—$C_{3-6}$cycloalkyl,
(k) —NH—C(=O)—O—$C_{1-4}$alkyl, and
(l) —NH—C(=O)—O—$C_{1-4}$alkylaryl,
wherein each of choices (a) to (l) is optionally substituted with 1 to 3 substituents independently selected from the group consisting of:
(i) —$C_{1-4}$alkyl,
(ii) -halogen,
(iii) —OH,
(iv) —O—$C_{1-4}$alkyl,
(v) —SH, and
(vi) —S—$C_{1-4}$alkyl;
$R^{10}$ and $R^{11}$ are each —$C_{1-4}$alkyl, or
$R^{10}$, $R^{11}$ and the carbon atom to which they are attached together form a $C_{3-6}$cycloalkyl or a 4- to 6-membered heterocycle, and
$R^{12}$ is —OH.

10. A compound of claim 1 having the formula (Ib):

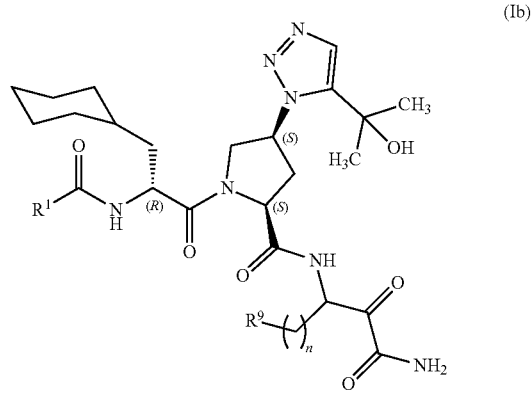

(Ib)

or a pharmaceutically acceptable salt, solvate, solvate of the salt or prodrug thereof, wherein $R^1$ is selected from the group consisting of:
(a) -aryl, and
(b) -heteroaryl;
wherein the aryl and heteroaryl of choices (a) and (b) are each optionally substituted with 1 to 3 substituents independently selected from the group consisting of:
(i) -halogen,
(ii) —CN,
(iii) —C(O)R⁸,
(iv) —CONR⁵R⁶, (v) —OH,
(vi) —O—$C_{1-6}$alkyl,
(vii) —S(O)$_p$—$C_{1-6}$alkyl,
(viii) —S(O)$_2$NR$^5$R$^6$,
(ix) —NHC(O)R$^8$,
(x) —NHC(O)OR$^8$,
(xi) —NHSO$_2$C$_{1-6}$alkyl, and
(xii) C$_{1-4}$alkyl;
wherein each of the alkyl group of choices (vi), (vii), and (xi) is optionally substituted with 1 to 5 substituents independently selected from -halogen, -haloC$_{1-4}$alkyl, —COR$^8$, —CO$_2$R$^8$, —CONR$^5$R$^6$, —NR$^5$R$^6$, —OH, —O—C$_{1-4}$alkyl, —SH and —S—C$_{1-4}$alkyl;
R$^9$ is selected from the group consisting of:
(m) —NH—C(=O)—NH—C$_{1-4}$alkyl,
(n) —NH—C(=O)—N(C$_{1-4}$alkyl)$_2$,
(o) —NH—C(=O)—NH—C$_{3-5}$alkenyl,
(p) —NH—C(=O)—NH—C$_{3-5}$alkynyl,
(q) —NH—C(=O)—NH—C$_{3-6}$cycloalkyl,
(r) —NH—C(=O)—NH-aryl,
(s) —NH—C(=O)—NH-heterocycle,
(t) —NH—C(=O)—NH-heteroaryl,
(u) —NH—C(=O)—NH—SO$_2$—C$_{1-4}$alkyl,
(v) —NH—C(=O)—NH—SO$_2$—C$_{3-6}$cycloalkyl,
(w) —NH—C(=O)—O—C$_{1-4}$alkyl, and
(x) —NH—C(=O)—O—C$_{1-4}$alkylaryl,
wherein each of choices (a) to (l) is optionally substituted with 1 to 3 substituents independently selected from the group consisting of:
(vii) —C$_{1-4}$alkyl,
(viii) -halogen,
(ix) —OH,
(x) —O—C$_{1-4}$alkyl,
(xi) —SH, and
(xii) —S—C$_{1-4}$alkyl; and
n is 1 to 5.

11. A compound of claim 10 wherein n is 4.
12. A compound of claim 10 wherein R$^1$ is phenyl optionally substituted with 1 to 3 substituents independently selected from the group consisting of:
(i) -halogen,
(ii) —CN,
(iii) —C(O)R$^8$,
(iv) —CONR$^5$R$^6$,
(v) —OH,
(vi) —O—C$_{1-6}$alkyl,
(vii) —S(O)$_p$—C$_{1-6}$alkyl, and
(viii) —S(O)$_2$NR$^5$R$^6$;
wherein each of the alkyl group of choices (vi) and (vii) is optionally substituted with 1 to 5 substituents independently selected from -halogen, -haloC$_{1-4}$alkyl, —COR$^8$, —CO$_2$R$^8$, —CONH$_2$, —OH, and —O—C$_{1-4}$alkyl.
13. A compound of claim 10 wherein R$^1$ is naphthyl.
14. A compound of claim 10 wherein R$^1$ is selected from the group consisting of:
(a) 5- or 6-membered monocyclic heteroaryl ring having a heteroatom selected from N, O and S, and optionally 1, 2 or 3 additional N atoms; and
(b) 8-, 9-, or 10-membered fused bicyclic heteroaryl ring having a heteroatom selected from N, O and S, and optionally 1, 2 or 3 additional N atoms;
wherein each of choices (a) and (b) is optionally substituted with a group selected from: OH and C$_{1-4}$alkyl.
15. A compound of claim 1 selected from the group consisting of:

(2S)-1-((R)-2-(2-naphthamido)-3-cyclohexylpropanoyl)-N-(1-amino-4-methyl-1,2-dioxopentan-3-yl)pyrrolidine-2-carboxamide;
methyl (3-((S)-1-((R)-2-(2-naphthamido)-3-cyclohexylpropanoyl)pyrrolidine-2-carboxamido)-4-methyl-2-oxopentanoyl)glycinate;
(2S)-1-((R)-2-(2-naphthamido)-3-cyclohexylpropanoyl)-N-(1-((2-methoxyethyl)amino)-4-methyl-1,2-dioxopentan-3-yl)pyrrolidine-2-carboxamide;
(2S,4R)-1-((R)-2-(2-naphthamido)-3-cyclohexylpropanoyl)-N-(1-amino-4-methyl-1,2-dioxopentan-3-yl)-4-phenylpyrrolidine-2-carboxamide;
(2S,4R)-1-((R)-2-(2-naphthamido)-3-cyclohexylpropanoyl)-N-(1-amino-4-methyl-1,2-dioxopentan-3-yl)-4-(piperidin-1-yl)pyrrolidine-2-carboxamide;
(2S,4R)-1-((R)-2-(2-naphthamido)-3-cyclohexylpropanoyl)-N-(1-amino-7-(3-cyclohexylureido)-2-hydroxy-1-oxoheptan-3-yl)-4-(piperidin-1-yl)pyrrolidine-2-carboxamide;
(2S,4R)-1-((R)-2-(2-naphthamido)-3-cyclohexylpropanoyl)-N-(4-amino-1-cyclobutyl-3,4-dioxobutan-2-yl)-4-(piperidin-1-yl)pyrrolidine-2-carboxamide;
(2S,4R)-1-((R)-2-(2-naphthamido)-3-cyclohexylpropanoyl)-N-(1-amino-4-methyl-1,2-dioxohexan-3-yl)-4-(piperidin-1-yl)pyrrolidine-2-carboxamide;
(2S,4R)-1-((R)-2-(2-naphthamido)-3-cyclohexylpropanoyl)-N-(4-amino-3,4-dioxo-1-phenylbutan-2-yl)-4-(piperidin-1-yl)pyrrolidine-2-carboxamide;
(2S,4S)-1-((R)-2-(2-naphthamido)-3-cyclohexylpropanoyl)-N-(4-amino-1-cyclobutyl-3,4-dioxobutan-2-yl)-4-(piperidin-1-yl)pyrrolidine-2-carboxamide;
(2S,4S)-1-((R)-2-(2-naphthamido)-3-cyclohexylpropanoyl)-N-(1-amino-7-(3-cyclopropylureido)-1,2-dioxoheptan-3-yl)-4-(5-(2-hydroxypropan-2-yl)-1H-1,2,3-triazol-1-yl)pyrrolidine-2-carboxamide;
(2S,4S)-1-((R)-2-(2-naphthamido)-3-cyclohexylpropanoyl)-N-(1-amino-7-(3-isobutylureido)-1,2-dioxoheptan-3-yl)-4-(5-(2-hydroxypropan-2-yl)-1H-1,2,3-triazol-1-yl)pyrrolidine-2-carboxamide;
(2S,4S)-1-((R)-2-(2-naphthamido)-3-cyclohexylpropanoyl)-N-(1-amino-7-(3-cyclohexylureido)-1,2-dioxoheptan-3-yl)-4-(5-(2-hydroxypropan-2-yl)-1H-1,2,3-triazol-1-yl)pyrrolidine-2-carboxamide;
(2S,4S)-1-((R)-2-(2-naphthamido)-3-cyclohexylpropanoyl)-N-(1-amino-1,2-dioxo-7-(3-(pyridin-4-yl)ureido)heptan-3-yl)-4-(5-(2-hydroxypropan-2-yl)-1H-1,2,3-triazol-1-yl)pyrrolidine-2-carboxamide;
(2S,4S)-1-((R)-2-(2-naphthamido)-3-cyclohexylpropanoyl)-N-(1-amino-7-(3-ethylureido)-1,2-dioxoheptan-3-yl)-4-(5-(2-hydroxypropan-2-yl)-1H-1,2,3-triazol-1-yl)pyrrolidine-2-carboxamide;
(2S,4S)-1-((R)-2-(2-naphthamido)-3-cyclohexylpropanoyl)-N-(1-amino-7-(3-(1-methyl-1H-pyrazol-3-yl)ureido)-1,2-dioxoheptan-3-yl)-4-(5-(2-hydroxypropan-2-yl)-1H-1,2,3-triazol-1-yl)pyrrolidine-2-carboxamide;
(2S,4S)-1-((R)-2-(2-naphthamido)-3-cyclohexylpropanoyl)-N-(1-amino-7-(3-(isoxazol-3-yl)ureido)-1,2-dioxoheptan-3-yl)-4-(5-(2-hydroxypropan-2-yl)-1H-1,2,3-triazol-1-yl)pyrrolidine-2-carboxamide;
(2S,4S)-1-((R)-2-(2-naphthamido)-3-cyclohexylpropanoyl)-N-(1-amino-1,2-dioxo-7-(3-(tetrahydro-2H-pyran-4-yl)ureido)heptan-3-yl)-4-(5-(2-hydroxypropan-2-yl)-1H-1,2,3-triazol-1-yl)pyrrolidine-2-carboxamide;
(2S,4S)-1-((R)-2-(2-naphthamido)-3-cyclohexylpropanoyl)-N-(1-amino-1,2-dioxo-7-(3-(pyrimidin-5-yl)

ureido)heptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-7-(3-(1-oxidotetrahydro-2H-thiopyran-4-yl)ureido)-1,2-dioxoheptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-1,2-dioxo-7-(3-(tetrahydro-2H-thiopyran-4-yl)ureido)heptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-1,2-dioxo-7-(3-(pyridin-3-yl)ureido)heptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-1,2-dioxo-7-(3-(pyridin-2-yl)ureido)heptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-1,2-dioxo-7-(3-(prop-2-yn-1-yl)ureido)heptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-7-(3-(5-(tert-butyl)isoxazol-3-yl)ureido)-1,2-dioxoheptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(7-(3-allylureido)-1-amino-1,2-dioxoheptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-7-(3-(cyanomethyl)ureido)-1,2-dioxoheptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-7-(3-cyclobutylureido)-1,2-dioxoheptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-1,2-dioxo-7-((trifluoromethyl)sulfonamido)heptan-3-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-amino-7-(3-(cyclopropyl sulfonyl)ureido)-1,2-dioxoheptan-3-yl)-4-(5-(2-hydroxypropan-2-yl)-1H-1,2,3-triazol-1-yl)pyrrolidine-2-carboxamide;

benzyl (5-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (5-((2S,4S)-1-((R)-2-(2-naphthamido)-3-cyclohexylpropanoyl)-4-(4-(2-hydroxypropan-2-yl)-1H-1,2,3-triazol-1-yl)pyrrolidine-2-carboxamido)-7-amino-6,7-dioxoheptyl)carbamate;

benzyl (5-((2S,4R)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (5-((2S,4R)-1-((R)-2-(2-naphthamido)-3-cyclohexylpropanoyl)-4-(4-(2-hydroxypropan-2-yl)-1H-1,2,3-triazol-1-yl)pyrrolidine-2-carboxamido)-7-amino-6,7-dioxoheptyl)carbamate;

(2S,4S)-1-((R)-2-(2-naphthamido)-3-cyclohexylpropanoyl)-N-(1-amino-1,2-dioxohex-5-en-3-yl)-4-(5-(2-hydroxypropan-2-yl)-1H-1,2,3-triazol-1-yl)pyrrolidine-2-carboxamide;

N-((2R)-1-((2S,4S)-2-((7-(3-propargylureido)-1-amino-1,2-dioxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)isonicotinamide;

(2S,4S)—N-(7-(3-propargylureido)-1-amino-1,2-dioxoheptan-3-yl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide;

(2S,4S)—N-(1-amino-1,2-dioxo-7-(3-(prop-2-yn-1-yl)ureido)heptan-3-yl)-1-((R)-3-cyclohexyl-2-(4-(2,2,2-trifluoro-1,1-dihydroxyethyl)benzamido)propanoyl)-4-(5-(2-hydroxypropan-2-yl)-1H-1,2,3-triazol-1-yl)pyrrolidine-2-carboxamide;

benzyl (5-((2S,4S)-1-((R)-2-(1H-benzo[d]imidazole-2-carboxamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (7-amino-5-((2S,4S)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (5-((2S,4S)-1-((R)-2-(1H-benzo[d]imidazole-4-carboxamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (5-((2S,4S)-1-((R)-2-(1H-benzo[d]imidazole-6-carboxamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (7-amino-5-((2S,4S)-1-((R)-3-cyclohexyl-2-(1,6-naphthyridine-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1,6-naphthyridine-8-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1,8-naphthyridine-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoxaline-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinazoline-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoxaline-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1,5-naphthyridine-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1,6-naphthyridine-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1,8-naphthyridine-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1,7-naphthyridine-3-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1,5-naphthyridine-3-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoxaline-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(4-oxo-3,4-dihydroquinazoline-7-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1,5-naphthyridine-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1-methyl-1H-imidazole-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1-methyl-1H-imidazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1-methyl-1H-imidazole-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-pyrrolo[3,2-c]pyridine-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-indole-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-indole-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-indole-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-indazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-indazole-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-indazole-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-indazole-7-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (5-((2S,4S)-1-((R)-2-(1-naphthamido)-3-cyclohexylpropanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (7-amino-5-((2S,4S)-1-((R)-3-cyclohexyl-2-(isoxazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(oxazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(oxazole-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-2-(3-carbamoylbenzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-2-(4-carbamoylbenzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-2-(2-cyanobenzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-2-(3-cyanobenzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-2-(4-cyanobenzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(2-fluorobenzamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(4-fluorobenzamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(2-methoxybenzamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(3-methoxybenzamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(4-methoxybenzamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(2-((methylperoxy)thio)benzamido)-propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(3-((methylperoxy)thio)benzamido)-propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(4-((difluoromethyl)sulfonyl)benzamido)-propanoyl)-4-

(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(4-((2-methoxyethyl)sulfonyl)benzamido)-propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-2-(4-((2-amino-2-oxoethyl)sulfonyl)benzamido)-3-cyclohexylpropanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(4-(isopropylsulfonyl)benzamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(nicotinamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(picolinamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(isonicotinamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(pyrimidine-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(isoquinoline-1-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoline-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoline-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(isoquinoline-5-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(isoquinoline-8-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoline-8-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoline-2-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1-oxo-1,2-dihydroisoquinoline-3-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(isoquinoline-3-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoline-3-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(2-oxo-1,2-dihydroquinoline-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(isoquinoline-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(isoquinoline-7-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(imidazo[1,2-a]pyridine-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(quinoline-7-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(pyrido[2,3-b]pyrazine-8-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(pyrido[2,3-b]pyrazine-6-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(pyrido[2,3-b]pyrazine-7-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1H-1,2,3-triazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

benzyl (7-amino-5-((2S,4S)-1-((R)-3-cyclohexyl-2-(1-methyl-1H-1,2,3-triazole-4-carboxamido)propanoyl)-4-(5-(2-hydroxypropan-2-yl)-1H-1,2,3-triazol-1-yl)pyrrolidine-2-carboxamido)-6,7-dioxoheptyl)carbamate;

(2S,4S)—N-(1-amino-7-(3-cyclopropylureido)-1,2-dioxoheptan-3-yl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide;

(2S,4S)—N-(1-amino-7-(3-cyclopropylureido)-1,2-dioxoheptan-3-yl)-1-((R)-2-(4-cyanobenzamido)-3-cyclohexylpropanoyl)-4-(5-(2-hydroxypropan-2-yl)-1H-1,2,3-triazol-1-yl)pyrrolidine-2-carboxamide;

N-((2R)-1-((2S,4S)-2-((1-amino-7-(3-cyclopropylureido)-1,2-dioxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)imidazo[1,2-a]pyridine-6-carboxamide;

N-((2R)-1-((2S,4S)-2-((1-amino-7-(3-cyclopropylureido)-1,2-dioxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)quinoline-3-carboxamide;

(2S,4S)-1-((R)-2-(4-((2-amino-2-oxoethyl)sulfonyl)benzamido)-3-cyclohexylpropanoyl)-N-(1-amino-7-(3-cyclopropylureido)-1,2-dioxoheptan-3-yl)-4-(5-(2-hydroxypropan-2-yl)-1H-1,2,3-triazol-1-yl)pyrrolidine-2-carboxamide;

(2S,4S)—N-(1-amino-7-(3-cyclopropylureido)-1,2-dioxoheptan-3-yl)-1-((R)-3-cyclohexyl-2-(4-((difluoromethyl)sulfonyl)benzamido)propanoyl)-4-(5-(2-hydroxypropan-2-yl)-1H-1,2,3-triazol-1-yl)pyrrolidine-2-carboxamide;

N-((2R)-1-((2S,4S)-2-((1-amino-7-(3-cyclopropylureido)-1,2-dioxoheptan-3-yl)carbamoyl)-4-(5-(2-hydroxypropan-2-yl)-1H-1,2,3-triazol-1-yl)pyrrolidin-1-yl)-3-cyclohexyl-1-oxopropan-2-yl)-1H-indazole-7-carboxamide;

(2S,4S)—N-(1-amino-7-(3-cyclopropylureido)-1,2-dioxoheptan-3-yl)-1-((R)-3-cyclohexyl-2-(4-((2-methoxyethyl)sulfonyl)benzamido)propanoyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(4-amino-1-(4-nitrophenyl)-3,4-dioxobutan-2-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(4-acetamidophenyl)-4-amino-3,4-dioxobutan-2-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(4-amino-1-(4-(3-cyclohexylureido)phenyl)-3,4-dioxobutan-2-yl)-4-(5-(2-hydroxypropan-2-yl)-1H-1,2,3-triazol-1-yl)pyrrolidine-2-carboxamide;

benzyl (2-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)-4-amino-3,4-dioxobutyl)carbamate;

benzyl (7-amino-5-((3S)-2-((R)-3-cyclohexyl-2-(4-(methylsulfonyl)benzamido)propanoyl)-2-azabicyclo[2.2.1]heptane-3-carboxamido)-6,7-dioxoheptyl)carbamate;

benzyl (5-((2S,4S)-1-(2-(2-naphthamido)-4-((1S,4R)-bicyclo[2.2.1]heptan-2-yl)butanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (5-((2S,4S)-1-((R)-2-(2-naphthamido)-3-(((benzyloxy)carbonyl)amino)propanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (5-((2S,4S)-1-(2-(2-naphthamido)-3-(tetrahydro-2H-pyran-4-yl)propanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (5-((2S,4S)-1-(2-(2-naphthamido)-3-((3S,5S,7S)-adamantan-1-yl)propanoyl)-4-(5-(2-hydroxypropan-2-yl)-1H-1,2,3-triazol-1-yl)pyrrolidine-2-carboxamido)-7-amino-6,7-dioxoheptyl)carbamate;

benzyl (5-((2S,4S)-1-(2-(2-naphthamido)-3-((1S,2R,5S)-6,6-dimethylbicyclo[3.1.1]heptan-2-yl)propanoyl)-4-(5-(2-hydroxypropan-2-yl)-1H-1,2,3-triazol-1-yl)pyrrolidine-2-carboxamido)-7-amino-6,7-dioxoheptyl)carbamate; and benzyl (5-((2S,4S)-1-(2-(2-naphthamido)-3-(3-methyloxetan-3-yl)propanoyl)-4-(5-(2-hydroxypropan-2-yl)-1H-1,2,3-triazol-1-yl)pyrrolidine-2-carboxamido)-7-amino-6,7-dioxoheptyl)carbamate;

or a pharmaceutically acceptable salt, solvate, salt of the solvate or prodrug thereof.

16. A pharmaceutical composition comprising a compound of claim 1 and a pharmaceutically acceptable carrier.

* * * * *